US007962316B2

(12) United States Patent
Jackson et al.

(10) Patent No.: US 7,962,316 B2
(45) Date of Patent: Jun. 14, 2011

(54) METHOD OF DESIGNING SIRNAS FOR GENE SILENCING

(75) Inventors: Aimee L. Jackson, Seattle, WA (US); Steven R. Bartz, Seattle, WA (US); Julja Burchard, Mount Vernon, WA (US); Peter S. Linsley, Seattle, WA (US); Wei Ge, Redmond, WA (US); Guy L. Cavet, Burlingame, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1035 days.

(21) Appl. No.: 10/577,696

(22) PCT Filed: Oct. 27, 2004

(86) PCT No.: PCT/US2004/035636
§ 371 (c)(1),
(2), (4) Date: Mar. 12, 2007

(87) PCT Pub. No.: WO2005/042708
PCT Pub. Date: May 12, 2005

(65) Prior Publication Data
US 2008/0234941 A1    Sep. 25, 2008

Related U.S. Application Data

(60) Provisional application No. 60/572,314, filed on May 17, 2004, provisional application No. 60/515,180, filed on Oct. 27, 2003.

(51) Int. Cl.
G06F 17/10     (2006.01)
G06F 7/60      (2006.01)
(52) U.S. Cl. ................ 703/2; 702/19; 703/11; 707/723; 707/748; 536/23.1
(58) Field of Classification Search ........................ None
See application file for complete search history.

(56) References Cited

U.S. PATENT DOCUMENTS

| 6,506,559 B1 | 1/2003 | Fire et al. | |
|---|---|---|---|
| 2002/0086356 A1 | 7/2002 | Tuschl et al. | |
| 2002/0162126 A1 | 10/2002 | Beach et al. | |
| 2003/0143597 A1 | 7/2003 | Finney et al. | |
| 2003/0166282 A1* | 9/2003 | Brown et al. | 435/455 |
| 2003/0175950 A1* | 9/2003 | McSwiggen | 435/325 |
| 2003/0194725 A1 | 10/2003 | Greener et al. | |

FOREIGN PATENT DOCUMENTS

| WO | WO 02/44321 | 6/2002 |
|---|---|---|
| WO | WO 03/006477 | 1/2003 |
| WO | 03/070193 A2 | 8/2003 |
| WO | WO 03/065281 A1 | 8/2003 |

OTHER PUBLICATIONS

Levenkova et al. "Gene Specific siRNA Selector", 2004, Bioinformatics, vol. 20, No. 3, pp. 430-432.*

Aza-Blanc et al. (2003). "Identification of Modulators of TRAIL-Induced Apoptosis via RNAi-Based Phenotypic Screening". Mol. Cell 12(3):627-637.
Bass (2000). "Double-Stranded RNA as a Template for Gene Silencing". Cell 101(3):235-238.
Boden et al. (2003). "Promoter Choice Affects the Potency of HIV-1 Specific RNA Interference". Nucleic Acids Res. 31(17):5033-5038.
Brummelkamp et al. (2002). "A System for Stable Expression of Short Interfering RNAs in Mammalian Cells". Science 296(5567):550-553.
Campbell (1994). "Advances in Statistical Methodology for the Evaluation of Diagnostic and Laboratory Tests". Stat. Med. 13(May 7):499-508.
Couzin (2002). "Breakthrough of the Year. Small RNAs Make Big Splash". Science 298(5602):2296-2297.
Elbashir et al. (2001). "Duplexes of 21-Nucleotide RNAs Mediate RNA Interference in Cultured Mammalian Cells". Nature 411(6836):494-498.
Elbashir et al. (2001). "Functional Anatomy of siRNAs for Mediating Efficient RNAi in *Drosophila melanogaster* Embryo Lysate". EMBO J 20(23):6877-6888.
Elbashir et al. (2001). "RNA Interference Is Mediated By 21- and 22-Nucleotide RNAs". Genes Dev. 15(2):188-200.
Fire et al. (1998). "Potent and Specific Genetic Interference by Double-Stranded RNA in *Caenorhabditis elegans* ". Nature 391(6669):806-811.
Grant (1999). "Dissecting The Mechanisms Of Posttranscriptional Gene Silencing: Divide And Conquer". Cell 96(3):303-306.
Gribskov et al. (1987). "Profile Analysis: Detection Of Distantly Related Proteins". Proc. Natl. Acad. Sci. U S A 84(13):4355-4358.
Gribskov et al. (1990). "Profile Analysis". Methods Enzymol. 183:146-159.
Gribskov et al. (1996). "Use Of Receiver Operating Characteristic (ROC) Analysis To Evaluate Sequence Matching". Comput. Chem. 20(1):25-33.
Grishok et al. (2001). "Genes And Mechanisms Related To RNA Interference Regulate Expression Of The Small Temporal RNAs That Control *C. elegans* Developmental Timing". Cell 106(I):23-34.
Guo et al. (1995). "par-1, A Gene Required for Establishing Polarity in *C. elegans* Embryos, Encodes A Putative Ser/Thr Kinase That is Asymmetrically Distributed". Cell 81(4):611-620.
Hammond et al. (2001). "Argonaute2, A Link Between Genetic and Biochemical Analyses of RNAi". Science 293(5532):1146-1150.
Hannon (2002). "RNA Interference". Nature 418(6894):244-251.
Henikoff et al. (1994). "Position-Based Sequence Weights". J. Mol. Biol. 243(4):574-578.

(Continued)

*Primary Examiner* — Carolyn L. Smith
(74) *Attorney, Agent, or Firm* — Christensen O'Connor Johnson Kindness PLLC

(57) ABSTRACT

The present invention provides a method for identifying siRNA target motifs in a transcript using a position-specific score matrix approach. The invention also provides a method for identifying off-target genes of an siRNA using a position-specific score matrix approach. The invention further provides a method for designing siRNAs with higher silencing efficacy and specificity. The invention also provides a library of siRNAs comprising siRNAs with high silencing efficacy and specificity.

37 Claims, 27 Drawing Sheets

OTHER PUBLICATIONS

Hutvagner et al. (2001). "A Cellular Function for the RNA-Interference Enzyme Dicer In The Maturation Of The let-7 Small Temporal RNA". Science 293(5531):834-838.

Hutvagner et al. (2002). "A microRNA in a Multiple-Turnover RNAi Enzyme Complex". Science 297(5589):2056-2060.

Kawasaki et al. (2003). "Short Hairpin Type of dsRNAs that are Controlled by tRNA(Val) Promoter Significantly induce RNAi-mediated Gene Silencing in the Cytoplasm of Human Cells". Nucleic Acids Res. 31(2):700-707.

Ketting et al. (2001). "Dicer Functions in RNA Interference and in Synthesis of Small RNA Involved in Developmental Timing in *C. Elegans*". Genes Dev. 15(20):2654-2659.

Krogh et al. (1994). "Hidden Markov Models in Computational Biology. Applications To Protein Modeling". J. Mol. Biol. 235(5):1501-1531.

Kwak et al. (2003). "RNA Interference With Small Hairpin RNAs Transcribed From A Human U6 Promoter-Driven DNA Vector". J. Pharmacol. Sci. 93(2):214-217.

Lau et al. (2001). "An Abundant Class Of Tiny RNAs With Probable Regulatory Roles in *Caenorhabditis elegans*". Science 294(5543):858-862.

Lee et al. (1993). "The *C. elegans* Heterochronic Gene lin-4 Encodes Small RNAs With Antisense Complementarity To lin-14". Cell 75(5):843-854.

Lee et al. (2001). "An Extensive Class of Small RNAs in *Caenorhabditis elegans*". Science 294(5543):862-864.

Lewis et al. (2002). "Efficient Delivery Of siRNA For Inhibition Of Gene Expression In Postnatal Mice". Nat. Genet. 32(1):107-108.

Martinez et al. (2002). "Single-Stranded Antisense siRNAs Guide Target RNA Cleavage In RNAi". Cell 110(5):563-574.

Martinez et al. (2002). "Synthetic Small Inhibiting RNAs: Efficient Tools To Inactivate Oncogenic Mutations And Restore p53 Pathways". Proc. Natl. Acad. Sci. U S A 99(23):14849-14854.

McCaffrey et al. (2002). "RNA Interference in Adult Mice". Nature 418(6893):38-39.

McManus et al. (2002). "Gene Silencing in Mammals by Small Interfering RNAs". Nat. Rev. Genet. 3(10):737-747.

Metz (1986). "ROC Methodology In Radiologic Imaging". Invest. Radiol. 21(9):720-733.

Miyagishi et al. (2002). "U6 Promoter-Driven siRNAs With Four Uridine 3' Overhangs Efficiently Suppress Targeted Gene Expression In Mammalian Cells". Nat. Biotechno. 20(5):497-500.

Mourelatos et al. (2002). "miRNPs: A Novel Class Of Ribonucleoproteins Containing Numerous microRNAs". Genes Dev. 16(6):720-728.

Paddison et al. (2002). "RNA Interference: The New Somatic Cell Genetics?". Cancer Cell 2(I):17-23.

Paddison et al. (2002). "Short Hairpin RNAs (shRNAs) Induce Sequence-Specific Silencing In Mammalian Cells". Genes Dev. 16(8):948-958.

Paddison et al. (2002). "Stable Suppression Of Gene Expression By RNAi in Mammalian Cells". Proc. Natl. Acad. Sci. U S A 99(3):1443-1448.

Paul et al. (2002). "Effective Expression Of Small Interfering RNA In Human Cells". Nat. Biotechnol. 20(5):505-508.

Petcherski et al. (2000). "LAG-3 Is A Putative Transcriptional Activator In The *C. elegans* Notch Pathway". Nature 405(6784):364-368.

Reinhart et al. (2000). "The 21-Nucleotide let-7 RNA Regulates Developmental Timing in *Caenorhabditis elegans*". Nature 403(6772):901-906.

Rubinson et al. (2003). "A Lentivirus-Based System to Functionally Silence Genes in Primary Mammalian Cells, Stem Cells and Transgenic Mice by RNA Interference". Nat. Genet. 33(3):401-406.

Salzberg et al. (1998). "Microbial Gene Identification Using Interpolated Markov Models". Nucleic Acids Res. 26(2):544-548.

Song et al. (2003). "RNA Interference Targeting Fas Protects Mice From Fulminant Hepatitis". Nat. Med. 9(3):347-351.

Sorensen et al. (2003). "Gene Silencing By Systemic Delivery Of Synthetic siRNAs In Adult Mice". J. Mol. Biol. 327(4):761-766.

Sui et al. (2002). "A DNA Vector-Based RNAi Technology To Suppress Gene Expression In Mammalian Cells". Proc. Natl. Acad. Sci. U S A 99(8):5515-5520.

Tabara et al. (1999). "The rde-1 Gene, RNA Interference, And Transposon Silencing in *C. elegans*". Cell 99(2):I23-32.

Tiscornia et al. (2003). "A General Method For Gene Knockdown In Mice By Using Lentiviral Vectors Expressing Small Interfering RNA". Proc. Natl. Acad. Sci. U S A 100(4):1844-1848.

Tuschl et al. (1999). "Targeted mRNA Degradation By Double-Stranded RNA In Vitro". Genes Dev. 13(24):3191-3197.

Wightman et al. (1993). "Posttranscriptional Regulation Of The Heterochronic Gene lin-14 by lin- 4 Mediates Temporal Pattern Formation In *C. elegans*". Cell 75(5):855-862.

Wilda et al. (2002). "Killing Of Leukemic Cells With A BCR/ABL Fusion Gene By RNA Interference (RNAi)". Oncogene 21(37):5716-5724.

Williams et al. (2002). "Argonautei Is Required For Efficient RNA Interference In *Drosophila* Embryos". Proc. Natl. Acad. Sci. U S A 99(10):6889-6894.

Xia et al. (2002). "siRNA-Mediated Gene Silencing in Vitro and in Vivo". Nat. Biotechnol. 20(10):1006-1010.

Yu et al. (2002). "RNA Interference by Expression of Short-Interfering RNAs and Hairpin RNAs in Mammalian Cells". Proc. Natl. Acad. Sci. U S A 99(9):6047-6052.

Zamore et al. (2000). "RNAi: Double-Stranded RNA Directs the ATP-Dependent Cleavage of mRNA at 21 to 23 Nucleotide Intervals". Cell 101(1):25-33.

Zeng (2002). "Both Natural and Designed Micro RNAs Can Inhibit the Expression of Cognate mRNAs When Expressed in Human Cells". Mol. Cell 9(6)1327-1333.

Zijlstra et al. (1989). "Germ-Line Transmission of a Disrupted Beta 2-Microgobulin Gene Produced by Homologous Recombination in Embryonic Stem Cells". Nature 342(6248):435-438.

Levenkova et al. 2004, "Gene specific siRNA selector," Bioinformatics, 20(3):430-2.

Supplementary European Search Report dated Jun. 5, 2008 for EP 04810056.4-2401, European national stage of International Application No. PCT/US2004/035636.

Barash et al., 2001, "A Simple Hyper-Geometric Approach for Discovering Putative Transcription Factor Binding Sites," Lecture Notes in Computer Science, Springer Verlag, 2149, pp. 278-293.

Harborth et al., 2003, "Sequence, chemical, and structural variation of small interfering RNAs and short hairpin RNAs and the effect on mammalian gene silencing," Antisense & Nucleic Acid Drug Development, 13, pp. 83-105.

Klein et al., 2003, "RSEARCH: Finding homologs of single structured RNA sequences," BMC Bioinformatics, 4, pp. 44.1-44.16.

Lim et al., 2003, "The microRNAs of *Caenorhabditis elegans*," Genes and Development, 17, pp. 991-1008.

\* cited by examiner

| Position | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| NM_018461 | C | C | A | A | A | A | G | G | T | C | A | T | T | A | C | T | C | A | G |
| NM_018130 | G | A | T | C | C | T | G | A | T | C | A | T | T | A | T | C | T | A | G |
| NM_005861 | C | T | C | C | A | G | G | C | T | C | A | T | T | G | C | C | G | C | G |
| Contig46927_RC | A | T | T | T | T | T | G | G | T | G | A | T | C | A | C | C | G | A | G |
| Contig52414_RC | A | T | C | C | G | G | A | G | T | T | A | T | T | A | C | G | A | A | G |
| NM_001887 | A | A | C | C | G | T | G | C | C | T | A | T | T | A | C | C | A | G | C |
| NM_004034 | A | C | G | A | G | T | G | G | A | G | A | T | T | A | C | C | G | A | A |
| NM_001156 | A | C | G | A | G | T | G | G | A | G | A | T | T | A | C | C | G | A | A |
| NM_002570 | T | G | T | T | C | T | A | A | T | T | T | T | T | A | C | C | G | A | T |
| Contig54761_RC | T | A | A | A | A | T | C | T | T | T | T | T | A | C | C | G | A | A |   |
| Contig53248_RC | G | T | G | G | C | C | T | T | T | T | T | T | T | A | C | C | G | A | T |
| Contig55337_RC | T | G | A | G | A | A | A | A | A | A | G | T | T | A | C | C | G | A | A |

FIG. 6

SEQUENCE LISTING

```
<160> NUMBER OF SEQ ID NOS: 990

<210> SEQ ID NO 1
<211> LENGTH: 19
<212> TYPE: DNA
<213> ORGANISM: Artificial Sequence
<220> FEATURE:
<223> OTHER INFORMATION: an example of siRNA

<400> SEQUENCE: 1
gcgttaatgt gataatata                                              19

<210> SEQ ID NO 2
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 2
tgttgtccgg ctgatggac                                              19

<210> SEQ ID NO 3
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 3
actcttactg ctctccagt                                              19

<210> SEQ ID NO 4
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 4
cttaacacgg atgctggtg                                              19

<210> SEQ ID NO 5
<211> LENGTH: 19
<212> TYPE: DNA
```

```
<213> ORGANISM: Artificial Sequence
<220> FEATURE:
<223> OTHER INFORMATION: DNA sequence corresponding to siRNA sense
      strand in construction of siRNA library

<400> SEQUENCE: 5
ggagagcttt ctaggacct                                                    19

<210> SEQ ID NO 6
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 6
agtcatcccg cagagccgc                                                    19

<210> SEQ ID NO 7
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 7
atcgtagtgc ttgtactta                                                    19

<210> SEQ ID NO 8
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 8
ggagacgtac cgctgcatc                                                    19

<210> SEQ ID NO 9
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 9
gcagtgattg ctcagcagc                                                    19

<210> SEQ ID NO 10
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 10
gagtttaccg accaccaag                                                    19

<210> SEQ ID NO 11
<211> LENGTH: 19
<212> TYPE: DNA
<213> ORGANISM: Artificial Sequence
<220> FEATURE:
```

```
<223> OTHER INFORMATION: DNA sequence corresponding to siRNA sense
      strand in construction of siRNA library

<400> SEQUENCE: 11
tgcggatgcc attcagtgg                                                        19

<210> SEQ ID NO 12
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 12
cacggttggc agagtctat                                                        19

<210> SEQ ID NO 13
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 13
gcaagttgag ctctaccgc                                                        19

<210> SEQ ID NO 14
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 14
tggccagcgc ttactggaa                                                        19

<210> SEQ ID NO 15
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 15
gttcaaaagc tggatgatc                                                        19

<210> SEQ ID NO 16
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 16
ggcctctata cccctcaaa                                                        19

<210> SEQ ID NO 17
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library
```

<400> SEQUENCE: 17
agaaccgaat cgtctagag                                                19

<210> SEQ ID NO 18
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 18
cacgatgcat agccatcct                                                19

<210> SEQ ID NO 19
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 19
cagagacaga atctacact                                                19

<210> SEQ ID NO 20
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 20
caacagaagg ttgtcttgt                                                19

<210> SEQ ID NO 21
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 21
ttgtgtgtgg gaccgtaat                                                19

<210> SEQ ID NO 22
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 22
gctcacggtc attaccgag                                                19

<210> SEQ ID NO 23
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 23
cctgaggaac attactcgg                                                    19

<210> SEQ ID NO 24
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 24
tgctgacctc tgttacctc                                                    19

<210> SEQ ID NO 25
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 25
cgacacggcc tgtgtagct                                                    19

<210> SEQ ID NO 26
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 26
cggcagccag agcatgtac                                                    19

<210> SEQ ID NO 27
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 27
ccagaacttg cagcaactg                                                    19

<210> SEQ ID NO 28
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 28
cctcacggtc atccgcggc                                                    19

<210> SEQ ID NO 29
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 29
ctacgccctg gtcatcttc                                                    19

```
<210> SEQ ID NO 30
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 30
tctcaaggat attgggctt                                                     19

<210> SEQ ID NO 31
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 31
ggatattggg ctttacaac                                                     19

<210> SEQ ID NO 32
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 32
cattactcgg ggggccatc                                                     19

<210> SEQ ID NO 33
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 33
aatgctgacc tctgttacc                                                     19

<210> SEQ ID NO 34
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 34
ctggatcgta agaaggcag                                                     19

<210> SEQ ID NO 35
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 35
tggaaggtga aaggtcacc                                                     19
```

```
<210> SEQ ID NO 36
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 36
ggacaactgc agctactct                                                19

<210> SEQ ID NO 37
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 37
tacggactca ccttgcttg                                                19

<210> SEQ ID NO 38
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 38
gtatatacat tcagctgac                                                19

<210> SEQ ID NO 39
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 39
ggaacacccc ccgcttatc                                                19

<210> SEQ ID NO 40
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 40
gtggccgatc cttatgatc                                                19

<210> SEQ ID NO 41
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 41
atgtgattgg tctgttgga                                                19

<210> SEQ ID NO 42
<211> LENGTH: 19
```

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 42
gtcatcagct ttgtgccac                                                   19

<210> SEQ ID NO 43
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 43
taattcacag ggacctaaa                                                   19

<210> SEQ ID NO 44
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 44
tgcctacttt gctcagtac                                                   19

<210> SEQ ID NO 45
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 45
cctacagaga actgcggtt                                                   19

<210> SEQ ID NO 46
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 46
ttctccgagg tctaaagta                                                   19

<210> SEQ ID NO 47
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 47
ccagtggccg atccttatg                                                   19

<210> SEQ ID NO 48
<211> LENGTH: 19
<212> TYPE: DNA
<213> ORGANISM: Artificial Sequence
```

```
<220> FEATURE:
<223> OTHER INFORMATION: DNA sequence corresponding to siRNA sense
      strand in construction of siRNA library

<400> SEQUENCE: 48
ggcctttcca cgggaactc                                                    19

<210> SEQ ID NO 49
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 49
ctgaagaagc tactgcttg                                                    19

<210> SEQ ID NO 50
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 50
gacatgcgaa tgacactag                                                    19

<210> SEQ ID NO 51
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 51
agaggaactc tctgcaagc                                                    19

<210> SEQ ID NO 52
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 52
aaactgggag gctacttac                                                    19

<210> SEQ ID NO 53
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 53
actgacaaca aagtgcagc                                                    19

<210> SEQ ID NO 54
<211> LENGTH: 19
<212> TYPE: DNA
<213> ORGANISM: Artificial Sequence
<220> FEATURE:
<223> OTHER INFORMATION: DNA sequence corresponding to siRNA sense
``` strand in construction of siRNA library

<400> SEQUENCE: 54
ctcacattgt ccaccagga                                                  19

<210> SEQ ID NO 55
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 55
gacctgtgcc ttttagaga                                                  19

<210> SEQ ID NO 56
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 56
gacttcattg acagtggcc                                                  19

<210> SEQ ID NO 57
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 57
aaaggacaac tgcagctac                                                  19

<210> SEQ ID NO 58
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 58
tggaggggaa tgctcagaa                                                  19

<210> SEQ ID NO 59
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 59
taaagatggc actttcccg                                                  19

<210> SEQ ID NO 60
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

```
<400> SEQUENCE: 60
aaggcagcta aaggaagtg                                                    19

<210> SEQ ID NO 61
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 61
tattgggcca gcagattac                                                    19

<210> SEQ ID NO 62
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 62
ttatgacgct aggccacaa                                                    19

<210> SEQ ID NO 63
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 63
ggagaaagat ccctttgag                                                    19

<210> SEQ ID NO 64
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 64
acaaaaacgg agatccgtc                                                    19

<210> SEQ ID NO 65
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 65
ataagcagca agaaacggc                                                    19

<210> SEQ ID NO 66
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 66
```

-continued gaatttcgggctactttgg                                          19

<210> SEQ ID NO 67
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 67
cgcaccttcc atgtggaga                                         19

<210> SEQ ID NO 68
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 68
agacgttttt gtgctgtgg                                         19

<210> SEQ ID NO 69
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 69
gctggagaac ctcatgctg                                         19

<210> SEQ ID NO 70
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 70
ctctaccact gaagagttg                                         19

<210> SEQ ID NO 71
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 71
aagtgggtcg taagaacca                                         19

<210> SEQ ID NO 72
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 72
gaagctgtcc ctgctaaat                                         19

```
<210> SEQ ID NO 73
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 73
gaagagatcc cagtgcttc                                                    19

<210> SEQ ID NO 74
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 74
tctgaaagtg accagctca                                                    19

<210> SEQ ID NO 75
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 75
gaaaatgaag ctttgcggg                                                    19

<210> SEQ ID NO 76
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 76
aagaagaacc agtggttcg                                                    19

<210> SEQ ID NO 77
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 77
ccgagttatt catcgagac                                                    19

<210> SEQ ID NO 78
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 78
aagagaccta cctccggat                                                    19

<210> SEQ ID NO 79
```

-continued

```
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 79
aatatcctca ggggtggag                                                  19

<210> SEQ ID NO 80
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 80
gtgcctcttg ttgcagaga                                                  19

<210> SEQ ID NO 81
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 81
gaagctctcc agaccattt                                                  19

<210> SEQ ID NO 82
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 82
agaagctgtg gatcttagg                                                  19

<210> SEQ ID NO 83
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 83
tgatgcacat catggtggc                                                  19

<210> SEQ ID NO 84
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 84
ctaggaaacc tcaggctta                                                  19

<210> SEQ ID NO 85
<211> LENGTH: 19
<212> TYPE: DNA
```

```
<213> ORGANISM: Artificial Sequence
<220> FEATURE:
<223> OTHER INFORMATION: DNA sequence corresponding to siRNA sense
      strand in construction of siRNA library

<400> SEQUENCE: 85
gcgaatctct gcctttcga                                                   19

<210> SEQ ID NO 86
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 86
cagtcaagct ggctgactt                                                   19

<210> SEQ ID NO 87
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 87
ggatctgatg cgccagttt                                                   19

<210> SEQ ID NO 88
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 88
gcacaactcc tgcaaattc                                                   19

<210> SEQ ID NO 89
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 89
gatggaagag cctctaaga                                                   19

<210> SEQ ID NO 90
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 90
acgaaaagct gcttgagag                                                   19

<210> SEQ ID NO 91
<211> LENGTH: 19
<212> TYPE: DNA
<213> ORGANISM: Artificial Sequence
<220> FEATURE:
```

```
<223> OTHER INFORMATION: DNA sequence corresponding to siRNA sense
      strand in construction of siRNA library

<400> SEQUENCE: 91
gaagaccatc tgtggcacc                                                    19

<210> SEQ ID NO 92
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 92
tcagggacca gctttactg                                                    19

<210> SEQ ID NO 93
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 93
gttaccaaga gcctctttg                                                    19

<210> SEQ ID NO 94
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 94
aaccaaagtg aactggctg                                                    19

<210> SEQ ID NO 95
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 95
gatcggccac ttccttttc                                                    19

<210> SEQ ID NO 96
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 96
agagatctgg gcctcatgt                                                    19

<210> SEQ ID NO 97
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library
```

```
<400> SEQUENCE: 97
agttcgatca gcagctgtt                                              19

<210> SEQ ID NO 98
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 98
tagattgttc caggacacg                                              19

<210> SEQ ID NO 99
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 99
gaagttggat gccagctgt                                              19

<210> SEQ ID NO 100
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 100
tggtgatcac tccaggtag                                              19

<210> SEQ ID NO 101
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 101
tgtccctttc agagacagc                                              19

<210> SEQ ID NO 102
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 102
gacgtcaaac gtaaacagc                                              19

<210> SEQ ID NO 103
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 103
```
aagttcatgt cagggctgg                                                19

<210> SEQ ID NO 104
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 104
caaagatgcc cttctgaac                                                19

<210> SEQ ID NO 105
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 105
aatgcgcaaa ttcagcgag                                                19

<210> SEQ ID NO 106
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 106
gcacaaaagc ttgtctcca                                                19

<210> SEQ ID NO 107
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 107
ttgcagattt tgggtggtc                                                19

<210> SEQ ID NO 108
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 108
acagtcttag gaatcgtgc                                                19

<210> SEQ ID NO 109
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 109
aggacttcgc ccataagag                                                19

```
<210> SEQ ID NO 110
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 110
caacctccag gatacactc                                               19

<210> SEQ ID NO 111
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 111
ccaactttct agctgctgt                                               19

<210> SEQ ID NO 112
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 112
gaatgtgagc gtagagtgg                                               19

<210> SEQ ID NO 113
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 113
ccattggtta ctgacgtgg                                               19

<210> SEQ ID NO 114
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 114
aacccaaacc tccacaatc                                               19

<210> SEQ ID NO 115
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 115
gaaagaagca gttgacctc                                               19
```

```
<210> SEQ ID NO 116
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 116
ctaaaagctg ggtggactc                                              19

<210> SEQ ID NO 117
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 117
gaaagcacct ctttgtgtg                                              19

<210> SEQ ID NO 118
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 118
tgaggccttg gaactcaag                                              19

<210> SEQ ID NO 119
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 119
cctcttggtc gaccttagt                                              19

<210> SEQ ID NO 120
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 120
gcacccagga cttccattt                                              19

<210> SEQ ID NO 121
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 121
gaaactgcag ctatcttcc                                              19

<210> SEQ ID NO 122
<211> LENGTH: 19
```

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 122
gttacaatga ggctgatgc                                                        19

<210> SEQ ID NO 123
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 123
tcacgactcg ctgaactgt                                                        19

<210> SEQ ID NO 124
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 124
gaccgaccct gaagcagaa                                                        19

<210> SEQ ID NO 125
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 125
ttccaggagt atgctgttt                                                        19

<210> SEQ ID NO 126
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 126
ggaacttctg cacaaggag                                                        19

<210> SEQ ID NO 127
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 127
tgttgacgga cagcctatt                                                        19

<210> SEQ ID NO 128
<211> LENGTH: 19
<212> TYPE: DNA
<213> ORGANISM: Artificial Sequence
```

```
<220> FEATURE:
<223> OTHER INFORMATION: DNA sequence corresponding to siRNA sense
      strand in construction of siRNA library

<400> SEQUENCE: 128
ggcattggca tctgctttt                                                  19

<210> SEQ ID NO 129
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 129
gtgaatgaga cactccagt                                                  19

<210> SEQ ID NO 130
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 130
gagctggtgt ctgattgtt                                                  19

<210> SEQ ID NO 131
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 131
gtgtaagcag ctgaggtct                                                  19

<210> SEQ ID NO 132
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 132
ctgcccaaag aaattcgga                                                  19

<210> SEQ ID NO 133
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 133
atttgcccgc gcatttgtg                                                  19

<210> SEQ ID NO 134
<211> LENGTH: 19
<212> TYPE: DNA
<213> ORGANISM: Artificial Sequence
<220> FEATURE:
<223> OTHER INFORMATION: DNA sequence corresponding to siRNA sense
``` strand in construction of siRNA library

<400> SEQUENCE: 134
agaagatgaa tggtctggc					19

<210> SEQ ID NO 135
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 135
aacgggcgat tatctctgg					19

<210> SEQ ID NO 136
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 136
gacttagagc tgggaatct					19

<210> SEQ ID NO 137
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 137
agttgaggag gtttctgca					19

<210> SEQ ID NO 138
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 138
ggattatatc cagcagctc					19

<210> SEQ ID NO 139
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 139
gtggctggat tcatgttcc					19

<210> SEQ ID NO 140
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

```
<400> SEQUENCE: 140
caaggcatcc gttatatct                                                    19

<210> SEQ ID NO 141
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 141
accaggattt ggagtggat                                                    19

<210> SEQ ID NO 142
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 142
ctgaagaagc agtcgcagt                                                    19

<210> SEQ ID NO 143
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 143
atcgattctg ctcctctag                                                    19

<210> SEQ ID NO 144
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 144
tgcctgaaag agacttgtg                                                    19

<210> SEQ ID NO 145
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 145
tcttggacgt gattggact                                                    19

<210> SEQ ID NO 146
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 146
```
agaaaacctg gattcccac                                                19

<210> SEQ ID NO 147
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 147
accacagaac attctggtg                                                19

<210> SEQ ID NO 148
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 148
gaaagccaga caacttctg                                                19

<210> SEQ ID NO 149
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 149
ctctcagtga aagtgccaa                                                19

<210> SEQ ID NO 150
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 150
gacactgcct gcttttact                                                19

<210> SEQ ID NO 151
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 151
aagaacctgg tgaaagtcc                                                19

<210> SEQ ID NO 152
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 152
gaagtgcagc aggttaaga                                                19

<210> SEQ ID NO 153
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 153
agccgagttg taactatcc                                                    19

<210> SEQ ID NO 154
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 154
gatcacagtg gcaatggaa                                                    19

<210> SEQ ID NO 155
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 155
aaactcttgg aagtggtgc                                                    19

<210> SEQ ID NO 156
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 156
atgaatccac agctctacc                                                    19

<210> SEQ ID NO 157
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 157
gaatggaagc ctgaactga                                                    19

<210> SEQ ID NO 158
<211> LENGTH: 19
<212> TYPE: DNA
<213> ORGANISM: Artificial Sequence
<220> FEATURE:
<223> OTHER INFORMATION: DNA sequence corresponding to siRNA sense strand in construction of siRNA library

<400> SEQUENCE: 158
agacatcatg gagtccagc                                                    19

<210> SEQ ID NO 159

<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 159
caagttctcc atcaagtcc                                              19

<210> SEQ ID NO 160
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 160
ggaatagtat gcgcagctt                                              19

<210> SEQ ID NO 161
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 161
gtgattcaga tggagctag                                              19

<210> SEQ ID NO 162
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 162
cacccgtaca tcaatgtct                                              19

<210> SEQ ID NO 163
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 163
tcattggaag aacagcggc                                              19

<210> SEQ ID NO 164
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 164
aagaagacgt tcagcgaca                                              19

<210> SEQ ID NO 165
<211> LENGTH: 19
<212> TYPE: DNA

<213> ORGANISM: Artificial Sequence
<220> FEATURE:
<223> OTHER INFORMATION: DNA sequence corresponding to siRNA sense
      strand in construction of siRNA library

<400> SEQUENCE: 165
aaaaagcctg cccttggtt                                              19

<210> SEQ ID NO 166
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 166
cttgcaacgt ctgttagag                                              19

<210> SEQ ID NO 167
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 167
ctgaaggctt ccttacaag                                              19

<210> SEQ ID NO 168
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 168
cagaagttgt ggaatgagg                                              19

<210> SEQ ID NO 169
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 169
gcaatgagga cagcttgtg                                              19

<210> SEQ ID NO 170
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 170
tgtagctttc cactggagt                                              19

<210> SEQ ID NO 171
<211> LENGTH: 19
<212> TYPE: DNA
<213> ORGANISM: Artificial Sequence
<220> FEATURE:

```
<223> OTHER INFORMATION: DNA sequence corresponding to siRNA sense
      strand in construction of siRNA library

<400> SEQUENCE: 171
tctccttgtg aacagcaac                                                   19

<210> SEQ ID NO 172
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 172
agtgaagaac ctggggtac                                                   19

<210> SEQ ID NO 173
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 173
gttccaccag cattgttcc                                                   19

<210> SEQ ID NO 174
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 174
gaatgagatg caggtgctc                                                   19

<210> SEQ ID NO 175
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 175
caattcgtcg gaggcatca                                                   19

<210> SEQ ID NO 176
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 176
ggggagtttg ctggacttt                                                   19

<210> SEQ ID NO 177
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library
```

```
<400> SEQUENCE: 177
gcagtgcctg cctatgaaa                                                    19

<210> SEQ ID NO 178
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 178
ctagacctag acctagact                                                    19

<210> SEQ ID NO 179
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 179
gaggatgtca acggttatg                                                    19

<210> SEQ ID NO 180
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 180
caaagtcttg gccagaatc                                                    19

<210> SEQ ID NO 181
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 181
gatcgagctg gctgtctttt                                                   19

<210> SEQ ID NO 182
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 182
ggtcttaaag aaggacgtc                                                    19

<210> SEQ ID NO 183
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 183
```
tgaggacgac ctatttgag                                              19

<210> SEQ ID NO 184
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 184
tgagctggtg gattatcac                                              19

<210> SEQ ID NO 185
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 185
ctggtacaag gcagagctt                                              19

<210> SEQ ID NO 186
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 186
ccggaacgtc taagagtca                                              19

<210> SEQ ID NO 187
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 187
tacagaaaag tttggccgg                                              19

<210> SEQ ID NO 188
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 188
aatgaagcct ttgtggctg                                              19

<210> SEQ ID NO 189
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 189
gtgcacattc ctgctgtct                                              19

<210> SEQ ID NO 190
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 190
cctccctatt cagaaagct                                              19

<210> SEQ ID NO 191
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 191
gactttgaaa ttggtcgcc                                              19

<210> SEQ ID NO 192
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 192
cacccaaaag agcaagcag                                              19

<210> SEQ ID NO 193
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 193
taagcctggt ggtgatctt                                              19

<210> SEQ ID NO 194
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 194
aaggtcttta cgccagtac                                              19

<210> SEQ ID NO 195
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 195
ggaatgtatc cgagcactg                                              19

```
<210> SEQ ID NO 196
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 196
ggactctgaa gatgtacct                                                19

<210> SEQ ID NO 197
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 197
ggcatactag tacaagtgg                                                19

<210> SEQ ID NO 198
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 198
gaaaagactc ctggctgtg                                                19

<210> SEQ ID NO 199
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 199
ctttgaatgc cagggggaac                                               19

<210> SEQ ID NO 200
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 200
ccaaggaacc tgctttgat                                                19

<210> SEQ ID NO 201
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 201
gactcagacc actgcttca                                                19

<210> SEQ ID NO 202
<211> LENGTH: 19
```

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 202
gctgctgttg gaccacttt                                                  19

<210> SEQ ID NO 203
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 203
tgccaactga agaggatga                                                  19

<210> SEQ ID NO 204
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 204
tgatcactgc ttccccgat                                                  19

<210> SEQ ID NO 205
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 205
atatcgacga ttgtccagg                                                  19

<210> SEQ ID NO 206
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 206
aggcaagccc tgcaagaat                                                  19

<210> SEQ ID NO 207
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 207
cacttacacc tgtgtgtgc                                                  19

<210> SEQ ID NO 208
<211> LENGTH: 19
<212> TYPE: DNA
<213> ORGANISM: Artificial Sequence
```

```
<220> FEATURE:
<223> OTHER INFORMATION: DNA sequence corresponding to siRNA sense
      strand in construction of siRNA library

<400> SEQUENCE: 208
tatcagaccg gacctctat                                                  19

<210> SEQ ID NO 209
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 209
attgaccacc aggtttctg                                                  19

<210> SEQ ID NO 210
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 210
cttacaaaag ggagcacac                                                  19

<210> SEQ ID NO 211
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 211
gtctcagctt ctgcggtat                                                  19

<210> SEQ ID NO 212
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 212
aggattttgt ggcctccat                                                  19

<210> SEQ ID NO 213
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 213
tccaggttga aggcattca                                                  19

<210> SEQ ID NO 214
<211> LENGTH: 19
<212> TYPE: DNA
<213> ORGANISM: Artificial Sequence
<220> FEATURE:
<223> OTHER INFORMATION: DNA sequence corresponding to siRNA sense
```

-continued strand in construction of siRNA library

<400> SEQUENCE: 214
ttggcaaagg ctccttgta                                           19

<210> SEQ ID NO 215
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 215
ccatctgctt gagctactt                                           19

<210> SEQ ID NO 216
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 216
gttgacttac ctgacggac                                           19

<210> SEQ ID NO 217
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 217
gacatcccga gtctataag                                           19

<210> SEQ ID NO 218
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 218
tggaggagaa ttaggcctt                                           19

<210> SEQ ID NO 219
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 219
gcacaaggag gtcttcttc                                           19

<210> SEQ ID NO 220
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

```
<400> SEQUENCE: 220
cagatcactc caggcatag                                              19

<210> SEQ ID NO 221
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 221
atgtgtggtg actgctttg                                              19

<210> SEQ ID NO 222
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 222
tgacatcatt gtgctggcc                                              19

<210> SEQ ID NO 223
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 223
cgttccgatc ctctatact                                              19

<210> SEQ ID NO 224
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 224
tgaccaaaga tgacctgtg                                              19

<210> SEQ ID NO 225
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 225
gagaaagaat ggggtcggt                                              19

<210> SEQ ID NO 226
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 226
```
cgacatccag aagttgtca                                                19

<210> SEQ ID NO 227
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 227
tgaggagcag attgccact                                                19

<210> SEQ ID NO 228
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 228
gaggtacaat tgcgaatat                                                19

<210> SEQ ID NO 229
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 229
tactacgtcg gacagagtt                                                19

<210> SEQ ID NO 230
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 230
aactacaata acgccactg                                                19

<210> SEQ ID NO 231
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 231
gccacagtcg tcttgctgt                                                19

<210> SEQ ID NO 232
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 232
gggcggcttt gccaagtgc                                                19

```
<210> SEQ ID NO 233
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 233
cacgcctcat cctctacaa                                                    19

<210> SEQ ID NO 234
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 234
gagacctacc tccggatca                                                    19

<210> SEQ ID NO 235
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 235
cccaccacag ctagaactt                                                    19

<210> SEQ ID NO 236
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 236
ctattcccag tcagaggcg                                                    19

<210> SEQ ID NO 237
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 237
cagtagagga gccgtcaaa                                                    19

<210> SEQ ID NO 238
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 238
cagttcacta ttacgcaga                                                    19

<210> SEQ ID NO 239
```

```
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 239
tgttacgaga tgacagatt                                               19

<210> SEQ ID NO 240
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 240
aacccagagg atcgtccca                                               19

<210> SEQ ID NO 241
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 241
ctgtttggag aaaaccctc                                               19

<210> SEQ ID NO 242
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 242
gacaacccaa accagagtc                                               19

<210> SEQ ID NO 243
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 243
gtcttgactg ggatgaaaa                                               19

<210> SEQ ID NO 244
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 244
accagagtct tttgacagg                                               19

<210> SEQ ID NO 245
<211> LENGTH: 19
<212> TYPE: DNA
```

```
<213> ORGANISM: Artificial Sequence
<220> FEATURE:
<223> OTHER INFORMATION: DNA sequence corresponding to siRNA sense
      strand in construction of siRNA library

<400> SEQUENCE: 245
tagaccaccc attgcttcc                                                    19

<210> SEQ ID NO 246
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 246
agagccttcg aaggcttca                                                    19

<210> SEQ ID NO 247
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 247
gaccatagca tccgccatg                                                    19

<210> SEQ ID NO 248
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 248
tagctctgct agaggagga                                                    19

<210> SEQ ID NO 249
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 249
acagaacggc tgaatagcc                                                    19

<210> SEQ ID NO 250
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 250
gagaatgaga gcctgactg                                                    19

<210> SEQ ID NO 251
<211> LENGTH: 19
<212> TYPE: DNA
<213> ORGANISM: Artificial Sequence
<220> FEATURE:
```

<223> OTHER INFORMATION: DNA sequence corresponding to siRNA sense
     strand in construction of siRNA library

<400> SEQUENCE: 251
ggaaacagag tgcctctct                                                19

<210> SEQ ID NO 252
<211> LENGTH: 19
<212> TYPE: DNA
<213> ORGANISM: Artificial Sequence
<220> FEATURE:
<223> OTHER INFORMATION: DNA sequence corresponding to siRNA sense
     strand in construction of siRNA library

<400> SEQUENCE: 252
ccactcagct cagatcatg                                                19

<210> SEQ ID NO 253
<211> LENGTH: 19
<212> TYPE: DNA
<213> ORGANISM: Artificial Sequence
<220> FEATURE:
<223> OTHER INFORMATION: DNA sequence corresponding to siRNA sense
     strand in construction of siRNA library

<400> SEQUENCE: 253
tctggtctct tgcaaaagg                                                19

<210> SEQ ID NO 254
<211> LENGTH: 19
<212> TYPE: DNA
<213> ORGANISM: Artificial Sequence
<220> FEATURE:
<223> OTHER INFORMATION: DNA sequence corresponding to siRNA sense
     strand in construction of siRNA library

<400> SEQUENCE: 254
atttttgcgg cgccagaat                                                19

<210> SEQ ID NO 255
<211> LENGTH: 19
<212> TYPE: DNA
<213> ORGANISM: Artificial Sequence
<220> FEATURE:
<223> OTHER INFORMATION: DNA sequence corresponding to siRNA sense
     strand in construction of siRNA library

<400> SEQUENCE: 255
gaaaaacgga ggtcgcgtt                                                19

<210> SEQ ID NO 256
<211> LENGTH: 19
<212> TYPE: DNA
<213> ORGANISM: Artificial Sequence
<220> FEATURE:
<223> OTHER INFORMATION: DNA sequence corresponding to siRNA sense
     strand in construction of siRNA library

<400> SEQUENCE: 256
gaaaacaaat gccccgtgc                                                19

<210> SEQ ID NO 257
<211> LENGTH: 19
<212> TYPE: DNA
<213> ORGANISM: Artificial Sequence
<220> FEATURE:
<223> OTHER INFORMATION: DNA sequence corresponding to siRNA sense
     strand in construction of siRNA library

```
<400> SEQUENCE: 257
tggcactcat cactgtcat                                                    19

<210> SEQ ID NO 258
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 258
tgagaacagt gaccagcag                                                    19

<210> SEQ ID NO 259
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 259
gggcccagga ctgttgatg                                                    19

<210> SEQ ID NO 260
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 260
agagatgggc attgtttcc                                                    19

<210> SEQ ID NO 261
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 261
gctcatggag atgtttggt                                                    19

<210> SEQ ID NO 262
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 262
agcattgctg tttcacgcc                                                    19

<210> SEQ ID NO 263
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 263
```

```
ttgagctgct gcaacggtc                                                    19
```

<210> SEQ ID NO 264
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 264

```
gtccccacat tccaagtca                                                    19
```

<210> SEQ ID NO 265
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 265

```
cctctctgga atttgtgcc                                                    19
```

<210> SEQ ID NO 266
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 266

```
caagtacttc tccaacatt                                                    19
```

<210> SEQ ID NO 267
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 267

```
tggaggaaca tgtgtgtcc                                                    19
```

<210> SEQ ID NO 268
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 268

```
ttactgcagg aacccagac                                                    19
```

<210> SEQ ID NO 269
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 269

```
tggctttgaa tctttggcc                                                    19
```

```
<210> SEQ ID NO 270
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 270
aggtgcactg cagttcaac                                               19

<210> SEQ ID NO 271
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 271
ttcagctagt acaggtcct                                               19

<210> SEQ ID NO 272
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 272
ttgattcctc gcgacatct                                               19

<210> SEQ ID NO 273
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 273
gcttttccca tgatctcca                                               19

<210> SEQ ID NO 274
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 274
cttggcatgg aacattgtg                                               19

<210> SEQ ID NO 275
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 275
gcctcagaaa gggattgct                                               19
```

<210> SEQ ID NO 276
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 276
gctctggatg tgcacacat                                              19

<210> SEQ ID NO 277
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 277
gtgtctcaaa ggagctttc                                              19

<210> SEQ ID NO 278
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 278
attcaacggg ctcttgtgc                                              19

<210> SEQ ID NO 279
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 279
gatcgatggc tacgagtgt                                              19

<210> SEQ ID NO 280
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 280
catcccctac aagatcgag                                              19

<210> SEQ ID NO 281
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 281
gcaactttgg tctcctttc                                              19

<210> SEQ ID NO 282
<211> LENGTH: 19

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 282
gcaattggct gtgatgctc                                                      19

<210> SEQ ID NO 283
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 283
gagacaagtt aactcgtgc                                                      19

<210> SEQ ID NO 284
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 284
tcctggcaag aaagcttga                                                      19

<210> SEQ ID NO 285
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 285
aaacctctac acgttctgc                                                      19

<210> SEQ ID NO 286
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 286
ctaaaggtga aaagctccg                                                      19

<210> SEQ ID NO 287
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 287
gatctggaag accacccaa                                                      19

<210> SEQ ID NO 288
<211> LENGTH: 19
<212> TYPE: DNA
<213> ORGANISM: Artificial Sequence
```

```
-continued

<220> FEATURE:
<223> OTHER INFORMATION: DNA sequence corresponding to siRNA sense
      strand in construction of siRNA library

<400> SEQUENCE: 288
cagaacccaa aagggtaag                                                  19

<210> SEQ ID NO 289
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 289
aggaaatagg cagggtgtg                                                  19

<210> SEQ ID NO 290
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 290
agcagtgctg atgataagg                                                  19

<210> SEQ ID NO 291
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 291
aagccattgg tgaagagag                                                  19

<210> SEQ ID NO 292
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 292
tgtgtcattg ctctccaag                                                  19

<210> SEQ ID NO 293
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 293
gcagatgagc aaggatgct                                                  19

<210> SEQ ID NO 294
<211> LENGTH: 19
<212> TYPE: DNA
<213> ORGANISM: Artificial Sequence
<220> FEATURE:
<223> OTHER INFORMATION: DNA sequence corresponding to siRNA sense
``` strand in construction of siRNA library

<400> SEQUENCE: 294
gtacatccat gtggccaaa					19

<210> SEQ ID NO 295
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 295
tgggtcatga aagctgcca					19

<210> SEQ ID NO 296
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 296
gaacaccgtt aacacctcc					19

<210> SEQ ID NO 297
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 297
ataacaggag agatccagc					19

<210> SEQ ID NO 298
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 298
tggtgtcctt gaggttgtc					19

<210> SEQ ID NO 299
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 299
acctgtctct tggatattc					19

<210> SEQ ID NO 300
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

```
<400> SEQUENCE: 300
taaatgtgat ttgccttct                                             19

<210> SEQ ID NO 301
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 301
gaagttatgg aattccttt                                             19

<210> SEQ ID NO 302
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 302
caccatgtcc tgaattcat                                             19

<210> SEQ ID NO 303
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 303
tcaagcacct tcattctgc                                             19

<210> SEQ ID NO 304
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 304
cgagttttat gatgacgcc                                             19

<210> SEQ ID NO 305
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 305
atacgtccag gccctcttt                                             19

<210> SEQ ID NO 306
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 306
```

| | | |
|---|---|---|
| tgcagcactt caaggtgct | | 19 |

<210> SEQ ID NO 307
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 307

| | | |
|---|---|---|
| cgggcagacc ggcatgttt | | 19 |

<210> SEQ ID NO 308
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 308

| | | |
|---|---|---|
| gacatgagaa cctggctca | | 19 |

<210> SEQ ID NO 309
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 309

| | | |
|---|---|---|
| cttgcaggcc ttgtttgtg | | 19 |

<210> SEQ ID NO 310
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 310

| | | |
|---|---|---|
| taatacagct ggggacgac | | 19 |

<210> SEQ ID NO 311
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 311

| | | |
|---|---|---|
| agaacctcgg ctacaacgt | | 19 |

<210> SEQ ID NO 312
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 312

| | | |
|---|---|---|
| tcggctacaa cgtgaccaa | | 19 |

<210> SEQ ID NO 313
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 313
tccgcatctc catgtgcca                                                19

<210> SEQ ID NO 314
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 314
tcacaaagtg tgctgggtt                                                19

<210> SEQ ID NO 315
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 315
ccaggaggaa ttcaaaggt                                                19

<210> SEQ ID NO 316
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 316
gctcaccatc tgaggaaga                                                19

<210> SEQ ID NO 317
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 317
tgacagtgga gcctgtgta                                                19

<210> SEQ ID NO 318
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 318
ctttctgaat ggggagcct                                                19

<210> SEQ ID NO 319

<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 319
tacacacacc agagtgatg                                                  19

<210> SEQ ID NO 320
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 320
atgaaggaga gtgatcacc                                                  19

<210> SEQ ID NO 321
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 321
aatggcagtg aaacaccct                                                  19

<210> SEQ ID NO 322
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 322
aagtttgtgt cccagacac                                                  19

<210> SEQ ID NO 323
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 323
aatggcttcc gctgcctct                                                  19

<210> SEQ ID NO 324
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 324
gaacatggcc aagggtgag                                                  19

<210> SEQ ID NO 325
<211> LENGTH: 19
<212> TYPE: DNA

```
<213> ORGANISM: Artificial Sequence
<220> FEATURE:
<223> OTHER INFORMATION: DNA sequence corresponding to siRNA sense
      strand in construction of siRNA library

<400> SEQUENCE: 325
gagtctggga cctccttct                                                    19

<210> SEQ ID NO 326
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 326
ccagggagac tccggcccc                                                    19

<210> SEQ ID NO 327
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 327
gggaccgtca tggcgtcgc                                                    19

<210> SEQ ID NO 328
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 328
atttaatttg gcagagcgg                                                    19

<210> SEQ ID NO 329
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 329
gctcaaggaa aacatacac                                                    19

<210> SEQ ID NO 330
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 330
tactaaacag attgatgtt                                                    19

<210> SEQ ID NO 331
<211> LENGTH: 19
<212> TYPE: DNA
<213> ORGANISM: Artificial Sequence
<220> FEATURE:
```

<223> OTHER INFORMATION: DNA sequence corresponding to siRNA sense
      strand in construction of siRNA library

<400> SEQUENCE: 331
tactgataat ggtactgaa                                                    19

<210> SEQ ID NO 332
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 332
aggagtgata attaaaggt                                                    19

<210> SEQ ID NO 333
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 333
gttttctctg ttacaatac                                                    19

<210> SEQ ID NO 334
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 334
tggaaatata aatcaatcc                                                    19

<210> SEQ ID NO 335
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 335
actaactaga atcctccag                                                    19

<210> SEQ ID NO 336
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 336
aaactctgag tacattgga                                                    19

<210> SEQ ID NO 337
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

```
<400> SEQUENCE: 337
taactgttca agaagagca                                                    19

<210> SEQ ID NO 338
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 338
aagaagaata tatcacatc                                                    19

<210> SEQ ID NO 339
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 339
agttgaccaa cacaatgca                                                    19

<210> SEQ ID NO 340
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 340
tacatgaact acaagaaaa                                                    19

<210> SEQ ID NO 341
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 341
gactaagctt aattgcttt                                                    19

<210> SEQ ID NO 342
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 342
ggggcagtat actgaagaa                                                    19

<210> SEQ ID NO 343
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 343
```

```
ttcttgtata ttattaagt                                                  19

<210> SEQ ID NO 344
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 344
tctataattt atattcttt                                                  19

<210> SEQ ID NO 345
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 345
tacaaagaat aaattttct                                                  19

<210> SEQ ID NO 346
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 346
cagcgcagct tcgggagca                                                  19

<210> SEQ ID NO 347
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 347
cggagttgca gctcccgga                                                  19

<210> SEQ ID NO 348
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 348
ggcaagattg tgcctaagt                                                  19

<210> SEQ ID NO 349
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 349
gggagaagat gtccatgga                                                  19
```

<210> SEQ ID NO 350
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 350
gacttcgtgt tcgtggtgt                                                    19

<210> SEQ ID NO 351
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 351
gcccgatact acctacggc                                                    19

<210> SEQ ID NO 352
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 352
ggactggcaa ccaaagtcg                                                    19

<210> SEQ ID NO 353
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 353
tgtatcatgt ataccttgt                                                    19

<210> SEQ ID NO 354
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 354
ttcttgccta aaagagacc                                                    19

<210> SEQ ID NO 355
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 355
tccagaagat gcttcagac                                                    19

```
<210> SEQ ID NO 356
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 356
acgagctgct taatgacga                                                  19

<210> SEQ ID NO 357
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 357
tcgattgctc ccagcagcc                                                  19

<210> SEQ ID NO 358
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 358
cacagtcctc aataaaggc                                                  19

<210> SEQ ID NO 359
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 359
caatgcctcc aagccctcg                                                  19

<210> SEQ ID NO 360
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 360
agtgggtgga ctattcgga                                                  19

<210> SEQ ID NO 361
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 361
tacatgagcg agcacttgc                                                  19

<210> SEQ ID NO 362
<211> LENGTH: 19
```

```
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 362
ctcaaggcct cctaatagc                                                    19

<210> SEQ ID NO 363
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 363
ccgcggtgcc atgtctgca                                                    19

<210> SEQ ID NO 364
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 364
cccctccccc tcaacccca                                                    19

<210> SEQ ID NO 365
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 365
attttctaga aaacggtaa                                                    19

<210> SEQ ID NO 366
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 366
gaggggcgaa gtttcggca                                                    19

<210> SEQ ID NO 367
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 367
ctgggaccgg gaagccgga                                                    19

<210> SEQ ID NO 368
<211> LENGTH: 19
<212> TYPE: DNA
<213> ORGANISM: Artificial Sequence
```

```
<220> FEATURE:
<223> OTHER INFORMATION: DNA sequence corresponding to siRNA sense
      strand in construction of siRNA library

<400> SEQUENCE: 368
cttctacttc tgttggcag                                                 19

<210> SEQ ID NO 369
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 369
acttactatt cagactgca                                                 19

<210> SEQ ID NO 370
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 370
gccctcaccc acagtagcc                                                 19

<210> SEQ ID NO 371
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 371
cagaggaatg cacacccag                                                 19

<210> SEQ ID NO 372
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 372
gattgattag atctcttga                                                 19

<210> SEQ ID NO 373
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 373
gtgagtatta tcccagttg                                                 19

<210> SEQ ID NO 374
<211> LENGTH: 19
<212> TYPE: DNA
<213> ORGANISM: Artificial Sequence
<220> FEATURE:
<223> OTHER INFORMATION: DNA sequence corresponding to siRNA sense
``` strand in construction of siRNA library

<400> SEQUENCE: 374
atctggggtg ctgattgct                                              19

<210> SEQ ID NO 375
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 375
gtgacagtgg cagtacgcg                                              19

<210> SEQ ID NO 376
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 376
tcagactgaa gttgttaga                                              19

<210> SEQ ID NO 377
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 377
gttggctaga attgggaaa                                              19

<210> SEQ ID NO 378
<211> LENGTH: 19
<212> TYPE: DNA
<213> ORGANISM: Artificial Sequence
<220> FEATURE:
<223> OTHER INFORMATION: DNA sequence corresponding to siRNA sense
      strand in construction of siRNA library

<400> SEQUENCE: 378
gaagaccata gcatccgcc                                              19

<210> SEQ ID NO 379
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 379
caggtaaagt cagagacat                                              19

<210> SEQ ID NO 380
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 380

```
gggattgacg gcagtaaga                                              19

<210> SEQ ID NO 381
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 381
cactgaatgt gggaggtga                                              19

<210> SEQ ID NO 382
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 382
gtctgggtgg aaattcaaa                                              19

<210> SEQ ID NO 383
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 383
catctttgct gaatcgaaa                                              19

<210> SEQ ID NO 384
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 384
cagggatgct gtttggata                                              19

<210> SEQ ID NO 385
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 385
ccctgtgtgg gactcctaa                                              19

<210> SEQ ID NO 386
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 386
ggtgttcgcg ggcaagatt                                              19

<210> SEQ ID NO 387
<211> LENGTH: 19
<212> TYPE: DNA
<213> ORGANISM: Artificial Sequence
<220> FEATURE:
```

```
<223> OTHER INFORMATION: NM_005030 (PLK)

<400> SEQUENCE: 387
cgcctcatcc tctacaatg                                                19

<210> SEQ ID NO 388
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 388
gttctttact tctggctat                                                19

<210> SEQ ID NO 389
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 389
ctccttaaat atttccgca                                                19

<210> SEQ ID NO 390
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 390
ctgagcctga ggcccgata                                                19

<210> SEQ ID NO 391
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 391
caaattatgt gtttccgaa                                                19

<210> SEQ ID NO 392
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 392
cgcatgtgct ggcagtata                                                19

<210> SEQ ID NO 393
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 393
ccgaagattt cacagtcaa                                                19

<210> SEQ ID NO 394
```

-continued

```
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 394
accattgatt ctgttactt                                                19

<210> SEQ ID NO 395
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 395
accgcaaagt ctttgagaa                                                19

<210> SEQ ID NO 396
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 396
gtcctgacat gctgtttga                                                19

<210> SEQ ID NO 397
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 397
ggaattcaat gatgtgtat                                                19

<210> SEQ ID NO 398
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 398
gctgttgact ggaagaaca                                                19

<210> SEQ ID NO 399
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 399
ctcctgagat catgctgaa                                                19

<210> SEQ ID NO 400
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 400
```

```
ccatttcagt ccatcattc                                               19

<210> SEQ ID NO 401
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 401
cagattatgc gtctgacag                                               19

<210> SEQ ID NO 402
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 402
cgcttatctc attaacagg                                               19

<210> SEQ ID NO 403
<211> LENGTH: 19
<212> TYPE: DNA
<213> ORGANISM: Artificial Sequence
<220> FEATURE:
<223> OTHER INFORMATION: NM_004523 (KIF11)

<400> SEQUENCE: 403
gagcccagat caaccttta                                               19

<210> SEQ ID NO 404
<211> LENGTH: 19
<212> TYPE: DNA
<213> ORGANISM: Artificial Sequence
<220> FEATURE:
<223> OTHER INFORMATION: NM_004523 (KIF11)

<400> SEQUENCE: 404
ctgacaagag ctcaaggaa                                               19

<210> SEQ ID NO 405
<211> LENGTH: 19
<212> TYPE: DNA
<213> ORGANISM: Artificial Sequence
<220> FEATURE:
<223> OTHER INFORMATION: NM_004523 (KIF11)

<400> SEQUENCE: 405
ggcattaaca cactggaga                                               19

<210> SEQ ID NO 406
<211> LENGTH: 19
<212> TYPE: DNA
<213> ORGANISM: Artificial Sequence
<220> FEATURE:
<223> OTHER INFORMATION: NM_004523 (KIF11)

<400> SEQUENCE: 406
gatggcagct caaagcaaa                                               19

<210> SEQ ID NO 407
<211> LENGTH: 19
<212> TYPE: DNA
<213> ORGANISM: Artificial Sequence
<220> FEATURE:
```

<223> OTHER INFORMATION: NM_004523 (KIF11)

<400> SEQUENCE: 407
cagcagaaat ctaaggata                                                    19

<210> SEQ ID NO 408
<211> LENGTH: 19
<212> TYPE: DNA
<213> ORGANISM: Artificial Sequence
<220> FEATURE:
<223> OTHER INFORMATION: NM_004523 (KIF11)

<400> SEQUENCE: 408
cgttctggag ctgttgata                                                    19

<210> SEQ ID NO 409
<211> LENGTH: 19
<212> TYPE: DNA
<213> ORGANISM: Artificial Sequence
<220> FEATURE:
<223> OTHER INFORMATION: AK092024_NM_030932 (DIAPH3)

<400> SEQUENCE: 409
gcagtgattg ctcagcagc                                                    19

<210> SEQ ID NO 410
<211> LENGTH: 19
<212> TYPE: DNA
<213> ORGANISM: Artificial Sequence
<220> FEATURE:
<223> OTHER INFORMATION: AK092024_NM_030932 (DIAPH3)

<400> SEQUENCE: 410
gagtttaccg accaccaag                                                    19

<210> SEQ ID NO 411
<211> LENGTH: 19
<212> TYPE: DNA
<213> ORGANISM: Artificial Sequence
<220> FEATURE:
<223> OTHER INFORMATION: AK092024_NM_030932 (DIAPH3)

<400> SEQUENCE: 411
cacggttggc agagtctat                                                    19

<210> SEQ ID NO 412
<211> LENGTH: 19
<212> TYPE: DNA
<213> ORGANISM: Artificial Sequence
<220> FEATURE:
<223> OTHER INFORMATION: AK092024_NM_030932 (DIAPH3)

<400> SEQUENCE: 412
tgcggatgcc attcagtgg                                                    19

<210> SEQ ID NO 413
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 413
aaactgggag gctacttac                                                    19

<210> SEQ ID NO 414

```
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 414
ctcacattgt ccaccagga                                            19

<210> SEQ ID NO 415
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 415
gaccatagca tccgccatg                                            19

<210> SEQ ID NO 416
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 416
agagccttcg aaggcttca                                            19

<210> SEQ ID NO 417
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 417
tagaccaccc attgcttcc                                            19

<210> SEQ ID NO 418
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 418
actgacaaca aagtgcagc                                            19

<210> SEQ ID NO 419
<211> LENGTH: 19
<212> TYPE: DNA
<213> ORGANISM: Artificial Sequence
<220> FEATURE:
<223> OTHER INFORMATION: U53530 (DNCH1)

<400> SEQUENCE: 419
tggccagcgc ttactggaa                                            19

<210> SEQ ID NO 420
<211> LENGTH: 19
<212> TYPE: DNA
<213> ORGANISM: Artificial Sequence
<220> FEATURE:
<223> OTHER INFORMATION: U53530 (DNCH1)

<400> SEQUENCE: 420
```

-continued

```
gcaagttgag ctctaccgc                                               19

<210> SEQ ID NO 421
<211> LENGTH: 19
<212> TYPE: DNA
<213> ORGANISM: Artificial Sequence
<220> FEATURE:
<223> OTHER INFORMATION: NM_000859 (HMGCR)

<400> SEQUENCE: 421
ttgtgtgtgg gaccgtaat                                               19

<210> SEQ ID NO 422
<211> LENGTH: 19
<212> TYPE: DNA
<213> ORGANISM: Artificial Sequence
<220> FEATURE:
<223> OTHER INFORMATION: NM_000859 (HMGCR)

<400> SEQUENCE: 422
caacagaagg ttgtcttgt                                               19

<210> SEQ ID NO 423
<211> LENGTH: 19
<212> TYPE: DNA
<213> ORGANISM: Artificial Sequence
<220> FEATURE:
<223> OTHER INFORMATION: NM_000859 (HMGCR)

<400> SEQUENCE: 423
cagagacaga atctacact                                               19

<210> SEQ ID NO 424
<211> LENGTH: 19
<212> TYPE: DNA
<213> ORGANISM: Artificial Sequence
<220> FEATURE:
<223> OTHER INFORMATION: NM_000859 (HMGCR)

<400> SEQUENCE: 424
cacgatgcat agccatcct                                               19

<210> SEQ ID NO 425
<211> LENGTH: 19
<212> TYPE: DNA
<213> ORGANISM: Artificial Sequence
<220> FEATURE:
<223> OTHER INFORMATION: NM_000271 (NPC1)

<400> SEQUENCE: 425
gaggtacaat tgcgaatat                                               19

<210> SEQ ID NO 426
<211> LENGTH: 19
<212> TYPE: DNA
<213> ORGANISM: Artificial Sequence
<220> FEATURE:
<223> OTHER INFORMATION: NM_000271 (NPC1)

<400> SEQUENCE: 426
gccacagtcg tcttgctgt                                               19

<210> SEQ ID NO 427
<211> LENGTH: 19
<212> TYPE: DNA
<213> ORGANISM: Artificial Sequence
<220> FEATURE:
```

```
<223> OTHER INFORMATION: NM_000271 (NPC1)

<400> SEQUENCE: 427
tactacgtcg gacagagtt                                          19

<210> SEQ ID NO 428
<211> LENGTH: 19
<212> TYPE: DNA
<213> ORGANISM: Artificial Sequence
<220> FEATURE:
<223> OTHER INFORMATION: NM_000271 (NPC1)

<400> SEQUENCE: 428
aactacaata acgccactg                                          19

<210> SEQ ID NO 429
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 429
tactgataat ggtactgaa                                          19

<210> SEQ ID NO 430
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 430
tacatgaact acaagaaaa                                          19

<210> SEQ ID NO 431
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 431
gactaagctt aattgcttt                                          19

<210> SEQ ID NO 432
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 432
agttgaccaa cacaatgca                                          19

<210> SEQ ID NO 433
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 433
gttttctctg ttacaatac                                          19

<210> SEQ ID NO 434
```

```
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 434
aggagtgata attaaaggt                                                  19

<210> SEQ ID NO 435
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 435
aaactctgag tacattgga                                                  19

<210> SEQ ID NO 436
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 436
tactaaacag attgatgtt                                                  19

<210> SEQ ID NO 437
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 437
gctcaaggaa aacatacac                                                  19

<210> SEQ ID NO 438
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 438
ctggatcgta agaaggcag                                                  19

<210> SEQ ID NO 439
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 439
gacttcattg acagtggcc                                                  19

<210> SEQ ID NO 440
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 440
```

| | |
|---|---|
| ggacaactgc agctactct | 19 |

<210> SEQ ID NO 441
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 441

| | |
|---|---|
| ggggcagtat actgaagaa | 19 |

<210> SEQ ID NO 442
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 442

| | |
|---|---|
| gacctgtgcc ttttagaga | 19 |

<210> SEQ ID NO 443
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 443

| | |
|---|---|
| aaaggacaac tgcagctac | 19 |

<210> SEQ ID NO 444
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 444

| | |
|---|---|
| tacaaagaat aaattttct | 19 |

<210> SEQ ID NO 445
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 445

| | |
|---|---|
| tggaaggtga aggtcacc | 19 |

<210> SEQ ID NO 446
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 446

| | |
|---|---|
| taactgttca agaagagca | 19 |

<210> SEQ ID NO 447
<211> LENGTH: 19
<212> TYPE: DNA
<213> ORGANISM: Artificial Sequence
<220> FEATURE:

<223> OTHER INFORMATION: NM_004523 (KNSL1)

<400> SEQUENCE: 447
tctataattt atattcttt                                           19

<210> SEQ ID NO 448
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 448
gggaccgtca tggcgtcgc                                           19

<210> SEQ ID NO 449
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 449
ccagggagac tccggcccc                                           19

<210> SEQ ID NO 450
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 450
atttaatttg gcagagcgg                                           19

<210> SEQ ID NO 451
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 451
tggaaatata aatcaatcc                                           19

<210> SEQ ID NO 452
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 452
actaactaga atcctccag                                           19

<210> SEQ ID NO 453
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 453
aagaagaata tatcacatc                                           19

<210> SEQ ID NO 454

```
<211> LENGTH: 19
<212> TYPE: DNA
<213> ORGANISM: Artificial Sequence
<220> FEATURE:
<223> OTHER INFORMATION: NM_004523 (KNSL1)

<400> SEQUENCE: 454
ttcttgtata ttattaagt                                              19

<210> SEQ ID NO 455
<211> LENGTH: 19
<212> TYPE: DNA
<213> ORGANISM: Artificial Sequence
<220> FEATURE:
<223> OTHER INFORMATION: NM_004064 (CDKN1B)

<400> SEQUENCE: 455
gacgtcaaac gtaaacagc                                              19

<210> SEQ ID NO 456
<211> LENGTH: 19
<212> TYPE: DNA
<213> ORGANISM: Artificial Sequence
<220> FEATURE:
<223> OTHER INFORMATION: NM_004064 (CDKN1B)

<400> SEQUENCE: 456
tggtgatcac tccaggtag                                              19

<210> SEQ ID NO 457
<211> LENGTH: 19
<212> TYPE: DNA
<213> ORGANISM: Artificial Sequence
<220> FEATURE:
<223> OTHER INFORMATION: NM_004064 (CDKN1B)

<400> SEQUENCE: 457
tgtccctttc agagacagc                                              19

<210> SEQ ID NO 458
<211> LENGTH: 19
<212> TYPE: DNA
<213> ORGANISM: Artificial Sequence
<220> FEATURE:
<223> OTHER INFORMATION: NM_004073 (CNK)

<400> SEQUENCE: 458
gttaccaaga gcctctttg                                              19

<210> SEQ ID NO 459
<211> LENGTH: 19
<212> TYPE: DNA
<213> ORGANISM: Artificial Sequence
<220> FEATURE:
<223> OTHER INFORMATION: NM_004073 (CNK)

<400> SEQUENCE: 459
atcgtagtgc ttgtactta                                              19

<210> SEQ ID NO 460
<211> LENGTH: 19
<212> TYPE: DNA
<213> ORGANISM: Artificial Sequence
<220> FEATURE:
<223> OTHER INFORMATION: NM_004073 (CNK)

<400> SEQUENCE: 460
```

```
gaagaccatc tgtggcacc                                              19

<210> SEQ ID NO 461
<211> LENGTH: 19
<212> TYPE: DNA
<213> ORGANISM: Artificial Sequence
<220> FEATURE:
<223> OTHER INFORMATION: NM_004073 (CNK)

<400> SEQUENCE: 461
ggagacgtac cgctgcatc                                              19

<210> SEQ ID NO 462
<211> LENGTH: 19
<212> TYPE: DNA
<213> ORGANISM: Artificial Sequence
<220> FEATURE:
<223> OTHER INFORMATION: NM_004073 (CNK)

<400> SEQUENCE: 462
tcagggacca gctttactg                                              19

<210> SEQ ID NO 463
<211> LENGTH: 19
<212> TYPE: DNA
<213> ORGANISM: Artificial Sequence
<220> FEATURE:
<223> OTHER INFORMATION: NM_004073 (CNK)

<400> SEQUENCE: 463
agtcatcccg cagagccgc                                              19

<210> SEQ ID NO 464
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 464
ggccttttca cgggaactc                                              19

<210> SEQ ID NO 465
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 465
gaagctctcc agaccattt                                              19

<210> SEQ ID NO 466
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 466
tgcctacttt gctcagtac                                              19

<210> SEQ ID NO 467
<211> LENGTH: 19
<212> TYPE: DNA
<213> ORGANISM: Artificial Sequence
<220> FEATURE:
```

```
<223> OTHER INFORMATION: NM_001315 (MAPK14)

<400> SEQUENCE: 467
atgtgattgg tctgttgga                                              19

<210> SEQ ID NO 468
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 468
gtcatcagct ttgtgccac                                              19

<210> SEQ ID NO 469
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 469
cctacagaga actgcggtt                                              19

<210> SEQ ID NO 470
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 470
ccagtggccg atccttatg                                              19

<210> SEQ ID NO 471
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 471
gtgcctcttg ttgcagaga                                              19

<210> SEQ ID NO 472
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 472
ttctccgagg tctaaagta                                              19

<210> SEQ ID NO 473
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 473
taattcacag ggacctaaa                                              19

<210> SEQ ID NO 474
```

```
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 474
gtggccgatc cttatgatc                                                  19

<210> SEQ ID NO 475
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 475
gtatatacat tcagctgac                                                  19

<210> SEQ ID NO 476
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 476
aatatcctca ggggtggag                                                  19

<210> SEQ ID NO 477
<211> LENGTH: 19
<212> TYPE: DNA
<213> ORGANISM: Artificial Sequence
<220> FEATURE:
<223> OTHER INFORMATION: NM_001315 (MAPK14)

<400> SEQUENCE: 477
ggaacacccc ccgcttatc                                                  19

<210> SEQ ID NO 478
<211> LENGTH: 19
<212> TYPE: DNA
<213> ORGANISM: Artificial Sequence
<220> FEATURE:
<223> OTHER INFORMATION: NM_006101 (HEC)

<400> SEQUENCE: 478
ctgaaggctt ccttacaag                                                  19

<210> SEQ ID NO 479
<211> LENGTH: 19
<212> TYPE: DNA
<213> ORGANISM: Artificial Sequence
<220> FEATURE:
<223> OTHER INFORMATION: NM_006101 (HEC)

<400> SEQUENCE: 479
agaaccgaat cgtctagag                                                  19

<210> SEQ ID NO 480
<211> LENGTH: 19
<212> TYPE: DNA
<213> ORGANISM: Artificial Sequence
<220> FEATURE:
<223> OTHER INFORMATION: NM_006101 (HEC)

<400> SEQUENCE: 480
```

-continued

| | |
|---|---|
| cagaagttgt ggaatgagg | 19 |

<210> SEQ ID NO 481
<211> LENGTH: 19
<212> TYPE: DNA
<213> ORGANISM: Artificial Sequence
<220> FEATURE:
<223> OTHER INFORMATION: NM_006101 (HEC)

<400> SEQUENCE: 481

| | |
|---|---|
| gttcaaaagc tggatgatc | 19 |

<210> SEQ ID NO 482
<211> LENGTH: 19
<212> TYPE: DNA
<213> ORGANISM: Artificial Sequence
<220> FEATURE:
<223> OTHER INFORMATION: NM_006101 (HEC)

<400> SEQUENCE: 482

| | |
|---|---|
| ggcctctata cccctcaaa | 19 |

<210> SEQ ID NO 483
<211> LENGTH: 19
<212> TYPE: DNA
<213> ORGANISM: Artificial Sequence
<220> FEATURE:
<223> OTHER INFORMATION: NM_006101 (HEC)

<400> SEQUENCE: 483

| | |
|---|---|
| cttgcaacgt ctgttagag | 19 |

<210> SEQ ID NO 484
<211> LENGTH: 19
<212> TYPE: DNA
<213> ORGANISM: Artificial Sequence
<220> FEATURE:
<223> OTHER INFORMATION: NM_000314 (PTEN)

<400> SEQUENCE: 484

| | |
|---|---|
| cccaccacag ctagaactt | 19 |

<210> SEQ ID NO 485
<211> LENGTH: 19
<212> TYPE: DNA
<213> ORGANISM: Artificial Sequence
<220> FEATURE:
<223> OTHER INFORMATION: NM_000314 (PTEN)

<400> SEQUENCE: 485

| | |
|---|---|
| cagtagagga gccgtcaaa | 19 |

<210> SEQ ID NO 486
<211> LENGTH: 19
<212> TYPE: DNA
<213> ORGANISM: Artificial Sequence
<220> FEATURE:
<223> OTHER INFORMATION: NM_000314 (PTEN)

<400> SEQUENCE: 486

| | |
|---|---|
| ctattcccag tcagaggcg | 19 |

<210> SEQ ID NO 487
<211> LENGTH: 19
<212> TYPE: DNA
<213> ORGANISM: Artificial Sequence
<220> FEATURE:

```
<223> OTHER INFORMATION: NM_000314 (PTEN)

<400> SEQUENCE: 487
taaagatggc actttcccg                                                19

<210> SEQ ID NO 488
<211> LENGTH: 19
<212> TYPE: DNA
<213> ORGANISM: Artificial Sequence
<220> FEATURE:
<223> OTHER INFORMATION: NM_000314 (PTEN)

<400> SEQUENCE: 488
aaggcagcta aaggaagtg                                                19

<210> SEQ ID NO 489
<211> LENGTH: 19
<212> TYPE: DNA
<213> ORGANISM: Artificial Sequence
<220> FEATURE:
<223> OTHER INFORMATION: NM_000314 (PTEN)

<400> SEQUENCE: 489
tggaggggaa tgctcagaa                                                19

<210> SEQ ID NO 490
<211> LENGTH: 19
<212> TYPE: DNA
<213> ORGANISM: Artificial Sequence
<220> FEATURE:
<223> OTHER INFORMATION: NM_000075 (CDK4)

<400> SEQUENCE: 490
gcgaatctct gcctttcga                                                19

<210> SEQ ID NO 491
<211> LENGTH: 19
<212> TYPE: DNA
<213> ORGANISM: Artificial Sequence
<220> FEATURE:
<223> OTHER INFORMATION: NM_000075 (CDK4)

<400> SEQUENCE: 491
cagtcaagct ggctgactt                                                19

<210> SEQ ID NO 492
<211> LENGTH: 19
<212> TYPE: DNA
<213> ORGANISM: Artificial Sequence
<220> FEATURE:
<223> OTHER INFORMATION: NM_000075 (CDK4)

<400> SEQUENCE: 492
ggatctgatg cgccagttt                                                19

<210> SEQ ID NO 493
<211> LENGTH: 19
<212> TYPE: DNA
<213> ORGANISM: Artificial Sequence
<220> FEATURE:
<223> OTHER INFORMATION: NM_000075 (CDK4)

<400> SEQUENCE: 493
tgttgtccgg ctgatggac                                                19

<210> SEQ ID NO 494
```

-continued

```
<211> LENGTH: 19
<212> TYPE: DNA
<213> ORGANISM: Artificial Sequence
<220> FEATURE:
<223> OTHER INFORMATION: NM_006622 (SNK)

<400> SEQUENCE: 494
tgttacgaga tgacagatt                                               19

<210> SEQ ID NO 495
<211> LENGTH: 19
<212> TYPE: DNA
<213> ORGANISM: Artificial Sequence
<220> FEATURE:
<223> OTHER INFORMATION: NM_006622 (SNK)

<400> SEQUENCE: 495
aacccagagg atcgtccca                                               19

<210> SEQ ID NO 496
<211> LENGTH: 19
<212> TYPE: DNA
<213> ORGANISM: Artificial Sequence
<220> FEATURE:
<223> OTHER INFORMATION: NM_006622 (SNK)

<400> SEQUENCE: 496
cagttcacta ttacgcaga                                               19

<210> SEQ ID NO 497
<211> LENGTH: 19
<212> TYPE: DNA
<213> ORGANISM: Artificial Sequence
<220> FEATURE:
<223> OTHER INFORMATION: NM_139164 (STARD4)

<400> SEQUENCE: 497
accagagtct tttgacagg                                               19

<210> SEQ ID NO 498
<211> LENGTH: 19
<212> TYPE: DNA
<213> ORGANISM: Artificial Sequence
<220> FEATURE:
<223> OTHER INFORMATION: NM_139164 (STARD4)

<400> SEQUENCE: 498
ctgtttggag aaaaccctc                                               19

<210> SEQ ID NO 499
<211> LENGTH: 19
<212> TYPE: DNA
<213> ORGANISM: Artificial Sequence
<220> FEATURE:
<223> OTHER INFORMATION: NM_139164 (STARD4)

<400> SEQUENCE: 499
gacaacccaa accagagtc                                               19

<210> SEQ ID NO 500
<211> LENGTH: 19
<212> TYPE: DNA
<213> ORGANISM: Artificial Sequence
<220> FEATURE:
<223> OTHER INFORMATION: NM_139164 (STARD4)

<400> SEQUENCE: 500
```

-continued gtcttgactg ggatgaaaa                                              19

<210> SEQ ID NO 501
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 501
gggagaagat gtccatgga                                              19

<210> SEQ ID NO 502
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 502
ccgagttatt catcgagac                                              19

<210> SEQ ID NO 503
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 503
gagacctacc tccggatca                                              19

<210> SEQ ID NO 504
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 504
tccagaagat gcttcagac                                              19

<210> SEQ ID NO 505
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 505
cacgcctcat cctctacaa                                              19

<210> SEQ ID NO 506
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 506
gacttcgtgt tcgtggtgt                                              19

<210> SEQ ID NO 507
<211> LENGTH: 19
<212> TYPE: DNA
<213> ORGANISM: Artificial Sequence
<220> FEATURE:

<223> OTHER INFORMATION: NM_005030 (PLK)

<400> SEQUENCE: 507
gggcggcttt gccaagtgc                               19

<210> SEQ ID NO 508
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 508
acgagctgct taatgacga                               19

<210> SEQ ID NO 509
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 509
ggactggcaa ccaaagtcg                               19

<210> SEQ ID NO 510
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 510
gcccgatact acctacggc                               19

<210> SEQ ID NO 511
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 511
cggagttgca gctcccgga                               19

<210> SEQ ID NO 512
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 512
aagagaccta cctccggat                               19

<210> SEQ ID NO 513
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 513
agtgggtgga ctattcgga                               19

<210> SEQ ID NO 514

<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 514
tgtatcatgt ataccttgt                                                   19

<210> SEQ ID NO 515
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 515
aagaagaacc agtggttcg                                                   19

<210> SEQ ID NO 516
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 516
ggcaagattg tgcctaagt                                                   19

<210> SEQ ID NO 517
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 517
ccgcggtgcc atgtctgca                                                   19

<210> SEQ ID NO 518
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 518
ctcaaggcct cctaatagc                                                   19

<210> SEQ ID NO 519
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 519
cagcgcagct tcgggagca                                                   19

<210> SEQ ID NO 520
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 520

-continued cacagtcctc aataaaggc                                            19

<210> SEQ ID NO 521
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 521
cccctccccc tcaacccca                                            19

<210> SEQ ID NO 522
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 522
tcgattgctc ccagcagcc                                            19

<210> SEQ ID NO 523
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 523
ttcttgccta aaagagacc                                            19

<210> SEQ ID NO 524
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 524
tacatgagcg agcacttgc                                            19

<210> SEQ ID NO 525
<211> LENGTH: 19
<212> TYPE: DNA
<213> ORGANISM: Artificial Sequence
<220> FEATURE:
<223> OTHER INFORMATION: NM_005030 (PLK)

<400> SEQUENCE: 525
caatgcctcc aagccctcg                                            19

<210> SEQ ID NO 526
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 526
ggatattggg ctttacaac                                            19

<210> SEQ ID NO 527
<211> LENGTH: 19
<212> TYPE: DNA
<213> ORGANISM: Artificial Sequence
<220> FEATURE:

-continued

<223> OTHER INFORMATION: NM_000875 (IGF1R)

<400> SEQUENCE: 527
cttgcagcaa ctgtgggac                                              19

<210> SEQ ID NO 528
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 528
gctcacggtc attaccgag                                              19

<210> SEQ ID NO 529
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 529
gatgattcag atggccgga                                              19

<210> SEQ ID NO 530
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 530
cgacacggcc tgtgtagct                                              19

<210> SEQ ID NO 531
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 531
aatgctgacc tctgttacc                                              19

<210> SEQ ID NO 532
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 532
tctcaaggat attgggctt                                              19

<210> SEQ ID NO 533
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 533
cattactcgg ggggccatc                                              19

<210> SEQ ID NO 534

```
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 534
tgctgacctc tgttacctc                                               19

<210> SEQ ID NO 535
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 535
ctacgccctg gtcatcttc                                               19

<210> SEQ ID NO 536
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 536
cctcacggtc atccgcggc                                               19

<210> SEQ ID NO 537
<211> LENGTH: 19
<212> TYPE: DNA
<213> ORGANISM: Artificial Sequence
<220> FEATURE:
<223> OTHER INFORMATION: NM_000875 (IGF1R)

<400> SEQUENCE: 537
cctgaggaac attactcgg                                               19

<210> SEQ ID NO 538
<211> LENGTH: 19
<212> TYPE: DNA
<213> ORGANISM: Artificial Sequence
<220> FEATURE:
<223> OTHER INFORMATION: NM_001813 (CENPE)

<400> SEQUENCE: 538
ggagagcttt ctaggacct                                               19

<210> SEQ ID NO 539
<211> LENGTH: 19
<212> TYPE: DNA
<213> ORGANISM: Artificial Sequence
<220> FEATURE:
<223> OTHER INFORMATION: NM_001813 (CENPE)

<400> SEQUENCE: 539
gaagagatcc cagtgcttc                                               19

<210> SEQ ID NO 540
<211> LENGTH: 19
<212> TYPE: DNA
<213> ORGANISM: Artificial Sequence
<220> FEATURE:
<223> OTHER INFORMATION: NM_001813 (CENPE)

<400> SEQUENCE: 540
```
actcttactg ctctccagt                                           19

<210> SEQ ID NO 541
<211> LENGTH: 19
<212> TYPE: DNA
<213> ORGANISM: Artificial Sequence
<220> FEATURE:
<223> OTHER INFORMATION: NM_001813 (CENPE)

<400> SEQUENCE: 541
tctgaaagtg accagctca                                           19

<210> SEQ ID NO 542
<211> LENGTH: 19
<212> TYPE: DNA
<213> ORGANISM: Artificial Sequence
<220> FEATURE:
<223> OTHER INFORMATION: NM_001813 (CENPE)

<400> SEQUENCE: 542
gaaaatgaag ctttgcggg                                           19

<210> SEQ ID NO 543
<211> LENGTH: 19
<212> TYPE: DNA
<213> ORGANISM: Artificial Sequence
<220> FEATURE:
<223> OTHER INFORMATION: NM_001813 (CENPE)

<400> SEQUENCE: 543
cttaacacgg atgctggtg                                           19

<210> SEQ ID NO 544
<211> LENGTH: 19
<212> TYPE: DNA
<213> ORGANISM: Artificial Sequence
<220> FEATURE:
<223> OTHER INFORMATION: NM_004958 (FRAP1)

<400> SEQUENCE: 544
cttgcaggcc ttgtttgtg                                           19

<210> SEQ ID NO 545
<211> LENGTH: 19
<212> TYPE: DNA
<213> ORGANISM: Artificial Sequence
<220> FEATURE:
<223> OTHER INFORMATION: NM_004958 (FRAP1)

<400> SEQUENCE: 545
caacctccag gatacactc                                           19

<210> SEQ ID NO 546
<211> LENGTH: 19
<212> TYPE: DNA
<213> ORGANISM: Artificial Sequence
<220> FEATURE:
<223> OTHER INFORMATION: NM_004958 (FRAP1)

<400> SEQUENCE: 546
gacatgagaa cctggctca                                           19

<210> SEQ ID NO 547
<211> LENGTH: 19
<212> TYPE: DNA
<213> ORGANISM: Artificial Sequence
<220> FEATURE:

<223> OTHER INFORMATION: NM_004958 (FRAP1)

<400> SEQUENCE: 547
ccaactttct agctgctgt						19

<210> SEQ ID NO 548
<211> LENGTH: 19
<212> TYPE: DNA
<213> ORGANISM: Artificial Sequence
<220> FEATURE:
<223> OTHER INFORMATION: NM_004958 (FRAP1)

<400> SEQUENCE: 548
aggacttcgc ccataagag						19

<210> SEQ ID NO 549
<211> LENGTH: 19
<212> TYPE: DNA
<213> ORGANISM: Artificial Sequence
<220> FEATURE:
<223> OTHER INFORMATION: NM_004958 (FRAP1)

<400> SEQUENCE: 549
taatacagct ggggacgac						19

<210> SEQ ID NO 550
<211> LENGTH: 19
<212> TYPE: DNA
<213> ORGANISM: Artificial Sequence
<220> FEATURE:
<223> OTHER INFORMATION: NM_005163 (AKT1)

<400> SEQUENCE: 550
gctggagaac ctcatgctg						19

<210> SEQ ID NO 551
<211> LENGTH: 19
<212> TYPE: DNA
<213> ORGANISM: Artificial Sequence
<220> FEATURE:
<223> OTHER INFORMATION: NM_005163 (AKT1)

<400> SEQUENCE: 551
cgcaccttcc atgtggaga						19

<210> SEQ ID NO 552
<211> LENGTH: 19
<212> TYPE: DNA
<213> ORGANISM: Artificial Sequence
<220> FEATURE:
<223> OTHER INFORMATION: NM_005163 (AKT1)

<400> SEQUENCE: 552
agacgttttt gtgctgtgg						19

<210> SEQ ID NO 553
<211> LENGTH: 19
<212> TYPE: DNA
<213> ORGANISM: Artificial Sequence
<220> FEATURE:
<223> OTHER INFORMATION: NM_002358 (MAD2L1)

<400> SEQUENCE: 553
tacggactca ccttgcttg						19

<210> SEQ ID NO 554

```
<211> LENGTH: 19
<212> TYPE: DNA
<213> ORGANISM: Artificial Sequence
<220> FEATURE:
<223> OTHER INFORMATION: NM_000551 (VHL)

<400> SEQUENCE: 554
ggcattggca tctgctttt                                               19

<210> SEQ ID NO 555
<211> LENGTH: 19
<212> TYPE: DNA
<213> ORGANISM: Artificial Sequence
<220> FEATURE:
<223> OTHER INFORMATION: NM_000551 (VHL)

<400> SEQUENCE: 555
gtgaatgaga cactccagt                                               19

<210> SEQ ID NO 556
<211> LENGTH: 19
<212> TYPE: DNA
<213> ORGANISM: Artificial Sequence
<220> FEATURE:
<223> OTHER INFORMATION: NM_000551 (VHL)

<400> SEQUENCE: 556
tgttgacgga cagcctatt                                               19

<210> SEQ ID NO 557
<211> LENGTH: 19
<212> TYPE: DNA
<213> ORGANISM: Artificial Sequence
<220> FEATURE:
<223> OTHER INFORMATION: NM_000551 (VHL)

<400> SEQUENCE: 557
gatctggaag accacccaa                                               19

<210> SEQ ID NO 558
<211> LENGTH: 19
<212> TYPE: DNA
<213> ORGANISM: Artificial Sequence
<220> FEATURE:
<223> OTHER INFORMATION: NM_000551 (VHL)

<400> SEQUENCE: 558
aggaaatagg cagggtgtg                                               19

<210> SEQ ID NO 559
<211> LENGTH: 19
<212> TYPE: DNA
<213> ORGANISM: Artificial Sequence
<220> FEATURE:
<223> OTHER INFORMATION: inNM_000551 (VHL)

<400> SEQUENCE: 559
cagaacccaa aagggtaag                                               19

<210> SEQ ID NO 560
<211> LENGTH: 19
<212> TYPE: DNA
<213> ORGANISM: Artificial Sequence
<220> FEATURE:
<223> OTHER INFORMATION: NM_001654 (ARAF1)

<400> SEQUENCE: 560
```

```
gtccccacat tccaagtca                                                19
```

<210> SEQ ID NO 561
<211> LENGTH: 19
<212> TYPE: DNA
<213> ORGANISM: Artificial Sequence
<220> FEATURE:
<223> OTHER INFORMATION: NM_001654 (ARAF1)

<400> SEQUENCE: 561

```
gaatgagatg caggtgctc                                                19
```

<210> SEQ ID NO 562
<211> LENGTH: 19
<212> TYPE: DNA
<213> ORGANISM: Artificial Sequence
<220> FEATURE:
<223> OTHER INFORMATION: NM_001654 (ARAF1)

<400> SEQUENCE: 562

```
gttccaccag cattgttcc                                                19
```

<210> SEQ ID NO 563
<211> LENGTH: 19
<212> TYPE: DNA
<213> ORGANISM: Artificial Sequence
<220> FEATURE:
<223> OTHER INFORMATION: NM_001654 (ARAF1)

<400> SEQUENCE: 563

```
cctctctgga atttgtgcc                                                19
```

<210> SEQ ID NO 564
<211> LENGTH: 19
<212> TYPE: DNA
<213> ORGANISM: Artificial Sequence
<220> FEATURE:
<223> OTHER INFORMATION: NM_001654 (ARAF1)

<400> SEQUENCE: 564

```
agtgaagaac ctggggtac                                                19
```

<210> SEQ ID NO 565
<211> LENGTH: 19
<212> TYPE: DNA
<213> ORGANISM: Artificial Sequence
<220> FEATURE:
<223> OTHER INFORMATION: NM_001654 (ARAF1)

<400> SEQUENCE: 565

```
ttgagctgct gcaacggtc                                                19
```

<210> SEQ ID NO 566
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 566

```
gaacatggcc aagggtgag                                                19
```

<210> SEQ ID NO 567
<211> LENGTH: 19
<212> TYPE: DNA
<213> ORGANISM: Artificial Sequence
<220> FEATURE:

<223> OTHER INFORMATION: NM_000435 (NOTCH3)

<400> SEQUENCE: 567
gagtctggga cctccttct                                      19

<210> SEQ ID NO 568
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 568
aatggcttcc gctgcctct                                      19

<210> SEQ ID NO 569
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 569
tgatcactgc ttccccgat                                      19

<210> SEQ ID NO 570
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 570
tgccaactga agaggatga                                      19

<210> SEQ ID NO 571
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 571
gctgctgttg gaccacttt                                      19

<210> SEQ ID NO 572
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 572
ccaaggaacc tgctttgat                                      19

<210> SEQ ID NO 573
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 573
gactcagacc actgcttca                                      19

<210> SEQ ID NO 574

-continued

```
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 574
ctttgaatgc cagggggaac                                              19

<210> SEQ ID NO 575
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 575
gcaactttgg tctcctttc                                               19

<210> SEQ ID NO 576
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 576
gagacaagtt aactcgtgc                                               19

<210> SEQ ID NO 577
<211> LENGTH: 19
<212> TYPE: DNA
<213> ORGANISM: Artificial Sequence
<220> FEATURE:
<223> OTHER INFORMATION: NM_000435 (NOTCH3)

<400> SEQUENCE: 577
gcaattggct gtgatgctc                                               19

<210> SEQ ID NO 578
<211> LENGTH: 19
<212> TYPE: DNA
<213> ORGANISM: Artificial Sequence
<220> FEATURE:
<223> OTHER INFORMATION: NM_012193 (FZD4)

<400> SEQUENCE: 578
ccatctgctt gagctactt                                               19

<210> SEQ ID NO 579
<211> LENGTH: 19
<212> TYPE: DNA
<213> ORGANISM: Artificial Sequence
<220> FEATURE:
<223> OTHER INFORMATION: NM_012193 (FZD4)

<400> SEQUENCE: 579
ttggcaaagg ctccttgta                                               19

<210> SEQ ID NO 580
<211> LENGTH: 19
<212> TYPE: DNA
<213> ORGANISM: Artificial Sequence
<220> FEATURE:
<223> OTHER INFORMATION: NM_012193 (FZD4)

<400> SEQUENCE: 580
```

-continued agaacctcgg ctacaacgt                                           19

<210> SEQ ID NO 581
<211> LENGTH: 19
<212> TYPE: DNA
<213> ORGANISM: Artificial Sequence
<220> FEATURE:
<223> OTHER INFORMATION: NM_012193 (FZD4)

<400> SEQUENCE: 581
tcggctacaa cgtgaccaa                                           19

<210> SEQ ID NO 582
<211> LENGTH: 19
<212> TYPE: DNA
<213> ORGANISM: Artificial Sequence
<220> FEATURE:
<223> OTHER INFORMATION: NM_012193 (FZD4)

<400> SEQUENCE: 582
gttgacttac ctgacggac                                           19

<210> SEQ ID NO 583
<211> LENGTH: 19
<212> TYPE: DNA
<213> ORGANISM: Artificial Sequence
<220> FEATURE:
<223> OTHER INFORMATION: NM_012193 (FZD4)

<400> SEQUENCE: 583
tccgcatctc catgtgcca                                           19

<210> SEQ ID NO 584
<211> LENGTH: 19
<212> TYPE: DNA
<213> ORGANISM: Artificial Sequence
<220> FEATURE:
<223> OTHER INFORMATION: NM_007313 (ABL1)

<400> SEQUENCE: 584
gaatggaagc ctgaactga                                           19

<210> SEQ ID NO 585
<211> LENGTH: 19
<212> TYPE: DNA
<213> ORGANISM: Artificial Sequence
<220> FEATURE:
<223> OTHER INFORMATION: NM_007313 (ABL1)

<400> SEQUENCE: 585
caagttctcc atcaagtcc                                           19

<210> SEQ ID NO 586
<211> LENGTH: 19
<212> TYPE: DNA
<213> ORGANISM: Artificial Sequence
<220> FEATURE:
<223> OTHER INFORMATION: NM_007313 (ABL1)

<400> SEQUENCE: 586
ctaaaggtga aaagctccg                                           19

<210> SEQ ID NO 587
<211> LENGTH: 19
<212> TYPE: DNA
<213> ORGANISM: Artificial Sequence
<220> FEATURE:

```
<223> OTHER INFORMATION: NM_007313 (ABL1)

<400> SEQUENCE: 587
tcctggcaag aaagcttga                                               19

<210> SEQ ID NO 588
<211> LENGTH: 19
<212> TYPE: DNA
<213> ORGANISM: Artificial Sequence
<220> FEATURE:
<223> OTHER INFORMATION: NM_007313 (ABL1)

<400> SEQUENCE: 588
aaacctctac acgttctgc                                               19

<210> SEQ ID NO 589
<211> LENGTH: 19
<212> TYPE: DNA
<213> ORGANISM: Artificial Sequence
<220> FEATURE:
<223> OTHER INFORMATION: NM_007313 (ABL1)

<400> SEQUENCE: 589
agacatcatg gagtccagc                                               19

<210> SEQ ID NO 590
<211> LENGTH: 19
<212> TYPE: DNA
<213> ORGANISM: Artificial Sequence
<220> FEATURE:
<223> OTHER INFORMATION: NM_017412 (FZD3)

<400> SEQUENCE: 590
cagatcactc caggcatag                                               19

<210> SEQ ID NO 591
<211> LENGTH: 19
<212> TYPE: DNA
<213> ORGANISM: Artificial Sequence
<220> FEATURE:
<223> OTHER INFORMATION: NM_017412 (FZD3)

<400> SEQUENCE: 591
atgtgtggtg actgctttg                                               19

<210> SEQ ID NO 592
<211> LENGTH: 19
<212> TYPE: DNA
<213> ORGANISM: Artificial Sequence
<220> FEATURE:
<223> OTHER INFORMATION: NM_017412 (FZD3)

<400> SEQUENCE: 592
agagatgggc attgtttcc                                               19

<210> SEQ ID NO 593
<211> LENGTH: 19
<212> TYPE: DNA
<213> ORGANISM: Artificial Sequence
<220> FEATURE:
<223> OTHER INFORMATION: NM_017412 (FZD3)

<400> SEQUENCE: 593
agcattgctg tttcacgcc                                               19

<210> SEQ ID NO 594
```

```
<211> LENGTH: 19
<212> TYPE: DNA
<213> ORGANISM: Artificial Sequence
<220> FEATURE:
<223> OTHER INFORMATION: NM_017412 (FZD3)

<400> SEQUENCE: 594
gctcatggag atgtttggt                                              19

<210> SEQ ID NO 595
<211> LENGTH: 19
<212> TYPE: DNA
<213> ORGANISM: Artificial Sequence
<220> FEATURE:
<223> OTHER INFORMATION: NM_005633 (SOS1)

<400> SEQUENCE: 595
tggtgtcctt gaggttgtc                                              19

<210> SEQ ID NO 596
<211> LENGTH: 19
<212> TYPE: DNA
<213> ORGANISM: Artificial Sequence
<220> FEATURE:
<223> OTHER INFORMATION: NM_005633 (SOS1)

<400> SEQUENCE: 596
tatcagaccg gacctctat                                              19

<210> SEQ ID NO 597
<211> LENGTH: 19
<212> TYPE: DNA
<213> ORGANISM: Artificial Sequence
<220> FEATURE:
<223> OTHER INFORMATION: NM_005633 (SOS1)

<400> SEQUENCE: 597
cttacaaaag ggagcacac                                              19

<210> SEQ ID NO 598
<211> LENGTH: 19
<212> TYPE: DNA
<213> ORGANISM: Artificial Sequence
<220> FEATURE:
<223> OTHER INFORMATION: NM_005633 (SOS1)

<400> SEQUENCE: 598
gaacaccgtt aacacctcc                                              19

<210> SEQ ID NO 599
<211> LENGTH: 19
<212> TYPE: DNA
<213> ORGANISM: Artificial Sequence
<220> FEATURE:
<223> OTHER INFORMATION: NM_005633 (SOS1)

<400> SEQUENCE: 599
ataacaggag agatccagc                                              19

<210> SEQ ID NO 600
<211> LENGTH: 19
<212> TYPE: DNA
<213> ORGANISM: Artificial Sequence
<220> FEATURE:
<223> OTHER INFORMATION: NM_005633 (SOS1)

<400> SEQUENCE: 600
```

-continued

```
attgaccacc aggtttctg                                                19

<210> SEQ ID NO 601
<211> LENGTH: 19
<212> TYPE: DNA
<213> ORGANISM: Artificial Sequence
<220> FEATURE:
<223> OTHER INFORMATION: NM_005417 (SRC)

<400> SEQUENCE: 601
caattcgtcg gaggcatca                                                19

<210> SEQ ID NO 602
<211> LENGTH: 19
<212> TYPE: DNA
<213> ORGANISM: Artificial Sequence
<220> FEATURE:
<223> OTHER INFORMATION: NM_005417 (SRC)

<400> SEQUENCE: 602
gcagtgcctg cctatgaaa                                                19

<210> SEQ ID NO 603
<211> LENGTH: 19
<212> TYPE: DNA
<213> ORGANISM: Artificial Sequence
<220> FEATURE:
<223> OTHER INFORMATION: NM_005417 (SRC)

<400> SEQUENCE: 603
ggggagtttg ctggacttt                                                19

<210> SEQ ID NO 604
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 604
gatcgagctg gctgtctttt                                               19

<210> SEQ ID NO 605
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 605
gctcaccatc tgaggaaga                                                19

<210> SEQ ID NO 606
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 606
ggtcttaaag aaggacgtc                                                19

<210> SEQ ID NO 607
<211> LENGTH: 19
<212> TYPE: DNA
<213> ORGANISM: Artificial Sequence
<220> FEATURE:
```

<223> OTHER INFORMATION: NM_005400 (PRKCE)

<400> SEQUENCE: 607
tcacaaagtg tgctgggtt                   19

<210> SEQ ID NO 608
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 608
ccaggaggaa ttcaaaggt                   19

<210> SEQ ID NO 609
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 609
tgaggacgac ctatttgag                   19

<210> SEQ ID NO 610
<211> LENGTH: 19
<212> TYPE: DNA
<213> ORGANISM: Artificial Sequence
<220> FEATURE:
<223> OTHER INFORMATION: NM_002388 (MCM3)

<400> SEQUENCE: 610
gtctcagctt ctgcggtat                   19

<210> SEQ ID NO 611
<211> LENGTH: 19
<212> TYPE: DNA
<213> ORGANISM: Artificial Sequence
<220> FEATURE:
<223> OTHER INFORMATION: NM_002388 (MCM3)

<400> SEQUENCE: 611
gtacatccat gtggccaaa                   19

<210> SEQ ID NO 612
<211> LENGTH: 19
<212> TYPE: DNA
<213> ORGANISM: Artificial Sequence
<220> FEATURE:
<223> OTHER INFORMATION: NM_002388 (MCM3)

<400> SEQUENCE: 612
aggattttgt ggcctccat                   19

<210> SEQ ID NO 613
<211> LENGTH: 19
<212> TYPE: DNA
<213> ORGANISM: Artificial Sequence
<220> FEATURE:
<223> OTHER INFORMATION: NM_002388 (MCM3)

<400> SEQUENCE: 613
tgggtcatga aagctgcca                   19

<210> SEQ ID NO 614

-continued

```
<211> LENGTH: 19
<212> TYPE: DNA
<213> ORGANISM: Artificial Sequence
<220> FEATURE:
<223> OTHER INFORMATION: NM_002388 (MCM3)

<400> SEQUENCE: 614
tccaggttga aggcattca                                                    19

<210> SEQ ID NO 615
<211> LENGTH: 19
<212> TYPE: DNA
<213> ORGANISM: Artificial Sequence
<220> FEATURE:
<223> OTHER INFORMATION: NM_002388 (MCM3)

<400> SEQUENCE: 615
gcagatgagc aaggatgct                                                    19

<210> SEQ ID NO 616
<211> LENGTH: 19
<212> TYPE: DNA
<213> ORGANISM: Artificial Sequence
<220> FEATURE:
<223> OTHER INFORMATION: NM_004380 (CREBBP)

<400> SEQUENCE: 616
gaaaaacgga ggtcgcgtt                                                    19

<210> SEQ ID NO 617
<211> LENGTH: 19
<212> TYPE: DNA
<213> ORGANISM: Artificial Sequence
<220> FEATURE:
<223> OTHER INFORMATION: NM_004380 (CREBBP)

<400> SEQUENCE: 617
gacatcccga gtctataag                                                    19

<210> SEQ ID NO 618
<211> LENGTH: 19
<212> TYPE: DNA
<213> ORGANISM: Artificial Sequence
<220> FEATURE:
<223> OTHER INFORMATION: NM_004380 (CREBBP)

<400> SEQUENCE: 618
tggaggagaa ttaggcctt                                                    19

<210> SEQ ID NO 619
<211> LENGTH: 19
<212> TYPE: DNA
<213> ORGANISM: Artificial Sequence
<220> FEATURE:
<223> OTHER INFORMATION: NM_004380 (CREBBP)

<400> SEQUENCE: 619
atttttgcgg cgccagaat                                                    19

<210> SEQ ID NO 620
<211> LENGTH: 19
<212> TYPE: DNA
<213> ORGANISM: Artificial Sequence
<220> FEATURE:
<223> OTHER INFORMATION: NM_004380 (CREBBP)

<400> SEQUENCE: 620
```

```
gcacaaggag gtcttcttc                                                    19

<210> SEQ ID NO 621
<211> LENGTH: 19
<212> TYPE: DNA
<213> ORGANISM: Artificial Sequence
<220> FEATURE:
<223> OTHER INFORMATION: NM_004380 (CREBBP)

<400> SEQUENCE: 621
gaaaacaaat gccccgtgc                                                    19

<210> SEQ ID NO 622
<211> LENGTH: 19
<212> TYPE: DNA
<213> ORGANISM: Artificial Sequence
<220> FEATURE:
<223> OTHER INFORMATION: NM_006219 (PIK3CB)

<400> SEQUENCE: 622
caaagatgcc cttctgaac                                                    19

<210> SEQ ID NO 623
<211> LENGTH: 19
<212> TYPE: DNA
<213> ORGANISM: Artificial Sequence
<220> FEATURE:
<223> OTHER INFORMATION: NM_006219 (PIK3CB)

<400> SEQUENCE: 623
gtgcacattc ctgctgtct                                                    19

<210> SEQ ID NO 624
<211> LENGTH: 19
<212> TYPE: DNA
<213> ORGANISM: Artificial Sequence
<220> FEATURE:
<223> OTHER INFORMATION: NM_006219 (PIK3CB)

<400> SEQUENCE: 624
aagttcatgt cagggctgg                                                    19

<210> SEQ ID NO 625
<211> LENGTH: 19
<212> TYPE: DNA
<213> ORGANISM: Artificial Sequence
<220> FEATURE:
<223> OTHER INFORMATION: NM_006219 (PIK3CB)

<400> SEQUENCE: 625
aatgcgcaaa ttcagcgag                                                    19

<210> SEQ ID NO 626
<211> LENGTH: 19
<212> TYPE: DNA
<213> ORGANISM: Artificial Sequence
<220> FEATURE:
<223> OTHER INFORMATION: NM_006219 (PIK3CB)

<400> SEQUENCE: 626
aatgaagcct ttgtggctg                                                    19

<210> SEQ ID NO 627
<211> LENGTH: 19
<212> TYPE: DNA
<213> ORGANISM: Artificial Sequence
<220> FEATURE:
```

-continued

<223> OTHER INFORMATION: NM_006219 (PIK3CB)

<400> SEQUENCE: 627
tacagaaaag tttggccgg                                                19

<210> SEQ ID NO 628
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 628
ctaggaaacc tcaggctta                                                19

<210> SEQ ID NO 629
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 629
ttcagctagt acaggtcct                                                19

<210> SEQ ID NO 630
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 630
tgatgcacat catggtggc                                                19

<210> SEQ ID NO 631
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 631
agaagctgtg gatcttagg                                                19

<210> SEQ ID NO 632
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 632
aggtgcactg cagttcaac                                                19

<210> SEQ ID NO 633
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 633
tggctttgaa tctttggcc                                                19

<210> SEQ ID NO 634

```
<211> LENGTH: 19
<212> TYPE: DNA
<213> ORGANISM: Artificial Sequence
<220> FEATURE:
<223> OTHER INFORMATION: NM_002086 (GRB2)

<400> SEQUENCE: 634
ctggtacaag gcagagctt                                                    19

<210> SEQ ID NO 635
<211> LENGTH: 19
<212> TYPE: DNA
<213> ORGANISM: Artificial Sequence
<220> FEATURE:
<223> OTHER INFORMATION: NM_002086 (GRB2)

<400> SEQUENCE: 635
cgggcagacc ggcatgttt                                                    19

<210> SEQ ID NO 636
<211> LENGTH: 19
<212> TYPE: DNA
<213> ORGANISM: Artificial Sequence
<220> FEATURE:
<223> OTHER INFORMATION: NM_002086 (GRB2)

<400> SEQUENCE: 636
ccggaacgtc taagagtca                                                    19

<210> SEQ ID NO 637
<211> LENGTH: 19
<212> TYPE: DNA
<213> ORGANISM: Artificial Sequence
<220> FEATURE:
<223> OTHER INFORMATION: NM_002086 (GRB2)

<400> SEQUENCE: 637
atacgtccag gccctcttt                                                    19

<210> SEQ ID NO 638
<211> LENGTH: 19
<212> TYPE: DNA
<213> ORGANISM: Artificial Sequence
<220> FEATURE:
<223> OTHER INFORMATION: NM_002086 (GRB2)

<400> SEQUENCE: 638
tgagctggtg gattatcac                                                    19

<210> SEQ ID NO 639
<211> LENGTH: 19
<212> TYPE: DNA
<213> ORGANISM: Artificial Sequence
<220> FEATURE:
<223> OTHER INFORMATION: NM_002086 (GRB2)

<400> SEQUENCE: 639
tgcagcactt caaggtgct                                                    19

<210> SEQ ID NO 640
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 640
```

```
tgacagtgga gcctgtgta                                                19

<210> SEQ ID NO 641
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 641
ctagacctag acctagact                                                19

<210> SEQ ID NO 642
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 642
ctttctgaat ggggagcct                                                19

<210> SEQ ID NO 643
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 643
gaggatgtca acggttatg                                                19

<210> SEQ ID NO 644
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 644
caaagtcttg gccagaatc                                                19

<210> SEQ ID NO 645
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 645
tacacacacc agagtgatg                                                19

<210> SEQ ID NO 646
<211> LENGTH: 19
<212> TYPE: DNA
<213> ORGANISM: Artificial Sequence
<220> FEATURE:
<223> OTHER INFORMATION: NM_001903 (CTNNA1)

<400> SEQUENCE: 646
cgttccgatc ctctatact                                                19

<210> SEQ ID NO 647
<211> LENGTH: 19
<212> TYPE: DNA
<213> ORGANISM: Artificial Sequence
<220> FEATURE:
```

```
<223> OTHER INFORMATION: NM_001903 (CTNNA1)

<400> SEQUENCE: 647
aagccattgg tgaagagag                                              19

<210> SEQ ID NO 648
<211> LENGTH: 19
<212> TYPE: DNA
<213> ORGANISM: Artificial Sequence
<220> FEATURE:
<223> OTHER INFORMATION: NM_001903 (CTNNA1)

<400> SEQUENCE: 648
tgtgtcattg ctctccaag                                              19

<210> SEQ ID NO 649
<211> LENGTH: 19
<212> TYPE: DNA
<213> ORGANISM: Artificial Sequence
<220> FEATURE:
<223> OTHER INFORMATION: NM_001903 (CTNNA1)

<400> SEQUENCE: 649
agcagtgctg atgataagg                                              19

<210> SEQ ID NO 650
<211> LENGTH: 19
<212> TYPE: DNA
<213> ORGANISM: Artificial Sequence
<220> FEATURE:
<223> OTHER INFORMATION: NM_001903 (CTNNA1)

<400> SEQUENCE: 650
tgaccaaaga tgacctgtg                                              19

<210> SEQ ID NO 651
<211> LENGTH: 19
<212> TYPE: DNA
<213> ORGANISM: Artificial Sequence
<220> FEATURE:
<223> OTHER INFORMATION: NM_001903 (CTNNA1)

<400> SEQUENCE: 651
tgacatcatt gtgctggcc                                              19

<210> SEQ ID NO 652
<211> LENGTH: 19
<212> TYPE: DNA
<213> ORGANISM: Artificial Sequence
<220> FEATURE:
<223> OTHER INFORMATION: NM_003600 (STK6)

<400> SEQUENCE: 652
cacccaaaag agcaagcag                                              19

<210> SEQ ID NO 653
<211> LENGTH: 19
<212> TYPE: DNA
<213> ORGANISM: Artificial Sequence
<220> FEATURE:
<223> OTHER INFORMATION: NM_003600 (STK6)

<400> SEQUENCE: 653
gcacaaaagc ttgtctcca                                              19

<210> SEQ ID NO 654
```

```
<211> LENGTH: 19
<212> TYPE: DNA
<213> ORGANISM: Artificial Sequence
<220> FEATURE:
<223> OTHER INFORMATION: NM_003600 (STK6)

<400> SEQUENCE: 654
cctccctatt cagaaagct                                              19

<210> SEQ ID NO 655
<211> LENGTH: 19
<212> TYPE: DNA
<213> ORGANISM: Artificial Sequence
<220> FEATURE:
<223> OTHER INFORMATION: NM_003600 (STK6)

<400> SEQUENCE: 655
acagtcttag gaatcgtgc                                              19

<210> SEQ ID NO 656
<211> LENGTH: 19
<212> TYPE: DNA
<213> ORGANISM: Artificial Sequence
<220> FEATURE:
<223> OTHER INFORMATION: NM_003600 (STK6)

<400> SEQUENCE: 656
gactttgaaa ttggtcgcc                                              19

<210> SEQ ID NO 657
<211> LENGTH: 19
<212> TYPE: DNA
<213> ORGANISM: Artificial Sequence
<220> FEATURE:
<223> OTHER INFORMATION: NM_003600 (STK6)

<400> SEQUENCE: 657
ttgcagattt tgggtggtc                                              19

<210> SEQ ID NO 658
<211> LENGTH: 19
<212> TYPE: DNA
<213> ORGANISM: Artificial Sequence
<220> FEATURE:
<223> OTHER INFORMATION: NM_003161 (RPS6KB1)

<400> SEQUENCE: 658
gacactgcct gcttttact                                              19

<210> SEQ ID NO 659
<211> LENGTH: 19
<212> TYPE: DNA
<213> ORGANISM: Artificial Sequence
<220> FEATURE:
<223> OTHER INFORMATION: NM_003161 (RPS6KB1)

<400> SEQUENCE: 659
ctctcagtga aagtgccaa                                              19

<210> SEQ ID NO 660
<211> LENGTH: 19
<212> TYPE: DNA
<213> ORGANISM: Artificial Sequence
<220> FEATURE:
<223> OTHER INFORMATION: NM_003161 (RPS6KB1)

<400> SEQUENCE: 660
```
gctttcccca tgatctcca                    19

<210> SEQ ID NO 661
<211> LENGTH: 19
<212> TYPE: DNA
<213> ORGANISM: Artificial Sequence
<220> FEATURE:
<223> OTHER INFORMATION: NM_003161 (RPS6KB1)

<400> SEQUENCE: 661
ttgattcctc gcgacatct                    19

<210> SEQ ID NO 662
<211> LENGTH: 19
<212> TYPE: DNA
<213> ORGANISM: Artificial Sequence
<220> FEATURE:
<223> OTHER INFORMATION: NM_003161 (RPS6KB1)

<400> SEQUENCE: 662
gaaagccaga caacttctg                    19

<210> SEQ ID NO 663
<211> LENGTH: 19
<212> TYPE: DNA
<213> ORGANISM: Artificial Sequence
<220> FEATURE:
<223> OTHER INFORMATION: NM_003161 (RPS6KB1)

<400> SEQUENCE: 663
cttggcatgg aacattgtg                    19

<210> SEQ ID NO 664
<211> LENGTH: 19
<212> TYPE: DNA
<213> ORGANISM: Artificial Sequence
<220> FEATURE:
<223> OTHER INFORMATION: AF308602 (NOTCH1)

<400> SEQUENCE: 664
gatcgatggc tacgagtgt                    19

<210> SEQ ID NO 665
<211> LENGTH: 19
<212> TYPE: DNA
<213> ORGANISM: Artificial Sequence
<220> FEATURE:
<223> OTHER INFORMATION: AF308602 (NOTCH1)

<400> SEQUENCE: 665
cacttacacc tgtgtgtgc                    19

<210> SEQ ID NO 666
<211> LENGTH: 19
<212> TYPE: DNA
<213> ORGANISM: Artificial Sequence
<220> FEATURE:
<223> OTHER INFORMATION: AF308602 (NOTCH1)

<400> SEQUENCE: 666
aggcaagccc tgcaagaat                    19

<210> SEQ ID NO 667
<211> LENGTH: 19
<212> TYPE: DNA
<213> ORGANISM: Artificial Sequence
<220> FEATURE:

-continued

<223> OTHER INFORMATION: AF308602 (NOTCH1)

<400> SEQUENCE: 667
catcccctac aagatcgag                                                    19

<210> SEQ ID NO 668
<211> LENGTH: 19
<212> TYPE: DNA
<213> ORGANISM: Artificial Sequence
<220> FEATURE:
<223> OTHER INFORMATION: AF308602 (NOTCH1)

<400> SEQUENCE: 668
atatcgacga ttgtccagg                                                    19

<210> SEQ ID NO 669
<211> LENGTH: 19
<212> TYPE: DNA
<213> ORGANISM: Artificial Sequence
<220> FEATURE:
<223> OTHER INFORMATION: AF308602 (NOTCH1)

<400> SEQUENCE: 669
attcaacggg ctcttgtgc                                                    19

<210> SEQ ID NO 670
<211> LENGTH: 19
<212> TYPE: DNA
<213> ORGANISM: Artificial Sequence
<220> FEATURE:
<223> OTHER INFORMATION: NM_016231 (NLK)

<400> SEQUENCE: 670
ccactcagct cagatcatg                                                    19

<210> SEQ ID NO 671
<211> LENGTH: 19
<212> TYPE: DNA
<213> ORGANISM: Artificial Sequence
<220> FEATURE:
<223> OTHER INFORMATION: NM_016231 (NLK)

<400> SEQUENCE: 671
gcaatgagga cagcttgtg                                                    19

<210> SEQ ID NO 672
<211> LENGTH: 19
<212> TYPE: DNA
<213> ORGANISM: Artificial Sequence
<220> FEATURE:
<223> OTHER INFORMATION: NM_016231 (NLK)

<400> SEQUENCE: 672
tgtagctttc cactggagt                                                    19

<210> SEQ ID NO 673
<211> LENGTH: 19
<212> TYPE: DNA
<213> ORGANISM: Artificial Sequence
<220> FEATURE:
<223> OTHER INFORMATION: NM_016231 (NLK)

<400> SEQUENCE: 673
tctccttgtg aacagcaac                                                    19

<210> SEQ ID NO 674

```
<211> LENGTH: 19
<212> TYPE: DNA
<213> ORGANISM: Artificial Sequence
<220> FEATURE:
<223> OTHER INFORMATION: NM_016231 (NLK)

<400> SEQUENCE: 674
ggaaacagag tgcctctct                                                   19

<210> SEQ ID NO 675
<211> LENGTH: 19
<212> TYPE: DNA
<213> ORGANISM: Artificial Sequence
<220> FEATURE:
<223> OTHER INFORMATION: NM_016231 (NLK)

<400> SEQUENCE: 675
tctggtctct tgcaaaagg                                                   19

<210> SEQ ID NO 676
<211> LENGTH: 19
<212> TYPE: DNA
<213> ORGANISM: Artificial Sequence
<220> FEATURE:
<223> OTHER INFORMATION: NM_001253 (CDC5L)

<400> SEQUENCE: 676
aagaagacgt tcagcgaca                                                   19

<210> SEQ ID NO 677
<211> LENGTH: 19
<212> TYPE: DNA
<213> ORGANISM: Artificial Sequence
<220> FEATURE:
<223> OTHER INFORMATION: NM_001253 (CDC5L)

<400> SEQUENCE: 677
aaaaagcctg cccttggtt                                                   19

<210> SEQ ID NO 678
<211> LENGTH: 19
<212> TYPE: DNA
<213> ORGANISM: Artificial Sequence
<220> FEATURE:
<223> OTHER INFORMATION: NM_001253 (CDC5L)

<400> SEQUENCE: 678
tcattggaag aacagcggc                                                   19

<210> SEQ ID NO 679
<211> LENGTH: 19
<212> TYPE: DNA
<213> ORGANISM: Artificial Sequence
<220> FEATURE:
<223> OTHER INFORMATION: NM_003391 (WNT2)

<400> SEQUENCE: 679
gtgtctcaaa ggagctttc                                                   19

<210> SEQ ID NO 680
<211> LENGTH: 19
<212> TYPE: DNA
<213> ORGANISM: Artificial Sequence
<220> FEATURE:
<223> OTHER INFORMATION: NM_003391 (WNT2)

<400> SEQUENCE: 680
```

-continued gcctcagaaa gggattgct                                                19

<210> SEQ ID NO 681
<211> LENGTH: 19
<212> TYPE: DNA
<213> ORGANISM: Artificial Sequence
<220> FEATURE:
<223> OTHER INFORMATION: NM_003391 (WNT2)

<400> SEQUENCE: 681
agaagatgaa tggtctggc                                                19

<210> SEQ ID NO 682
<211> LENGTH: 19
<212> TYPE: DNA
<213> ORGANISM: Artificial Sequence
<220> FEATURE:
<223> OTHER INFORMATION: NM_003391 (WNT2)

<400> SEQUENCE: 682
gctctggatg tgcacacat                                                19

<210> SEQ ID NO 683
<211> LENGTH: 19
<212> TYPE: DNA
<213> ORGANISM: Artificial Sequence
<220> FEATURE:
<223> OTHER INFORMATION: NM_003391 (WNT2)

<400> SEQUENCE: 683
aacgggcgat tatctctgg                                                19

<210> SEQ ID NO 684
<211> LENGTH: 19
<212> TYPE: DNA
<213> ORGANISM: Artificial Sequence
<220> FEATURE:
<223> OTHER INFORMATION: NM_003391 (WNT2)

<400> SEQUENCE: 684
atttgcccgc gcatttgtg                                                19

<210> SEQ ID NO 685
<211> LENGTH: 19
<212> TYPE: DNA
<213> ORGANISM: Artificial Sequence
<220> FEATURE:
<223> OTHER INFORMATION: NM_002387 (MCC)

<400> SEQUENCE: 685
agttgaggag gtttctgca                                                19

<210> SEQ ID NO 686
<211> LENGTH: 19
<212> TYPE: DNA
<213> ORGANISM: Artificial Sequence
<220> FEATURE:
<223> OTHER INFORMATION: NM_002387 (MCC)

<400> SEQUENCE: 686
gacttagagc tgggaatct                                                19

<210> SEQ ID NO 687
<211> LENGTH: 19
<212> TYPE: DNA
<213> ORGANISM: Artificial Sequence
<220> FEATURE:

```
<223> OTHER INFORMATION: NM_002387 (MCC)

<400> SEQUENCE: 687
ggattatatc cagcagctc                                            19

<210> SEQ ID NO 688
<211> LENGTH: 19
<212> TYPE: DNA
<213> ORGANISM: Artificial Sequence
<220> FEATURE:
<223> OTHER INFORMATION: NM_002387 (MCC)

<400> SEQUENCE: 688
gagaatgaga gcctgactg                                            19

<210> SEQ ID NO 689
<211> LENGTH: 19
<212> TYPE: DNA
<213> ORGANISM: Artificial Sequence
<220> FEATURE:
<223> OTHER INFORMATION: NM_002387 (MCC)

<400> SEQUENCE: 689
tagctctgct agaggagga                                            19

<210> SEQ ID NO 690
<211> LENGTH: 19
<212> TYPE: DNA
<213> ORGANISM: Artificial Sequence
<220> FEATURE:
<223> OTHER INFORMATION: NM_002387 (MCC)

<400> SEQUENCE: 690
acagaacggc tgaatagcc                                            19

<210> SEQ ID NO 691
<211> LENGTH: 19
<212> TYPE: DNA
<213> ORGANISM: Artificial Sequence
<220> FEATURE:
<223> OTHER INFORMATION: NM_005978 (S100A2)

<400> SEQUENCE: 691
ggaacttctg cacaaggag                                            19

<210> SEQ ID NO 692
<211> LENGTH: 19
<212> TYPE: DNA
<213> ORGANISM: Artificial Sequence
<220> FEATURE:
<223> OTHER INFORMATION: NM_005978 (S100A2)

<400> SEQUENCE: 692
gggcccagga ctgttgatg                                            19

<210> SEQ ID NO 693
<211> LENGTH: 19
<212> TYPE: DNA
<213> ORGANISM: Artificial Sequence
<220> FEATURE:
<223> OTHER INFORMATION: NM_005978 (S100A2)

<400> SEQUENCE: 693
tgagaacagt gaccagcag                                            19

<210> SEQ ID NO 694
```

-continued

<211> LENGTH: 19
<212> TYPE: DNA
<213> ORGANISM: Artificial Sequence
<220> FEATURE:
<223> OTHER INFORMATION: NM_005978 (S100A2)

<400> SEQUENCE: 694
tggcactcat cactgtcat                                                19

<210> SEQ ID NO 695
<211> LENGTH: 19
<212> TYPE: DNA
<213> ORGANISM: Artificial Sequence
<220> FEATURE:
<223> OTHER INFORMATION: NM_005978 (S100A2)

<400> SEQUENCE: 695
gaccgaccct gaagcagaa                                                19

<210> SEQ ID NO 696
<211> LENGTH: 19
<212> TYPE: DNA
<213> ORGANISM: Artificial Sequence
<220> FEATURE:
<223> OTHER INFORMATION: NM_005978 (S100A2)

<400> SEQUENCE: 696
ttccaggagt atgctgttt                                                19

<210> SEQ ID NO 697
<211> LENGTH: 19
<212> TYPE: DNA
<213> ORGANISM: Artificial Sequence
<220> FEATURE:
<223> OTHER INFORMATION: NM_033360 (KRAS2)

<400> SEQUENCE: 697
gaagttatgg aattcctt                                                 19

<210> SEQ ID NO 698
<211> LENGTH: 19
<212> TYPE: DNA
<213> ORGANISM: Artificial Sequence
<220> FEATURE:
<223> OTHER INFORMATION: NM_033360 (KRAS2)

<400> SEQUENCE: 698
ggactctgaa gatgtacct                                                19

<210> SEQ ID NO 699
<211> LENGTH: 19
<212> TYPE: DNA
<213> ORGANISM: Artificial Sequence
<220> FEATURE:
<223> OTHER INFORMATION: NM_033360 (KRAS2)

<400> SEQUENCE: 699
ggcatactag tacaagtgg                                                19

<210> SEQ ID NO 700
<211> LENGTH: 19
<212> TYPE: DNA
<213> ORGANISM: Artificial Sequence
<220> FEATURE:
<223> OTHER INFORMATION: NM_033360 (KRAS2)

<400> SEQUENCE: 700
acctgtctct tggatattc                                              19

<210> SEQ ID NO 701
<211> LENGTH: 19
<212> TYPE: DNA
<213> ORGANISM: Artificial Sequence
<220> FEATURE:
<223> OTHER INFORMATION: NM_033360 (KRAS2)

<400> SEQUENCE: 701
taaatgtgat ttgccttct                                              19

<210> SEQ ID NO 702
<211> LENGTH: 19
<212> TYPE: DNA
<213> ORGANISM: Artificial Sequence
<220> FEATURE:
<223> OTHER INFORMATION: NM_033360 (KRAS2)

<400> SEQUENCE: 702
gaaaagactc ctggctgtg                                              19

<210> SEQ ID NO 703
<211> LENGTH: 19
<212> TYPE: DNA
<213> ORGANISM: Artificial Sequence
<220> FEATURE:
<223> OTHER INFORMATION: NM_139049 (MAPK8)

<400> SEQUENCE: 703
ggaatagtat gcgcagctt                                              19

<210> SEQ ID NO 704
<211> LENGTH: 19
<212> TYPE: DNA
<213> ORGANISM: Artificial Sequence
<220> FEATURE:
<223> OTHER INFORMATION: NM_139049 (MAPK8)

<400> SEQUENCE: 704
gtgattcaga tggagctag                                              19

<210> SEQ ID NO 705
<211> LENGTH: 19
<212> TYPE: DNA
<213> ORGANISM: Artificial Sequence
<220> FEATURE:
<223> OTHER INFORMATION: NM_139049 (MAPK8)

<400> SEQUENCE: 705
caccatgtcc tgaattcat                                              19

<210> SEQ ID NO 706
<211> LENGTH: 19
<212> TYPE: DNA
<213> ORGANISM: Artificial Sequence
<220> FEATURE:
<223> OTHER INFORMATION: NM_139049 (MAPK8)

<400> SEQUENCE: 706
cgagttttat gatgacgcc                                              19

<210> SEQ ID NO 707
<211> LENGTH: 19
<212> TYPE: DNA
<213> ORGANISM: Artificial Sequence
<220> FEATURE:

<223> OTHER INFORMATION: NM_139049 (MAPK8)

<400> SEQUENCE: 707
cacccgtaca tcaatgtct                    19

<210> SEQ ID NO 708
<211> LENGTH: 19
<212> TYPE: DNA
<213> ORGANISM: Artificial Sequence
<220> FEATURE:
<223> OTHER INFORMATION: NM_139049 (MAPK8)

<400> SEQUENCE: 708
tcaagcacct tcattctgc                    19

<210> SEQ ID NO 709
<211> LENGTH: 19
<212> TYPE: DNA
<213> ORGANISM: Artificial Sequence
<220> FEATURE:
<223> OTHER INFORMATION: NM_002658 (PLAU)

<400> SEQUENCE: 709
caagtacttc tccaacatt                    19

<210> SEQ ID NO 710
<211> LENGTH: 19
<212> TYPE: DNA
<213> ORGANISM: Artificial Sequence
<220> FEATURE:
<223> OTHER INFORMATION: NM_002658 (PLAU)

<400> SEQUENCE: 710
gagctggtgt ctgattgtt                    19

<210> SEQ ID NO 711
<211> LENGTH: 19
<212> TYPE: DNA
<213> ORGANISM: Artificial Sequence
<220> FEATURE:
<223> OTHER INFORMATION: NM_002658 (PLAU)

<400> SEQUENCE: 711
ctgcccaaag aaattcgga                    19

<210> SEQ ID NO 712
<211> LENGTH: 19
<212> TYPE: DNA
<213> ORGANISM: Artificial Sequence
<220> FEATURE:
<223> OTHER INFORMATION: NM_002658 (PLAU)

<400> SEQUENCE: 712
gtgtaagcag ctgaggtct                    19

<210> SEQ ID NO 713
<211> LENGTH: 19
<212> TYPE: DNA
<213> ORGANISM: Artificial Sequence
<220> FEATURE:
<223> OTHER INFORMATION: NM_002658 (PLAU)

<400> SEQUENCE: 713
tggaggaaca tgtgtgtcc                    19

<210> SEQ ID NO 714

```
<211> LENGTH: 19
<212> TYPE: DNA
<213> ORGANISM: Artificial Sequence
<220> FEATURE:
<223> OTHER INFORMATION: NM_002658 (PLAU)

<400> SEQUENCE: 714
ttactgcagg aacccagac                                                19

<210> SEQ ID NO 715
<211> LENGTH: 19
<212> TYPE: DNA
<213> ORGANISM: Artificial Sequence
<220> FEATURE:
<223> OTHER INFORMATION: NM_016195 (MPHOSPH1)

<400> SEQUENCE: 715
agaggaactc tctgcaagc                                                19

<210> SEQ ID NO 716
<211> LENGTH: 19
<212> TYPE: DNA
<213> ORGANISM: Artificial Sequence
<220> FEATURE:
<223> OTHER INFORMATION: NM_016195 (MPHOSPH1)

<400> SEQUENCE: 716
aagtttgtgt cccagacac                                                19

<210> SEQ ID NO 717
<211> LENGTH: 19
<212> TYPE: DNA
<213> ORGANISM: Artificial Sequence
<220> FEATURE:
<223> OTHER INFORMATION: NM_016195 (MPHOSPH1)

<400> SEQUENCE: 717
ctgaagaagc tactgcttg                                                19

<210> SEQ ID NO 718
<211> LENGTH: 19
<212> TYPE: DNA
<213> ORGANISM: Artificial Sequence
<220> FEATURE:
<223> OTHER INFORMATION: NM_016195 (MPHOSPH1)

<400> SEQUENCE: 718
gacatgcgaa tgacactag                                                19

<210> SEQ ID NO 719
<211> LENGTH: 19
<212> TYPE: DNA
<213> ORGANISM: Artificial Sequence
<220> FEATURE:
<223> OTHER INFORMATION: NM_016195 (MPHOSPH1)

<400> SEQUENCE: 719
aatggcagtg aaacaccct                                                19

<210> SEQ ID NO 720
<211> LENGTH: 19
<212> TYPE: DNA
<213> ORGANISM: Artificial Sequence
<220> FEATURE:
<223> OTHER INFORMATION: NM_016195 (MPHOSPH1)

<400> SEQUENCE: 720
```

| | |
|---|---|
| atgaaggaga gtgatcacc | 19 |

<210> SEQ ID NO 721
<211> LENGTH: 19
<212> TYPE: DNA
<213> ORGANISM: Artificial Sequence
<220> FEATURE:
<223> OTHER INFORMATION: NM_020168 (PAK6)

<400> SEQUENCE: 721

| | |
|---|---|
| cgacatccag aagttgtca | 19 |

<210> SEQ ID NO 722
<211> LENGTH: 19
<212> TYPE: DNA
<213> ORGANISM: Artificial Sequence
<220> FEATURE:
<223> OTHER INFORMATION: NM_020168 (PAK6)

<400> SEQUENCE: 722

| | |
|---|---|
| gagaaagaat ggggtcggt | 19 |

<210> SEQ ID NO 723
<211> LENGTH: 19
<212> TYPE: DNA
<213> ORGANISM: Artificial Sequence
<220> FEATURE:
<223> OTHER INFORMATION: NM_020168 (PAK6)

<400> SEQUENCE: 723

| | |
|---|---|
| tgaggagcag attgccact | 19 |

<210> SEQ ID NO 724
<211> LENGTH: 19
<212> TYPE: DNA
<213> ORGANISM: Artificial Sequence
<220> FEATURE:
<223> OTHER INFORMATION: NM_000051 (ATM)

<400> SEQUENCE: 724

| | |
|---|---|
| tagattgttc caggacacg | 19 |

<210> SEQ ID NO 725
<211> LENGTH: 19
<212> TYPE: DNA
<213> ORGANISM: Artificial Sequence
<220> FEATURE:
<223> OTHER INFORMATION: NM_000051 (ATM)

<400> SEQUENCE: 725

| | |
|---|---|
| agttcgatca gcagctgtt | 19 |

<210> SEQ ID NO 726
<211> LENGTH: 19
<212> TYPE: DNA
<213> ORGANISM: Artificial Sequence
<220> FEATURE:
<223> OTHER INFORMATION: NM_000051 (ATM)

<400> SEQUENCE: 726

| | |
|---|---|
| gaagttggat gccagctgt | 19 |

<210> SEQ ID NO 727
<211> LENGTH: 19
<212> TYPE: DNA
<213> ORGANISM: Artificial Sequence
<220> FEATURE:

<223> OTHER INFORMATION: NM_001259 (CDK6)

<400> SEQUENCE: 727
tcttggacgt gattggact                                                  19

<210> SEQ ID NO 728
<211> LENGTH: 19
<212> TYPE: DNA
<213> ORGANISM: Artificial Sequence
<220> FEATURE:
<223> OTHER INFORMATION: NM_001259 (CDK6)

<400> SEQUENCE: 728
accacagaac attctggtg                                                  19

<210> SEQ ID NO 729
<211> LENGTH: 19
<212> TYPE: DNA
<213> ORGANISM: Artificial Sequence
<220> FEATURE:
<223> OTHER INFORMATION: NM_001259 (CDK6)

<400> SEQUENCE: 729
agaaaacctg gattcccac                                                  19

<210> SEQ ID NO 730
<211> LENGTH: 19
<212> TYPE: DNA
<213> ORGANISM: Artificial Sequence
<220> FEATURE:
<223> OTHER INFORMATION: NM_004856 (KNSL5)

<400> SEQUENCE: 730
gaatgtgagc gtagagtgg                                                  19

<210> SEQ ID NO 731
<211> LENGTH: 19
<212> TYPE: DNA
<213> ORGANISM: Artificial Sequence
<220> FEATURE:
<223> OTHER INFORMATION: NM_004856 (KNSL5)

<400> SEQUENCE: 731
ccattggtta ctgacgtgg                                                  19

<210> SEQ ID NO 732
<211> LENGTH: 19
<212> TYPE: DNA
<213> ORGANISM: Artificial Sequence
<220> FEATURE:
<223> OTHER INFORMATION: NM_004856 (KNSL5)

<400> SEQUENCE: 732
aacccaaacc tccacaatc                                                  19

<210> SEQ ID NO 733
<211> LENGTH: 19
<212> TYPE: DNA
<213> ORGANISM: Artificial Sequence
<220> FEATURE:
<223> OTHER INFORMATION: NM_004856 (KNSL5)

<400> SEQUENCE: 733
acaaaaacgg agatccgtc                                                  19

<210> SEQ ID NO 734

```
<211> LENGTH: 19
<212> TYPE: DNA
<213> ORGANISM: Artificial Sequence
<220> FEATURE:
<223> OTHER INFORMATION: NM_004856 (KNSL5)

<400> SEQUENCE: 734
gaatttcggg ctactttgg                                                  19

<210> SEQ ID NO 735
<211> LENGTH: 19
<212> TYPE: DNA
<213> ORGANISM: Artificial Sequence
<220> FEATURE:
<223> OTHER INFORMATION: NM_004856 (KNSL5)

<400> SEQUENCE: 735
ataagcagca agaaacggc                                                  19

<210> SEQ ID NO 736
<211> LENGTH: 19
<212> TYPE: DNA
<213> ORGANISM: Artificial Sequence
<220> FEATURE:
<223> OTHER INFORMATION: NM_004972 (JAK2)

<400> SEQUENCE: 736
agccgagttg taactatcc                                                  19

<210> SEQ ID NO 737
<211> LENGTH: 19
<212> TYPE: DNA
<213> ORGANISM: Artificial Sequence
<220> FEATURE:
<223> OTHER INFORMATION: NM_004972 (JAK2)

<400> SEQUENCE: 737
aagaacctgg tgaaagtcc                                                  19

<210> SEQ ID NO 738
<211> LENGTH: 19
<212> TYPE: DNA
<213> ORGANISM: Artificial Sequence
<220> FEATURE:
<223> OTHER INFORMATION: NM_004972 (JAK2)

<400> SEQUENCE: 738
gaagtgcagc aggttaaga                                                  19

<210> SEQ ID NO 739
<211> LENGTH: 19
<212> TYPE: DNA
<213> ORGANISM: Artificial Sequence
<220> FEATURE:
<223> OTHER INFORMATION: NM_005026 (PIK3CD)

<400> SEQUENCE: 739
gatcggccac ttccttttc                                                  19

<210> SEQ ID NO 740
<211> LENGTH: 19
<212> TYPE: DNA
<213> ORGANISM: Artificial Sequence
<220> FEATURE:
<223> OTHER INFORMATION: NM_005026 (PIK3CD)

<400> SEQUENCE: 740
```

```
agagatctgg gcctcatgt                                          19

<210> SEQ ID NO 741
<211> LENGTH: 19
<212> TYPE: DNA
<213> ORGANISM: Artificial Sequence
<220> FEATURE:
<223> OTHER INFORMATION: NM_005026 (PIK3CD)

<400> SEQUENCE: 741
aaccaaagtg aactggctg                                          19

<210> SEQ ID NO 742
<211> LENGTH: 19
<212> TYPE: DNA
<213> ORGANISM: Artificial Sequence
<220> FEATURE:
<223> OTHER INFORMATION: NM_014885 (APC10)

<400> SEQUENCE: 742
caaggcatcc gttatatct                                          19

<210> SEQ ID NO 743
<211> LENGTH: 19
<212> TYPE: DNA
<213> ORGANISM: Artificial Sequence
<220> FEATURE:
<223> OTHER INFORMATION: NM_014885 (APC10)

<400> SEQUENCE: 743
accaggattt ggagtggat                                          19

<210> SEQ ID NO 744
<211> LENGTH: 19
<212> TYPE: DNA
<213> ORGANISM: Artificial Sequence
<220> FEATURE:
<223> OTHER INFORMATION: NM_014885 (APC10)

<400> SEQUENCE: 744
gtggctggat tcatgttcc                                          19

<210> SEQ ID NO 745
<211> LENGTH: 19
<212> TYPE: DNA
<213> ORGANISM: Artificial Sequence
<220> FEATURE:
<223> OTHER INFORMATION: NM_005733 (RAB6KIFL)

<400> SEQUENCE: 745
gaagctgtcc ctgctaaat                                          19

<210> SEQ ID NO 746
<211> LENGTH: 19
<212> TYPE: DNA
<213> ORGANISM: Artificial Sequence
<220> FEATURE:
<223> OTHER INFORMATION: NM_005733 (RAB6KIFL)

<400> SEQUENCE: 746
ctctaccact gaagagttg                                          19

<210> SEQ ID NO 747
<211> LENGTH: 19
<212> TYPE: DNA
<213> ORGANISM: Artificial Sequence
<220> FEATURE:
```

<223> OTHER INFORMATION: NM_005733 (RAB6KIFL)

<400> SEQUENCE: 747
aagtgggtcg taagaacca                                                19

<210> SEQ ID NO 748
<211> LENGTH: 19
<212> TYPE: DNA
<213> ORGANISM: Artificial Sequence
<220> FEATURE:
<223> OTHER INFORMATION: NM_007054 (KIF3A)

<400> SEQUENCE: 748
ggagaaagat ccctttgag                                                19

<210> SEQ ID NO 749
<211> LENGTH: 19
<212> TYPE: DNA
<213> ORGANISM: Artificial Sequence
<220> FEATURE:
<223> OTHER INFORMATION: NM_007054 (KIF3A)

<400> SEQUENCE: 749
tattgggcca gcagattac                                                19

<210> SEQ ID NO 750
<211> LENGTH: 19
<212> TYPE: DNA
<213> ORGANISM: Artificial Sequence
<220> FEATURE:
<223> OTHER INFORMATION: NM_007054 (KIF3A)

<400> SEQUENCE: 750
ttatgacgct aggccacaa                                                19

<210> SEQ ID NO 751
<211> LENGTH: 19
<212> TYPE: DNA
<213> ORGANISM: Artificial Sequence
<220> FEATURE:
<223> OTHER INFORMATION: NM_020242 (KNSL7)

<400> SEQUENCE: 751
gcacaactcc tgcaaattc                                                19

<210> SEQ ID NO 752
<211> LENGTH: 19
<212> TYPE: DNA
<213> ORGANISM: Artificial Sequence
<220> FEATURE:
<223> OTHER INFORMATION: NM_020242 (KNSL7)

<400> SEQUENCE: 752
gatggaagag cctctaaga                                                19

<210> SEQ ID NO 753
<211> LENGTH: 19
<212> TYPE: DNA
<213> ORGANISM: Artificial Sequence
<220> FEATURE:
<223> OTHER INFORMATION: NM_020242 (KNSL7)

<400> SEQUENCE: 753
acgaaaagct gcttgagag                                                19

<210> SEQ ID NO 754

```
<211> LENGTH: 19
<212> TYPE: DNA
<213> ORGANISM: Artificial Sequence
<220> FEATURE:
<223> OTHER INFORMATION: NM_001184 (ATR)

<400> SEQUENCE: 754
tcacgactcg ctgaactgt                                                  19

<210> SEQ ID NO 755
<211> LENGTH: 19
<212> TYPE: DNA
<213> ORGANISM: Artificial Sequence
<220> FEATURE:
<223> OTHER INFORMATION: NM_001184 (ATR)

<400> SEQUENCE: 755
gaaactgcag ctatcttcc                                                  19

<210> SEQ ID NO 756
<211> LENGTH: 19
<212> TYPE: DNA
<213> ORGANISM: Artificial Sequence
<220> FEATURE:
<223> OTHER INFORMATION: NM_001184 (ATR)

<400> SEQUENCE: 756
gttacaatga ggctgatgc                                                  19

<210> SEQ ID NO 757
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 757
attttctaga aaacggtaa                                                  19

<210> SEQ ID NO 758
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 758
gaggggcgaa gtttcggca                                                  19

<210> SEQ ID NO 759
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 759
ctgggaccgg gaagccgga                                                  19

<210> SEQ ID NO 760
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 760
```

-continued

```
cttctacttc tgttggcag                                                19

<210> SEQ ID NO 761
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 761
acttactatt cagactgca                                                19

<210> SEQ ID NO 762
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 762
gccctcaccc acagtagcc                                                19

<210> SEQ ID NO 763
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 763
cagaggaatg cacacccag                                                19

<210> SEQ ID NO 764
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 764
gattgattag atctcttga                                                19

<210> SEQ ID NO 765
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 765
gtgagtatta tcccagttg                                                19

<210> SEQ ID NO 766
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 766
atctggggtg ctgattgct                                                19

<210> SEQ ID NO 767
<211> LENGTH: 19
<212> TYPE: DNA
<213> ORGANISM: Artificial Sequence
<220> FEATURE:
```

<223> OTHER INFORMATION: NM_014875 (KIF14)

<400> SEQUENCE: 767
gtgacagtgg cagtacgcg                                        19

<210> SEQ ID NO 768
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 768
tcagactgaa gttgttaga                                        19

<210> SEQ ID NO 769
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 769
gttggctaga attgggaaa                                        19

<210> SEQ ID NO 770
<211> LENGTH: 19
<212> TYPE: DNA
<213> ORGANISM: Artificial Sequence
<220> FEATURE:
<223> OTHER INFORMATION: NM_014875 (KIF14)

<400> SEQUENCE: 770
gaagaccata gcatccgcc                                        19

<210> SEQ ID NO 771
<211> LENGTH: 19
<212> TYPE: DNA
<213> ORGANISM: Artificial Sequence
<220> FEATURE:
<223> OTHER INFORMATION: NM_001274 (CHEK1)

<400> SEQUENCE: 771
tgcctgaaag agacttgtg                                        19

<210> SEQ ID NO 772
<211> LENGTH: 19
<212> TYPE: DNA
<213> ORGANISM: Artificial Sequence
<220> FEATURE:
<223> OTHER INFORMATION: NM_001274 (CHEK1)

<400> SEQUENCE: 772
atcgattctg ctcctctag                                        19

<210> SEQ ID NO 773
<211> LENGTH: 19
<212> TYPE: DNA
<213> ORGANISM: Artificial Sequence
<220> FEATURE:
<223> OTHER INFORMATION: NM_001274 (CHEK1)

<400> SEQUENCE: 773
ctgaagaagc agtcgcagt                                        19

<210> SEQ ID NO 774

```
<211> LENGTH: 19
<212> TYPE: DNA
<213> ORGANISM: Artificial Sequence
<220> FEATURE:
<223> OTHER INFORMATION: NM_001274 (CHEK1)

<400> SEQUENCE: 774
gatcacagtg gcaatggaa                                                   19

<210> SEQ ID NO 775
<211> LENGTH: 19
<212> TYPE: DNA
<213> ORGANISM: Artificial Sequence
<220> FEATURE:
<223> OTHER INFORMATION: NM_001274 (CHEK1)

<400> SEQUENCE: 775
atgaatccac agctctacc                                                   19

<210> SEQ ID NO 776
<211> LENGTH: 19
<212> TYPE: DNA
<213> ORGANISM: Artificial Sequence
<220> FEATURE:
<223> OTHER INFORMATION: NM_001274 (CHEK1)

<400> SEQUENCE: 776
aaactcttgg aagtggtgc                                                   19

<210> SEQ ID NO 777
<211> LENGTH: 19
<212> TYPE: DNA
<213> ORGANISM: Artificial Sequence
<220> FEATURE:
<223> OTHER INFORMATION: NM_000546 (TP53)

<400> SEQUENCE: 777
gcacccagga cttccattt                                                   19

<210> SEQ ID NO 778
<211> LENGTH: 19
<212> TYPE: DNA
<213> ORGANISM: Artificial Sequence
<220> FEATURE:
<223> OTHER INFORMATION: NM_000546 (TP53)

<400> SEQUENCE: 778
cctcttggtc gaccttagt                                                   19

<210> SEQ ID NO 779
<211> LENGTH: 19
<212> TYPE: DNA
<213> ORGANISM: Artificial Sequence
<220> FEATURE:
<223> OTHER INFORMATION: NM_000546 (TP53)

<400> SEQUENCE: 779
tgaggccttg gaactcaag                                                   19

<210> SEQ ID NO 780
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 780
```

-continued

| | | |
|---|---|---|
| agcgcctggg cctggatga | | 19 |

<210> SEQ ID NO 781
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 781

| | | |
|---|---|---|
| accgggcagc atcgtctcc | | 19 |

<210> SEQ ID NO 782
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 782

| | | |
|---|---|---|
| cagcggccag agaaggaaa | | 19 |

<210> SEQ ID NO 783
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 783

| | | |
|---|---|---|
| cagaaggaag agtgtatgt | | 19 |

<210> SEQ ID NO 784
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 784

| | | |
|---|---|---|
| tgcagtgtaa agtctgcaa | | 19 |

<210> SEQ ID NO 785
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 785

| | | |
|---|---|---|
| gcgcatcggc caaacggcc | | 19 |

<210> SEQ ID NO 786
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 786

| | | |
|---|---|---|
| attgcagaga cttcatctg | | 19 |

<210> SEQ ID NO 787
<211> LENGTH: 19
<212> TYPE: DNA
<213> ORGANISM: Artificial Sequence
<220> FEATURE:

```
<223> OTHER INFORMATION: NM_005400 (PRKCE)

<400> SEQUENCE: 787
gaagagccgg tactcaccc                                              19

<210> SEQ ID NO 788
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 788
agtactggcc gacctgggc                                              19

<210> SEQ ID NO 789
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 789
ggatgcagaa ggtcactgc                                              19

<210> SEQ ID NO 790
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 790
cgtgagcttg aagcccaca                                              19

<210> SEQ ID NO 791
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 791
cacaaagtgt gctgggtta                                              19

<210> SEQ ID NO 792
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 792
gacgaagcaa ttgtaaagc                                              19

<210> SEQ ID NO 793
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 793
cacccttcaa accacgcat                                              19

<210> SEQ ID NO 794
```

```
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 794
gtcagcatct tgaaagctt                                                19

<210> SEQ ID NO 795
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 795
caaccgagga gaggagcac                                                19

<210> SEQ ID NO 796
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 796
tacattgccc tcaatgtgg                                                19

<210> SEQ ID NO 797
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 797
gaggaatcgc caaagtact                                                19

<210> SEQ ID NO 798
<211> LENGTH: 19
<212> TYPE: DNA
<213> ORGANISM: Artificial Sequence
<220> FEATURE:
<223> OTHER INFORMATION: NM_005400 (PRKCE)

<400> SEQUENCE: 798
gggatttgaa actggacaa                                                19

<210> SEQ ID NO 799
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 799
ttacacgttc atgtgctgg                                                19

<210> SEQ ID NO 800
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 800
```

-continued cacaatccat gaacagcat                                            19

<210> SEQ ID NO 801
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 801
caatcaaacc tgaacaggc                                            19

<210> SEQ ID NO 802
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 802
cagttcaaca gccacacac                                            19

<210> SEQ ID NO 803
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 803
gtgttacaag gcttatcta                                            19

<210> SEQ ID NO 804
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 804
gatcctatgg ttcgaggtt                                            19

<210> SEQ ID NO 805
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 805
ctccaaataa tgacaagca                                            19

<210> SEQ ID NO 806
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 806
actttgcctt tccatttgc                                            19

<210> SEQ ID NO 807
<211> LENGTH: 19
<212> TYPE: DNA
<213> ORGANISM: Artificial Sequence
<220> FEATURE:

<223> OTHER INFORMATION: NM_006218 (PIK3CA)

<400> SEQUENCE: 807
agaatatcag ggcaagtac                                                    19

<210> SEQ ID NO 808
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 808
ttggatcttc cacacaatt                                                    19

<210> SEQ ID NO 809
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 809
agtaggcaac cgtgaagaa                                                    19

<210> SEQ ID NO 810
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 810
cagggcttgc tgtctcctc                                                    19

<210> SEQ ID NO 811
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 811
gagcccaaga atgcacaaa                                                    19

<210> SEQ ID NO 812
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 812
gccagaacaa gtaattgct                                                    19

<210> SEQ ID NO 813
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 813
ggatgcccta cagggcttg                                                    19

<210> SEQ ID NO 814

-continued

```
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 814
tcaaattatt cgtattatg                                               19

<210> SEQ ID NO 815
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 815
gaattggaga tcgtcacaa                                               19

<210> SEQ ID NO 816
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 816
tgaggtggtg cgaaattct                                               19

<210> SEQ ID NO 817
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 817
gatttacggc aagatatgc                                               19

<210> SEQ ID NO 818
<211> LENGTH: 19
<212> TYPE: DNA
<213> ORGANISM: Artificial Sequence
<220> FEATURE:
<223> OTHER INFORMATION: NM_006218 (PIK3CA)

<400> SEQUENCE: 818
tgatgaatac ttcctagaa                                               19

<210> SEQ ID NO 819
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 819
gctgctggga ctatgccca                                               19

<210> SEQ ID NO 820
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 820
```

-continued

| | |
|---|---|
| atctgcacaa ttgatgtct | 19 |

<210> SEQ ID NO 821
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 821

| | |
|---|---|
| ctttgaactg gaccaaggt | 19 |

<210> SEQ ID NO 822
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 822

| | |
|---|---|
| catcatgccc actgcaggc | 19 |

<210> SEQ ID NO 823
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 823

| | |
|---|---|
| aactttccag ctggaaccc | 19 |

<210> SEQ ID NO 824
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 824

| | |
|---|---|
| tgaaggaaat tagtgctgg | 19 |

<210> SEQ ID NO 825
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 825

| | |
|---|---|
| aattcgccag cggttcagg | 19 |

<210> SEQ ID NO 826
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 826

| | |
|---|---|
| accagagctt caagactgt | 19 |

<210> SEQ ID NO 827
<211> LENGTH: 19
<212> TYPE: DNA
<213> ORGANISM: Artificial Sequence
<220> FEATURE:

<223> OTHER INFORMATION: NM_001982 (ERBB3)

<400> SEQUENCE: 827
gaggctacag actctgcct                                          19

<210> SEQ ID NO 828
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 828
tggagccaga actagacct                                          19

<210> SEQ ID NO 829
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 829
acactgtaca agctctacg                                          19

<210> SEQ ID NO 830
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 830
taatggtcac tgctttggg                                          19

<210> SEQ ID NO 831
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 831
acaggcactc ctggagata                                          19

<210> SEQ ID NO 832
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 832
gtttaggaca aacactggt                                          19

<210> SEQ ID NO 833
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 833
gattactggc atagcaggc                                          19

<210> SEQ ID NO 834

<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 834
atgaatacat gaaccggag                                                    19

<210> SEQ ID NO 835
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 835
cacttaatcg gccacgtgg                                                    19

<210> SEQ ID NO 836
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 836
ggcctgtcct cctgacaag                                                    19

<210> SEQ ID NO 837
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 837
tctgcggagt catgagggc                                                    19

<210> SEQ ID NO 838
<211> LENGTH: 19
<212> TYPE: DNA
<213> ORGANISM: Artificial Sequence
<220> FEATURE:
<223> OTHER INFORMATION: NM_001982 (ERBB3)

<400> SEQUENCE: 838
tagacctaga cttggaagc                                                    19

<210> SEQ ID NO 839
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 839
gatttcaggt ctccctgtc                                                    19

<210> SEQ ID NO 840
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 840
gccacagtgg ttatctcca                                                    19

<210> SEQ ID NO 841
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 841
gcaatccctt ccctcctgt                                                    19

<210> SEQ ID NO 842
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 842
tctctgatcc tgaagtgaa                                                    19

<210> SEQ ID NO 843
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 843
catcaatgtg aagcaggtc                                                    19

<210> SEQ ID NO 844
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 844
catgagcttg ctgctttcc                                                    19

<210> SEQ ID NO 845
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 845
aacgtgttgt gcctgctga                                                    19

<210> SEQ ID NO 846
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 846
ctgctttcca gggtgtgtt                                                    19

<210> SEQ ID NO 847
<211> LENGTH: 19
<212> TYPE: DNA
<213> ORGANISM: Artificial Sequence
<220> FEATURE:

<223> OTHER INFORMATION: NM_004283 (RAB3D)

<400> SEQUENCE: 847
gcggccaggg ccaagccgc                                              19

<210> SEQ ID NO 848
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 848
cttctagctt agaaccatt                                              19

<210> SEQ ID NO 849
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 849
cagggtgtgt tgagggtgg                                              19

<210> SEQ ID NO 850
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 850
ctctttctca ggtcctgca                                              19

<210> SEQ ID NO 851
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 851
cttgtgccaa gatggcatc                                              19

<210> SEQ ID NO 852
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 852
gcaccatcac cacggccta                                              19

<210> SEQ ID NO 853
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 853
cgcggacgac tccttcact                                              19

<210> SEQ ID NO 854

```
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 854
tcatccaggg aaggcggcg                                                  19

<210> SEQ ID NO 855
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 855
gacactgacg tgcatgagc                                                  19

<210> SEQ ID NO 856
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 856
ccctcccagg ccctgttta                                                  19

<210> SEQ ID NO 857
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 857
aggtcttcga gcgcctggt                                                  19

<210> SEQ ID NO 858
<211> LENGTH: 19
<212> TYPE: DNA
<213> ORGANISM: Artificial Sequence
<220> FEATURE:
<223> OTHER INFORMATION: NM_004283 (RAB3D)

<400> SEQUENCE: 858
cctctttctc aggtcctgc                                                  19

<210> SEQ ID NO 859
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 859
ttgcccggga gcacttgtg                                                  19

<210> SEQ ID NO 860
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 860
```

```
cgtgtgcgac gggcacggc                                                  19

<210> SEQ ID NO 861
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 861
attaggtctt aaagtagtt                                                  19

<210> SEQ ID NO 862
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 862
agccctgact ttaaggata                                                  19

<210> SEQ ID NO 863
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 863
tgtggagccc gaaccgacg                                                  19

<210> SEQ ID NO 864
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 864
gcgacgggca cggcgggcg                                                  19

<210> SEQ ID NO 865
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 865
gattatatgg gtatatatt                                                  19

<210> SEQ ID NO 866
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 866
ttagaaggag cacagttat                                                  19

<210> SEQ ID NO 867
<211> LENGTH: 19
<212> TYPE: DNA
<213> ORGANISM: Artificial Sequence
<220> FEATURE:
```

<223> OTHER INFORMATION: NM_003620 (PPM1D)

<400> SEQUENCE: 867
ccggccagcc ggccatggc                                            19

<210> SEQ ID NO 868
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 868
gagcagataa cactagtgc                                            19

<210> SEQ ID NO 869
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 869
agatgccatc tcaatgtgc                                            19

<210> SEQ ID NO 870
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 870
gcggcacagt ttgcccggg                                            19

<210> SEQ ID NO 871
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 871
cgtagcaatg ccttctcag                                            19

<210> SEQ ID NO 872
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 872
tatatgggta tatattcat                                            19

<210> SEQ ID NO 873
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 873
gctgctaatt cccaacatt                                            19

<210> SEQ ID NO 874

```
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 874
acaactgcca gtgtggtca                                               19

<210> SEQ ID NO 875
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 875
ttgaccctca gaagcacaa                                               19

<210> SEQ ID NO 876
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 876
gtcttaaagt agttactcc                                               19

<210> SEQ ID NO 877
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 877
atgctccgag cagataaca                                               19

<210> SEQ ID NO 878
<211> LENGTH: 19
<212> TYPE: DNA
<213> ORGANISM: Artificial Sequence
<220> FEATURE:
<223> OTHER INFORMATION: NM_003620 (PPM1D)

<400> SEQUENCE: 878
gcgcctagtg tgtctcccg                                               19

<210> SEQ ID NO 879
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 879
tagccatcca gctgctttc                                               19

<210> SEQ ID NO 880
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 880
```

-continued ttctcattgg aagggactc                                                19

<210> SEQ ID NO 881
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 881
cacgcatctt ggcaaagag                                                19

<210> SEQ ID NO 882
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 882
tagcttggag gacttgttt                                                19

<210> SEQ ID NO 883
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 883
actcaattgt acctgcagc                                                19

<210> SEQ ID NO 884
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 884
ctaagtgctg ctgtttctt                                                19

<210> SEQ ID NO 885
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 885
gcaaagccgg agagatgat                                                19

<210> SEQ ID NO 886
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 886
cctcttcaca gacctcttt                                                19

<210> SEQ ID NO 887
<211> LENGTH: 19
<212> TYPE: DNA
<213> ORGANISM: Artificial Sequence
<220> FEATURE:

```
<223> OTHER INFORMATION: NM_022048 (CSNK1G1)

<400> SEQUENCE: 887
gaagggactc ctctttggg                                                19

<210> SEQ ID NO 888
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 888
gagagctcag attaggtaa                                                19

<210> SEQ ID NO 889
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 889
cacgtagatt ctggtgcat                                                19

<210> SEQ ID NO 890
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 890
atgagtattt acggaccct                                                19

<210> SEQ ID NO 891
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 891
ggtgggaccc aacttcagg                                                19

<210> SEQ ID NO 892
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 892
agagctgaat gttgatgat                                                19

<210> SEQ ID NO 893
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 893
gattctggtg catctgcaa                                                19

<210> SEQ ID NO 894
```

```
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 894
aacttcaggg ttggcaaga                                                   19

<210> SEQ ID NO 895
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 895
tctcgaatgg aatacgtgc                                                   19

<210> SEQ ID NO 896
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 896
ccgaggagag tgggaaatt                                                   19

<210> SEQ ID NO 897
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 897
gggagcccac tccaatgca                                                   19

<210> SEQ ID NO 898
<211> LENGTH: 19
<212> TYPE: DNA
<213> ORGANISM: Artificial Sequence
<220> FEATURE:
<223> OTHER INFORMATION: NM_022048 (CSNK1G1)

<400> SEQUENCE: 898
gtcaagccag agaacttcc                                                   19

<210> SEQ ID NO 899
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 899
ttagcagttt cctggtctc                                                   19

<210> SEQ ID NO 900
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 900
```
atgtgagaag agcatcagg                                              19

<210> SEQ ID NO 901
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 901
agcagtgtgt tccattggc                                              19

<210> SEQ ID NO 902
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 902
ggatcctgtt ctcacattc                                              19

<210> SEQ ID NO 903
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 903
cagcagtgat gaagaagga                                              19

<210> SEQ ID NO 904
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 904
gataactatg cttaaggga                                              19

<210> SEQ ID NO 905
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 905
tggacttcac ctcctcact                                              19

<210> SEQ ID NO 906
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 906
ttgaagtctg gatcctgtt                                              19

<210> SEQ ID NO 907
<211> LENGTH: 19
<212> TYPE: DNA
<213> ORGANISM: Artificial Sequence
<220> FEATURE:

```
<223> OTHER INFORMATION: NM_000082 (CKN1)

<400> SEQUENCE: 907
aggaacttta tagtggtag                                                      19

<210> SEQ ID NO 908
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 908
aagtgatgga cttcacctc                                                      19

<210> SEQ ID NO 909
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 909
tgtttataca gtttactca                                                      19

<210> SEQ ID NO 910
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 910
gaagggagat acatgttat                                                      19

<210> SEQ ID NO 911
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 911
gggtttggag gaccctctt                                                      19

<210> SEQ ID NO 912
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 912
atatgtctcc agtctccac                                                      19

<210> SEQ ID NO 913
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 913
gatggacttc acctcctca                                                      19

<210> SEQ ID NO 914
```

```
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 914
tgaaagtatg ggatacaaa                                                    19

<210> SEQ ID NO 915
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 915
atgtaaagca gtgtgttcc                                                    19

<210> SEQ ID NO 916
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 916
tctacagggt cacagacaa                                                    19

<210> SEQ ID NO 917
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 917
gaggccatca gtattgact                                                    19

<210> SEQ ID NO 918
<211> LENGTH: 19
<212> TYPE: DNA
<213> ORGANISM: Artificial Sequence
<220> FEATURE:
<223> OTHER INFORMATION: NM_000082 (CKN1)

<400> SEQUENCE: 918
actgtttggt agcagttgg                                                    19

<210> SEQ ID NO 919
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 919
aggaggaggc gaaggagac                                                    19

<210> SEQ ID NO 920
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 920
```
ctacgtcacc accacggag                                              19

<210> SEQ ID NO 921
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 921
tcgcctaatt ccaaggaa                                               19

<210> SEQ ID NO 922
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 922
caagtatgta gtaaagcat                                              19

<210> SEQ ID NO 923
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 923
aagctggtca cccttctgc                                              19

<210> SEQ ID NO 924
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 924
cacagaaggt ggcttggat                                              19

<210> SEQ ID NO 925
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 925
tggaatctag ccgatggaa                                              19

<210> SEQ ID NO 926
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 926
ataaacagaa tggaactgg                                              19

<210> SEQ ID NO 927
<211> LENGTH: 19
<212> TYPE: DNA
<213> ORGANISM: Artificial Sequence
<220> FEATURE:

-continued

<223> OTHER INFORMATION: NM_002843 (PTPRJ)

<400> SEQUENCE: 927
cctggagagc tgctcctct                                              19

<210> SEQ ID NO 928
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 928
aactttaagt tggcagaac                                              19

<210> SEQ ID NO 929
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 929
acacagtgga gatctttgc                                              19

<210> SEQ ID NO 930
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 930
cagtacacac ggcccagca                                              19

<210> SEQ ID NO 931
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 931
ttgaacaggg aagaaccaa                                              19

<210> SEQ ID NO 932
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 932
attatgttga ctaaatgtg                                              19

<210> SEQ ID NO 933
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 933
tgactcaaga ctcaagact                                              19

<210> SEQ ID NO 934

```
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 934
aactttcggt ccagaccca                                                 19

<210> SEQ ID NO 935
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 935
ggccagacca cggtgttcc                                                 19

<210> SEQ ID NO 936
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 936
tcactggaac ctggccgga                                                 19

<210> SEQ ID NO 937
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 937
acacaggagg gagctggca                                                 19

<210> SEQ ID NO 938
<211> LENGTH: 19
<212> TYPE: DNA
<213> ORGANISM: Artificial Sequence
<220> FEATURE:
<223> OTHER INFORMATION: NM_002843 (PTPRJ)

<400> SEQUENCE: 938
tgttctcatt tgatcaggg                                                 19

<210> SEQ ID NO 939
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 939
tcatccggga gaagtacat                                                 19

<210> SEQ ID NO 940
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 940
```

-continued acccaactat accaaggaa                                              19

<210> SEQ ID NO 941
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 941
cctgcatgaa ccagaagca                                              19

<210> SEQ ID NO 942
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 942
ctgcgggagg tctttgaga                                              19

<210> SEQ ID NO 943
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 943
gcctctttga tgtgtaccg                                              19

<210> SEQ ID NO 944
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 944
gacaacatga gaaatcgtg                                              19

<210> SEQ ID NO 945
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 945
gccacccagt gaaagcaaa                                              19

<210> SEQ ID NO 946
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 946
caggaacact ttccatcgc                                              19

<210> SEQ ID NO 947
<211> LENGTH: 19
<212> TYPE: DNA
<213> ORGANISM: Artificial Sequence
<220> FEATURE:

<223> OTHER INFORMATION: NM_004037 (AMPD2)

<400> SEQUENCE: 947
tgtgggagag gcagctgcc                                                19

<210> SEQ ID NO 948
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 948
gccgtgaaca gacgctgcg                                                19

<210> SEQ ID NO 949
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 949
aaatatccct ttaagaagc                                                19

<210> SEQ ID NO 950
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 950
gtaaagagcc actggctgg                                                19

<210> SEQ ID NO 951
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 951
cgtcctgcat gaaccagaa                                                19

<210> SEQ ID NO 952
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 952
gctcagcaac aacagcctc                                                19

<210> SEQ ID NO 953
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 953
cacatcatca aggaggtga                                                19

<210> SEQ ID NO 954

```
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 954
ctcattgttg tttgggctc                                                    19

<210> SEQ ID NO 955
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 955
aagctcagct cctgcgata                                                    19

<210> SEQ ID NO 956
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 956
tgcgatatgt gtgagctgg                                                    19

<210> SEQ ID NO 957
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 957
ctgggcccat ccaccacct                                                    19

<210> SEQ ID NO 958
<211> LENGTH: 19
<212> TYPE: DNA
<213> ORGANISM: Artificial Sequence
<220> FEATURE:
<223> OTHER INFORMATION: NM_004037 (AMPD2)

<400> SEQUENCE: 958
gaaggaccag ctagcctgg                                                    19

<210> SEQ ID NO 959
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 959
tatttcattt cttgtcaat                                                    19

<210> SEQ ID NO 960
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 960
```

-continued

```
gacgagggat ggagagagg                                              19

<210> SEQ ID NO 961
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 961
agtagattgt atagcttta                                              19

<210> SEQ ID NO 962
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 962
tatagataac tcatctaaa                                              19

<210> SEQ ID NO 963
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 963
aagaactttg cagtgagct                                              19

<210> SEQ ID NO 964
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 964
gaattagaac aaagccgaa                                              19

<210> SEQ ID NO 965
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 965
tgtgctatca atgagttct                                              19

<210> SEQ ID NO 966
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 966
acacctgacg agggatgga                                              19

<210> SEQ ID NO 967
<211> LENGTH: 19
<212> TYPE: DNA
<213> ORGANISM: Artificial Sequence
<220> FEATURE:
```

<223> OTHER INFORMATION: NM_016218 (POLK)

<400> SEQUENCE: 967
tgcatctaca gtttcatct                                                19

<210> SEQ ID NO 968
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 968
acacacctga cgagggatg                                                19

<210> SEQ ID NO 969
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 969
tggatagcac aaaggagaa                                                19

<210> SEQ ID NO 970
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 970
agggtgcatc agtctggaa                                                19

<210> SEQ ID NO 971
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 971
tatagcttta gtagatact                                                19

<210> SEQ ID NO 972
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 972
tgtttctact gcagaagaa                                                19

<210> SEQ ID NO 973
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 973
gttgtttcta ctgcagaag                                                19

<210> SEQ ID NO 974

-continued

```
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 974
ctgacaaaga taagtttgt                                                    19

<210> SEQ ID NO 975
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 975
gcatcagtct ggaagcctt                                                    19

<210> SEQ ID NO 976
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 976
ctcaggatct acagaaaga                                                    19

<210> SEQ ID NO 977
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 977
aaggagattt ggtgttcgt                                                    19

<210> SEQ ID NO 978
<211> LENGTH: 19
<212> TYPE: DNA
<213> ORGANISM: Artificial Sequence
<220> FEATURE:
<223> OTHER INFORMATION: NM_016218 (POLK)

<400> SEQUENCE: 978
tagtgcacat tgacatgga                                                    19

<210> SEQ ID NO 979
<211> LENGTH: 19
<212> TYPE: DNA
<213> ORGANISM: Artificial Sequence
<220> FEATURE:
<223> OTHER INFORMATION: an example of transcript of off-target
      gene from NM_018461

<400> SEQUENCE: 979
ccaaaaggtc attactcag                                                    19

<210> SEQ ID NO 980
<211> LENGTH: 19
<212> TYPE: DNA
<213> ORGANISM: Artificial Sequence
<220> FEATURE:
<223> OTHER INFORMATION: an example of transcript of off-target
      gene from NM_018130
```

```
<400> SEQUENCE: 980
gatcctgatc attatctag                                              19

<210> SEQ ID NO 981
<211> LENGTH: 19
<212> TYPE: DNA
<213> ORGANISM: Artificial Sequence
<220> FEATURE:
<223> OTHER INFORMATION: an example of transcript of off-target
      gene from NM_005861

<400> SEQUENCE: 981
ctccaggctc attgccgcg                                              19

<210> SEQ ID NO 982
<211> LENGTH: 19
<212> TYPE: DNA
<213> ORGANISM: Artificial Sequence
<220> FEATURE:
<223> OTHER INFORMATION: an example of transcript of off-target
      gene from Contig46927_RC

<400> SEQUENCE: 982
atttttggtg atcaccgag                                              19

<210> SEQ ID NO 983
<211> LENGTH: 19
<212> TYPE: DNA
<213> ORGANISM: Artificial Sequence
<220> FEATURE:
<223> OTHER INFORMATION: an example of transcript of off-target
      gene from Contig52414_RC

<400> SEQUENCE: 983
atccggagtt attacgaag                                              19

<210> SEQ ID NO 984
<211> LENGTH: 19
<212> TYPE: DNA
<213> ORGANISM: Artificial Sequence
<220> FEATURE:
<223> OTHER INFORMATION: an example of transcript of off-target
      gene from NM_001887

<400> SEQUENCE: 984
aaccgtgcct attaccagc                                              19

<210> SEQ ID NO 985
<211> LENGTH: 19
<212> TYPE: DNA
<213> ORGANISM: Artificial Sequence
<220> FEATURE:
<223> OTHER INFORMATION: an example of transcript of off-target
      gene from NM_004034

<400> SEQUENCE: 985
acgagtggag attaccgaa                                              19

<210> SEQ ID NO 986
<211> LENGTH: 19
<212> TYPE: DNA
<213> ORGANISM: Artificial Sequence
<220> FEATURE:
<223> OTHER INFORMATION: an example of transcript of off-target
      gene from NM_001156

<400> SEQUENCE: 986
```

```
acgagtggag attaccgaa                                                    19

<210> SEQ ID NO 987
<211> LENGTH: 19
<212> TYPE: DNA
<213> ORGANISM: Artificial Sequence
<220> FEATURE:
<223> OTHER INFORMATION: an example of transcript of off-target
      gene from NM_002570

<400> SEQUENCE: 987
tgttctaatt tttaccgat                                                    19

<210> SEQ ID NO 988
<211> LENGTH: 19
<212> TYPE: DNA
<213> ORGANISM: Artificial Sequence
<220> FEATURE:
<223> OTHER INFORMATION: an example of transcript of off-target
      gene from Contig54761_RC

<400> SEQUENCE: 988
taaaaatctt tttaccgaa                                                    19

<210> SEQ ID NO 989
<211> LENGTH: 19
<212> TYPE: DNA
<213> ORGANISM: Artificial Sequence
<220> FEATURE:
<223> OTHER INFORMATION: an example of transcript of off-target
      gene from Contig53248_RC

<400> SEQUENCE: 989
gtggcctttt tttaccgat                                                    19

<210> SEQ ID NO 990
<211> LENGTH: 19
<212> TYPE: DNA
<213> ORGANISM: Artificial Sequence
<220> FEATURE:
<223> OTHER INFORMATION: an example of transcript of off-target
      gene from Contig55337_RC

<400> SEQUENCE: 990
tgagaaaaaa gttaccgaa                                                    19
```

METHOD OF DESIGNING SIRNAS FOR GENE SILENCING

This application claims the benefit under 35 U.S.C. §119 (e) of U.S. Provisional Patent Application No. 60/572,314, filed on May 17, 2004, and U.S. Provisional Patent Application No. 60/515,180, filed on Oct. 27, 2003, each of which is incorporated by reference herein in its entirety.

1. FIELD OF THE INVENTION

The present invention relates to methods for identifying siRNA target motifs in a transcript. The invention also relates to methods for identifying off-target genes of an siRNA. The invention further relates to methods for designing siRNAs with higher silencing efficacy and specificity. The invention also relates to a library of siRNAs comprising siRNAs with high silencing efficacy and specificity.

2. BACKGROUND OF THE INVENTION

RNA interference (RNAi) is a potent method to suppress gene expression in mammalian cells, and has generated much excitement in the scientific community (Couzin, 2002, *Science* 298:2296-2297; McManus et al., 2002, *Nat. Rev. Genet.* 3, 737-747; Hannon, G. J., 2002, *Nature* 418, 244-251; Paddison et al., 2002, *Cancer Cell* 2, 17-23). RNA interference is conserved throughout evolution, from *C. elegans* to humans, and is believed to function in protecting cells from invasion by RNA viruses. When a cell is infected by a dsRNA virus, the dsRNA is recognized and targeted for cleavage by an RNaseIII-type enzyme termed Dicer. The Dicer enzyme "dices" the RNA into short duplexes of 21 nt, termed siRNAs or short-interfering RNAs, composed of 19 nt of perfectly paired ribonucleotides with two unpaired nucleotides on the 3' end of each strand. These short duplexes associate with a multiprotein complex termed RISC, and direct this complex to mRNA transcripts with sequence similarity to the siRNA As a result, nucleases present in the RISC complex cleave the mRNA transcript, thereby abolishing expression of the gene product. In the case of viral infection, this mechanism would result in destruction of viral transcripts, thus preventing viral synthesis. Since the siRNAs are double-stranded, either strand has the potential to associate with RISC and direct silencing of transcripts with sequence similarity.

Specific gene silencing promises the potential to harness human genome data to elucidate gene function, identify drug targets, and develop more specific therapeutics. Many of these applications assume a high degree of specificity of siRNAs for their intended targets. Cross-hybridization with transcripts containing partial identity to the siRNA sequence may elicit phenotypes reflecting silencing of unintended transcripts in addition to the target gene. This could confound the identification of the gene implicated in the phenotype. Numerous reports in the literature purport the exquisite specificity of siRNAs, suggesting a requirement for near-perfect identity with the siRNA sequence (Elbashir et al., 2001. *EMBO J.* 20:6877-6888; Tuschl et al., 1999, *Genes Dev.* 13:3191-3197; Hutvagner et al., *Sciencexpress* 297:2056-2060). One recent report suggests that perfect sequence complementarity is required for siRNA-targeted transcript cleavage, while partial complementarity will lead to translational repression without transcript degradation, in the manner of microRNAs (Hutvagner et al., *Sciencexpress* 297:2056-2060).

The biological function of small regulatory RNAs, including siRNAs and miRNAs is not well understood. One prevailing question regards the mechanism by which the distinct silencing pathways of these two classes of regulatory RNA are determined. miRNAs are regulatory RNAs expressed from the genome, and are processed from precursor stem-loop structures to produce single-stranded nucleic acids that bind to sequences in the 3' UTR of the target mRNA (Lee et al., 1993, *Cell* 75:843-854; Reinhart et al., 2000, *Nature* 403:901-906; Lee et al., 2001, *Science* 294:862-864; Lau et al., 2001, *Science* 294:858-862; Hutvagner et al., 2001, *Science* 293:834-838). miRNAs bind to transcript sequences with only partial complementarity (Zeng et al., 2002, *Molec. Cell* 9:1327-1333) and repress translation without affecting steady-state RNA levels (Lee et al., 1993, *Cell* 75:843-854; Wightman et al., 1993, *Cell* 75:855-862). Both miRNAs and siRNAs are processed by Dicer and associate with components of the RNA-induced silencing complex (Hutvagner et al., 2001, *Science* 293:834-838; Grishok et al., 2001, *Cell* 106: 23-34; Ketting et al., 2001, *Genes Dev.* 15:2654-2659; Williams et al., 2002, *Proc. Natl. Acad Sci USA* 99:6889-6894; Hammond et al., 2001, *Science* 293:1146-1150; Mourlatos et al., 2002, *Genes Dev.* 16:720-728). A recent report (Hutvagner et al., 2002, *Sciencexpress* 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

It has also been shown that siRNA and shRNA can be used to silence genes in vivo. The ability to utilize siRNA and shRNA for gene silencing in vivo has the potential to enable selection and development of siRNAs for therapeutic use. A recent report highlights the potential therapeutic application of siRNAs. Fas-mediated apoptosis is implicated in a broad spectrum of liver diseases, where lives could be saved by inhibiting apoptotic death of hepatocytes. Song (Song et al. 2003, *Nat. Medicine* 9, 347-351) injected mice intravenously with siRNA targeted to the Fas receptor. The Fas gene was silenced in mouse hepatocytes at the mRNA and protein levels, prevented apoptosis, and protected the mice from hepatitis-induced liver damage. Thus, silencing Fas expression holds therapeutic promise to prevent liver injury by protecting hepatocytes from cytotoxicity. As another example, injected mice intraperitoneally with siRNA targeting TNF-a. Lipopolysaccharide-induced TNF-a gene expression was inhibited, and these mice were protected from sepsis. Collectively, these results suggest that siRNAs can function in vivo, and may hold potential as therapeutic drugs (Sorensen et al., 2003, *J. Mol. Biol.* 327, 761-766).

Martinez et al. reported that RNA interference can be used to selectively target oncogenic mutations (Martinez et al., 2002, *Proc. Natl. Acad Sci. USA* 99:14849-14854). In this report, an siRNA that targets the region of the R248W mutant of p53 containing the point mutation was shown to silence the expression of the mutant p53 but not the wild-type p53.

Wilda et al. reported that an siRNA targeting the M-BCR/ABL fusion mRNA can be used to deplete the M-BCR/ABL mRNA and the M-BRC/ABL oncoprotein in leukemic cells (Wilda et al., 2002, *Oncogene* 21:5716-5724). However, the report also showed that applying the siRNA in combination with Imatinib, a small-molecule ABL kinase tyrosine inhibitor, to leukemic cells did not further increase in the induction of apoptosis.

U.S. Pat. No. 6,506,559 discloses a RNA interference process for inhibiting expression of a target gene in a cell. The process comprises introducing partially or fully doubled-stranded RNA having a sequence in the duplex region that is identical to a sequence in the target gene into the cell or into the extracellular environment. RNA sequences with insertions, deletions, and single point mutations relative to the target sequence are also found as effective for expression inhibition.

U.S. Patent Application Publication No. US 2002/0086356 discloses RNA interference in a *Drosophila* in vitro system using RNA segments 21-23 nucleotides (nt) in length. The patent application publication teaches that when these 21-23 nt fragments are purified and added back to *Drosophila* extracts, they mediate sequence-specific RNA interference in the absence of long dsRNA. The patent application publication also teaches that chemically synthesized oligonucleotides of the same or similar nature can also be used to target specific mRNAs for degradation in mammalian cells.

PCT publication WO 02/44321 discloses that double-stranded RNA (dsRNA) 19-23 nt in length induces sequence-specific post-transcriptional gene silencing in a *Drosophila* in vitro system. The PCT publication teaches that short interfering RNAs (siRNAs) generated by an RNase III-like processing reaction from long dsRNA or chemically synthesized siRNA duplexes with overhanging 3' ends mediate efficient target RNA cleavage in the lysate, and the cleavage site is located near the center of the region spanned by the guiding siRNA. The PCT publication also provides evidence that the direction of dsRNA processing determines whether sense or antisense-identical target RNA can be cleaved by the produced siRNP complex.

U.S. Patent Application Publication No. US 2002/0162126 discloses a method for attenuating expression of a target gene in cultured cells by introducing double stranded RNA (dsRNA) that comprises a nucleotide sequence that hybridizes under stringent conditions to a nucleotide sequence of the target gene into the cells in an amount sufficient to attenuate expression of the target gene.

PCT publication WO 03/006477 discloses engineered RNA precursors that when expressed in a cell are processed by the cell to produce targeted small interfering RNAs (siRNAs) that selectively silence targeted genes (by cleaving specific mRNAs) using the cell's own RNA interference (RNAi) pathway. The PCT publication teaches that by introducing nucleic acid molecules that encode these engineered RNA precursors into cells in vivo with appropriate regulatory sequences, expression of the engineered RNA precursors can be selectively controlled both temporally and spatially, i.e., at particular times and/or in particular tissues, organs, or cells.

Elbashir et al. disclosed a systematic analysis of the length, secondary structure, sugar backbone and sequence specificity of siRNA for RNAi (Elbashir et al., 2001. *EMBO J.* 20:6877-6888). Based on the analysis, Elbashir proposed rules for designing siRNAs.

Aza-Blanc et al. reported correlations between silencing efficacy and GC content of the 5' and 3' regions of the 19 bp target sequence (Aza-Blanc et al., 2003, Mol. Cell 12:627-637). It was found that siRNAs targeting sequences with a GC rich 5' and GC poor 3' perform the best.

Discussion or citation of a reference herein shall not be construed as an admission that such reference is prior art to the present invention.

3. SUMMARY OF THE INVENTION

In one aspect, the invention provides a method for selecting from a plurality of different siRNAs one or more siRNAs for silencing a target gene in an organism, each of the plurality of different siRNAs targeting a different target sequence in a transcript of the target gene, the method comprising (a) ranking the plurality of different siRNAs according to positional base compositions of a corresponding targeted sequence motifs in the transcript, wherein each targeted sequence motif comprises at least a portion of the target sequence of the corresponding siRNA and/or a second sequence in a sequence region flanking the target sequence; and (b) selecting one or more siRNAs from the ranked siRNAs. In a preferred embodiment, each sequence motif comprises the target sequence of the targeting siRNA. In another embodiment, the ranking step is carried out by (a1) determining a score for each different siRNA, wherein the score is calculated using a position-specific score matrix; and (a2) ranking the plurality of different siRNAs according to the score.

In one embodiment, each sequence motif is a nucleotide sequence of L nucleotides, L being an integer, and the position-specific score matrix is $\{\log(e_{ij}/p_{ij})\}$, where $e_{ij}$ is the weight of nucleotide i at position j, $p_{ij}$ is the weight of nucleotide i at position j in a random sequence, and i=G, C, A, U(T), j=1, ..., L. In another embodiment, each sequence motif is a nucleotide sequence of L nucleotides, L being an integer, and the position-specific score matrix is $\{\log(e_{ij}/p_{ij})\}$, where $e_{ij}$ is the weight of nucleotide i at position j, $p_{ij}$ is the weight of nucleotide i at position j in a random sequence, and i=G or C, A, U(T), j=1, ..., L.

In one embodiment, the score for each siRNA is calculated according to equation $$Score = \sum_{t=1}^{L} \ln(e_t / p_t)$$

wherein $e_t$ and $p_t$ are respectively weights of the nucleotide at position t in the sequence motif as determined according to the position-specific score matrix and in a random sequence.

In another embodiment, each sequence motif comprises the target sequence of the targeting siRNA and at least one flanking sequence. Preferably, each sequence motif comprises the target sequence of the targeting siRNA and a 5' flanking sequence and a 3' flanking sequence. In one embodiment, the 5' flanking sequence and the 3' flanking sequence are each a sequence of D nucleotides, D being an integer. In a specific embodiment, each target sequence is a sequence of 19 nucleotides, and each 5' flanking sequence and 3' flanking sequence are a sequence of 10 nucleotides. In another specific embodiment, each target sequence is a sequence of 19 nucleotides, and each 5' flanking sequence and 3' flanking sequence are a sequence of 50 nucleotides.

Preferably, the one or more siRNAs consist of at least 3 siRNAs. In another embodiment, the method further comprises a step of de-overlapping, comprising selecting a plurality of siRNAs among the at least 3 siRNAs such that siRNAs in the plurality are sufficiently different in a sequence diversity measure. In one embodiment, the diversity measure is a quantifiable measure, and the selecting in the de-overlapping step comprises selecting siRNAs having a difference in the sequence diversity measure between different selected siRNAs above a given threshold. In one embodiment, the sequence diversity measure is the overall GC content of the siRNAs. In one embodiment, the given threshold is 5%. In another embodiment, the sequence diversity measure is the distance between siRNAs along the length of the transcript sequence. In one embodiment, the threshold is 100 nucleotides. In still another embodiment, the sequence diversity measure is the identity of the leading dimer of the siRNAs, wherein each of the 16 possible leading dimers is assigned a score of 1-16, respectively. In one embodiment, the threshold is 0.5.

In another embodiment, the method further comprises a step of selecting one or more siRNAs based on silencing specificity, the step of selecting based on silencing specificity comprising, (i) for each of the plurality of siRNAs, predicting off-target genes of the siRNA from among a plurality of genes, wherein the off-target genes are genes other than the target gene and are directly silenced by the siRNA; (ii) ranking the plurality of siRNAs according to their respective numbers of off-target genes; and (iii) selecting one or more siRNAs for which the number of off-target genes is below a given threshold.

In one embodiment, the predicting comprises (i1) evaluating the sequence of each of the plurality of genes based on a predetermined siRNA sequence match pattern; and (i2) predicting the gene as an off-target gene if the gene comprise a sequence that matches the siRNA based on the sequence match patter In one embodiment, the step of evaluating comprises identifying an alignment of the siRNA to a sequence in a gene by a low stringency FastA alignment.

In one embodiment, each siRNA has L nucleotides in its duplex region, and the match pattern is represented by a position match position-specific score matrix (pmPSSM), the position match position-specific score matrix consisting of weights of different positions in an siRNA to match transcript sequence positions in an off-target transcript $\{P_j\}$, where $j=1, \ldots, L$, $P_j$ is the weight of a match at position $j$.

In another embodiment, the step (i1) comprises calculating a position match score pmScore according to equation $$pmScore = \sum_{i=1}^{L} \ln(E_i/0.25)$$

where $E_i = P_i$ if position i is a match and $E_i = (1-P_i)/3$ if position i is a mismatch; and the step (i2) comprises predicting the gene as an off-target gene if the position match score is greater than a given threshold.

In a preferred embodiment, L is 19, and the pmPSSM is given by Table I.

Preferably, the plurality of genes comprises all known unique genes of the organism other than the target gene.

In one embodiment, the position-specific score matrix (PSSM) is determined by a method comprising (aa) identifying a plurality of N siRNAs consisting of siRNAs having 19-nucleotide duplex region and having a silencing efficacy above a chosen threshold; (bb) identifying for each siRNA a functional sequence motif, the functional sequence motif comprising a 19-nucleotide target sequence of the siRNA and a 10-nucleotide 5' flanking sequence and a 10-nucleotide 3' flanking sequence; (cc) calculating a frequency matrix $\{f_{ij}\}$, where $i=G, C, A, U(T)$; $j=1, 2 \ldots, L$, and where $f_{ij}$ is the frequency of the ith nucleotide at the jth position, based on the siRNAs functional sequence motifs according to equation $$f_{ij} = \sum_{k=1}^{N} \delta_{ik}(j), \text{ where } \delta_{ik}(j) = \begin{cases} 1, \text{ if } k = i \\ 0, \text{ if } k \neq i \end{cases},$$

and (d) determining the PSSM by calculating $e_{ij}$ according to equation $$e_{ij} = \frac{f_{ij}}{N}.$$

In another embodiment, the position-specific score matrix (PSSM) is obtained by a method comprising (aa) initializing the PSSM with random weights; (bb) selecting randomly a weight $w_{ij}$ obtained in (aa); (cc) changing the value of the selected weight to generate a test psPSSM comprising the selected weight having the changed value; (dd) calculating a score for each of a plurality of siRNAs functional sequence motifs using the test PSSM according to equation $$Score = \sum_{k=1}^{L} \ln(w_k/p_k)$$

wherein the $w_k$ and $p_k$ are respectively weights of a nucleotide at position k in the functional sequence motif and in a random sequence; (ee) calculating correlation of the score and a metric of a characteristic of an siRNA among the plurality of siRNAs functional sequence motifs; (ff) repeating steps (cc)-(ee) for a plurality of different values of the selected weight in a given range and retain the value that corresponds to the best correlation for the selected weight; and (gg) repeating steps (bb)-(ff) for a chosen number of times; thereby determining the PSSM.

In one embodiment, the method further comprises selecting the plurality of siRNA functional sequence motifs by a method comprising (i) identifying a plurality of siRNAs consisting of siRNAs having different values in the metric; (ii) identifying a plurality of siRNA functional sequence motifs each corresponding to an siRNA in the plurality of siRNAs. In a preferred embodiment, the characteristic is silencing efficacy.

In one embodiment, the plurality of N siRNAs target a plurality of different genes having different transcript abundances in a cell.

In one embodiment, step (b) is carried out by selecting one or more siRNAs having the highest scores. In another embodiment, step (b) is carried out by selecting one or more siRNAs having a score closest to a predetermined value, wherein the predetermined value is the score value corresponding to the maximum median silencing efficacy of a plurality Of siRNA sequence motifs. In a preferred embodiment, the plurality of siRNA sequence motifs are sequence motifs in transcript having abundance level of less than about 3-5 copies per cell.

In another embodiment, step (b) is carried out by selecting one or more siRNAs having a score within a predetermined range, wherein the predetermined range is a score range corresponding to a plurality of siRNAs sequence motifs having a given level of silencing efficacy. In one embodiment, the silencing efficacy is above 50%, 75%, or 90% at an siRNA dose of about 100 nM.

In a preferred embodiment, the plurality of siRNA sequence motifs are sequence motifs in transcript having abundance level of less than about 3-5 copies per cell.

In another preferred embodiment, the plurality of N siRNAs comprises at least 10, 50, 100, 200, or 500 different siRNAs.

In another embodiment, the position-specific score matrix (PSSM) comprises $w_k$, $k=1, \ldots, L$, $w_k$ being a difference in probability of finding nucleotide G or C at sequence position k between a first type of siRNA and a second type of siRNA, and the score for each strand is calculated according to equation $$Score = \sum_{k=1}^{L} w_k.$$

In one embodiment, the first type of siRNA consists of one or more siRNAs having silencing efficacy no less than a first threshold and the second type of siRNA consists of one or more siRNAs having silencing efficacy less than a second threshold.

In one embodiment, the difference in probability is described by a sum of Gaussian curves, each of the Gaussian curves representing the difference in probability of finding a G or C at a different sequence position.

In one embodiment, the first and second threshold are both 75% at an siRNA dose of 100 nM.

In another aspect, the invention provides a method for selecting from a plurality of different siRNAs one or more siRNAs for silencing a target gene in an organism, each of the plurality of different siRNAs targeting a different target sequence in a transcript of the target gene, the method comprising (a) ranking the plurality of different siRNAs according to positional base composition of reverse complement sequences of sense strands of the siRNAs; and (b) selecting one or more siRNAs from the ranked siRNAs.

In one embodiment, the ranking step is carried out by (a1) determining a score for each different siRNA, wherein the score is calculated using a position-specific score matrix; and (a2) ranking the plurality of different siRNAs according to the score.

In one embodiment, the siRNA has a nucleotide sequence of L nucleotides in its duplex region, L being an integer, wherein the position-specific score matrix comprises $w_k$, k=1, . . . , L, $w_k$ being a difference in probability of finding nucleotide G or C at sequence position k between reverse complement of sense strand of a first type of siRNA and reverse complement of sense strand of a second type of siRNA, and the score for each reverse complement is calculated according to equation $$Score = \sum_{k=1}^{L} w_k.$$

In one embodiment, the first type of siRNA consists of one or more siRNAs having silencing efficacy no less than a first threshold and the second type of siRNA consists of one or more siRNAs having silencing efficacy less than a second threshold.

In another embodiment, the difference in probability is described by a sum of Gaussian curves, each of the Gaussian curves representing the difference in probability of finding a G or C at a different sequence position.

In one embodiment, the first and second threshold are both 75% at an siRNA dose of 100 nM.

In still another aspect, the invention provides a method for selecting from a plurality of different siRNAs one or more siRNAs for silencing a target gene in an organism, each of the plurality of different siRNAs targeting a different target sequence in a transcript of the target gene, the method comprising, (i) for each of the plurality of different siRNAs, predicting off-target genes of the siRNA from among a plurality of genes, wherein the off-target genes are genes other than the target gene and are directly silenced by the siRNA; (ii) ranking the plurality of different siRNAs according to the number of off-target genes; and (iii) selecting one or more siRNAs for which the number of off-target genes is below a given threshold.

In one embodiment, the predicting comprises (i1) evaluating the sequence of each of the plurality of genes based on a predetermined siRNA sequence match pattern; and (i2) predicting a gene as an off-target gene if the gene comprise a sequence that matches the siRNA based on the sequence match pattern.

In one embodiment, each siRNA has L nucleotides in its duplex region, and the sequence match pattern is represented by a position match position-specific score matrix (pmPSSM), the position match position-specific score matrix consisting of weights of different positions in an siRNA to match transcript sequence positions in an off-target transcript $\{P_j\}$, where j=1, . . . , L, $P_j$ is the weight of a match at position j.

In another embodiment, the step (i1) comprises calculating a position match score pmScore according to equation $$pmScore = \sum_{i=1}^{L} \ln(E_i / 0.25)$$

where $E_i = P_i$ if position i is a match and $E_i = (1-P_i)/3$ if position i is a mismatch; and the step (i2) comprises predicting the gene as an off-target gene if the position match score is greater than a given threshold.

In a preferred embodiment, L is 19, and the pmPSSM is given by Table I.

In one embodiment, the plurality of genes comprises all known unique genes of the organism other than the target gene.

In still another aspect, the invention provides a library of siRNAs, comprising a plurality of siRNAs for each of a plurality of different genes of an organism, wherein each siRNA achieves at least 75%, at least 80%, or at least 90% silencing of its target gene. In one embodiment, the plurality of siNRAs consists of at least 3, at least 5, or at least 10 siRNAs. In another embodiment, the plurality of different genes consists of at least 10, at least 100, at least 500, at least 1,000, at least 10,000, or at least 30,000 different genes.

In still another aspect, the invention provides a method for determining a base composition position-specific score matrix (bsPSSM) $\{\log(e_{ij}/p_{ij})\}$ for representing base composition patterns of siRNA functional sequence motifs of L nucleotides in transcripts, wherein i=G, C, A, U(T) and j=1, 2, . . . , L, and each siRNA functional sequence motif comprises at least a portion of the target sequence of the corresponding targeting siRNA and/or a sequence in a sequence region flanking the target sequence, the method comprising (a) identifying a plurality of N different siRNAs consisting of siRNAs having a silencing efficacy above a chosen threshold; (b) identifying a plurality of N corresponding siRNA functional sequence motifs, one for each different siRNA; (c) calculating a frequency matrix $\{f_{ij}\}$, where i=G, C, A, U(T); j=1, 2, . . . , L, and where $f_{ij}$ is the frequency of the ith nucleotide at the jth position, based on the plurality of N siRNAs functional sequence motifs according to equation $$f_{ij} = \sum_{k=1}^{N} \delta_{ik}(j),$$

$$\text{where } \delta_{ik}(j) = \begin{cases} 1, & \text{if } k = i \\ 0, & \text{if } k \neq i \end{cases},$$

and (d) determining the psPSSM by calculating $e_{ij}$ according to equation $$e_{ij} = \frac{f_{ij}}{N}.$$

In one embodiment, each siRNA functional motif comprises the target sequence of the corresponding targeting siRNA and one or both flanking sequences of the target sequence.

In one embodiment, each siRNA has M nucleotides in its duplex region, and each siRNA functional sequence motif consists of an siRNA target sequence of M nucleotides, a 5' flanking sequence of $D_1$ nucleotides and a 3' flanking sequence of $D_2$ nucleotides.

In a specific embodiment, each-siRNA has 19 nucleotides in its duplex region, and each siRNA functional sequence motif consists of an siRNA target sequence of 19 nucleotides, a 5' flanking sequence of 10 nucleotides and a 3' flanking sequence of 10 nucleotides. In another specific embodiment, each siRNA has 19 nucleotides in its duplex region, and each siRNA functional sequence motif consists of an siRNA target sequence of 19 nucleotides, a 5' flanking sequence of 50 nucleotides and a 3' flanking sequence of 50 nucleotides.

In one embodiment, the plurality of N siRNAs each targets a gene whose transcript abundance is within a given range. In one embodiment, the range is at least about 5, 10, or 100 transcripts per cell. In another embodiment, the range is less than about 3-5 transcripts per cell.

In another embodiment, the silencing threshold is 50%, 75%, or 90% at an siRNA dose of about 100 nM. In still another embodiment, the plurality of N siRNAs comprises 10, 50, 100, 200, or 500 different siRNAs.

In still another aspect, the invention provides a method for determining a base composition position-specific score matrix (bsPSSM) $\{w_{ij}\}$ for representing a base composition pattern representing a plurality of different siRNA functional sequence motifs of L nucleotides, wherein i=G, C, A, U(T) and j=1, 2, . . . , L, and each siRNA functional sequence motif comprises at least a portion of the target sequence of the corresponding targeting siRNA and/or a sequence in a sequence region flanking the siRNA target sequence, the method comprising (a) initializing the bsPSSM with random weights;.(b) selecting randomly a weight $w_{ij}$ obtained in (a); (c) changing the value of the selected weight to generate a test psPSSM comprising the selected weight having the changed value; (d) calculating a score for each of the plurality of siRNAs functional sequence motifs using the test psPSSM according to equation $$\text{Score} = \sum_{k=1}^{L} \ln(w_k / p_k)$$

wherein the $w_k$ and $p_k$ are respectively weights of a nucleotide at position k in the functional sequence motif and in a random sequence; (e) calculating correlation of the score and a metric characterizing an siRNA among the plurality of siRNAs functional sequence motifs; (f) repeating steps (c)-(e) for a plurality of different values of the selected weight in a given range and retain the value that corresponds to the best correlation for the selected weight; and (g) repeating steps (b)-(f) for a chosen number of times; thereby determining the psPSSM.

The invention also provides a method for determining a base composition position-specific score matrix (bsPSSM) $\{w_{ij}\}$ for representing a base composition pattern representing a plurality of different siRNA functional sequence motifs of L nucleotides, wherein i=G/C, A, U(T) and j=1, 2, . . . , L, and each siRNA functional sequence motif comprises a least a portion of the target sequence of the corresponding siRNA and/or a sequence in a sequence region flanking the siRNA target sequence, the method comprising (a) initializing the bsPSSM with random weights; (b) randomly selecting a weight $w_{ij}$ obtained in (a); (c) changing the value of the selected weight to generate a test psPSSM comprising the selected weight having the changed value; (d) calculating a score for each of the plurality of siRNA functional sequence motifs using the test psPSSM according to equation $$\text{Score} = \sum_{j=1}^{L} \ln(w_k / p_k)$$

wherein the $w_k$ and $p_k$ are respectively weights of a nucleotide at position k in the functional sequence motif and in a random sequence; (e) calculating a correlation of the score and a metric of a characteristic of an siRNA among the plurality of siRNAs functional sequence motifs; (f) repeating steps (c)-(e) for a plurality of different values of the selected weight in a given range and retain the value that corresponds to the best correlation for the selected weight; and (g) repeating steps (b)-(f) for a chosen number of times; thereby determining the psPSSM.

In one embodiment, each siRNA functional motif comprises the target sequence of the corresponding targeting siRNA and one or both flanking sequences of the target sequence.

In another embodiment, the method further comprises selecting the plurality of siRNA functional sequence motifs by a method comprising (i) identifying a plurality of siRNAs consisting of siRNAs having different values in the metric; (ii) identifying a plurality of siRNA functional sequence motifs each corresponding to an siRNA in the plurality of siRNAs.

In one embodiment, each siRNA has M nucleotides in its duplex region, and each siRNA functional sequence motif consists of an siRNA target sequence of M nucleotides, a 5' flanking sequence of $D_1$ nucleotides and a 3' flanking sequence of $D_2$ nucleotides.

In a specific embodiment, each siRNA has 19 nucleotides in its duplex region, and each siRNA functional sequence motif consists of an siRNA target sequence of 19 nucleotides, a 5' flanking sequence of 10 nucleotides and a 3' flanking sequence of 10 nucleotides. In another specific embodiment, each siRNA has 19 nucleotides in its duplex region, and each siRNA functional sequence motif consists of an siRNA target sequence of 19 nucleotides, a 5' flanking sequence of 50 nucleotides and a 3' flanking sequence of 50 nucleotides.

In one embodiment, the metric is silencing efficacy.

In one embodiment, the plurality of N siRNAs each targets a gene whose transcript abundance is within a given range. In one embodiment, the range is at least about 5, 10, or 100 transcripts per cell. In another embodiment, the range is less than about 3-5 transcripts per cell. In another embodiment, the threshold is 50%, 75%, or 90% at an siRNA dose of about 100 nM.

In another embodiment, the method further comprises evaluating the psPSSM using an ROC (receiver operating characteristic) curve of the sensitivity of the psPSSM vs. the non-specificity of the psPSSM curve, the sensitivity of the PSSM being the proportion of true positives detected using the psPSSM as a fraction of total true positives, and the non-specificity of the PSSM being the proportion of false positives detected using the psPSSM as a fraction of total false positives.

In one embodiment, the plurality of siRNA functional sequence motifs consists of at least 50, at least 100, or at least 200 different siRNAs functional sequence motifs.

In still another embodiment, the method further comprises testing the psPSSM using another plurality of siRNA functional sequence motifs.

The invention also provides a method for determining a position match position-specific score matrix (pmPSSM) $\{E_i\}$ for representing position match pattern of an siRNA of L nucleotides with its target sequence in a transcript, wherein $E_i$ is a score of a match at position i, i=1, 2, ..., L, the method comprising (a) identifying a plurality of N siRNA off-target sequences, wherein each off-target sequence is a sequence on which the siRNA exhibits silencing activity; (b) calculating a position match weight matrix $\{P_i\}$, where i=1, 2, ..., L, based on the plurality of N siRNAs off-target sequences according to equation $$P_i = \frac{1}{N}\sum_{k=1}^{N} \delta_k(j),$$

where $\delta_k(j)$ is 1 if k is a match, and is 0 if k is a mismatch; and (c) determining the psPSSM by calculating $E_i$ such that $E_i = P_i$ if position i is a match and $E_i = (1-P_i)/3$ if position i is a mismatch.

In a preferred embodiment, L=19. In another preferred embodiment, the position match weight matrix is given by Table I.

The invention also provides a method for evaluating the relative activity of the two strands of an siRNA in off-target gene silencing, comprising comparing position specific base composition of the sense strand of the siRNA and position specific base composition of the antisense strand of the siRNA or reverse complement strand of the sense strand of the siRNA, wherein the antisense strand is the guiding strand for targeting the intended target sequence.

In one embodiment, the comparing is carried out by a method comprising (a) determining a score for the sense strand of the siRNA, wherein the score is calculated using a position-specific score matrix; (b) determining a score for the antisense strand of the siRNA or the reverse complement strand of the sense strand of the siRNA using the position-specific score matrix; and (c) comparing the score for the sense strand and the score for the antisense strand or the reverse complement strand of the sense strand, thereby evaluating strand preference of the siRNA.

In one embodiment, the siRNA has a nucleotide sequence of L nucleotides in its duplex region, L being an integer, wherein the position-specific score matrix is $\{w_{ij}\}$, where $w_{ij}$ is the weight of nucleotide i at position j, i=G, C, A, U(T), j=1, ..., L.

In another embodiment, the siRNA has a nucleotide sequence of L nucleotides in its duplex region, L being an integer, and the position-specific score matrix is $\{W_{ij}\}$, where $w_{ij}$ is the weight of nucleotide i at position j, i=G or C, A, U(T), j=1, ..., L.

In another embodiment, the position-specific score matrix is obtained by a method comprising (a) initializing the position-specific score matrix with random weights; (b) selecting randomly a weight $w_{ij}$ obtained in (a); (c) changing the value of the selected weight to generate a test position-specific score matrix comprising the selected weight having the changed value; (d) calculating a score for each of a plurality of siRNAs using the test position-specific score matrix according to equation $$\text{Score} = \sum_{j=1}^{L} \ln(w_j/p_j)$$

wherein the $w_j$ and $p_j$ are respectively weights of a nucleotide at position j in the siRNA and in a random sequence; (e) calculating correlation of the score with a metric of a characteristic of an siRNA among the plurality of siRNAs; (f) repeating steps (c)-(e) for a plurality of different values of the selected weight in a given range and retain the value that corresponds to the best correlation for the selected weight; and (g) repeating steps (b)-(f) for a chosen number of times; thereby determining the position-specific score matrix.

In one embodiment, the metric is siRNA silencing efficiency.

In one embodiment, the siRNA has 19 nucleotides in its duplex region.

In another embodiment, the siRNA has a nucleotide sequence of L nucleotides in its duplex region, L being an integer, wherein the position-specific score matrix comprises $w_k$, k=1, ..., L, $w_k$ being a difference in probability of finding nucleotide G or C at sequence position k between a first type of siRNA and a second type of siRNA, and the score for each strand is calculated according to equation $$\text{Score} = \sum_{k=1}^{L} w_k.$$

In one embodiment, the first type of siRNA consists of one or more siRNAs having silencing efficacy no less than a first threshold and the second type of siRNA consists of one or more siRNAs having silencing efficacy less than a second threshold, and the siRNA is determined as having antisense preference if the score determined in step (a) is greater than the score determined in step (b), or as having sense preference if the score determined in step (b) is greater than the score determined in step (a).

In another embodiment, the difference in probability is described by a sum of Gaussian curves, each of the Gaussian curves representing the difference in probability of finding a G or C at a different sequence position.

In one embodiment, the first and second threshold are both 75% at an siRNA dose of about 100 nM.

In still another aspect, the invention provides a computer system comprising a processor, and a memory coupled to the processor and encoding one or more programs, wherein the one or more programs cause the processor to carry out any one of the method of the invention.

In still another aspect, the invention provides a computer program product for use in conjunction with a computer having a processor and a memory connected to the processor, the computer program product comprising a computer readable storage medium having a computer program mechanism encoded thereon, wherein the computer program mechanism may be loaded into the memory of the computer and cause the computer to carry out any one of the method of the invention.

4. BRIEF DESCRIPTION OF FIGURES

FIGS. 1A-C show that base composition in and around an siRNA target sequence affects the silencing efficacy of the siRNA. A total of 377 siRNAs were tested by Taqman analysis for their ability to silence their target sequences 24 hr following transfection into HeLa cells. Median target silencing was ~75%. This dataset was divided into two subsets, one having less than median and one having equal to or greater than median silencing ability (referred to as "bad" and "good" siRNAs, respectively). Shown here are the mean difference within a window of 5 (i.e., averaged over all 5 bases) in GC content (FIG. 1A), A content (FIG. 1B), and U content (FIG. 1C) between good and bad siRNAs at different relative positions on a target sequence.

FIGS. 2A-C (A) GC content of good and bad siRNAs; (B) A content of good and bad siRNAs; (C) U content of good and bad siRNAs. The figures show average compositions of each base. For example, 0.5 on the y-axis corresponds to an average base content of 50%.

FIG. 3 shows the performance of an actual siRNA base composition model used in the siRNA design method of the invention. siRNA efficacy data were subdivided into two pairs of training and test sets. Different PSSMs were optimized on each of the training sets and verified on the test sets. The performance of each PSSM was evaluated by its ability to distinguish good siRNAs (true positives) and bad siRNAs (false positives) as an increasing number of siRNAs were selected from a list ranked by PSSM score. Shown are Receiver Operating Characteristics (ROC) curves demonstrating the performance of two different PSSMs on their respective training and test sets (heavy black and dotted gray lines, respectively). The expected performance of the PSSMs on randomized data is shown for comparison (i.e., no improvement in selection ability, 45° line).

FIG. 4 demonstrates the predictive ability of PSSMs on an independent experimental data set. New siRNAs were designed for five genes by the standard method as described in Elbashir et al., 2001, Nature 411:494-8, with the addition of the specificity prediction method disclosed in this application, and by the PSSM based efficacy and specificity prediction method of the invention. The top free ranked siRNAs per gene were selected for each method and purchased from Dharmacon. All six siRNAs for each of the five genes were then tested for their ability to silence their target sequences. Shown is a histogram of the number of siRNAs that silence their respective target genes by a specified amount. Solid curve, silencing by siRNAs designed by the present method; dashed curve, silencing by siRNAs designed by the standard method; dotted gray curve, silencing by the data set of 377 siRNAs.

FIGS. 5A-C show mean weights of GC, A or U from the two ensembles of base composition PSSM trained and tested with siRNAs in set 1 and set 2, respectively. FIG. 5A mean weights for GC, FIG. 5B mean weights for A, FIG. 5C mean weights for U. siRNAs in set 1 and set 2 are shown in Table II.

FIG. 6 shows an example of alignments of transcripts of off-target genes to the core 19mer of an siRNA oligo sequence. Off-target genes were selected from the Human 25 k v2.2.1 microarray by selecting for kinetic patterns of transcript abundance consistent with direct effects of siRNA oligos. The left hand column lists transcript sequence identifiers. Alignments were generated with FASTA and edited by hand. The black boxes and grey area demonstrate the higher level of sequence similarity in the 3' half of the alignment.

FIG. 7 shows a position match position-specific scoring matrix for predicting off-target effects. The chart shows the weight associated with each position in a matrix representing the alignment between an siRNA oligo and off-target transcripts. The weight represents the probability that a match will be observed at each position i along an alignment between an siRNA oligo and an observed off-target transcript.

Figure 10:
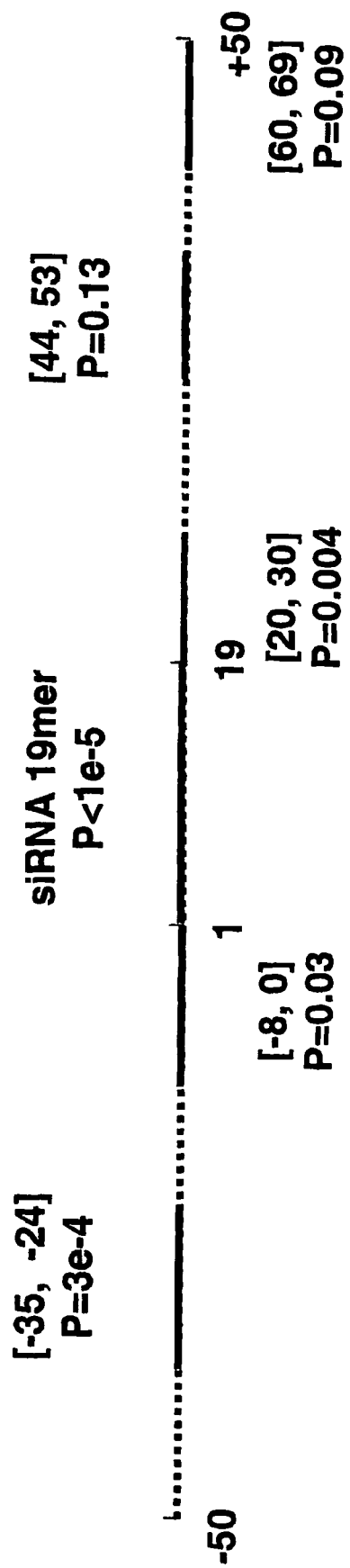

FIG. 10 illustrates sequence regions that can be used for distinguishing good and bad siRNAs. PSSMs were trained on chunks of sequence 10+ bases in length, from 50 bases upstream to 50 bases downstream of the siRNA 19mer, and tested on independent test sets. The performance of models trained on chunks of interest was compared with models trained on random sequences. Position 1 corresponds to the first 5' base in the duplex region of a 21 nt siRNA.

Figure 11A:
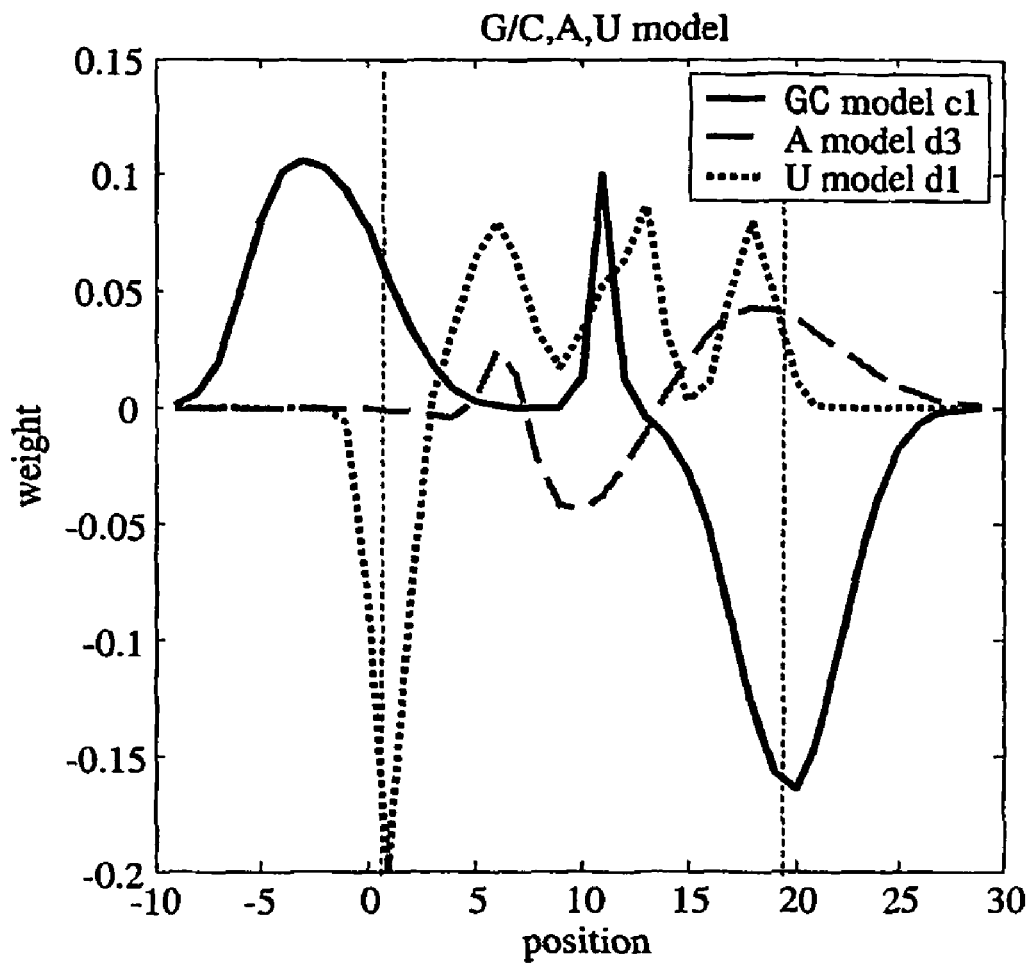
Figure 11B:
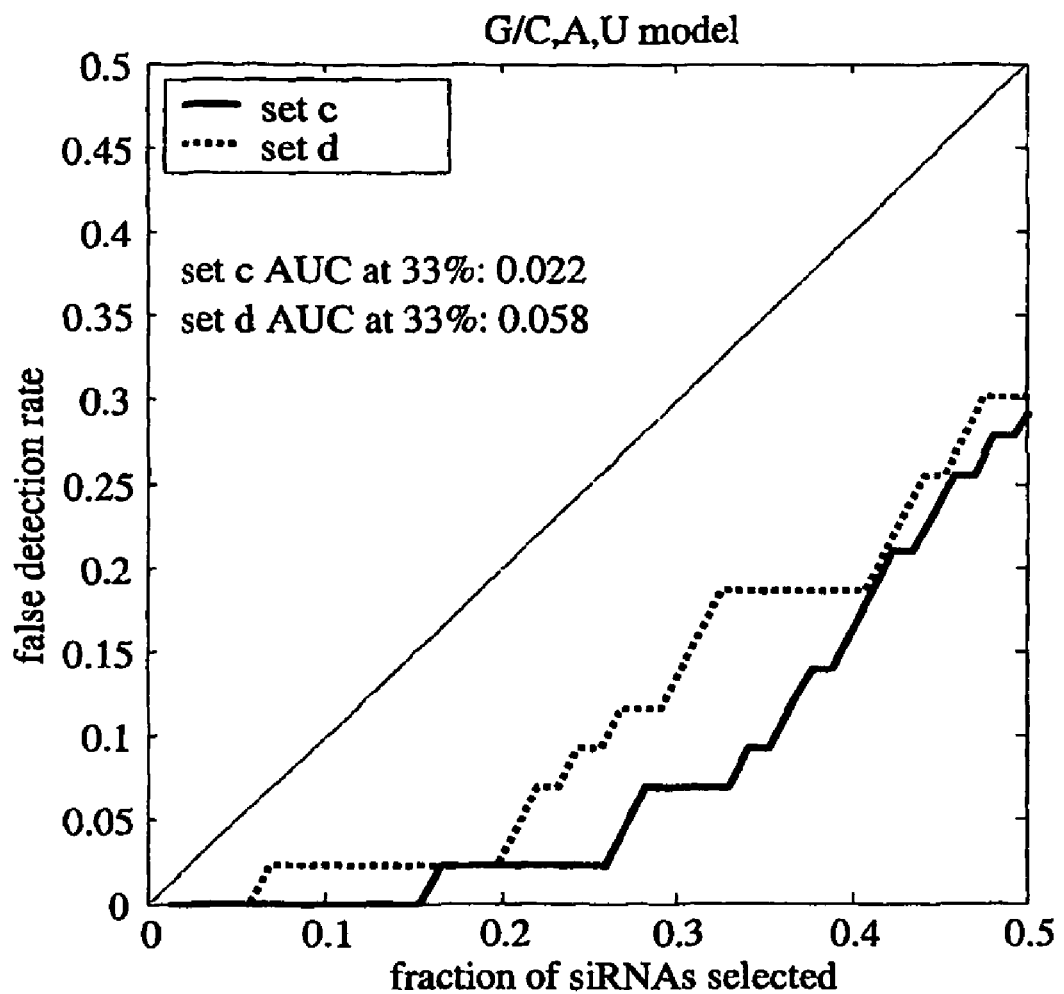

FIGS. 11A-B shows curve models for PSSM. 11A: an exemplary set of curve models for PSSM. 11B: the performance of the models on training and test sets.

Figure 12:
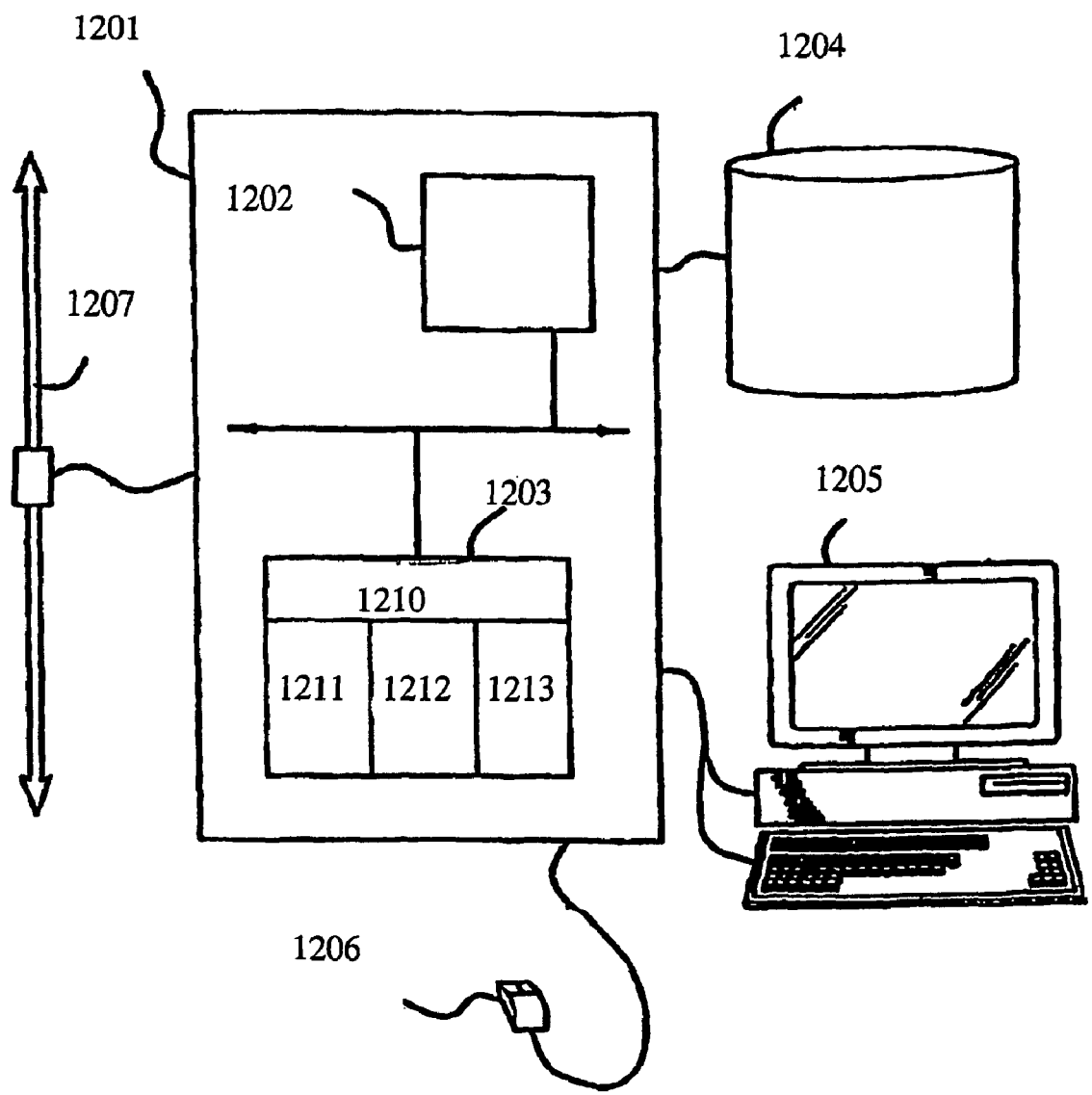

FIG. 12 illustrates an exemplary embodiment of a computer system useful for implementing the methods of the present invention.

Figure 13:
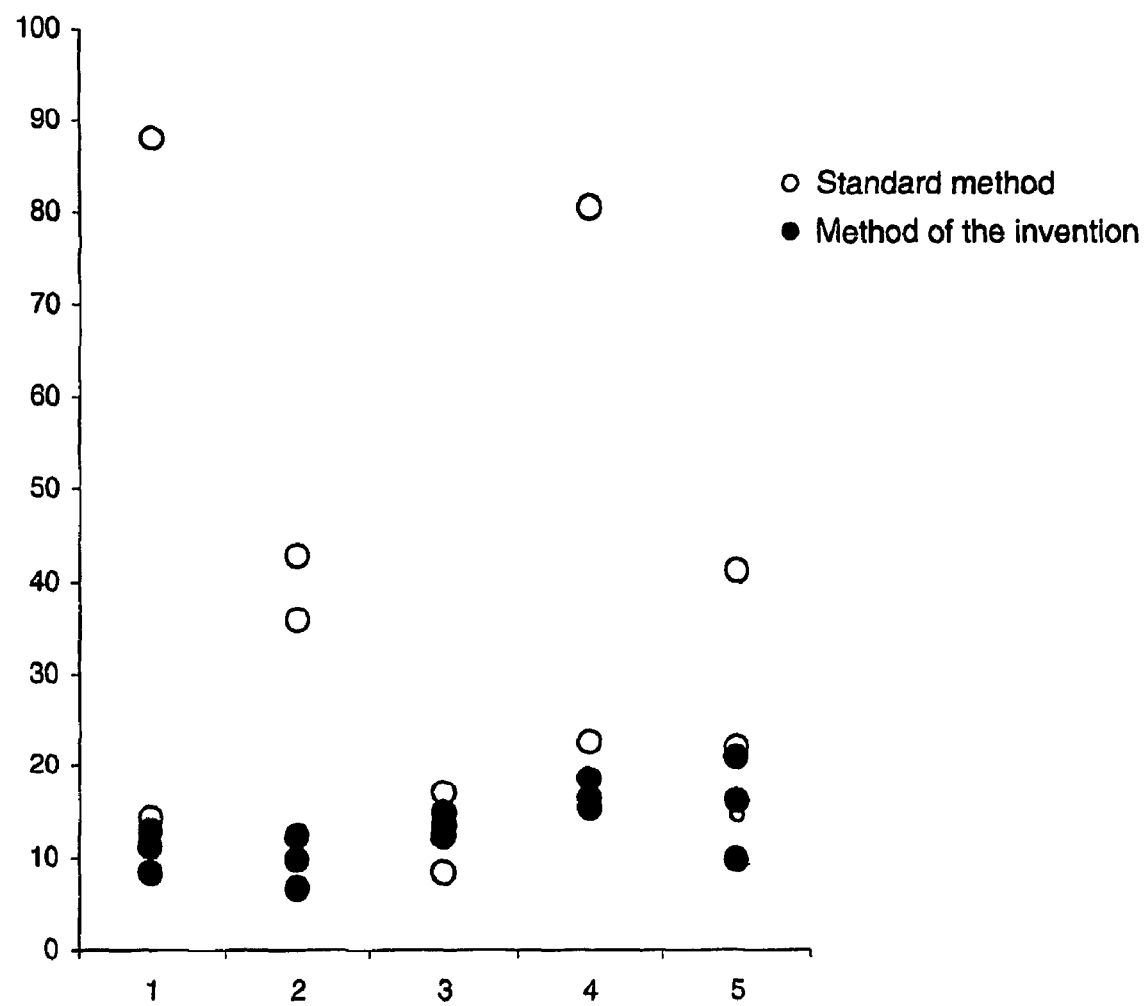

FIG. 13 shows a comparison of the distribution of silencing efficacies of the siRNAs among the 30 siRNAs designed using the method of the invention (solid circles) and siRNAs designed using the standard method (open circles). x-axis: 1, KIF14; 2, PLK; 3, IGF1R; 4, MAPK14; 5, KIF11.y-axis: RNA level. The siRNAs designed using the standard method to the 5 genes exhibited a broad distribution of silencing abilities, while those designed with the method of the invention show more consistent silencing within each gene, as well as across genes. A narrow distribution is very important for functional genomics with siRNAs.

Figure 14B:
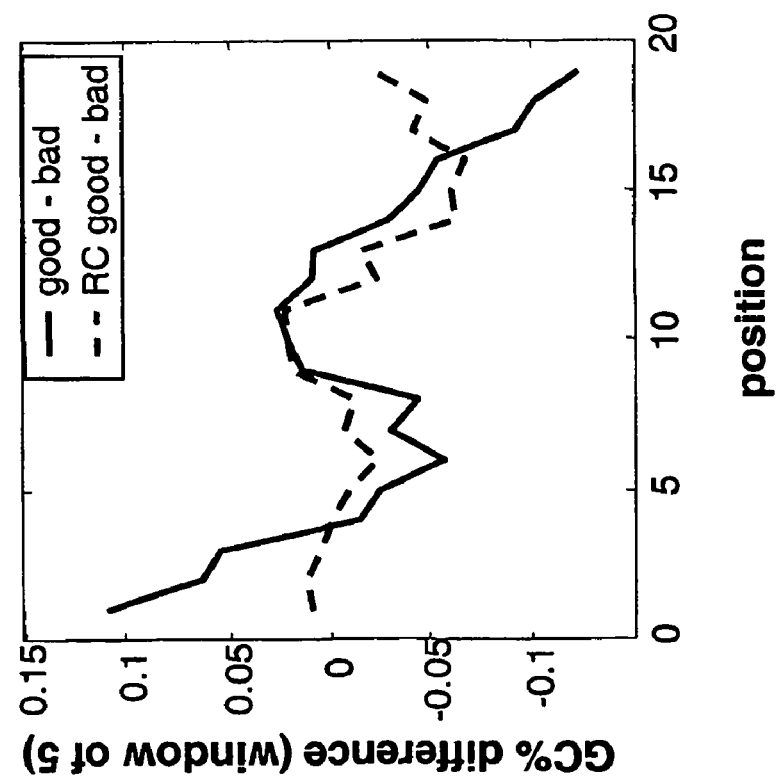
Figure 14A:
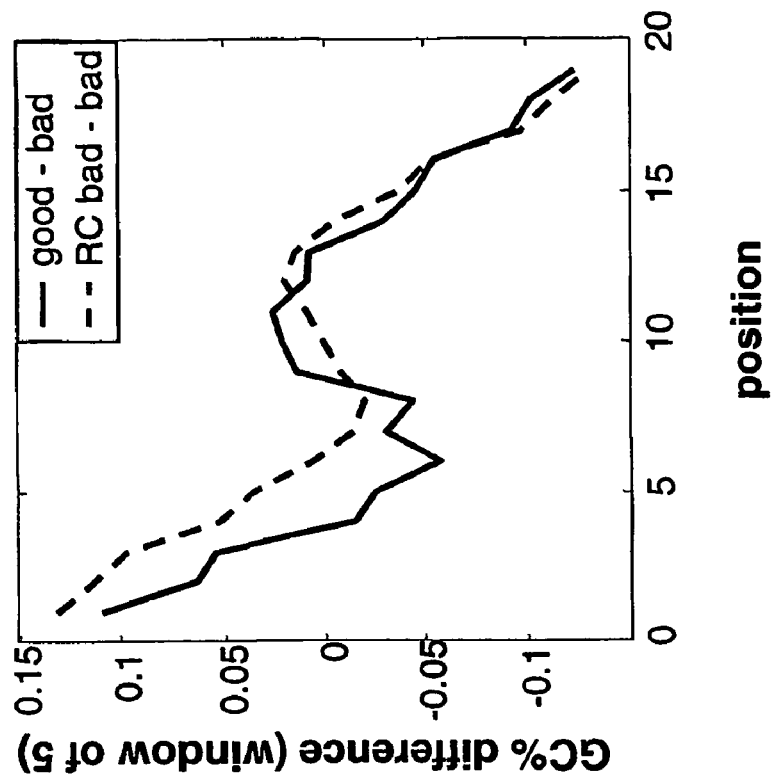

FIGS. 14A-B show a comparison of the GC content of siRNAs and their reverse complements with the GC content of bad siRNAs. The results indicate that bad siRNAs have sense strands similar to good siRNAs, while good siRNAs have sense strands similar to bad siRNAs. RC: reverse complement of the siRNA target sequence.

Figure 15:
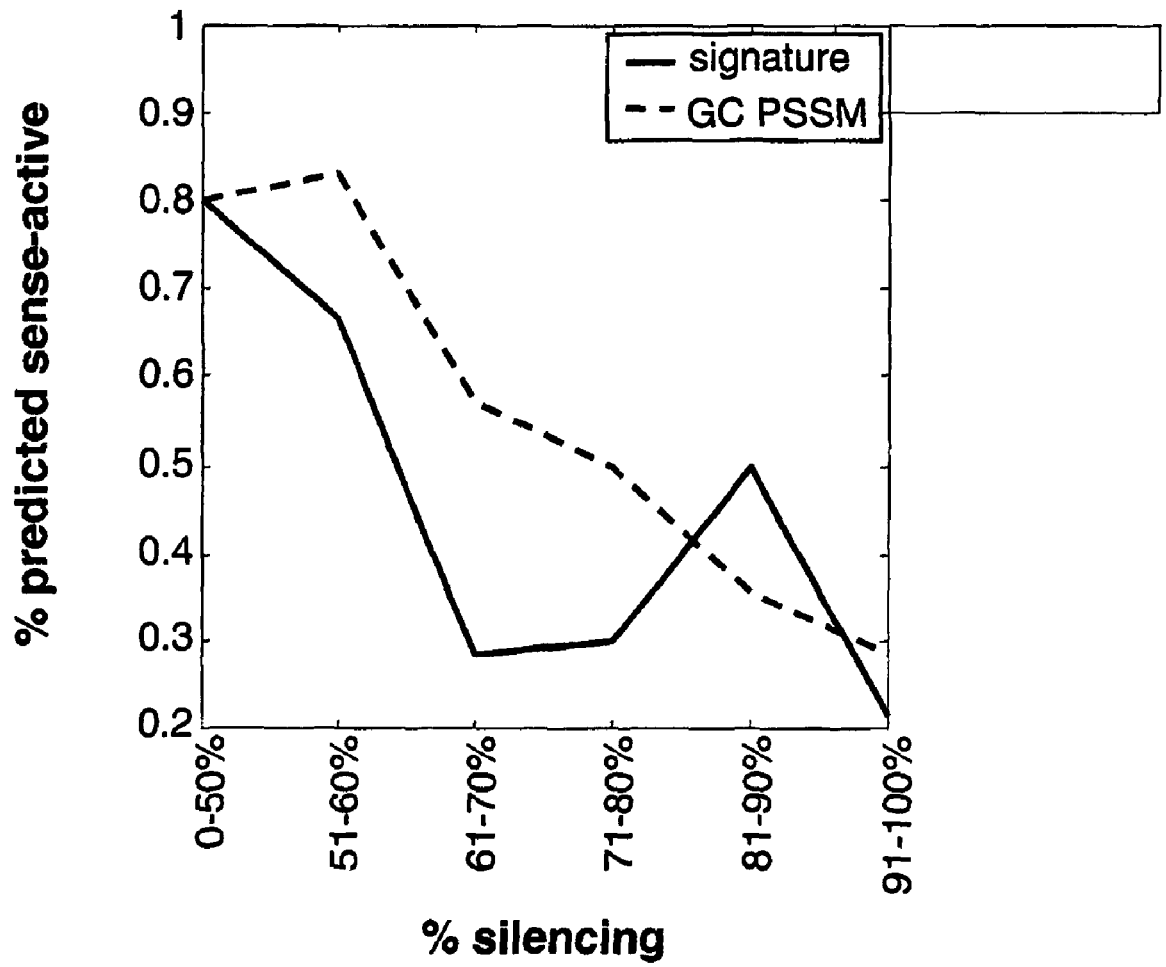

FIG. 15 shows that less effective siRNAs have active sense strands. Strand bias of 61 siRNAs was predicted from expression profiles by the 3'-biased method, and from comparison of the GC PSSM scores of the siRNAs and their reverse complements. Strand bias predictions were binned by siRNA silencing efficacy.

Figure 16:
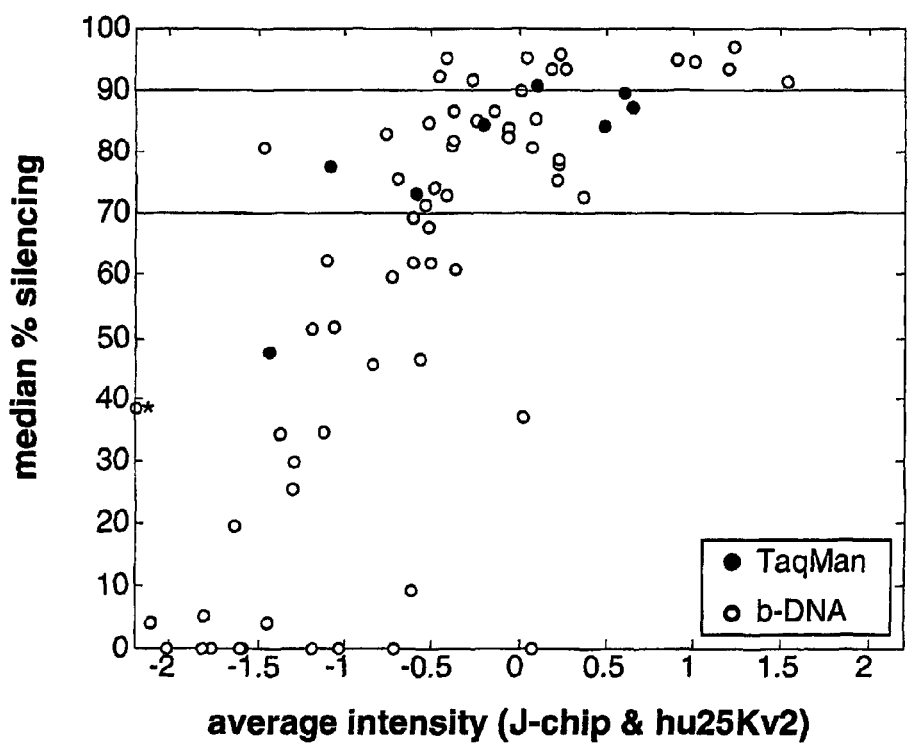

FIG. 16 shows that silencing efficacy relates to transcript expression level. A total of 222 siRNAs (3 siRNAs per gene for 74 genes) were tested by bDNA or Taqman analysis for their ability to silence their target sequences 24 hr following transfection into HeLa cells. Percent silencing (y-axis) was plotted as a function of transcript abundance (x-axis) measured as intensity on microarray. Shown is the median target silencing observed for 3 siRNAs per gene selected by the previous siRNA design algorithm. The dependence of silencing on gene expression level, as the average of intensities from 2 array types, is shown for 74 genes. TaqMan assays were used for 8 genes. b-DNA data is shown for the remaining 66 genes.

Figure 17:
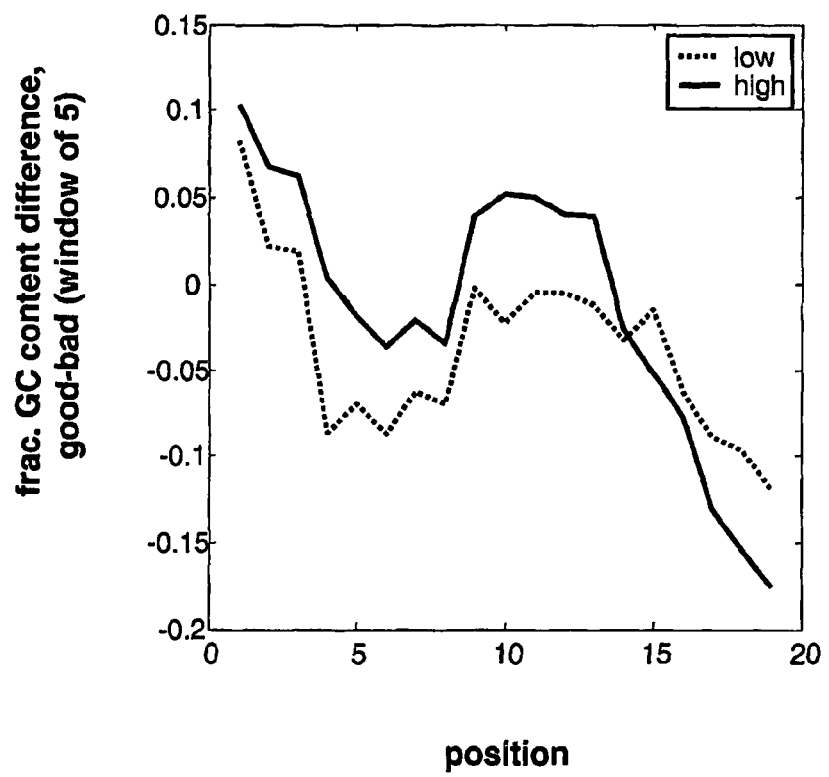

FIG. 17 shows that the silencing efficacy of an siRNA relates to its base composition. siRNAs to poorly-expressed genes were tested by bDNA analysis for their ability to silence their target sequences. Data were divided into subsets having less than 75% silencing and equal to or greater than 75% silencing (bad and good siRNAs, respectively). Shown here is the difference in GC content between good and bad siRNAs (y-axis) at each position in the siRNA sense strand (x-axis.) The dataset includes both poorly-expressed and highly-expressed genes from 570 siRNAs selected to 33 poorly- and 41 highly-expressed genes by Tuschl rules or randomized selection. The siRNA sequences are listed in Table IV. The GC profile for good siRNAs to poorly-expressed genes (gray dotted curve) shows some similar composition preferences to good siRNAs for well-expressed genes (black curve), but also some differences.

Figure 18:
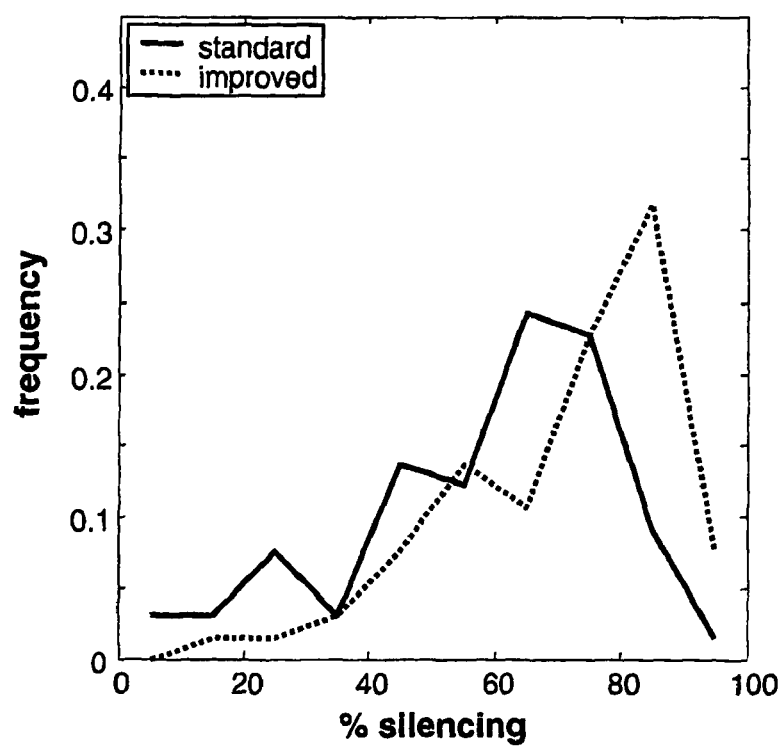

FIG. 18 shows the efficacy of newly design siRNAs. siRNAs were designed for 18 poorly-expressed genes by the standard method and by the new algorithm. Standard pipeline: selection for maximum pssm score; minimax filter for long off-target matches. Improved pipeline: selection for 1-3 G+C in sense 19mer bases 2-7, base 1 & 19 asymmetry, −300<pssm score<+200, and blast matches less than 16, 200 bases on either side of the 19mer are not repeat or low-complexity sequences. The top three ranked siRNAs per gene were selected for each method. All six siRNAs for each of the five genes were then tested for their ability to silence their target sequences. Shown is a histogram of the number of siRNAs silencing their target genes by a specified amount. Dotted curve, silencing by siRNAs designed by the new algorithm; solid curve, silencing by siRNAs designed by the standard method. Median silencing improved from 60% (standard algorithm) to 80% (new algorithm).

Figure 19:
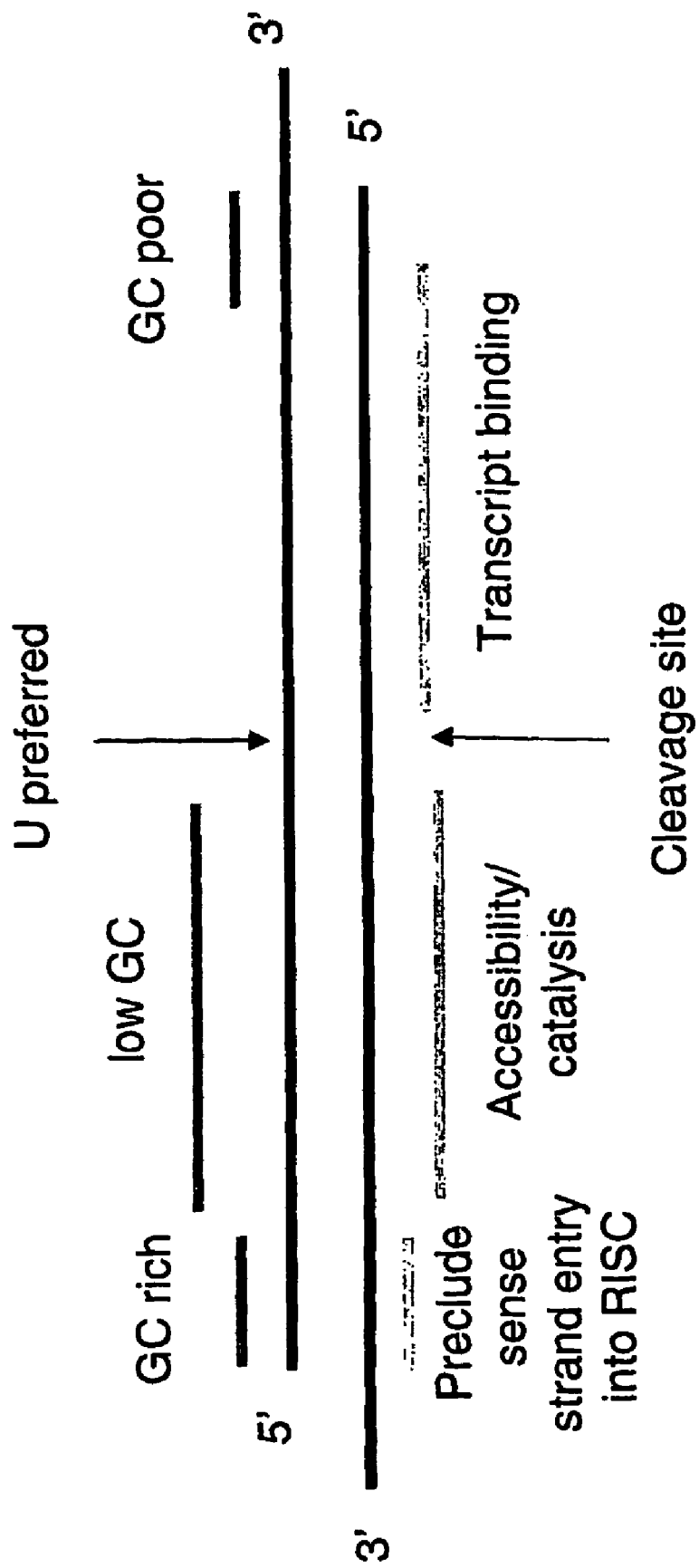

FIG. 19. Design features of efficacious siRNAs. Studies of design criteria that correlate with siRNA silencing efficacy have revealed a number of features that predict efficacy. These include a base asymmetry at the two termini to direct the antisense (guide) strand into RISC, a U at position 10 for effective cleavage of the transcript, a low GC stretch encompassing the center and 3' end of the guide strand for enhanced cleavage, and the "seed" region at the 5' end of the antisense strand implicated in transcript binding. Gray lines above the duplex indicate sequence preferences, light gray lines below the duplex indicate functional attributes.

Figure 20:
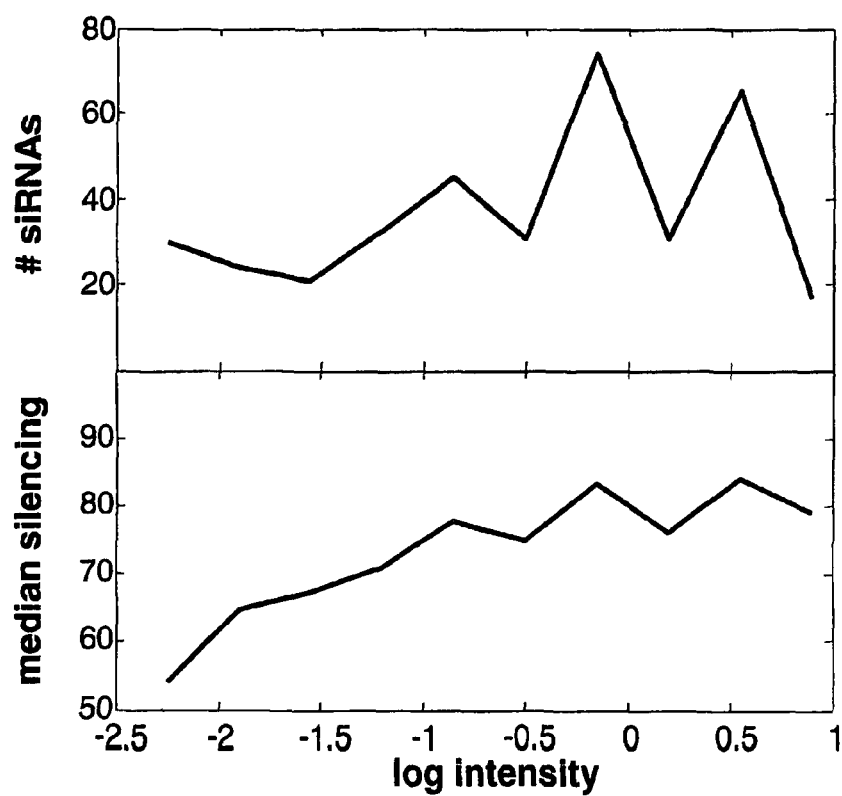

FIG. 20 shows expression vs. median silencing in 371 siRNAs. These are siRNAs from the original training set of 377 siRNAs. 6 siRNAs were not included in the analysis, as the expression level of their target gene was not available.

5. DETAILED DESCRIPTION OF THE INVENTION

The present invention provides a method for identifying siRNA target motifs in a transcript using a position-specific score matrix approach. The invention also provides a method for identifying off-target genes of an siRNA and for predicting specificity of an siRNA using a position-specific score matrix approach. The invention further provides a method for designing siRNAs with higher silencing efficacy and specificity. The invention also provides a library of siRNAs comprising siRNAs with high silencing efficacy and specificity.

In this application, an siRNA is often said to target a gene. It will be understood that when such a statement is made, it means that the siRNA is designed to target and cause degradation of a transcript of the gene. Such a gene is also referred to as a target gene of the siRNA, and the sequence in the transcript that is acted upon by the siRNA is referred to as the target sequence. For example, a 19-nucleotide sequence in a transcript which is identical to the sequence of the 19-nucleotide sequence in the sense strand of the duplex region of an siRNA is the target sequence of the siRNA. The antisense strand of the siRNA, i.e., the strand that acts upon the target sequence, is also referred to as the guiding strand. In the above example, the antisense strand of the 19-nucleotide duplex region of the siRNA is the guiding strand. In this application, features of an siRNA are often referred to with reference to its sequence, e.g., positional base composition. It will be understood that, unless specifically pointed out otherwise, such a reference is made to the sequence of the sense strand of the siRNA. In this application, a nucleotide or a sequence of nucleotides in an siRNA is often described with reference to the 5' or 3' end of the siRNA It will be understood that when such a description is employed, it refers to the 5' or 3' end of the sense strand of the siRNA. It will also be understood that, when a reference to the 3' end of the siRNA is made, it refers to the 3' duplex region of the siRNA, i.e., the two nucleotides of the 3' overhang are not included in the numbering of the nucleotides. In the application, an siRNA is also referred to as an oligo.

In this disclosure, design of siRNA is discussed in reference to silencing a sense strand target, i.e., transcript target sequence corresponding to the sense strand of the siRNA. It will be understood by one skilled person in the art that the methods of the invention are also applicable to the design of siRNA for silencing an antisense target (see, e.g., Martinez et al., 2002, Cell 110:563-574).

5.1. Methods of Identifying Sequence Motifs in a Gene for Targeting by a Small Interfering RNA The invention provides a method of identifying a sequence motif in a transcript which may be targeted by an siRNA for degradation of the transcript, e.g., a sequence motif that is likely to be a highly effective siRNA targeting site. Such a sequence motif is also referred to as an siRNA susceptible motif. The method can also be used for identifying a sequence motif in a transcript which may be less desirable for targeting by an siRNA, e.g., a sequence motif that is likely to be a less effective siRNA targeting site. Such a sequence motif is also referred to as an siRNA resistant motif.

In one embodiment, sequence features characteristic of a functional sequence motif, e.g., an siRNA susceptible sequence motif, are identified and a profile of the functional motif is built using, e.g., a library of siRNAs for which silencing efficacy of has been determined.

In one embodiment, the sequence region of interest is scanned to identify sequences that match the profile of the functional motif.

5.1.1. Sequence Profile and Target Silencing Efficacy

In a preferred embodiment, the profile of a functional sequence motif is represented using a position-specific score matrix (PSSM). A general discussion of PSSM can be found in, e.g., "Biological Sequence Analysis" by R. Durbin, S.

Eddy, A. Krogh, and G. Mitchison, Cambridge Univ. Press, 1998; and Henikoff et al., 1994, J Mol Biol. 243:574-8. A PSSM is a sequence motif descriptor which captures the characteristics of a functional sequence motif. In this disclosure, a PSSM is used to describe sequence motifs of the invention, e.g., a susceptible or resistant motif. A PSSM of an siRNA susceptible (resistant) motif is also referred to as a susceptible (resistant) PSSM. A skilled person in the art will know that a position-specific score matrix is also termed a position specific scoring matrix, a position weight matrix (PWM), or a Profile.

In the present invention, a functional motif can comprise one or more sequences in an siRNA target sequence. For example, the one or more sequences in an siRNA target sequence may be a sequence at 5' end of the target sequence, a sequence at 3' end of the target sequence. The one or more sequences in an siRNA target sequence may also be two stretches of sequences, one at 5' end of the target sequence and one at 3' end of the target sequence. A functional motif can also comprise one or more sequences in a sequence region that flanks the siRNA target sequence. Such one or more sequences can be directly adjacent to the siRNA target sequence. Such one or more sequences can also be separated from the siRNA target sequence by an intervening sequence. FIG. 10 illustrates some examples of functional motifs.

In one embodiment, a functional sequence motif, e.g., a susceptible or resistant sequence motif, comprises at least a portion of a sequence targeted by an siRNA. In one embodiment, the functional motif comprises a contiguous stretch of at least 7 nucleotides of the target sequence. In a preferred embodiment, the contiguous stretch is in a 3' region of the target sequence, e.g., beginning within 3 bases at the 3' end. In another embodiment, the contiguous stretch is in a 5' region of the target sequence. In another embodiment, the functional motif comprises a contiguous stretch of at least 3, 4, 5, 6, or 7 nucleotides in a 3' region of the target sequence and comprises a contiguous stretch of at least 3, 4, 5, 6, or 7 nucleotides in a 5' region of the target sequence. In still another embodiment, the functional motif comprises a contiguous stretch of at least 11 nucleotides in a central region of the target sequence. Sequence motifs comprise less than the full length of siRNA target sequence can be used for evaluating siRNA target transcripts that exhibit only partial sequence identify to an siRNA (International application No. PCT/US2004/015439 by Jackson et al., filed on May 17, 2004, which is incorporated herein by reference in its entirety). In a preferred embodiment, the functional motif comprises the full length siRNA target sequence.

The functional motif may also comprise a flanking sequence. The inventors have discovered that the sequence of such flanking region plays a role in determining the efficacy of silencing. In one embodiment, a functional sequence motif, e.g., a susceptible or resistant sequence motif, comprises at least a portion of a sequence targeted by an siRNA and one or more sequences in one or both flanking regions. Thus, a sequence motif can include an M nucleotides siRNA target sequence, a flanking sequence of $D_1$ nucleotides at one side of the siRNA target sequence and a flanking sequence of $D_2$ nucleotides at the other side of the siRNA target sequence where M, $D_1$ and $D_2$ are appropriate integers. In one embodiment, $D_1=D_2=D$. In one embodiment, M=19. In some preferred embodiments, $D_1$, $D_2$, or D is at least 5, 10, 20, 30, 50 nucleotides in length. In a specific embodiment, a susceptible or resistant sequence motif consists of an siRNA target sequence of 19 nucleotides and a flanking sequence of 10 nucleotides at either side of the siRNA target sequence. In another specific embodiment, a susceptible or resistant sequence motif consists of a 19 nucleotides siRNA target sequence and a 50 nucleotides flanking sequence at either side of the siRNA target sequence.

In another embodiment, a sequence motif can include an M nucleotides siRNA target sequence, and one or more of the following: a contiguous stretch of $D_1$ nucleotides flanking the 5' end of the target sequence, a contiguous stretch of $D_2$ nucleotides flanking the 3' end of the target sequence, a contiguous stretch of $D_3$ nucleotides which starts about 35 nucleotides upstream of the 5' end of the target sequence, a contiguous stretch of $D_4$ nucleotides which starts about 25 nucleotides downstream of the 3' end of the target sequence, and a contiguous stretch of $D_5$ nucleotides which starts about 60 nucleotides downstream of the 3' end of the target sequence, where $D_1$, $D_2$, $D_3$, $D_4$, and $D_5$ are appropriate integers. In one embodiment, $D_1=D_2=D$. In some preferred embodiments, each of $D_1$, $D_2$, $D_3$, $D_4$, and $D_5$ is at least 5, 10, or 20 nucleotides in length. The length of the functional motif is $L=M+D_1+D_2+D_3+D_4+D_5$. In a specific embodiment, the sequence motif include 19 nucleotides siRNA target sequence, a contiguous stretch of about 10 nucleotides flanking the 5' end of the target sequence, a contiguous stretch of about 10 nucleotides flanking the 3' end of the target sequence, a contiguous stretch of about 10 nucleotides which starts about 35 nucleotides upstream of the 5' end of the target sequence, a contiguous stretch of about 10 nucleotides which starts about 25 nucleotides downstream of the 3' end of the target sequence, and a contiguous stretch of about 10 nucleotides which starts about 60 nucleotides downstream of the 3' end of the target sequence (see FIG. 10).

In other embodiments, a functional sequence motif, e.g., a susceptible or resistant sequence motif, comprises one or more sequences in one or both flanking regions of an siRNA target sequence but does not comprise any siRNA target sequence. In one embodiment, the functional motif comprises a contiguous stretch of about 10 nucleotides flanking the 5' end of the target sequence. In another embodiment, the functional motif comprises a contiguous stretch of about 10 nucleotides flanking the 3' end of the target sequence. In a preferred embodiment, the functional motif comprises a contiguous stretch of about 10 nucleotides flanking the 5' end of the target sequence and a contiguous stretch of about 10 nucleotides flanking the 3' end of the target sequence. In one embodiment, the functional motif comprises a contiguous stretch of about 10 nucleotides which starts about 35 nucleotides upstream of the 5' end of the target sequence. In another embodiment, the functional motif comprises a contiguous stretch of about 10 nucleotides which starts about 25 nucleotides downstream of the 3' end of the target sequence. In still another embodiment, the functional motif comprises a contiguous stretch of about 10 nucleotides which starts about 60 nucleotides downstream of the 3' end of the target sequence. In a preferred embodiment, the functional motif comprises a contiguous stretch of about 10 nucleotides flanking the 5' end of the target sequence, a contiguous stretch of about 10 nucleotides flanking the 3' end of the target sequence, a contiguous stretch of about 10 nucleotides which starts about 35 nucleotides upstream of the 5' end of the target sequence, a contiguous stretch of about 10 nucleotides which starts about 25 nucleotides downstream of the 3' end of the target sequence, and a contiguous stretch of about 10 nucleotides which starts about 60 nucleotides downstream of the 3' end of the target sequence. Thus, a sequence motif can include a contiguous stretch of $D_1$ nucleotides flanking the 5' end of the target sequence, a contiguous stretch of $D_2$ nucleotides flanking the 3' end of the target sequence, a contiguous stretch of $D_3$ nucleotides which starts about 35 nucleotides upstream of the 5' end of the target sequence, a contiguous stretch of $D_4$ nucleotides which starts about 25 nucleotides downstream of the 3' end of the target sequence, and a contiguous stretch of $D_5$ nucleotides which starts about 60 nucleotides downstream of the 3' end of the target sequence, where $D_1$, $D_2$, $D_3$, $D_4$, and $D_5$ are appropriate integers. In some preferred embodiments, each of $D_1$, $D_2$, $D_3$, $D_4$, and $D_5$ is at least 5, 10, or 20 nucleotides in length. The length of the functional motif is $L=D_1+D_2+D_3+D_4+D_5$.

In one embodiment, the characteristics of a functional sequence motif are characterized using the frequency of each of G, C, A, U(or T) observed at each position along the sequence motif. In the disclosure, U(or T), or sometimes simply U(T), is used to indicate nucleotide U or T. The set of frequencies forms a frequency matrix, in which each element indicates the number of times that a given nucleotide has been observed at a given position. A frequency matrix representing a sequence motif of length L is a 4·L matrix $\{f_{ij}\}$, where i=G, C, A, U(T); j=1, 2, ..., L; where $f_{ij}$ is the frequency of the ith nucleotide at the jth position. A frequency matrix of a sequence motif can be derived or built from a set of N siRNA target sequences that exhibit a desired quality, e.g., a chosen level of susceptibility or resistance to siRNA silencing.

$$f_{ij} = \sum_{k=1}^{N} \delta_{ik}(j) \quad (1)$$

$$\text{where } \delta_{ik}(j) = \begin{cases} 1, & \text{if } k = i \\ 0, & \text{if } k \neq i \end{cases} \quad (2)$$

In embodiments in which a functional sequence motif consists of M nucleotides siRNA target sequence, a flanking sequence of $D_1$ nucleotides at one side of the siRNA target sequence and a flanking sequence of $D_2$ nucleotides at the other side of the siRNA target sequence, $L=M+D_1+D_2$. In embodiments in which the functional motif consists of M nucleotides siRNA target sequence, a contiguous stretch of $D_1$ nucleotides flaring the 5' end of the target sequence, a contiguous stretch of $D_2$ nucleotides flanking the 3' end of the target sequence, a contiguous stretch of $D_3$ nucleotides which starts about 35 nucleotides upstream of the 5' end of the target sequence, a contiguous stretch of $D_4$ nucleotides which starts about 25 nucleotides downstream of the 3' end of the target sequence, and a contiguous stretch of $D_5$ nucleotides which starts about 60 nucleotides downstream of the 3' end of the target sequence, $L=D_1+D_2+D_3+D_4+D_5$.

In another embodiment, the characteristics of a functional sequence motif are characterized using a set of weights, one for each nucleotide occurring at a position in the motif. In such an embodiment, a weight matrix $\{e_{ij}\}$, where i=G, C, A, U(T); j=1, 2, ..., L, can be used for representing a functional sequence motif of length L, where $e_{ij}$ is the weight of finding the ith nucleotide at the jth position. In one embodiment, the weight $e_{ij}$ is the probability of finding the ith nucleotide at the jth position in the functional sequence motif. When a probability is used for the weight, the matrix is also called a probability matrix. A probability matrix of a sequence motif can be derived from a frequency matrix according to equation $$e_{ij} = \frac{f_{ij}}{N} \quad (3)$$

In a preferred embodiment, a position-specific score matrix is used to characterize a functional sequence motif. The PSSM can be constructed using log likelihood values $\log(e_{ij}/p_{ij})$, where $e_{ij}$ is the weight of finding nucleotide i at position j, and $p_{ij}$ is the weight of finding nucleotide i at position j in a random sequence. In some embodiments, the probability of finding the ith nucleotide at the jth position in the functional sequence motif is used as $e_{ij}$, the probability of finding nucleotide i at position j in a random sequence is used as $p_{ij}$. The weight or probability $p_{ij}$ is an "a prior" weight or probability. In some embodiments, $p_{ij}=0.25$ for each possible nucleotide i∈{G, C, A, U(T)} at each position j. Thus, for a given sequence of length L, the sum of log likelihood ratios at all positions can be used as a score for evaluating if the given sequence is more or less likely to match the functional motif than to match a random sequence:

$$\text{Score} = \sum_{j=1}^{L} \ln(e_j / p_j) \quad (4)$$

wherein $e_j$ and $p_j$ are respectively weights of a nucleotide at position j in the functional sequence motif and in a random sequence. For example, if such a score is zero, the sequence has the same probability to match the sequence motif as to that to match a random sequence. A sequence is more likely to match the sequence motif if the ratio is greater than zero.

In another embodiment, when two or more different nucleotides are not to be distinguished, a PSSM with a reduced dimension can be used. For example, if the relative base compositions of G and C in a sequence motif are not to be distinguished, a PSSM can be a 3·L matrix $\{\log(E_{ij}/p_{ij})\}$, where i=G/C, A, U(T); j=1, 2, ..., L; where $E_{ij}$ is the weight, e.g., probability, of finding nucleotide i at position j, and $p_{ij}$ is the weight, e.g., probability, of finding nucleotide i at position j in a random sequence. Thus, in such cases, a PSSM has 3 sets of weights: GC-specific, A-specific and U-specific, e.g., if the base at a position is a G or a C, the natural logarithm of the ratio of the GC weight and the unbiased probability of finding a G or C at that position is used as the GC-specific weight for the position; and the natural logarithms of the position-specific A and T weights divided by the unbiased probability of respective base are used as the A- and T-specific weights for the position, respectively. The log likelihood ratio score is represented by Eq. (5):

$$\text{Score} = \sum_{j=1}^{L} \ln(E_j / p_j) \quad (5)$$

where $E_j$ is the weight assigned to a base—A, U or G/C—at position j, and $p_j=0.25$ for A or U and 0.5 for G/C.

In still another embodiment, when the relative base compositions of G and C in a sequence motif are not to be distinguished and the relative base compositions of A and T in the sequence motif are also not to be distinguished, a PSSM can be a 1·L matrix $\{\log(E_{ij}/p_{ij})\}$, where i=G/C; j=1, 2, ..., L; where $E_{ij}$ is the weight, e.g., probability, of finding nucleotide i at position j, and $p_{ij}$ is the weight, e.g., probability, of finding nucleotide i at position j in a random sequence. Thus, in such cases, a PSSM has 1 set of GC-specific weights: if the base at a position is a G or a C, the natural logarithm of the ratio of the GC weight and the unbiased probability of finding a G or C at that position is used as the GC-specific weight for the position. The log likelihood ratio score is represented by Eq. (5), except that $E_j$ is the weight assigned to a base—G/C—at position j, and $p_j$=0.50.

5.1.2. Methods of Determining a Profile

The invention provides methods of determining a PSSM of a functional sequence motif based on a plurality of siRNAs for which some quantity or quantities characterizing the siRNAs have been determined. For example, a plurality of siRNAs whose silencing efficacy has been determined can be used for determination of a PSSM of an siRNA susceptible or resistant sequence motif. In the disclosure, for simplicity reasons, efficacy is often used as a measure for classifying siRNAs. Efficacy of an siRNA is measured in the absence of other siRNAs designed to silence the target gene. It will be apparent to one skilled person in the art that the methods of the invention are equally applicable in cases where siRNAs are classified based on another measure. Such a plurality of siRNAs is also referred to as a library of siRNAs. In cases where the functional sequence motif of interest comprises one or more sequences in one or both flanking regions, a plurality of siRNA functional motifs, i.e., a sequence comprising the siRNA target sequence and the sequences in the flanking region(s) in a transcript, can be used to determine the PSSM of the functional motif. In a preferred embodiment, the siRNA functional sequence motif consists of an siRNA target sequence of 19 nucleotides and a flanking sequence of 10 nucleotides at either side of the siRNA target sequence. For simplicity reasons, in this disclosure, unless specified, the term "a library of siRNAs" is often used to referred to both a library of siRNAs and a library of siRNA functional motifs. It will be understood that in the latter cases, when the efficacy of an siRNA is referred to, it refers to the efficacy of the siRNA that targets the motif. Preferably, the plurality of siRNAs or siRNA target motifs comprises at least 10, 50, 100, 200, 500, 1000, or 10,000 different siRNAs or siRNA target motifs.

Each different siRNA in the plurality or library of siRNAs or siRNA functional motifs can have a different level of efficacy. In one embodiment, the plurality or library of siRNAs consists of siRNAs having a chosen level of efficacy. In another embodiment, the plurality or library of siRNAs comprises siRNAs having different levels of efficacy. In such an embodiment, siRNAs may be grouped into subsets, each consisting of siRNAs that have a chosen level of efficacy.

In one embodiment, a PSSM of an siRNA functional motif is determining using a plurality of siRNAs having a given efficacy. In one embodiment, a plurality of N siRNAs consisting of siRNAs having a silencing efficacy above a chosen threshold is used to determine a PSSM of an siRNA susceptible motif. The PSSM is determined based on the frequency of a nucleotide appeared at a position (see Section 5.1.1). The chosen threshold can be 50%, 75%, 80% or 90%. In another embodiment, a plurality of N siRNAs consisting of siRNAs having a silencing efficacy below a chosen threshold is used to determine a PSSM of an siRNA susceptible motif. The chosen threshold can be 5%, 10%, 20%, 50%, 75% or 90%. In a preferred embodiment, the PSSM has a reduced dimension with a weight for G/C.

In preferred embodiments, a PSSM of a susceptible or resistant motif is derived or built using a classifier approach with a set of N sequences. In such embodiments, a library of siRNAs comprising siRNAs having different levels of efficacy are used. In one embodiment, siRNAs in the library may be randomly grouped into subsets, each consisting of siRNAs that have different levels of efficacy, one subset is used as a training set for determining a PSSM and the other is used as a testing set for validating the PSSM. Different criteria can be used to divide the existing siRNA library into training and test sets. For an siRNA library in which a majority of siRNA oligos are designed with the standard method, which requires an AA dimer immediately before the 19mer oligo sequence, several partitions were used and more than one trained PSSMs (rather than single PSSMs) were combined to assign scores to the test oligos. An exemplary siRNA library and divisions of the library into training and test sets are shown in Table II.

In a preferred embodiment, the sequence motif consists of 39 bases in the transcript sequence, beginning 10 bases upstream of the 19mer siRNA target sequence and ending 10 bases downstream of the 19mer. The PSSM characterizing such a sequence motif is described in Section 5.1.1.

In a preferred embodiment, the PSSM is determined by an iterative process. A PSSM is initialized with random weights $\{e_{ij}\}$ or $\{E_{ij}\}$ within a given search range for all bases at all positions. In another preferred embodiment, PSSM is initialized to the smoothed mean base composition difference between good and bad siRNAs in the training set. As an example, a PSSM describing a 39 nucleotide sequence motif can have 117 elements. In another embodiment, the weights are optimized by comparing the correlation of scores generated to a quantity of interest, e.g., silencing efficacy, and selecting the PSSM whose score best correspond to that quantity. Improvement in PSSM performance is scored by comparing correlation values before and after a change in weights at any one position. In one embodiment, there is no minimum requirement for a change in correlation. Aggregate improvement is calculated as the difference between the final correlation and the initial correlation. In one embodiment, for a PSSM characterizing a 39mer sequence motif, the aggregate improvement threshold after 117 cycles for termination of optimization is a difference of 0.01.

In one embodiment, the weights are optimized to reflect base composition differences between good siRNAs, i.e., siRNAs having at least median efficacy, and bad siRNAs, i.e., siRNAs having below median efficacy, in the range of allowed values for weights. If the PSSM is initialized with a frequency matrix, the range of allowed values corresponds to the frequency matrix elements +/−0.05. If an unbiased search is used, the ranges of the allowed values for weights are 0.45-0.55 for G/C and 0.2-0.3 for A or U. In one embodiment, weights are allowed to vary from initial values by +/−0.05. If an unbiased search is used, the PSSM weights can be set to random initial values within the unbiased search range described above.

In one embodiment, the PSSM is determined by a random hill-climbing mutation optimization procedure. In each step of the process, one base at one position is randomly selected for optimization. For example, for a PSSM describing a 39 nucleotide sequence motif, the 39 bases become a vector of 117 weights: 39 G/C weights, 39 A weights and 39 U weights. One of these 117 weights is selected for optimization in each step, and is run through all values in the search range at that step. For each value in the search range, scores for a training set of siRNAs are calculated. The correlation of these scores with the silencing efficacy of the siRNAs is then calculated. The weight for that position which generate the best correlation between the scores and silencing efficacy is retained as the new weight at that position.

In one embodiment, the metric used to measure the effectiveness of the training and testing is the aggregate false detection rate (FDR) based on the ROC curve, and is computed as the average of the FDR scores of the top 33% oligos sorted by the scores given by the trained PSSM. In computing the FDR scores, those oligos with silencing levels less than the median are considered false, and those with silencing level higher than the median level are considered true. The "false detection rate" is the number of false positives selected divided by the total number of true positives, measured at each ranked position in a list. The false detection rate can be a function of the fraction of all siRNAs selected. In one embodiment, the area under the curve at 33% of the list selected as a single number representing performance. In one embodiment, all at-least-median siRNAs are called as "positives" and all worse-than-median siRNAs are called "negatives." Thus, half the data are positives and the other half are "false positives." In an ideal ranking, the area under the curve at 33% or even at 50% of the list selected should be 0. In contrast, a random ranking would cause equal numbers of true positives and false positives to be selected. This corresponds to an area under the curve of 0.17 at 33% of the list selected, or 0.25 at 50% of the list selected.

Correlations between % silencing and PSSM score are calculated according to method known in the art (see, e.g., Applied Multivariate Statistical Analysis, 4th ed., R. A. Johnson & E. W. Wichem, Prentice-hall, 1998).

The process is continued until the aggregate improvement over a plurality of iterations fell below a threshold.

In a preferred embodiment, a plurality of PSSMs are obtained for a functional sequence motif using an siRNA training set. In this disclosure, a plurality of PSSMs is also referred to as an "ensemble" of PSSMs. Each round of optimization may stop at a local optimum distinct from the global optimum. The particular local optimum reached is dependent on the history of random positions selected for optimization. A higher improvement threshold may not bring a PSSM optimized to a local optimum closer to the global optimum. Thus it is more effective to run multiple optimizations than one long optimization. Additional runs (e.g., up to 200) were found to enhance performance. Running more than 200 optimizations was not seen to provide further enhancements in performance. Empirically, scoring siRNAs via the average of multiple runs is less effective than scoring candidate siRNAs on the PSSMs generated by each run and then summing the scores. Thus, in one embodiment, the plurality of PSSMs are used individually or summed to generate a composite score for each sequence match. The plurality of matrices can be tested individually or as a composite on an independent set of siRNA target motifs with known silencing efficacy to evaluate the utility for identifying sequence motifs and in siRNA design. In a preferred embodiment, the plurality of PSSM consists of at least 2, 10, 50, 100, 200, or 500 PSSMs.

In a preferred embodiment, one or more different siRNA training sets are used to obtain one or more ensemble of PSSMS. These different ensembles of PSSMs may be used together in determining the score of a sequence motif.

Sequence weighting methods have been used in the art to reduce redundancy and emphasize diversity in multiple sequence alignment and searching applications. Each of these methods is based on a notion of distance between a sequence and an ancestral or generalized sequence. Here a different approach is presented, in which base weights on the diversity observed at each position in the alignment and the correlation between the base composition and the observed efficacy of the siRNAs, rather than on a sequence distance measure.

In still another embodiment, PSSMs are generated by a method which hypothesized dependency of the base composition of any one position on its neighboring positions, referred to as "curve models."

In one embodiment, curve models are generated as a sum of normal curves (i.e., Gaussian). It will be apparent to one skilled person in the art that other suitable curve functions, e.g., polynomials, can also be used. Each curve represents the probability of finding a particular base in a particular region. The value at each position in the summed normal curves is the weight given to that position for the base represented by the curve. The weights for each base present at each position in each siRNA and its flanking sequences are then summed to generate an siRNA's score, i.e., the score is $\Sigma w_i$. The score calculation can also be described as the dot product of the base content in the sequence with the weights in the curve model. As such, it is one way of representing the correlation of the sequence of interest with the model.

Curve models can be initialized to correspond to the major peaks and valleys present in the smoothed base composition difference between good and bad siRNAs, e.g., as described in FIGS. 1A-C and 5A-C. In one embodiment, curve models for G/C, A and U are obtained. In one embodiment, the initial model can be set up for the 3-peak G/C curve model as follows:

Peak 1
  mean: 1.5
  standard deviation: 2
  amplitude: 0.0455

Peak 1 mean, standard deviation and amplitude are set to correspond to the peak in the mean difference in GC content between good and bad siRNAs occurring within bases—2-5 of the siRNA target site in Set 1 training and test sets.

Peak 2
  mean: 11
  standard deviation: 0.5
  amplitude: 0.0337

Peak 2 mean, standard deviation and amplitude are set to correspond to the peak in the mean difference in GC content between good and bad siRNAs occurring within bases 10-12 of the siRNA target site in Set 1 training and test sets.

Peak 3
  mean: 18.5
  standard deviation: 4
  amplitude: −0.0548

Peak 3 mean, standard deviation and amplitude are set to correspond to the peak in the mean difference in GC content between good and bad siRNAs occurring within bases 12-25 of the siRNA target site in Set 1 training and test sets.

Peak height (amplitude), center position in the sequence (mean) and width (standard deviation) of a peak in a curve model can be adjusted. Curve models are optimized by adjusting the amplitude, mean and standard deviation of each peak over a preset grid of values. In one embodiment, curve models are optimized on several training sets and tested on several test sets, e.g., training sets and test sets as described in Table II. Each base—G/C, A and U(or T)—is optimized separately, and then combinations of optimized models are screened for best performance.

Preferably, optimization criteria for curve models are: (1) the fraction of good oligos in the top 10%, 15%, 20% and 33% of the scores, (2) the false detection rate at 33% and 50% of the siRNAs selected, and (3) the correlation coefficient of siRNA silencing vs. siRNA scores used as a tiebreaker.

When the model is trained, a grid of possible values for amplitude, mean and standard deviation of each peak is explored. The models with the top value or within the top range of values for any of the above criteria were selected and examined further.

In a preferred embodiment, G/C models are optimized with 3 or 4 peaks, A models are optimized with 3 peaks, and U models are optimized with 5 peaks. Exemplary ranges of parameters optimized for curve models are shown in Example 3, infra.

Figure 3:
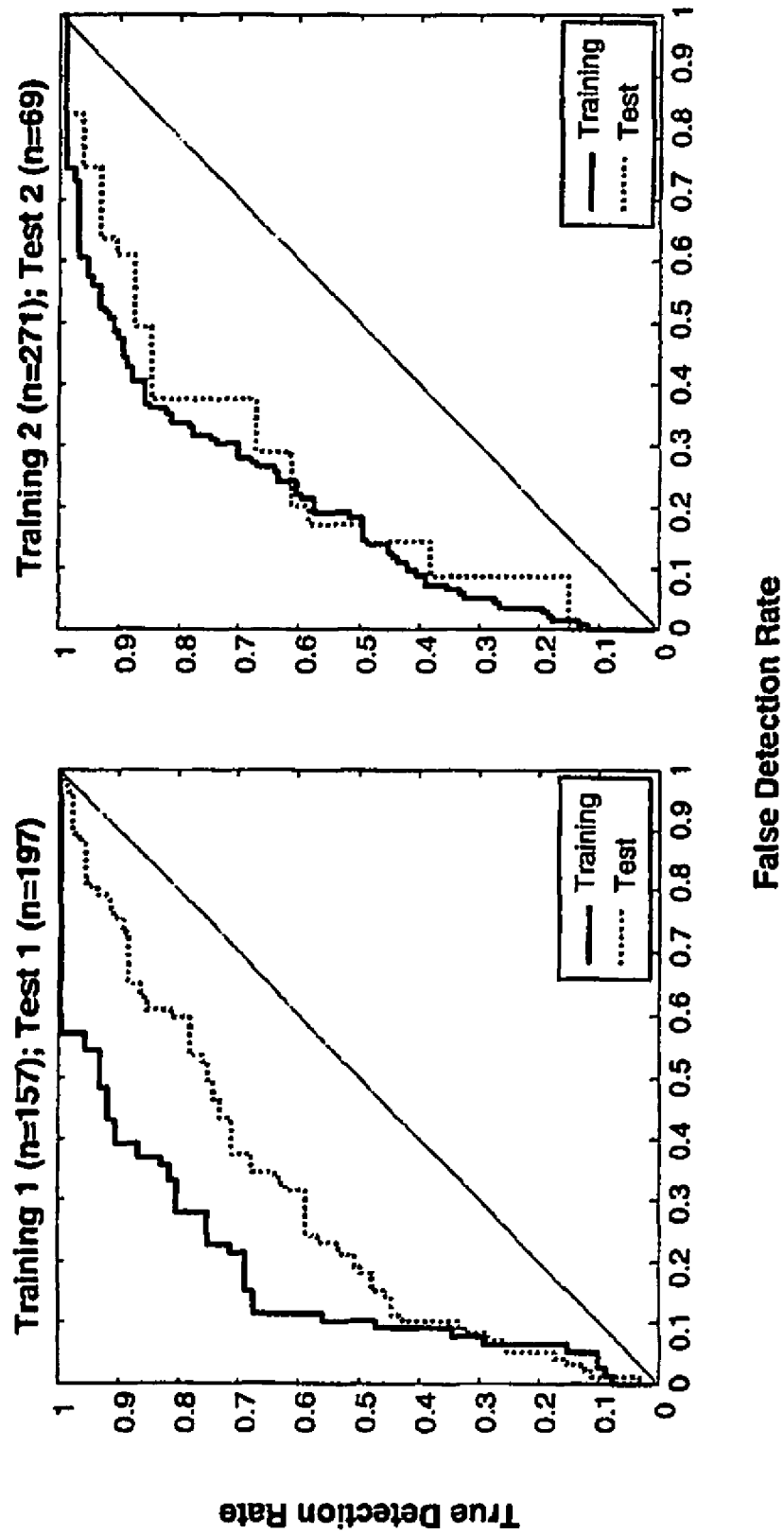
Figure 4:
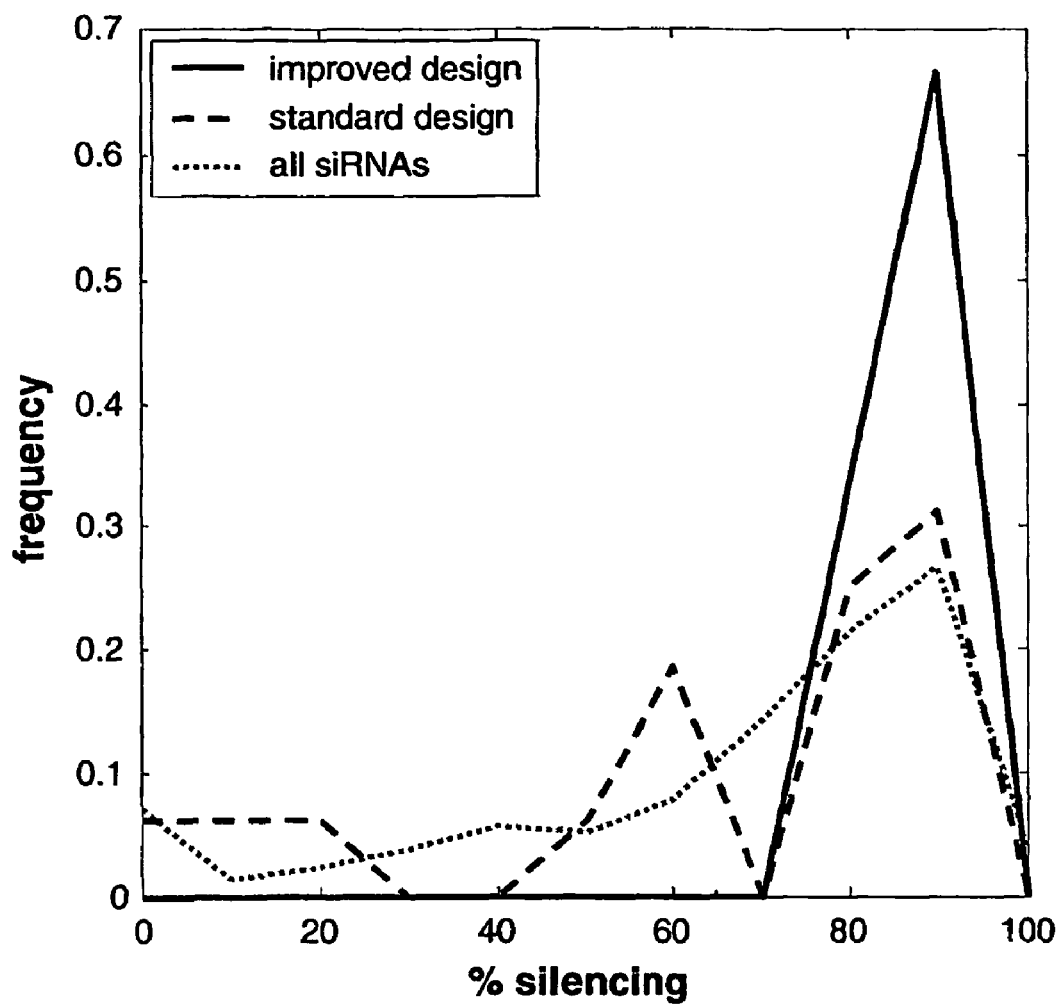
Figure 5A:
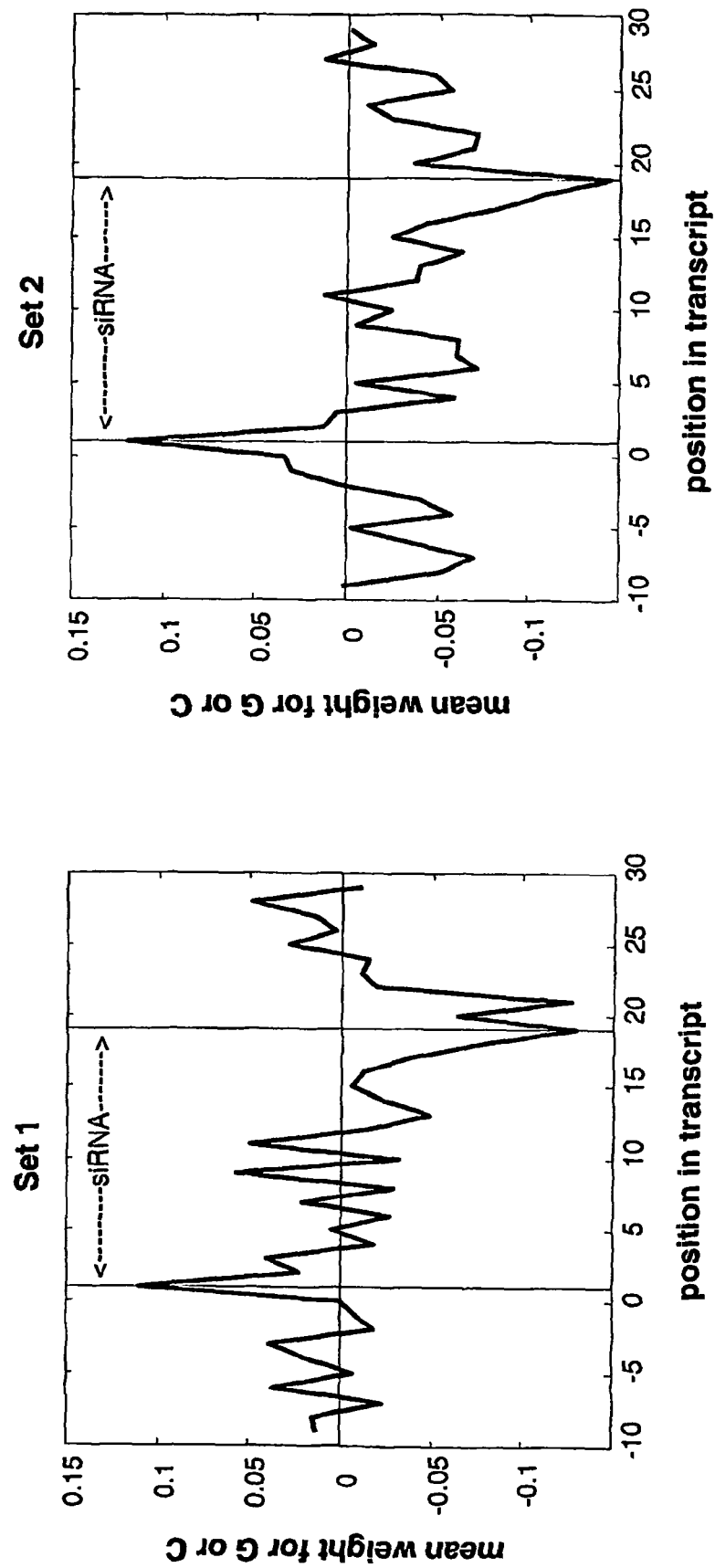
Figure 5B:
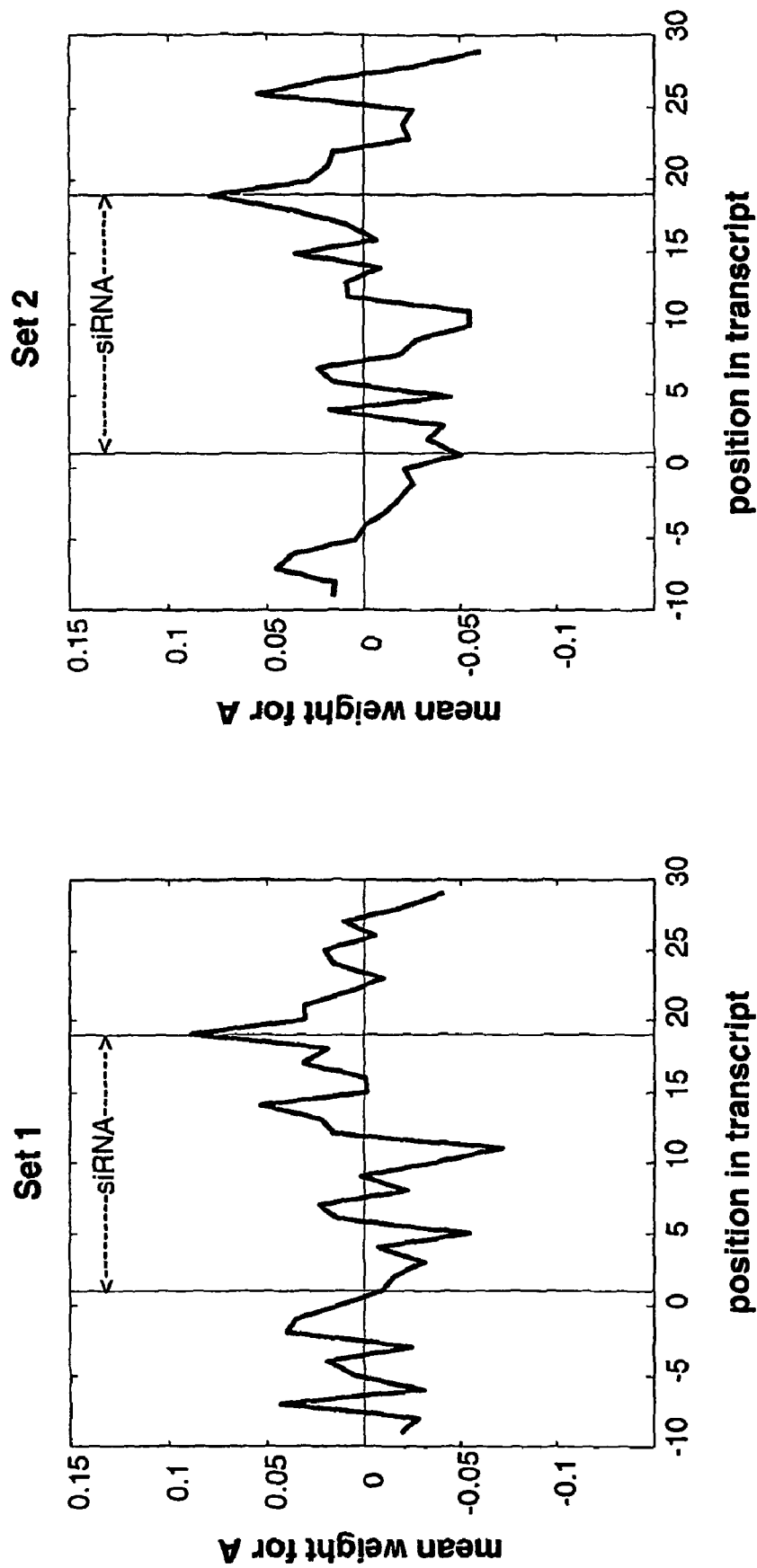
Figure 5C:
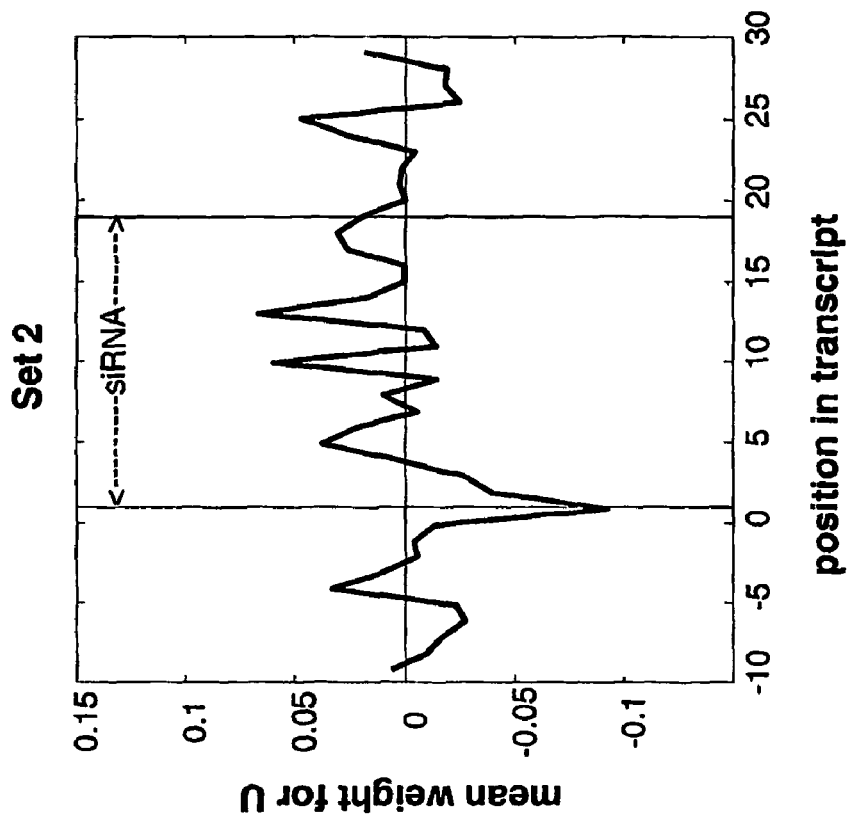
Figure 5C:
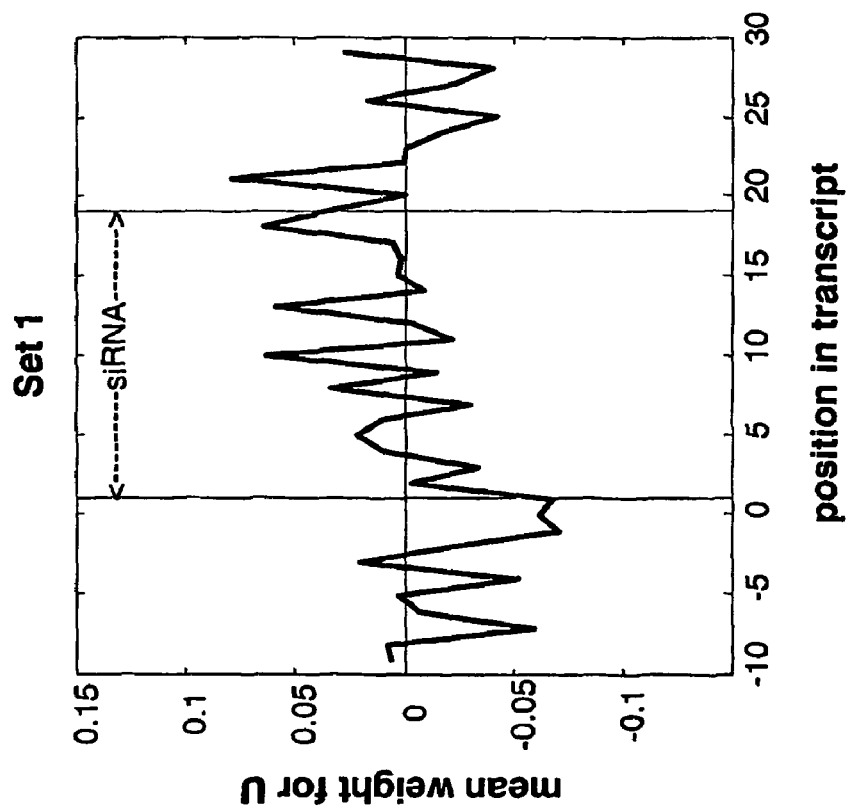

Preferably, the performance of the obtained PSSM is evaluated. In one embodiment, the PSSM is evaluated using an ROC (receiver operating characteristic) curve. An ROC curve is a plot of the sensitivity of a diagnostic test as a function of non-specificity. An ROC curve indicates the intrinsic properties of a test's diagnostic performance and can be used to compare relative merits of competing procedures. In one embodiment, the sensitivity of a PSSM is calculated as the proportion of true positives detected as a fraction of total true positives, whereas the non-specificity of the PSSM is calculated as the proportion of false positives detected as a fraction of total false positives (see, e.g., Campbell, 1994, Statistics in Medicine 13:499-508; Metz, 1986, Investigative Radiology 21:720-733; Gribskov et al., 1996, Computers Chem. 20:25-33). FIG. 3 shows ROC curves of the two PSSMs selected for the current best practice of the invention.

In another embodiment, the performance of a PSSM is evaluated by comparing a plurality of sequence motifs identified using the PSSM with a plurality of reference sequence motifs. The PSSM is used to obtain the plurality of sequence motifs by, e.g., scanning one or more transcripts and identifying sequence motifs that match the PSSM, e.g., with a score above a threshold. Preferably, the plurality comprises at least 3, 5, 10, 20 or 50 different sequence motifs. The reference sequence motifs can be from any suitable source. In one embodiment, a plurality of reference sequence motifs is obtained using a standard method (e.g., Elbashir et al., 2001, Nature. 411:494-8). The two pluralities are then compared using any standard method known in the art to determine if they are identical.

In a preferred embodiment, the two pluralities are compared using a Wilcoxon rank sum test. A Wilcoxon rank sum test tests if two pluralities of measurements are identical (see, e.g., Snedecor and Cochran, *Statistical Methods*, Eighth Edition, 1989, Iowa State University Press, pp. 142-144; McClave and Sincich, 2002, *Statistics*, Ninth Edition, Prentice Hall, Chapter 14). The Wilcoxon rank sum test can be considered a non-parametric equivalent of the unpaired t-test. It is used to test the hypothesis that two independent samples have come from the same population. Because it is non-parametric, it makes only limited assumptions about the distribution of the data. It assumes that the shape of the distribution is similar in the two groups. This is of particular relevance if the test is to be used as evidence that the median is significantly different between the groups.

The test ranks all the data from both groups. The smallest value is given a rank of 1, the second smallest is given a rank of 2, and so on. Where values are tied, they are given an average rank. The ranks for each group are added together (hence the term rank sum test). The sums of the ranks is compared with tabulated critical values to generate a p value. In a Wilkoxon rank sum test, p, a function of X, Y, and $\alpha$, is the probability of observing a result equal or more extreme than the one using the data (X and Y) if the null hypothesis is true. The value of p indicates the significance for testing the null hypothesis that the populations generating the two independent samples, X and Y, are identical. X and Y are vectors but can have different lengths, i.e., the samples can have different number of elements. The alternative hypothesis is that the median of the X population is shifted from the median of the Y population by a non-zero amount. $\alpha$ is a given level of significance and is a scalar between zero and one. In some embodiment, the default value of $\alpha$ is set to 0.05. If p is near zero, the null hypothesis may be rejected.

In one embodiment, the PSSM approach of the present invention was compared to the standard method (e.g., Elbashir et al., 2001, Nature 411:494-8) for its performance in identifying siRNAs having high efficacy. The results obtained with three siRNAs selected by each method are shown in FIG. 3. siRNAs selected by the method using the PSSM showed better median efficacy (88% as compared to 78% for the standard method siRNA) and were more uniform in their performance. The minimum efficacy was greatly improved (75% as compared to 12% for the standard method). The distribution of silencing efficacies of siRNAs designed using the algorithm based on PSSM was significantly better than that of the siRNAs designed using the standard method for the same genes (p=0.004, Wilcoxon rank sum test).

5.1.3. Alternative Method for Evaluating Silencing Efficacy of siRNAS

Position-specific scoring matrix approaches are the preferred method of representing siRNA functional motifs, e.g., siRNA susceptible and resistant motifs. However the information represented by PSSMs can also be represented by other methods which also provide weights for base-composition at particular positions. This section provides such methods for evaluating siRNA functional motifs.

5.1.3.1. Methods Based on Sequence Windows

A common method of weighting base-composition at positions in a sequence is to tally the number of a particular base or set of bases in a "window" of sequence positions. Alternatively, the tally is represented as a percentage. The number of values of such a score, referred to as a window score, depends on the size of the window. For example, scoring a window of size 5 for G/C content may give values of 0, 1, 2, 3, 4 or 5; or 0%, 20%, 40%, 60%, 80% or 100%.

An alternative method of scoring a window is to calculate the duplex melting temperature or $\Delta G$ for the bases in that window. These thermodynamic quantities reflect the composition of all bases in the window as well as their particular order. It is readily apparent to one of skill in the art that these thermodynamic quantities directly depend on the base composition of each window, and are dominated by the G/C content of the window while showing some variation with the order of the bases.

Figure 1A:
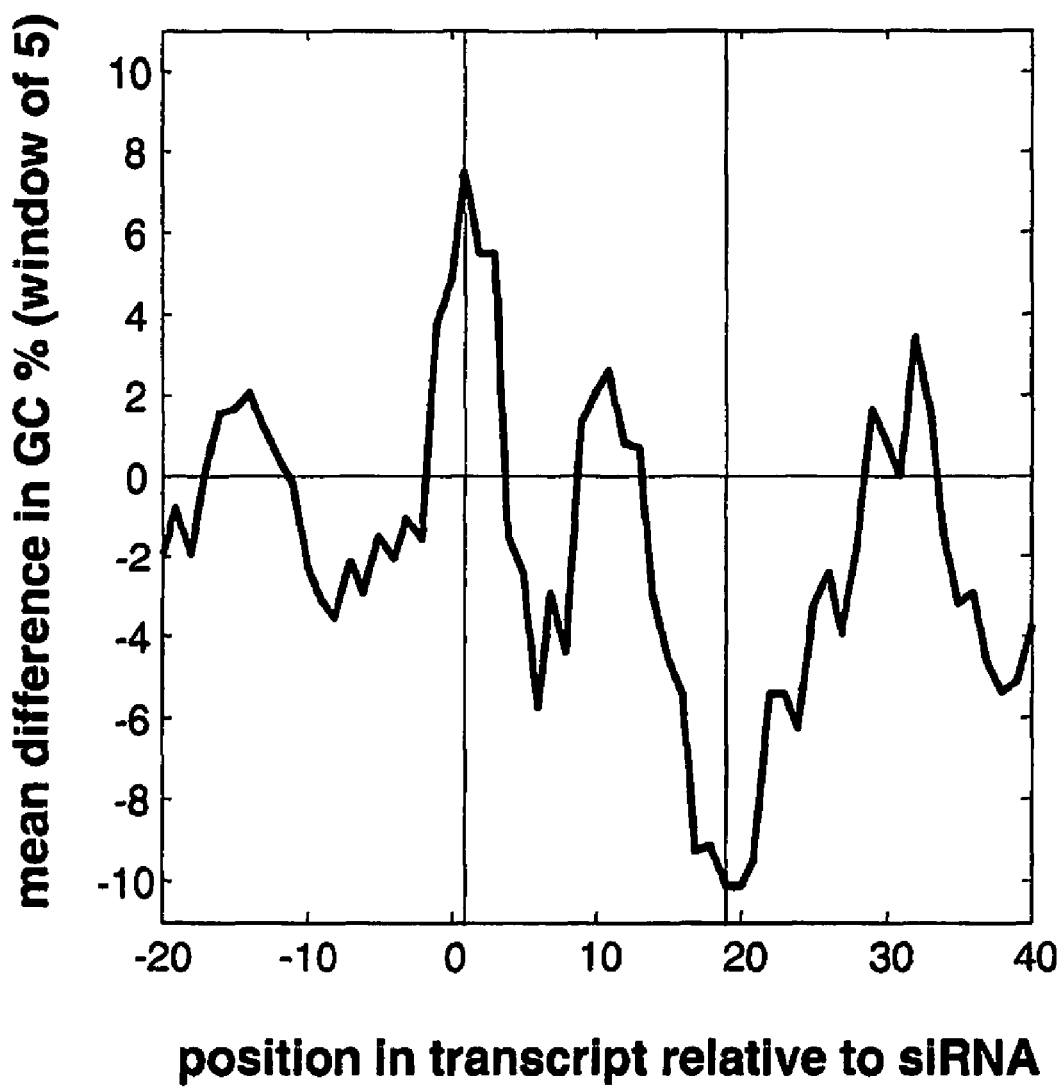
Figure 1B:
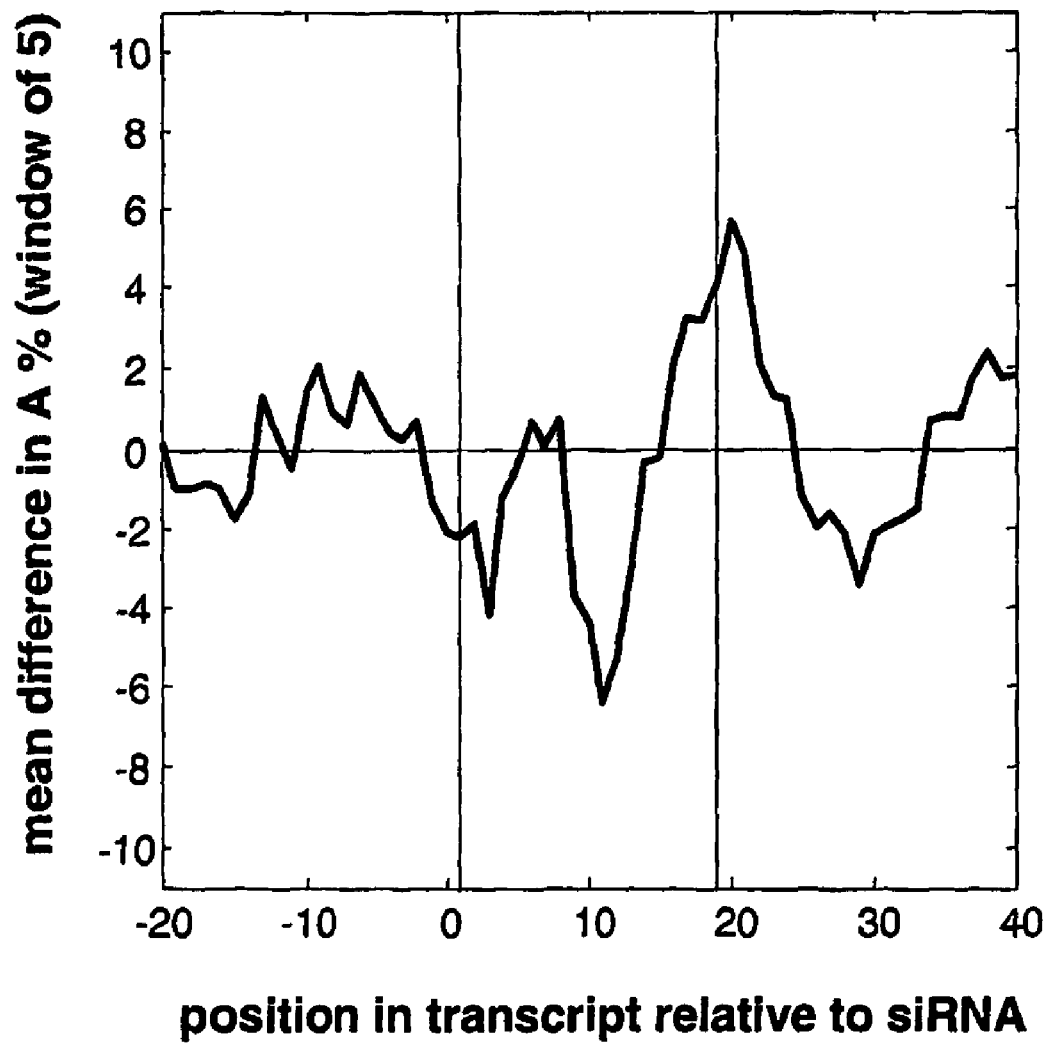
Figure 1C:
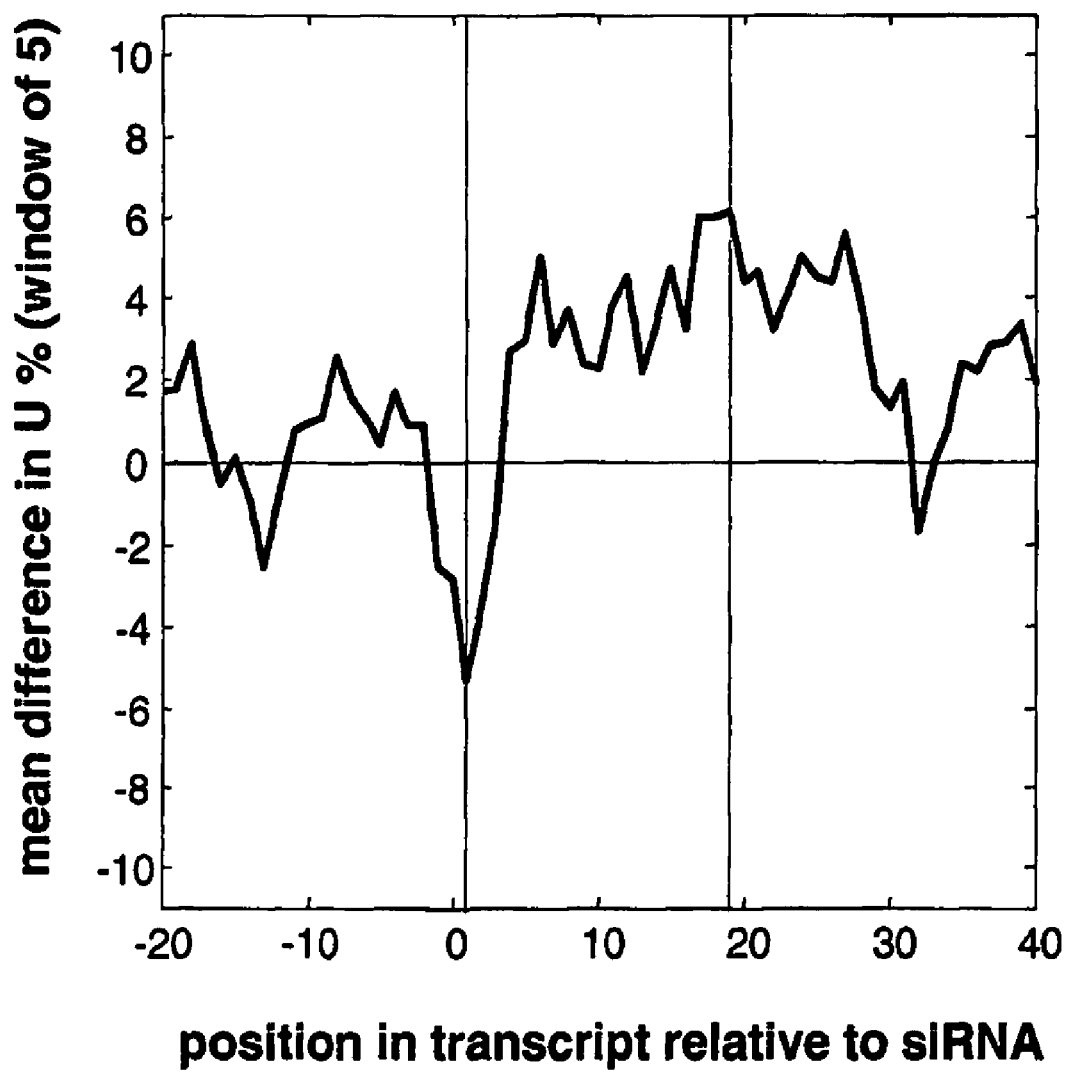

In one embodiment, the information represented by the base-composition differences, e.g., in FIGS. 1A, 1B and 1C, is represented by windows of base-composition corresponding to the positions to the peaks of increased or decreased composition of a particular base(s). These windows can be scored for content of the particular base(s), with increased or decreased base composition corresponding to sequences which are more or less functional or resistant for siRNA targeting. For example, a 5-base window of increased G/C content from base—1 to base 3 relative to the siRNA 19mer duplex, and a 16-base window of decreased G/C content from base 14 to base 29 relative to the siRNA 19mer duplex, can be used to represent some of the siRNA functional motif reflected in FIG. 1A.

The scores may be used directly as a classifier: in the example of a 5-base window, a 5-part classifier is automatically available. Scores can also be compared to a calculated or empirically derived threshold to use the window as a 2-part classifier. Windows can also be used in combination The scores of each sequence over multiple windows can be summed with or without normalization or weighting. In one embodiment, scores for each window are normalized by subtracting the mean score in a set of scores and then dividing by the standard deviation in the set of scores. In another embodiment, scores are weighted by the Pearson correlation coefficient obtained by comparing that window's score with the measured efficacy of a set of siRNAs. In another embodiment, scores are normalized, and then weighted before summation.

As an example of the use of windows to represent siRNA functional motifs, the following list of parameters was considered for prediction of siRNA efficacy:

1. Straight-forward parameters.

ATG_Dist—distance to the start codon.

STOP_Dist—distance to the end of the coding region

Coding_Percent—ATG_Dist as percentage of the length of coding region

End_Dist—distance to the end of the transcript

Total_Percent—start position as a percentage of the length of the transcript sequence.

2. Window-based parameters.

119 bases on the transcript sequence were considered (19mer plus 50 bases downstream and 50 bases upstream). Windows of sizes 3-10 were examined for each position from the beginning to the end of the 119-base chunk. The following items were counted for each window position:

a. Numbers of bases: A, C, G, or U.

b. Numbers of pairs of bases: M (A or C), R (A or G), W (A or U), S (C or G), Y (C or U), and K (G or U).

c. Numbers of various ordered dimers: AC, AT, AG, MM, RY, KM, SW, etc.

d. The longest stretches of the above one base or two-base units.

3. Motif-based parameters.

These parameters are also based on the 119-base chunks. The letters include the bases (A, C, G, U) and pairs of bases (M, R, W, S, Y, K).

(1). Position-Specific one-mer, dimers, or trimers.

(2). Numbers of 1mers to 7mers in four large regions: 50 bases upstream, 19mer proper, 50 bases downstream, and the whole 119mer region.

4. Structural parameters.

The structural parameters are based on the following regions.

the 19mer oligo proper (prefix: proper)

the 20mer immediate upstream the oligo (prefix: up20)

the 40mer immediate upstream the oligo the 60mer immediate upstream the oligo the 20mer immediate downstream the oligo (prefix: down20)

the 40mer immediate downstream the oligo the 60mer immediate downstream the oligo Base-pairing predicted by RNAStructure was examined and the following parameters were calculated:

the count of bulge loops (parameter bulge)

the total bases in the bulge loops (bulge_b)

the count of internal loops (internal)

the total bases in the internal loops (internal_b)

the count of hairpins (hairpin)

the total bases in the hairpins (hairpin_b)

the count of other motif regions (other)

the total bases in the other motif regions (other_b)

the total paired bases (total_pairs_b)

the total non-paired bases (total_nonpairs_b)

the longest stretch of paired bases (longest_pairs_b)

the longest stretch of non-paired bases (longest_nonpairs_b)

Thus, a total of 12*7=84 parameters were computed about the secondary structure motifs for each siRNA.

5. Parameters on off-target predictions.

10 different parameters were computed using the weighted FASTA score discussed in Section 5.2., the minimax score and the predicted duplex $\Delta G$ discussed in Section 5.4, using different conditions.

Parameters were normalized and weighted by the Pearson correlation coefficient of the scores with the silencing efficacy of the siRNAs examined. Various methods were used to select the parameters with the greatest predictive power for siRNA efficacy; the various methods agreed on the selection 1750 parameters. 1190 of these are window-based base composition parameters, 559 are motif-based base composition parameters, and only 1 structural parameter was selected. No other parameters were selected

5.1.3.2. Sequence Family Scoring Methods

Sequence consensus patterns, hidden Markov models and neural networks can also be used to represent siRNA functional motifs, e.g., siRNA susceptible or resistant motifs as an alternative to PSSMS.

First, an siRNA functional motifs, e.g., siRNA susceptible or resistant motif can be understood as a loose consensus sequence for a family of distantly related sequences—e.g. the family of functional siRNA target sites. Scoring sequences for similarity to a family consensus is well known in the art (Gribskov, M., McLachlan, A. D., and Esienberg, D. 1987. Profile analysis: detection of distantly related proteins. *PNAS* 84:4355-4358; Gribskov, M., Luthy, R., and Eisenberg, D. 1990. Profile analyisis. *Meth. Enzymol.* 183:146-159). Such scoring methods are most commonly referred to as "profiles", but may also be referred to as "templates" or "flexible patterns" or similar terms. Such methods are more or less statistical descriptions of the consensus of a multiple sequence alignment, using position-specific scores for particular bases or amino acids as well as for insertions or deletions in the sequence. Weights can be derived from the degree of conservation at each position. A difference between consensus profiles and PSSMs as the term is used in this text is that spacing can be flexible in consensus profiles: discontinuous portions of an siRNA functional motifs, e.g., siRNA susceptible or resistant motif can be found at varying distances to each other, with insertions or deletions permitted and scored as bases are.

Profile hidden Markov models are statistical models which also represent the consensus of a family of sequences. Krogh and colleagues (Krogh, A., Brown, M., Mian, I. S., Sjolander, K. and Haussler, D. 1994. Hidden Markov models in computational biology: Applications to protein modeling. *J. Mol Biol*.235:1501-1531) applied HMM techniques to modeling sequence profiles, adopting techniques from speech recognition studies (Rabiner, L. R. 1989. A tutorial on hidden Markov models and selected applications to speech recognition. *Proc. IEEE* 77:257-286). The use of hidden Markov models for analysis of biological sequences is now well known in the art and applications for hidden Markov model calculation are readily available; for example, the program HMMER (hmmer.wustl.edu).

Profile hidden Markov models differ from consensus profiles as described above in that profile hidden Markov models have a formal probabilistic basis for setting the weights for each base, insertion or deletion at each position. Hidden Markov models can also perform the alignment of unknown sequences for discovery of motifs as well as determining position-specific weights for said motifs, while consensus profiles are generally derived from previously aligned sequences.

Consensus profiles and profile hidden Markov models can assume that the base composition at a particular position is independent of the base composition of all other positions. This is similar to the random-hill-climbing PSSMs of this invention but distinct from the windows and curve model PSSMs.

To capture dependency of base composition at a particular position on the composition of neighboring positions, Markov models can be used as fixed-order Markov chains and interpolated Markov models. Salzberg and colleagues applied interpolated Markov models to finding genes in microbial genomes as an improvement over fixed-order Markov chains (Salzberg, S. L., Delcher, A. L., Kasif, S., and White, O. 1998. *Nucl. Acids Res.* 26:544-548). A fixed-order Markov chain predicts each base of a sequence as a function of a fixed number of bases preceding that position. The number of proceeding bases used to predict the next is known as the order of the Markov chain. Interpolated Markov models use a flexible number of preceeding bases to predict the base composition at a particular position. This permits training on smaller sequence sets. Sufficient predictive data may be available for n-mers of various lengths in a training set such that some predictions of succeeding bases can be made, while insufficient data may be available for all oligomers at any fixed length. Interpolated Markov models thus have more freedom to use preferable longer oligomers for prediction than fixed-order Markov chains, when said long oligomers are sufficiently frequent in the training set. Interpolated Markov models employ a weighted combination of probabilities from a plurality of oligomer lengths for classification of each base.

Fixed-order Markov chains and interpolated Markov models can represent siRNA functional motifs, e.g., siRNA susceptible or resistant motifs in terms of the dependency of the base-composition at a particular position on the composition of the preceding positions. An interpolated Markov model building process will discover the oligomers most predictive of siRNA functional or nonfunctional motifs.

Neural networks are also employed to score sequences for similarity to a family of sequences. A neural network is a statistical analysis tool used to build a model through an iterative leaning process. The trained network will then perform a classification task, dependent upon the desired output and the training input initially associated with that output. Typically a neural network program or computational device is supplied with a training set of sequences and sets up a state representing those sequences. The neural network is then tested for performance on a test set of sequences. Neural networks can be used to predict and model siRNA functional motifs, e.g., siRNA susceptible and resistant motifs. A disadvantage of neural networks is that the actual sequence features of a motif can be difficult or impossible to determine from examination of the state of the trained network.

5.1.4. Methods of Identifying Sequence Motifs in a Gene for Targeting by an siRNA The invention provides a method for identifying one or more sequence motifs in a transcript which are siRNA-susceptible or -resistant motifs. The corresponding functional or unfunctional siRNAs are thereby also provided by the method. In one embodiment, the sequence region of interest is scanned to identify sequences that match the profile of a functional motif. In one embodiment, a plurality of possible siRNA sequence motifs comprises siRNA sequence motifs tiled across the region at steps of a predetermined base intervals are evaluated to identify sequences that matched the profile. In a preferred embodiment, steps of 1, 5, 10, 15, or 19 base intervals are used. In a preferred embodiment, the entire transcript sequence is scanned. A score is calculated for each different sequence motif using a PSSM as described in Sections 5.1.1.-5.1.3. The sequences are then ranked according to the score. One or more sequences are then selected from the rank list. In one embodiment, siRNA sequence motifs having the highest scores are selected as siRNA-susceptible motifs. In another embodiment, siRNA sequence motifs having the lowest scores are selected as siRNA resistant motifs.

The inventors have discovered that the correlation between silencing efficacy and the base composition profiles of siRNA functional motifs may depend on one or more factors, e.g., the abundance of the target transcript. For example, the inventors have found that for silencing poorly-expressed genes. e.g., genes whose transcript levels are less than about 5 copies per cell, siRNA functional motifs having high GC content asymmetry at the two ends of the target sequence and having high GC content in the sequence regions flanking the target sequence have lower silencing efficiency than siRNA functional motifs having moderate GC content asymmetry at the two ends of the target sequence and low GC content in the flanking regions. The effect of target transcript abundance on silencing efficacy is illustrated in Example 6.

While not to be confirmed by any theory, the inventors reason that the silencing efficacy of a particular siRNA functional motif is a result of the interplay of a number of processes, including RISC formation and siRNA duplex unwinding, diffusion of the RISC and target mRNA, reaction of the RISC/target complex, which may include diffusion of the RISC along the target mRNA, cleavage reaction, and products dissociation, etc. Thus, the abundance of the transcript, the base composition profile of the siRNA, the base composition profile of the target sequence and flanking sequences, and the concentration of the siRNA and RISC in a cell may all affect silencing efficacy. Different processes may involve different sequence regions of an siRNA or siRNA sequence motif, i.e., different sequence regions of an siRNA or siRNA sequence motif may have different functions in transcript recognition, cleavage, and product release, siRNAs may be designed based on criteria that take one or more of such features into account. For example, bases near the 5' end of the guide strand are implicated in transcript binding (both on- and off-target transcripts), and have been shown to be sufficient for target RNA-binding energy. Weaker base pairing at the 5' end of the antisense strand (3' end of the duplex) encourages preferential interaction of the antisense strand with RISC, e.g., by facilitating unwinding of the siRNA duplex by a 5'-3' helicase component of RISC. A preference for U at position 10 of the sense strand of an siRNA has been associated with improved cleavage efficiency by RISC as it is in most endonucleases. Low GC content sequence flanking the cleavage site may enhance accessibility of the RISC/nuclease complex for cleavage, or release of the cleaved transcript, consistent with recent studies demonstrating that base pairs formed by the central and 3' regions of the siRNA guide strand provide a helical geometry required for catalysis. Thus, is the invention provides a method of identifying siRNA sequence motifs (and thus siRNAs) by obtaining siRNAs that have an optimal sequence composition in one or more sequence regions such that these siRNAs are optimal in one or more the siRNA functional processes. In one embodiment, the method comprises identifying siRNA sequence motifs whose overall sequence and/or different sequence regions have desired composition profiles. The method can be used to identify siRNAs motifs that have desired sequence composition in a particular region, thus are optimized for one functional process. The method can also be used to identify siRNAs that have desired sequence composition in a number of regions, thus are optimized for a number of functional processes.

In a preferred embodiment, a single siRNA functional profile, e.g., a profile as represented by a set of PSSMS, is obtained, e.g., by training with silencing efficacy data of a plurality of siRNAs that target genes having different transcript abundances using a method described in Section 5.1.2 or Section 5.1.3., and is used to evaluate siRNA sequence motifs in gene transcripts having abundances in all ranges. In one embodiment, the siRNA sequence motifs in gene transcripts having abundances in any range are evaluated based on the degree of similarity of their sequence base composition profiles to the profile or profiles represented by the set of PSSMS. In one embodiment, the PSSM scores of siRNA functional motifs for a gene of interest are obtained by a method described in Section 5.1.1. A predetermined reference value or reference range of values of the PSSM score is determined based on siRNAs that target genes having expression levels in different ranges. Methods for determining the reference value or range of reference value is described below. siRNA functional motifs in a particular gene are then ranked based on the closeness of their scores to the predetermined reference value or within the reference range. One or more siRNAs having scores closest to the predetermined value or within the reference range are then selected. In another embodiment, a predetermined reference value of the PSSM score or a reference range of the PSSM scores is used for genes having expression levels in a given range. The reference value or the reference range is determined based on siRNAs that target genes having expression levels in the range. siRNA functional motifs in a particular gene are then ranked based on the closeness of their scores to the predetermined reference value or within the reference range. One or more siRNAs having scores closest to the predetermined value or within the reference range are then selected.

The reference value or the reference range can be determined in various ways. In a preferred embodiment, correlation of PSSM scores of a plurality of siRNAs having one or more features, e.g., having particular efficiency in one or more siRNA functional processes, with silencing efficacy is evaluated. In a preferred embodiment, the feature is that the plurality of siRNAs targets poorly-expressed genes. The value of the score corresponding to maximum median silencing is used as the reference value. In a specific embodiment, the reference value is 0. One or more siRNAs having PSSM scores the closest to the reference score are selected.

In another embodiment, the range of scores corresponding to siRNAs having a given level of silencing efficacy, e.g., efficacy above 75%, is used as the range for the reference values. In one embodiment, effective siRNAs are found to have scores between −300 and +200 as long as the GC content in bases 2-7 is controlled. In a specific embodiment, a reference value of between −300 and +200 is used. One or more siRNAs having PSSM scores within the range are selected.

In another preferred embodiment, a particular score range within the range of PSSM scores of the plurality of siRNAs having one or more features, e.g., having particular efficiency in one or more siRNA functional processes, is used as the range of the reference value. In a preferred embodiment, the feature is that the plurality of siRNAs targets poorly-expressed genes. In one embodiment, a certain percentile in the range of PSSM scores is used as the range of the reference value, e.g., 90%, 80%, 70%, or 60%. In a specific embodiment, the combined PSSM score range in the training set has a maximum of 200, with 97% of the scores being 0 or below and 60% of the scores are below −300.

In still another preferred embodiment, a sum of scores from a plurality of sets of PSSMs (see Section 5.1.2) is used as the reference score. In a specific embodiment, the plurality of sets consists of the two sets of PSSMs described previously. The two sets of PSSMs differ in the base composition preferred for siRNAs, in particular with respect to the GC content of the 19mer and flanking sequences. With a combined score of 0, the PSSM sets are in balance in their preference for the siRNA.

In another preferred embodiment, in addition to the PSSM scores, the siRNA sequence motifs are also ranked according to GC content at positions corresponding to positions 2-7 of the corresponding siRNAs, and one or more siRNA sequence motifs that have a GC content approximately 0.15 to 0.5 (corresponding to 1-3 G or C) in the region are selected.

In still another preferred embodiment, siRNA sequence motifs having a G or C at the position corresponding to position 1 of the corresponding 19mer siRNA and a A or T at the position corresponding to position 19 of the corresponding 19mer siRNA are selected. In still another preferred embodiment, siRNAs motifs in which 200 bases on either side of the 19mer target region are not repeat or low-complexity sequences are selected.

In a specific embodiment, the siRNA sequence motifs selected in the following manner: (1) they are first ranked according to GC content at positions corresponding to positions 2-7 of the corresponding siRNAs, and one or sore siRNA sequence motifs that have a GC content approximately 0.15 to 0.5 (corresponding to 1-3 G or C) in the region are selected; (2) next, siRNA sequence motifs having a G or C at the position corresponding to position 1 of the corresponding 19mer siRNA and a A or T at the position corresponding to position 19 of the corresponding 19mer siRNA are selected; (3) siRNAs having PSSM scores in the range of −300 to 200 or most close to 0 are then selected; (4) number of off-target BLAST match less than 16 are then selected; and (5) siRNAs motifs in which 200 bases on either side of the 19mer target region are not repeat or low-complexity sequences are selected.

In another embodiment, a reference value or reference range for each of a plurality of different abundance ranges is determined. Selection of siRNA functional motifs in a gene of interest is achieved by using the appropriate reference value or reference range for the abundance range in which the gene of interest falls. In one embodiment, the plurality of different abundance ranges consists of two ranges: below about 3-5 copies per cell, corresponding to poorly-expressed genes, and above 5 copies per cell, corresponding to highly-expressed genes. The reference value or reference range can be determined for each abundance range using any one of the methods described above.

In another embodiment, a plurality of siRNA functional motif profiles are determined for a plurality of different transcript abundance ranges. Each such profile is determined based on silencing efficacy data of siRNAs that target genes having expression levels in a given range, i.e., genes whose transcript abundances fall within a given range, using a method described in Sections 5.1.2 and 5.1.3., supra. In one embodiment, a set of one or more PSSMs for genes having expression levels in a given range are trained as described in Section 5.1.2.using siRNAs that target genes having expression levels in the range. The PSSMs are then used for identifying siRNA functional motifs in a target gene whose expression level falls in the range, e.g., by ranking according to the PSSM scores obtained using a method described in Section 5.1.1. In a preferred embodiment, the transcript abundance ranges are divided into two ranges: below about 3-5 copies per cell, corresponding to poorly-expressed genes, and above 5 copies per cell, corresponding to highly-expressed genes. Two sets of PSSMs are obtained, one for each abundance range. siRNA functional motifs in a gene of interest can be identified using the set of PSSMs that is appropriate for the abundance of the gene of interest.

The invention also provides methods for evaluating the silencing efficacies of siRNA sequence motifs under different siRNA concentrations. For example, the methods described above for evaluating silencing efficacy of siRNA sequence motifs in transcripts having different abundances can be used for such purposes by replacing the abundance parameter with the concentration parameter. In one embodiment, a plurality of siRNA functional motif profiles are determined for a plurality of different siRNA concentration ranges. Each such profile can be determined based on silencing efficacy data of different concentration of siRNAs targeting genes having a different expression level or having an expression level in a different range. In one embodiment, such profiles are determined for transcripts having a given abundance or having a abundance within a range of abundances. Each such profile can be determined based on silencing efficacy data of different concentration of siRNAs targeting genes having the expression level or having an expression level in the range. In one embodiment, one or more PSSMs for a given siRNA concentration range are trained based on silencing efficacy data of siRNAs having a concentration in the range. The PSSMs can then be used for selecting siRNAs that have high efficiency at a concentration that falls in the concentration range. In a preferred embodiment, the transcript abundance ranges is selected to be below 5 copies per cell. In another embodiment, the transcript abundance ranges is selected to be above 5 copies per cell. The invention thus provides a method for selecting one or more siRNA functional motifs for targeting by siRNAs of a given concentration.

The methods can be used for identifying one or more siRNA functional motifs that can be targeted by siRNAs of a given concentration with desired silencing efficacy. The given concentration is preferably in the low nanomolar to sub-nanomolar range, more preferably in the picomolar range. In specific embodiments, the given concentration is 50 nmol, 20 nmol, 10 nmol, 5 nmol, 1 nmol, 0.5 nmol, 0.1 nmol, 0.05 nmol, or 0.01 nmol. The desired silencing efficacy is at least 50%, 75%, 90%, or 99% under a given concentration. Such methods are particularly useful for designing therapeutic siRNAs. For therapeutic uses, it is often desirable to identify siRNAs that can silence a target gene with high efficacy at sub-nanomolar to picomolar concentrations. The invention thus also provides a method for design of therapeutic siRNAs.

The invention also provides a method for determining if a gene is suitable for targeting by a therapeutic siRNA. In one embodiment, the desired siRNA concentration and the desired silencing efficacy are first determined. A plurality of possible siRNA sequence motifs in the transcript of the gene is evaluated using a method of this invention. One or more siRNA sequence motifs that exhibit the highest efficacy, e.g., having PSSM scores satisfying the above described criterion or criteria, are identified. The gene is determined as suitable for targeting by a therapeutic siRNA if the one or more siRNA sequence motifs can be targeted by the corresponding siRNAs with silencing efficacy above or equal to the desired efficacy. In one embodiment, the plurality of possible siRNA sequence motifs comprises siRNA sequence motifs that span or are tiled across a part of or the entire transcript at steps of a predetermined base intervals, e.g. at steps of 1, 5, 10, 15, or 19 base intervals. In a preferred embodiment, successive overlapping siRNA sequence motifs are tiled across the entire transcript sequence. In another preferred embodiment, successive overlapping siRNA sequence motifs tiled across a region of or the entire transcript sequence at steps of 1 base intervals.

5.2. Methods of Identifying Off-Target Genes of an siRNA

The invention also provides a method of identifying off-target genes of an siRNA. As used herein, an "off-target" gene is a gene which is directly silenced by an siRNA that is designed to target another gene (see, International application No. PCT/US2004/015439 by Jackson et al., filed on May 17, 2004, which is incorporated herein by reference in its entirety). An off-target gene can be silenced by either the sense strand or the antisense strand of the siRNA.

5.2.1. Sequence Match Profile and Off-Target Silencing

Microarray experiments suggest that most siRNA oligos result in downregulation of off-target genes through direct interactions between an siRNA and the off-target transcripts. While sequence similarity between dsRNA and transcripts appears to play a role in determining which off-target genes are affected, sequence similarity searches, even combined with thermodynamic models of hybridization, are insufficient to predict off-target effects accurately. However, alignment of off-target transcripts with offending siRNA sequences reveals that some base pairing interactions between the two appear to be more important than others (FIG. 6).

The invention provides a method of identifying potential off-target genes of an siRNA using a PSSM that describes the sequence match pattern between an siRNA and a sequence of an off-target gene (pmPSSM). In one embodiment, the sequence match pattern is represented by weights of different positions in an siRNA to match the corresponding target positions in off-target transcripts $\{P_i\}$, where $P_i$ is the weight of a match at position i, i=1, 2, ..., L, where L is the length of the siRNA. Such a match pattern can be determined based on the frequency with which each position in an siRNA is found to match affected off-target transcripts identified as direct targets of the siRNA by simultaneous downregulation with the intended target through kinetic analysis of expression profiles (see, International application No. PCT/US2004/015439 by Jackson et al., filed on May 17, 2004). A pmPSSM can be $\{E_{i,j}\}$, where $E_i=P_i$ if position i in the alignment is a match and $E_i=(1-P_i)/3$ if position i is a mismatch. An exemplary $\{P_i\}$ for a 19mer siRNA sequence is plotted in FIG. 7 and listed in Table I.

TABLE I

Weights of an exemplary pmPSSM for 21 nt siRNAs having a
19 nt duplex region

| | |
|---|---|
| 1 | 0.25 |
| 2 | 0.32 |
| 3 | 0.32 |
| 4 | 0.46 |
| 5 | 0.39 |
| 6 | 0.38 |
| 7 | 0.36 |
| 8 | 0.45 |

TABLE I-continued

Weights of an exemplary pmPSSM for 21 nt siRNAs having a 19 nt duplex region

| | |
|---|---|
| 9 | 0.61 |
| 10 | 0.47 |
| 11 | 0.76 |
| 12 | 0.96 |
| 13 | 0.94 |
| 14 | 0.81 |
| 15 | 0.92 |
| 16 | 0.94 |
| 17 | 0.89 |
| 18 | 0.78 |
| 19 | 0.58 |

In one embodiment, sequence match pattern of off-target transcripts are used to obtain a pmPSSM. Off-target genes of an siRNA can be identified using a method disclosed in International application No. PCT/US2004/015439 by Jackson et al., filed on May 17, 2004, which is incorporated herein by reference in its entirety. For example, off-target genes of an siRNA are identified based on silencing kinetics (see, e.g., International application No. PCT/US2004/015439 by Jackson et al., filed on May 17, 2004). A pmPSSM can then be generated using the frequency of matches found for each position. In one embodiment, the alignment shown in FIG. 6 and similar data for other siRNAs were combined to generate the exemplary position-specific scoring matrix for use in predicting off-target effects.

The degree of match between an siRNA and a sequence in a transcript can be evaluated with the pmPSSM using a score (also referred to as a position match score, pmScore) according to the following equation $$\text{Score} = \sum_{i=1}^{L} \ln(E_i/0.25) \quad (6)$$

where L is the length of the alignment, e.g., 19. A pmScore above a given threshold identifies the sequence as a potential off-target sequence.

Figure 8:
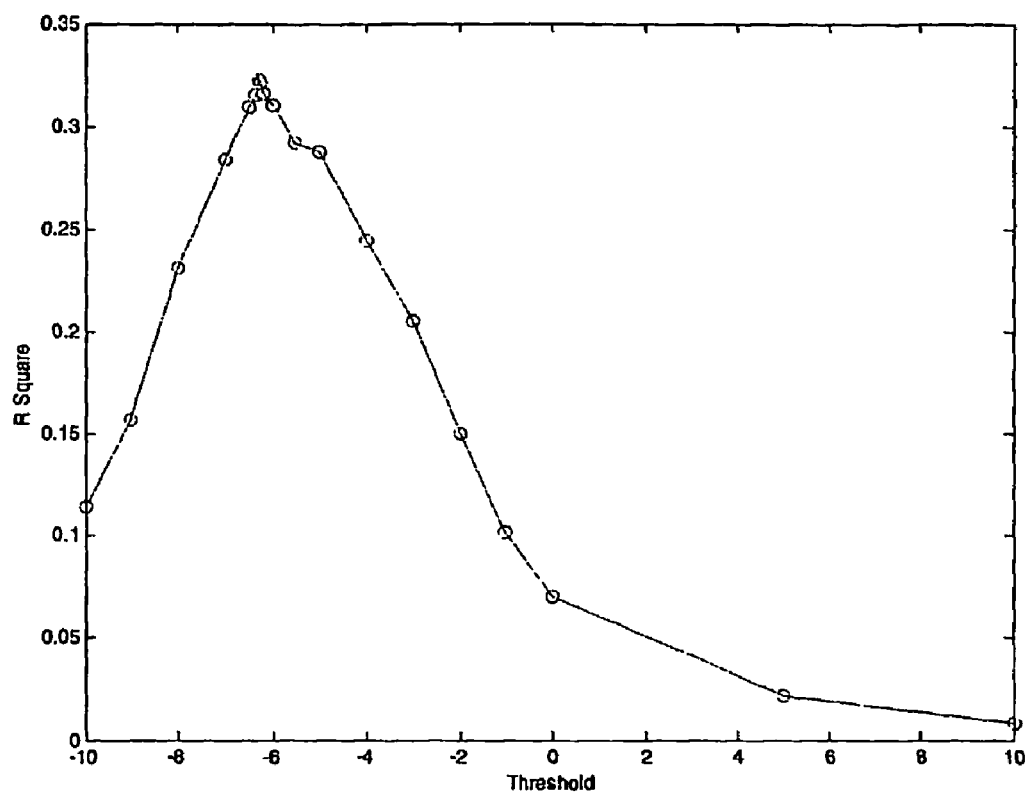
FIG. 8 shows optimization of the threshold score for predicting off-target effects of siRNAs. The $R^2$ values result from the correlation of number of alignments scoring above the threshold with number of observed off-target effects.

The inventors have discovered that for a given siRNA the number of alignments with a score above a threshold is predictive of the number of observed off-target effects. The score threshold can be optimized by maximizing the correlation between predicted and observed numbers of off-target effects (FIG. 8). The optimized threshold can be used to favor selection of siRNAs with relatively small numbers of predicted off-target effects.

5.2.2. Method of Identifying Off-Target Genes of an siRNA

Off-target genes of a given siRNA can be identified by first identifying off-target transcript sequences that align with the siRNA. Any suitable method for pair-wise is alignment, such as but not limited to BLAST and FASTA, can be used. The position-specific scoring matrix is then used to calculate position match scores for these alignments.

In a preferred embodiment, alignments are established with a low-stringency FASTA search and the score for each alignment is calculated according to Eq. 6. A score above a given threshold identifies the transcript comprising the sequence as a potential off-target gene.

The invention thus also provides a method of evaluating the silencing specificity of an siRNA. In one embodiment, potential off-target genes of the siRNA are identified. The total number of such off-target genes in the genome or a portion of the genome is then used as a measure of the silencing specificity of the siRNA.

5.3. Method for Prediction of Strand Preference of siRNAS

The invention provides a method for predicting strand preference and/or the efficacy and specificity of siRNAs based on position specific base composition of the siRNAs. The inventors have discovered that an siRNA whose base composition PSSM score (see Section 5.1.) is greater than the base composition PSSM (G/C PSSM) score of its reverse complement is predicted to have an antisense strand that is more active than its sense strand. In contrast, an siRNA whose base composition PSSM score is less than the base composition PSSM score of its reverse complement is predicted to have a sense strand that is more active than its antisense strand.

It has been shown that increased efficacy of an siRNA in silencing a sense-identical target gene corresponds to greater antisense strand activity and lesser sense strand activity. The inventors have discovered that base composition PSSMs can be used to distinguish siRNAs with strong sense strands as bad siRNAs from siRNAs with weak sense strands as good siRNAs. The reverse complements of bad siRNAs were seen to be even more different from the bad siRNAs themselves than are good siRNAs. On the average, the reverse complements of bad siRNAs had even stronger G/C content at the 5' end than the good siRNAs did and were similar in G/C content to good siRNAs at the 3' end. In contrast, the reverse complements of good siRNAs were seen to be substantially more similar to bad siRNAs than the good siRNAs were. On the average, the reverse complements of good siRNAs hardly differed from bad siRNAs in G/C content at the 5' end and were only slightly less G/C rich than bad siRNAs at the 3' end. These results indicate that the G/C PSSMS distinguish siRNAs with strong sense strands as bad siRNAs from siRNAs with weak sense strands as good siRNAs.

FIG. 14A shows the difference between the mean G/C content of the reverse complements of bad siRNAs with the mean G/C content of the bad siRNAs themselves, within the 19mer siRNA duplex region. The difference between the mean G/C content of good and bad siRNAs is shown for comparison. The curves are smoothed over a window of 5 (or portion of a window of 5, at the edges of the sequence).

FIG. 14B shows the difference between the mean G/C content of the reverse complements of good siRNAs with the mean G/C content of bad siRNAs, within the 19mer siRNA duplex region. The difference between the mean G/C content of good and bad siRNAs is shown for comparison. The curves are smoothed over a window of 5 (or portion of a window of 5, at the edges of the sequence).

In FIG. 15, siRNAs were binned by measured silencing efficacy, and the frequency of sense-active calls by the 3'-biased method and G/C PSSM method was compared. Although these techniques are based on different analyses, the agreement is quite good. Both show that a higher proportion of low-silencing siRNAs vs. high-silencing siRNAs are predicted to be sense active. The correlation coefficient for (siRNA G/C PSSM score—reverse complement G/C PSSM score) vs. $\log_{10}$(sense-identity score/antisense-identity score) is 0.59 for the set of 61 siRNAs binned in FIG. 15.

Thus, in one embodiment, the invention provides a method for predicting strand preference, i.e., which of the two strands is move active, of siRNAs based on position specific base composition of the siRNAs. In one embodiment, the method comprises evaluating the strand preference of an siRNA in gene silencing by comparing the base compositions of the sense and the antisense strands of the siRNA. In another embodiment, the method comprises evaluating the strand preference of an siRNA in gene silencing by comparing the base compositions of the sense and the reverse complement of the target sequence of the siRNA.

In one embodiment, the sequence of the antisense strand of an siRNA or the reverse complement of the target sequence of the siRNA in a transcript are compared with the target sequence using a PSSM approach (see Section 5.1.). An siRNA and its reverse complement are scored using a PSSM based on a smoothed G/C content difference between good and bad siRNAs within the duplex region as the weight matrix. In one embodiment, a base composition weight matrix as described by FIG. 14A is used as the weight matrix. In a preferred embodiment, the PSSM score of each strand can be calculated as the dot product of the siRNA strand G/C content with the G/C content difference matrix (as the score calculation method of curve model PSSMs). In one embodiment, an siRNA is identified as sense-active if its reverse complement PSSM score exceeded its own PSSM score.

In another embodiment, the 3'-biased method as described in International application No. PCT/US2004/015439 by Jackson et al., filed on May 17, 2004, which is incorporated herein by reference in its entirety, is used in conjunction with the PSSM score to determining the strand preference of an siRNA. In such an embodiment, an siRNA is identified as sense-active by the 3'-biased method of strand preference determination if the antisense-identical score exceeded the sense-identical score.

The method based on comparison of G/C PSSMs of siRNAs and their reverse complements for prediction of strand bias was tested by comparison with estimation of strand bias from siRNA expression profiles by the 3'-biased method.

The invention also provides a method for identifying siRNAs having good silencing efficacy. The method comprises identifying siRNAs having dominant antisense strand activity ("antisense-active" siRNAs) as siRNAs having good silencing efficacy and specificity (for silencing sense-identical target). In one embodiment, the method described in Section 5.1. is used to identify siRNAs having good sense strand (i.e., identifying siRNAs having good silencing efficacy towards an antisense-identical target). Such siRNAs are then eliminated from uses in silencing sense-identical targets. The method can also be used to eliminate siRNAs with dominant sense strand activity ("sense-active" siRNAs) as siRNAs having less efficacy and specificity for silencing sense-identical targets. In one embodiment, the method described in International application No. PCT/US2004/015439 by Jackson et al., filed on May 17, 2004, which is incorporated herein by reference in its entirety, is used to determine strand preference of an siRNA.

The reverse complements of bad siRNAs, on the average, appear to have a GC content profile which differs from that of bad siRNAs in the same manner as the GC content profile of good siRNAs differs from that of bad siRNAs. However, the reverse complements of bad siRNAs show even more extreme differences from bad siRNAs than do the good siRNAs.

This observation is in accord with the evidence in siRNA expression profiles that many bad siRNAs have active sense strands.

The combination of data and analysis thus suggests that the reverse complements of bad siRNAs form an alternative, or perhaps even more advantageous, model for effective siRNAs than the good siRNAs do. Thus, the invention also provides a method for selecting siRNAs based on the base composition of the sequence of a reverse complement of the sense strand of the siRNAs. In one embodiment, a plurality of different siRNAs designed for silencing a target gene in an organism at a different target sequence in a transcript of the target gene is ranked according to positional base composition of the reverse complement sequences of their sense strands. One or more siRNAs whose reverse complement sequences' positional base composition matches the positional base composition of desired siRNAs can then be selected. Preferably, the ranking of siRNAs is carried out by first determining a score for each different siRNA using a position-specific score matrix. The siRNAs are then ranked according to the score. Any method described in Section 5.1., supra, can be used to score reverse complement sequences. In one embodiment, for siRNAs that have a nucleotide sequence of L nucleotides in the duplex region, L being an integer, the position-specific score matrix comprises a difference in probability of finding nucleotide G or C at sequence position k between reverse complement of a first type of siRNA and reverse complement of a second type of siRNA designated as $w_k$, k=1, ..., L. The score for each reverse complement is calculated according to equation $$\text{Score} = \sum_{k=1}^{L} w_k \qquad (7)$$

The first type of siRNA can consist of one or more siRNAs having silencing efficacy no less than a first threshold, e.g., 75%, 80% or 90% at a suitable dose, e.g., 100 nM, and the second type of siRNA can consist of one or more siRNAs having silencing efficacy less than a second threshold, e.g., 25%, 50%, or 75% at a suitable dose, e.g., 100 nM. In a preferred embodiment, the difference in probability is described by a sum of Gaussian curves, each of said Gaussian curves representing the difference in probability of finding a G or C at a different sequence position.

The methods of this invention can also be applied to developing models, e.g., PSSMs, of siRNA functional motifs by training position-specific scoring matrices to distinguish between bad siRNAs and their reverse complements (see, e.g., Section 5.1.). A restriction in this analysis is that the reverse complements of bad siRNAs have no designated targets. Thus, in one embodiment, position-specific scoring matrices of 19mer siRNA duplex sequences are trained to distinguish between bad siRNAs and their reverse complements.

Flanking sequence training can be performed on off-target genes in the case of distinguishing between bad siRNAs and their reverse complements, as well as in the case of distinguishing between any two groups of siRNAs. In other words, the off-target activity of siRNAs can be hypothesized to have the same flanking sequence requirements as the on-target activity, as the same RNA-protein complexes are thought to be involved in both processes.

Thus, if the methods of the off-target application are used to identify genes directly down-regulated by an siRNA (i.e. through kinetic analysis of down-regulation to identify a group of genes down-regulated with the same half-life as the intended target), the regions flanking the alignment of the siRNA with the directly regulated off-target genes can be used to train and test models of flanking sequence requirements. These models can be developed by any of the methods of this invention: random hill-climbing PSSMs, curve-model PSSMs, good-bad difference frequency matrices, good-composition frequency matrices, and/or bad-composition frequency matrices, etc.

5.4. Methods of Designing siRNAS for Gene Silencing

The invention provides a method for designing siRNAs for gene silencing. The method can be used to design siRNAs that have full sequence homology to their respective target sequences in a target gene. The method can also be used to design siRNAs that have only partial sequence homology to a target gene. Methods and compositions for silencing a target gene using an siRNA that has only partial sequence homology to its target sequence in a target gene is disclosed in International application No. PCT/US2004/015439 by Jackson et al., filed on May 17, 2004, which is incorporated herein by reference in its entirety. For example, an siRNA that comprises a sense strand contiguous nucleotide sequence of 11-18 nucleotides that is identical to a sequence of a transcript of the target gene but the siRNA does not have full length homology to any sequences in the transcript may be used to silence the transcript Such contiguous nucleotide sequence is preferably in the central region of the siRNA molecules. A contiguous nucleotide sequence in the central region of an siRNA can be any continuous stretch of nucleotide sequence in the siRNA which does not begin at the 3' end. For example, a contiguous nucleotide sequence of 11 nucleotides can be the nucleotide sequence 2-12, 3-13, 4-14, 5-15, 6-16, 7-17, 8-18, or 9-19. In preferred embodiments, the contiguous nucleotide sequence is 11-16, 11-15, 14-15, 11, 12, or 13 nucleotides in length. Alternatively, an siRNA that comprises a 3' sense strand contiguous nucleotide sequence of 9-18 nucleotides which is identical to a sequence of a transcript of the target gene but which siRNA does not have full length sequence identity to any contiguous sequences in the transcript may also be used to silence the transcript. A 3' 9-18 nucleotide sequence is a continuous stretch of nucleotides that begins at the first paired base, i.e., it does not comprise the two base 3' overhang. In preferred embodiments, the contiguous nucleotide sequence is 9-16, 9-15, 9-12, 11, 10, or 9 nucleotides in length.

In preferred embodiments, the method of Section 5.1 is used for identifying from among a plurality of siRNAs one or more siRNAs that have high silencing efficacy. In one embodiment, each siRNA in the plurality of siRNAs is evaluated for silencing efficacy by base composition PSSMs. In one embodiment, this step comprises calculating one or more PSSM scores for each siRNA. The plurality of siRNAs are then ranked based on the score, and one or more siRNAs are selected using a method described in Section 5.1.4.

In other preferred embodiments, the method of Section 5.2 is used for identifying from among a plurality of siRNAs one or more siRNAs that have high silencing specificity. In one embodiment, alignments of each siRNA with sequences in each of a plurality of non-target transcripts are identified and evaluated with the pmPSSM approach (see Section 5.2.). A pmScore is calculated for each of the alignments. A pmScore above a given threshold identifies a sequence as a potential off-target sequence. Such a pmScore is also termed an alignment score. For example, when FASTA is used for the alignment, a pmScore can be a weighted FASTA alignment score. The transcript that comprises the potential off-target sequence is identified as a potential off-target transcript The total number of such off-target transcripts in the genome or a portion of the genome is used as a measure of the silencing specificity of the siRNA. One or more siRNAs having less off-target transcripts may then be selected.

The siRNAs having the desired levels of efficacy and specificity for a transcript can be further evaluated for sequence diversity. In this disclosure, sequence diversity is also referred to as "sequence variety" or simply "diversity" or "variety." Sequence diversity can be represented or measured based on some sequence characteristics. The siRNAs can be selected such that a plurality of siRNAs targeting a gene comprises siRNAs exhibiting sufficient difference in one or more of such diversity characteristics.

Preferably the sequence diversity characteristics used in the method of the invention are quantifiable. For example, sequence diversity can be measured based on GC content, the location of the siRNA target sequence along the length of the target transcript, or the two bases upstream of the siRNA duplex (i.e., the leading dimer, with 16 different possible leading dimers). The difference of two siRNAs can be measured as the difference between values of a sequence diversity measure. The diversity or variety of a plurality of siRNAs can be quantitatively represented by the minimum difference or spacing in a sequence diversity measure between different siRNAs in the plurality.

In the siRNA design method of the invention, the step of selection of siRNAs for diversity or variety is also referred to as a "de-overlap" step. In a preferred embodiment, for a sequence diversity measure that is quantifiable, the de-overlapping selects siRNAs having differences of a sequence diversity measure between two siRNAs above a given threshold. For example, de-overlapping by position establishes a minimum distance between selected oligos along the length of the transcript sequence. In one embodiment, siRNAs positioned at least 100 bases apart in the transcript are selected. De-overlapping by GC content establishes a minimum difference in GC content. In one embodiment, the minimum difference in GC content is 1%, 2% or 5%. De-overlapping by leading dimers establishes the probability of all or a portion of the 16 possible leading dimers among the selected siRNAs. In one embodiment, each of the 16 possible dimers is assigned a score of 1-16, and a 0.5 is used to selected all possible leading primer with equal probability.

In some embodiments, the candidates are preferably de-overlapped on GC content, with a minimum spacing of 5%, a maximum number of duplicates of each value of GC % of 100 and at least 200 candidates selected; more preferably they are de-overlapped on GC content with a minimum spacing of 5%, a maximum number of duplicates of each value of GC % of 80 and at least 200 candidates selected; and still more preferably they are de-overlapped on GC content with a minimum spacing of 5%, a maximum number of duplicates of each value of GC % of 60 and at least 200 candidates selected.

siRNAs can be further selected based additional selection criteria.

In one embodiment, siRNAs targeting sequences not common to all documented splice forms are eliminated.

In another embodiment, siRNAs targeting sequences overlapping with simple or interspersed repeat elements are eliminated.

In still another embodiment, siRNAs targeting sequences positioned at least 75 bases downstream of the translation start codon are selected.

In another embodiment, siRNAs targeting sequences overlapping or downstream of the stop codon are eliminated. This avoids targeting sequences absent in undocumented alternative polyadenylation forms.

In still another embodiment, siRNAs with GC content close to 50% are selected. In one embodiment, siRNAs with GC % <20% and >70% are eliminated. In another embodiment, 10% <GC % <90%, 20% <GC % <80%, 25% <GC % <75%, 30% <GC % <70% are retained.

In still another embodiment, siRNAs targeting sequence containing 4 consecutive guanosine, cytosine, adenine or uracil residues are eliminated. In still another embodiment, siRNAs targeting a sequence with a guanine or cytosine residue at the first position in the 19mer duplex region at the 5' end are selected. Such siRNAs target sequences that are effectively transcribed by RNA polymerase III.

In still another embodiment, siRNAs targeting a sequence containing recognition sites for one or more given restriction endonucleases, e.g., XhoI or EcoRI restriction endonucleases, are eliminated. This embodiment may be used to select siRNAs sequences for construction of the shRNA vectors.

In still another embodiment, the siRNAs are evaluated for binding energy. See WO 01/05935 for an exemplary method of determining binding energy. In a preferred embodiment, the binding energy is evaluated by calculating the nearest-neighbor 21 mer $\Delta G$.

In still another embodiment, the siRNAs are evaluated for binding specificity. See WO 01/05935 for an exemplary method of determining binding specificity of a 21mer. In a preferred embodiment, the binding specificity is evaluated by calculating a 21mer minimax score against the set of unique sequence representatives of genes of an organism, e.g., the set of unique sequences representatives for each cluster of $Homo$ $sapiens$ Unigene build 161 (ncbi website with the extension "nlm.nih.gov/entrez/query.fcgi?db=unigene")

In still another embodiment, the method for predicting strand preference and/or the efficacy and specificity of siRNAs based on position specific base composition of the siRNAs as described in Section 5.3. can be used to evaluate the siRNA candidates.

Figure 9:
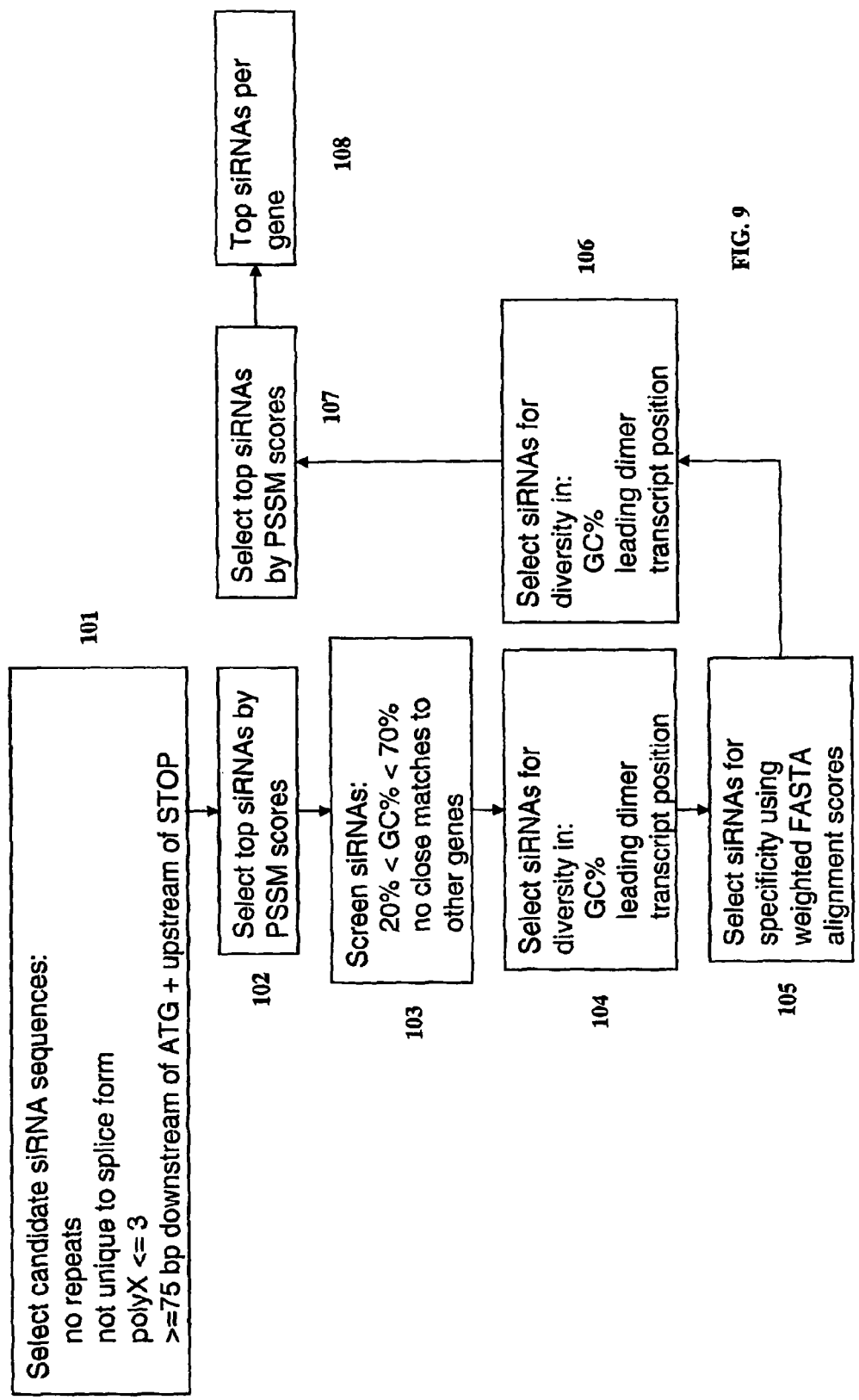
FIG. 9 shows a flow chart of an exemplary embodiment of the method for selecting siRNAs for use in silencing a gene.

A flow chart of an exemplary embodiment of the method used to select the siRNAs is shown in FIG. 9.

In step 101, siRNA sequences that target a transcript are selected. In one embodiment, all 19mer subsequences of the transcript are considered. The appropriate flanking sequences for each siRNA sequence are also obtained and considered. The siRNAs are evaluated against the following filters: (1) eliminating siRNAs targeting sequences not common to all documented splice forms; (2) eliminating siRNAs targeting sequences overlapping with simple or interspersed repeat elements; (3) eliminating siRNAs targeting sequences positioned within 75 bases downstream of the translation start codon; and (4) eliminating siRNAs overlapping or downstream of the stop codon.

For shRNA selection, the following steps are also taken: (5) eliminating siRNAs targeting sequence containing 4 consecutive guanosine, cytosine, adenine or uracil residues; (6) retaining siRNAs targeting a sequence with a guanine or cytosine residue at the first position in the 19mer duplex region at the 5' end; and (7) eliminating siRNAs targeting a sequence containing recognition sites for one or more given restriction enzymes, e.g., XhoI or EcoRI restriction endonucleases, if siRNAs sequences used in construction of the shRNA vectors.

Figure 2A:
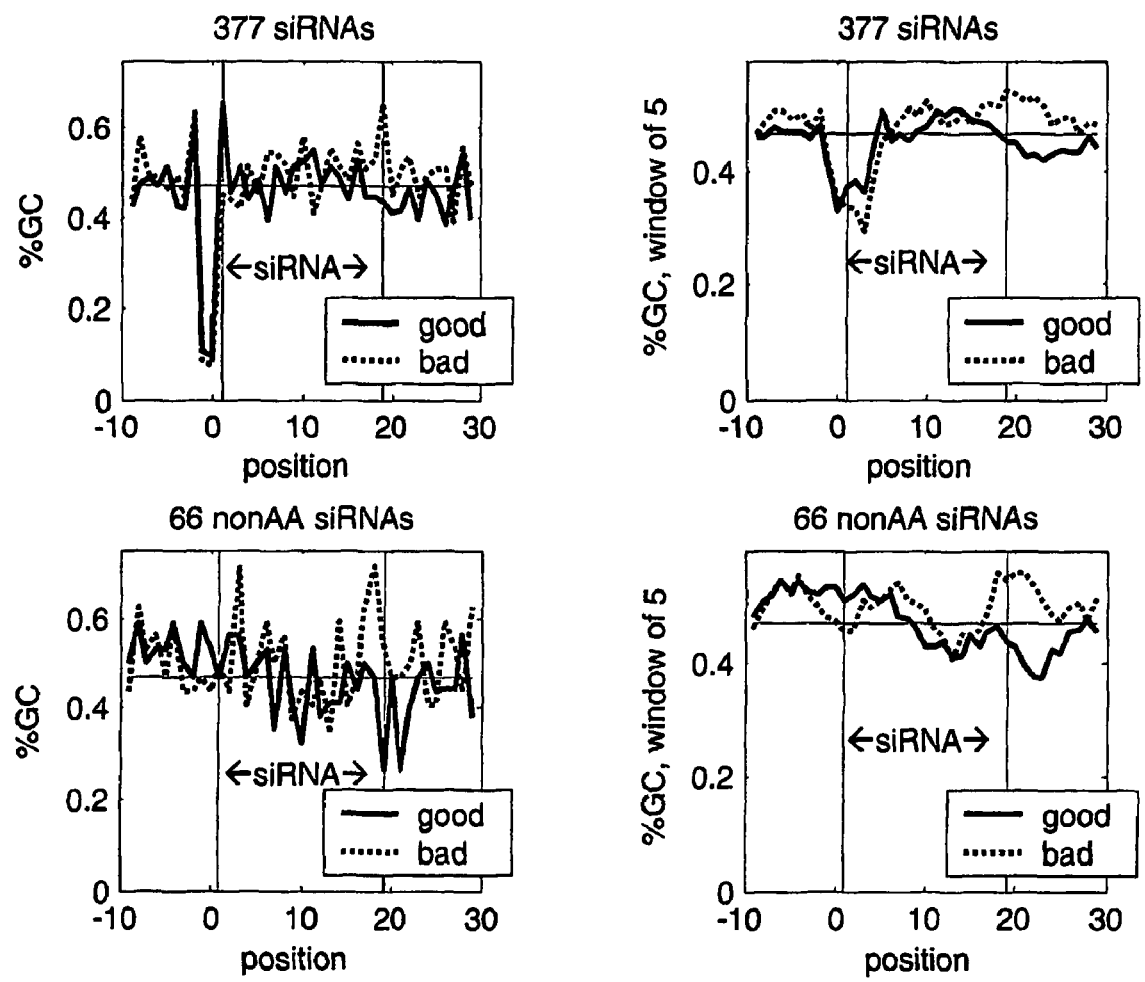
Figure 2B:
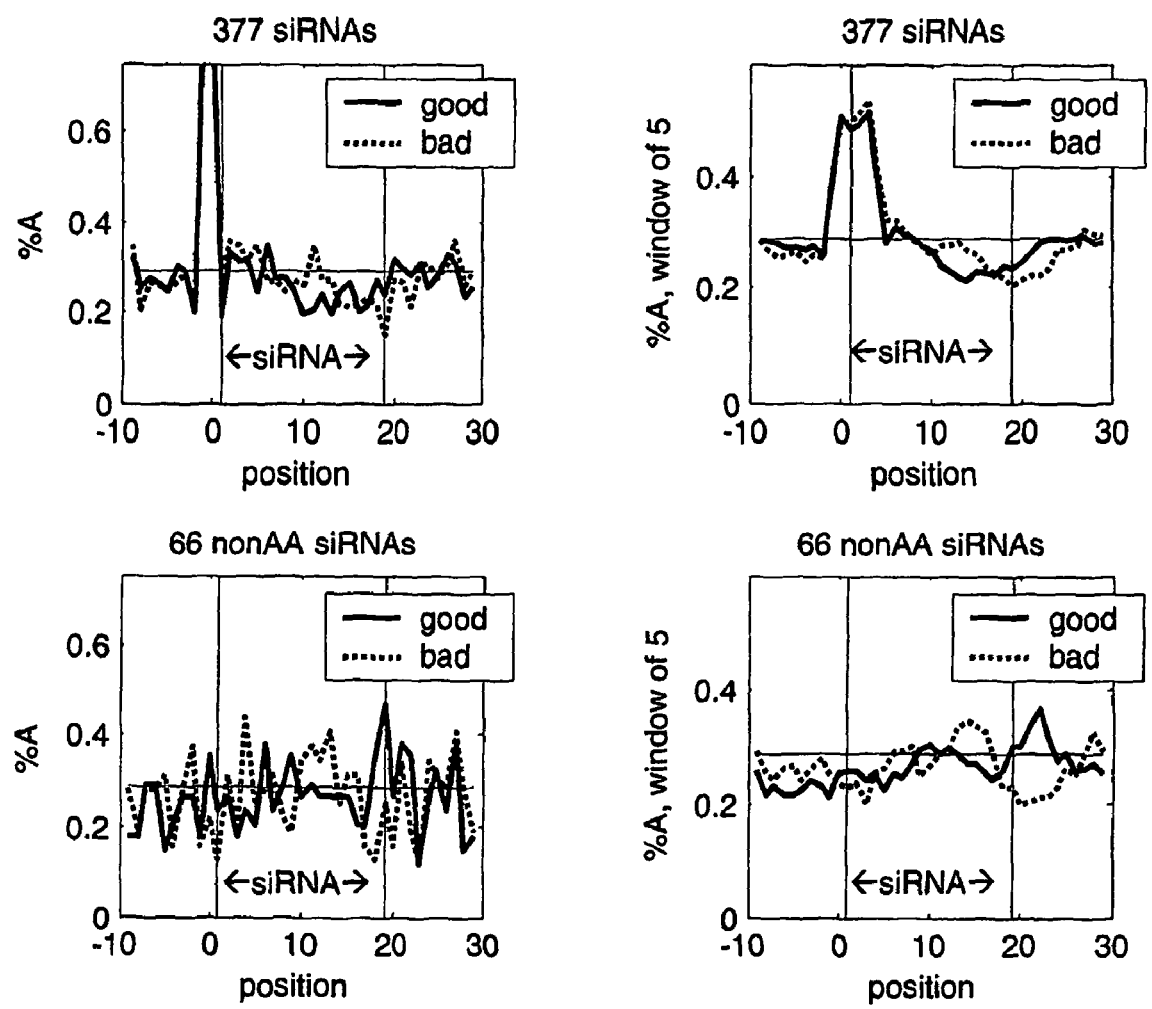
Figure 2C:
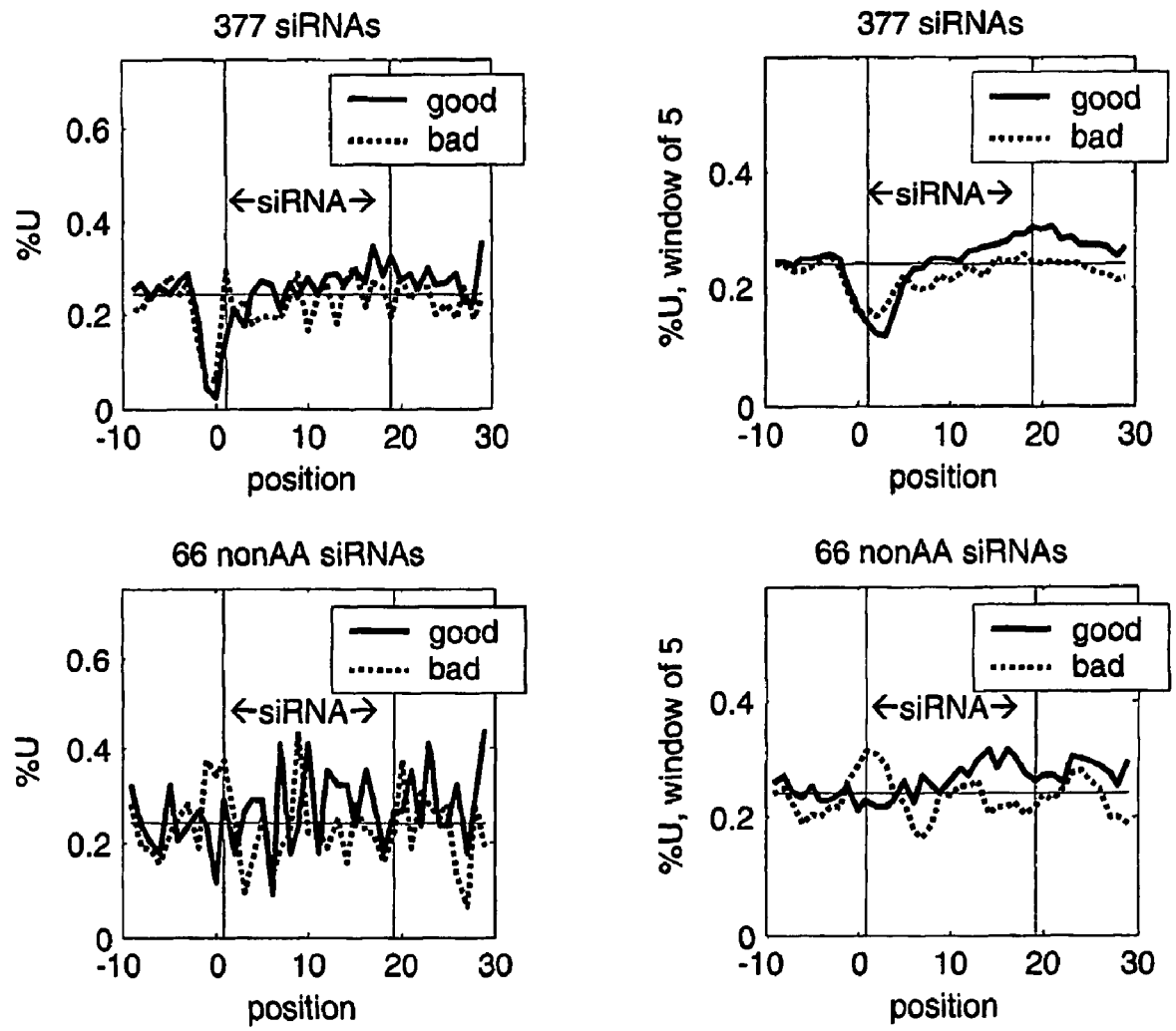

In step 102, the siRNA is evaluated for silencing efficacy by base composition PSSMs. In one embodiment, step 102 comprises calculating a first PSSM score, i.e., the PSSM-1 score, and a second PSSM score, i.e., the PSSM-2 score, for an siRNA. The two scores are sum to calculate the combined PSSM-1+PSSM-2 score for the siRNA. In one embodiment, the PSSMs used are those whose performance is shown in FIG. 2. The siRNA is retained if the combined score is above a given threshold.

The siRNA is then evaluated for its binding energy by calculating the nearest-neighbor 21mer $\Delta G$. The siRNA is then evaluated for binding specificity by calculating a 21mer minimax score against the set of unique sequence representatives of genes of an organism, e.g., the set of unique sequences representatives for each cluster of $Homo$ $sapiens$ Unigene build 161. See WO 01/05935 for methods of calculating the $\Delta G$ and the minimax score. In one embodiment, the parameters for the BLAST alignments and nearest-neighbor delta-G calculations based on the BLAST alignments, which are used to compute minimax scores, are as follows: -p blastn -e 100 -F F -W 11 -b 200 -v 10000 -S 3; and delta-G: temperature 66°; salt 1M; concentration 1 pM; type of nucleic acid, RNA. In one embodiment, the siRNA is eliminated if the (21mer $\Delta G$–21mer minimax)$\leq$0.5.

In step 103, siRNAs are screened for overall GC content. In one embodiment, siRNAs with GC content significantly deviated from 50%, e.g., GC % <20% and >70%, are eliminated.

In step 104, siRNAs are screened for diversity or variety. Position simply refers to the position of the oligo in the transcript sequence and is automatically provided by identifying the oligo. Variety is enforced in one or more "de-overlap" steps in the method. Briefly, de-overlapping selects for above-threshold spacing between selected oligos in some calculable parameter. To de-overlap, oligos are first ranked according to some parameter thought to distinguish better from poorer performers and then selected for spacing between oligos according to some other parameter. To begin, the top ranked oligo is selected. Then the ranked list is examined, and the next-best oligo with at least the minimum required spacing from the selected oligo is selected. Then the next-best oligo with at least the minimum spacing from the two selected oligos is also selected. The process continues until the desired number of oligos is selected. In one embodiment, multiple oligos may share the same value if a parameter is few-valued, and the number of oligos sharing the same value is limited by a set threshold. In one embodiment, if an insufficient number of oligos is selected in a first pass of de-overlapping, the spacing requirement can be relaxed until the desired number, or the set of all remaining available oligos, is selected.

For example, de-overlapping by position establishes a minimum distance between selected oligos along the length of the transcript sequence. In one embodiment, siRNAs are ranked by a PSSM score and the ranked siRNAs positioned at least 100 bases apart in the transcript are selected. De-overlapping by GC content establishes a minimum difference in GC content. In one embodiment, the minimum difference in GC content is 1%, 2% or 5%. Duplicates are allowed for few-valued parameters such as the GC % of a 19mer. De-overlapping by leading dimers establishes the probability of all or a portion of the 16 possible leading dimers among the selected siRNAs. In one embodiment, each of the 16 possible dimers is assigned a score of 1-16, and a 0.5 is used to selected all possible leading primer with equal probability, i.e., to distribute candidate siRNAs over all possible leading dimer values.

De-overlapping with different parameters may be combined.

In step 105, off-target activity of an siRNA is evaluated according to the method described in Section 5.2. Alignments of each siRNA with sequences in each of a plurality of non-target transcripts are identified and evaluated with a pmPSSM using a pmScore calculated according to equation (6). A pmScore above a given threshold identifies the sequence as a potential off-target sequence. The transcript that comprises the potential off-target sequence is identified as a potential off-target transcript The total number of such off-target transcripts in the genome or a portion of the genome is used as a measure of the silencing specificity of the siRNA. One or more siRNAs having less off-target transcripts are selected.

In one embodiment, transcripts of genes are scanned using FASTA with the parameters: KTUP 6 -r 3/-7 -g -6 -f -6 -d 14000 -b 14000 -E 7000.A pmScore is determined for each alignment as described in Section 5.2. The FASTA weighted score is used to: (1) quantify the nearest sequence match to the candidate siRNA; and (2) count the total matches to the candidate siRNA with weighted scores over a threshold. The total number of such off-target genes in the genome or a portion of the genome is then used as a measure of the silencing specificity of the siRNA.

In a preferred embodiment, the selected siRNAs are subjected to a second round of selection for variety (step 106), and re-ranked by their base composition PSSM scores (step 107). The desired number of siRNAs is retained from the top of this final ranking (step 108).

The invention also provides a method for selecting a plurality of siRNAs for each of a plurality of different genes, each siRNA achieving at least 75%, at least 80%, or at least 90% silencing of its target gene. The method described above is used to select a plurality of siRNAs for each of a plurality of genes. Preferably, the plurality of siNRAs consists of at least 3, 5, or 10 siRNAs. Preferably, the plurality of different genes consists of at least 100, 500, 1,000, 5,000, 10,000 or 30,000 different genes.

The invention also provides a library of siRNAs which comprises a plurality of siRNAs for each of a plurality of different genes, each siRNA achieves at least 75%, at least 80%, or at least 90% silencing of its target gene. The standard conditions are 100 nM siRNA, silencing assayed by TaqMan 24 hours post-transfection. Preferably, the plurality of siNRAs consists of at least 3, at least 5, or at least 10 siRNAs. Preferably, the plurality of different genes consists of at least 10, 100, 500, 1,000, 5,000, 10,000 or 30,000 different genes.

5.5. Methods and Compositions for RNA Interference and Cell Assays

Any standard method for gene silencing can be used in conjunction with the present invention, e.g., to carry out our gene silencing using siRNAs designed by a method described in the present invention (see, e.g., Guo et al., 1995, Cell 81:611-620; Fire et al., 1998, Nature 391:806-811; Grant, 1999, Cell 96:303-306; Tabara et al., 1999, Cell 99:123-132; Zamore et al., 2000, Cell 101:25-33; Bass, 2000, Cell 101:235-238; Petcherski et al., 2000, Nature 405:364-368; Elbashir et al., Nature 411:494-498; Paddison et al., Proc. Natl. Acad. Sci. USA 99:1443-1448). In one embodiment, gene silencing is induced by presenting the cell with the siRNA, mimicking the product of Dicer cleavage (see, e.g., Elbashir et al., 2001, *Nature* 411, 494-498; Elbashir et al., 2001, *Genes Dev.* 15, 188-200, all of which are incorporated by reference herein in their entirety). Synthetic siRMA duplexes maintain the ability to associate with RISC and direct silencing of mRNA transcripts. siRNAs can be chemically synthesized, or derived from cleavage of double-stranded RNA by recombinant Dicer. Cells can be transfected with the siRNA using standard method known in the art.

In one embodiment, siRNA transfection is carried out as follows: one day prior to transfection, 100 microliters of chosen cells, e.g., cervical cancer HeLa cells (ATCC, Cat. No. CCL-2), grown in DMEM/10% fetal bovine serum (Invitrogen, Carlsbad, Calif.) to approximately 90% confluency are seeded in a 96-well tissue culture plate (Corning, Corning, N.Y.) at 1500 cells/well. For each transfection 85 microliters of OptiMEM (Invitrogen) is mixed with 5 microliter of serially diluted siRNA (Dharma on, Denver) from a 20 micro molar stock. For each transfection 5 microliter OptiMEM is mixed with 5 microliter Oligofectamine reagent (Invitrogen) and incubated 5 minutes at room temperature. The 10 microliter OptiMEM/Oligofectamine mixture is dispensed into each tube with the OptiMEM/siRNA mixture, mixed and incubated 15-20 minutes at room temperature. 10 microliter of the transfection mixture is aliquoted into each well of the 96-well plate and incubated for 4 hours at 37° C. and 5% $CO_2$.

In one embodiment, RNA interference is carried out using pool of siRNAs. In a preferred embodiment, an siRNA pool containing at least k k=2, 3, 4, 5, 6 or 10) different siRNAs targeting a target gene at different sequence regions is used to transfect the cells. In another preferred embodiment, an siRNA pool containing at least k k=2, 3, 4, 5, 6 or 10) different siRNAs targeting two or more different target genes is used to supertransfect the cells. In a preferred embodiment, the total siRNA concentration of the pool is about the same as the concentration of a single siRNA when used individually, e.g., 100 nM. Preferably, the total concentration of the pool of siRNAs is an optimal concentration for silencing the intended target gene. An optimal concentration is a concentration further increase of which does not increase the level of silencing substantially. In one embodiment, the optimal concentration is a concentration further increase of which does not increase the level of silencing by more than 5%, 10% or 20%. In a preferred embodiment, the composition of the pool, including the number of different siRNAs in the pool and the concentration of each different siRNA, is chosen such that the pool of siRNAs causes less than 30%, 20%, 10% or 5%, 1%, 0.1% or 0.01% of silencing of any off-target genes. In another preferred embodiment, the concentration of each different siRNA in the pool of different siRNAs is about the same. In still another preferred embodiment, the respective concentrations of different siRNAs in the pool are different from each other by less than 5%, 10%, 20% or 50%. In still another preferred embodiment, at least one siRNA in the pool of different siRNAs constitutes more than 90%, 80%, 70%, 50%, or 20% of the total siRNA concentration in the pool. In still another preferred embodiment, none of the siRNAs in the pool of different siRNAs constitutes more than 90%, 80%, 70%, 50%, or 20% of the total siRNA concentration in the pool. In other embodiments, each siRNA in the pool has an concentration that is lower than the optimal concentration when used individually. In a preferred embodiment, each different siRNA in the pool has an concentration that is lower than the concentration of the siRNA that is effective to achieve at least 30%, 50%, 75%, 80%, 85%, 90% or 95% silencing when used in the absence of other siRNAs or in the absence of other siRNAs designed to silence the gene. In another preferred embodiment, each different siRNA in the pool has a concentration that causes less than 30%, 20%, 10% or 5% of silencing of the gene when used in the absence of other siRNAs or in the absence of other siRNAs designed to silence the gene. In a preferred embodiment, each siRNA has a concentration that causes less than 30%, 20%, 10% or 5% of silencing of the target gene when used alone, while the plurality of siRNAs causes at least 80% or 90% of silencing of the target gene.

Another method for gene silencing is to introduce into a cell an shRNA, for short hairpin RNA (see, e.g., Paddison et al., 2002, *Genes Dev.* 16, 948-958; Brummelknp et al., 2002, *Science* 296, 550-553; Sui, G. et al. 2002, *Proc. Natl. Acad. Sci. USA* 99, 5515-5520, all of which are incorporated by reference herein in their entirety), which can be processed in the cells into siRNA. In this method, a desired siRNA sequence is expressed from a plasmid (or virus) as an inverted repeat with an intervening loop sequence to form a hairpin structure. The resulting RNA transcript containing the hairpin is subsequently processed by Dicer to produce siRNAs for silencing. Plasmid-based shRNAs can be expressed stably in cells, allowing long-term gene silencing in cells both in vitro and in vivo, e.g., in animals (see, McCaffrey et al. 2002, *Nature* 418, 38-39; Xia et al., 2002, *Nat. Biotech.* 20, 1006-1010; Lewis et al., 2002, *Nat. Genetics* 32, 107-108; Rubinson et al., 2003, *Nat. Genetics* 33, 401-406; Tiscornia et al., 2003, *Proc. Natl. Acad. Sci USA* 100, 1844-1848, all of which are incorporated by reference herein in their entirety). Thus, in one embodiment, a plasmid-based shRNA is used.

In a preferred embodiment, shRNAs are expressed from recombinant vectors introduced either transiently or stably integrated into the genome (see, e.g., Paddison et al, 2002, *Genes Dev* 16:948-958; Sui et al., 2002, *Proc Natl Acad Sci U S A* 99:5515-5520; Yu et al., 2002, *Proc Natl Acad Sci U S A* 99:6047-6052; Miyagishi et al., 2002, *Nat Biotechnol* 20:497-500; Paul et al., 2002, *Nat Biotechnol* 20:505-508; Kwak et al., 2003, *J Pharmacol Sci* 93:214-217; Brummelkamp et al., 2002, *Science* 296:550-553; Boden et al., 2003, *Nucleic Acids Res* 31:5033-5038; Kawasaki et al., 2003, *Nucleic Acids Res* 31:700-707). The siRNA that disrupts the target gene can be expressed (via an shRNA) by any suitable vector which encodes the shRNA. The vector can also encode a marker which can be used for selecting clones in which the vector or a sufficient portion thereof is integrated in the host genome such that the shRNA is expressed. Any standard method known in the art can be used to deliver the vector into the cells. In one embodiment, cells expressing the shRNA are generated by transfecting suitable cells with a plasmid containing the vector. Cells can then be selected by the appropriate marker. Clones are then picked, and tested for knockdown. In a preferred embodiment, a plurality of recombinant vectors are introduced into the genome such that the expression level of the siRNA can be above a given value. Such an embodiment is particular useful for silencing genes whose transcript level is low in the cell.

In a preferred embodiment, the expression of the shRNA is under the control of an inducible promoter such that the silencing of its target gene can be turned on when desired. Inducible expression of an siRNA is particularly useful for targeting essential genes. In one embodiment, the expression of the shRNA is under the control of a regulated promoter that allows tuning of the silencing level of the target gene. This allows screening against cells in which the target gene is partially knocked out As used herein, a "regulated promoter" refers to a promoter that can be activated when an appropriate inducing agent is present. An "inducing agent" can be any molecule that can be used to activate transcription by activating the regulated promoter. An inducing agent can be, but is not limited to, a peptide or polypeptide, a hormone, or an organic small molecule. An analogue of an inducing agent, i.e., a molecule that activates the regulated promoter as the inducing agent does, can also be used. The level of activity of the regulated promoter induced by different analogues may be different, thus allowing more flexibility in tuning the activity level of the regulated promoter. The regulated promoter in the vector can be any mammalian transcription regulation system known in the art (see, e.g., Gossen et al, 1995, Science 268:1766-1769; Lucas et al, 1992, Annu. Rev. Biochem. 61:1131; Li et al., 1996, Cell 85:319-329; Saez et al., 2000, Proc. Natl. Acad. Sci. USA 97:14512-14517; and Pollock et al., 2000, Proc. Natl. Acad. Sci. USA 97:13221-13226). In preferred embodiments, the regulated promoter is regulated in a dosage and/or analogue dependent manner. In one embodiment, the level of activity of the regulated promoter is tuned to a desired level by a method comprising adjusting the concentration of the inducing agent to which the regulated promoter is responsive. The desired level of activity of the regulated promoter, as obtained by applying a particular concentration of the inducing agent, can be determined based on the desired silencing level of the target gene.

In one embodiment, a tetracycline regulated gene expression system is used (see, e.g., Gossen et al, 1995, Science 268: 1766-1769; U.S. Pat. No. 6,004,941). A tet regulated system utilizes components of the tet repressor/operator/inducer system of prokaryotes to regulate gene expression in eukaryotic cells. Thus, the invention provides methods for using the tet regulatory system for regulating the expression of an shRNA linked to one or more tet operator sequences. The methods involve introducing into a cell a vector encoding a fusion protein that activates transcription. The fusion protein comprises a first polypeptide that binds to a tet operator sequence in the presence of tetracycline or a tetracycline analogue operatively linked to a second polypeptide that activates transcription in cells. By modulating the concentration of a tetracycline, or a tetracycline analogue, expression of the tet operator-inked shRNA is regulated.

In other embodiments, an ecdyson regulated gene expression system (see, e.g., Saez et al., 2000, Proc. Natl. Acad. Sci. USA 97:14512-14517), or an MMTV glucocorticoid response element regulated gene expression system (see, e.g., Lucas et al, 1992, Annu. Rev. Biochem. 61:1131) may be used to regulate the expression of the shRNA.

In one embodiment, the pRETRO-SUPER (pRS) vector which encodes a puromycin-resistance marker and drives shRNA expression from an H1 (RNA Pol III) promoter is used The pRS-shRNA plasmid can be generated by any standard method known in the art. In one embodiment, the pRS-shRNA is deconvoluted from the library plasmid pool for a chosen gene by transforming bacteria with the pool and looking for clones containing only the plasmid of interest. Preferably, a 19mer siRNA sequence is used along with suitable forward and reverse primers for sequence specific PCR. Plasmids are identified by sequence specific PCR, and confirmed by sequencing. Cells expressing the shRNA are generated by transfecting suitable cells with the pRS-shRNA plasmid. Cells are selected by the appropriate marker, e.g., puromycin, and maintained until colonies are evident. Clones are then picked, and tested for knockdown. In another embodiment, an shRNA is expressed by a plasmid, e.g., a pRS-shRNA. The knockdown by the pRS-shRNA plasmid, can be achieved by transfecting cells using Lipofectanine 2000 (Invitrogen).

In yet another method, siRNAs can be delivered to an organ or tissue in an animal, such a human, in vivo (see, e.g., Song et al. 2003, *Nat. Medicine* 9, 347-351; Sorensen et al., 2003, *J. Mol. Biol.* 327, 761-766; Lewis et al., 2002, *Nat. Genetics* 32, 107-108, all of which are incorporated by reference herein in their entirety). In this method, a solution of siRNA is injected intravenously into the animal. The siRNA can then reach an organ or tissue of interest and effectively reduce the expression of the target gene in the organ or tissue of the animal.

The siRNAs can also be delivered to an organ or tissue using a gene therapy approach. Any of the methods for gene therapy available in the art can be used to deliver the siRNA. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann.

Rev. Biochem. 62:191-217; Robinson, 1993, TIBTECH 11(5):155-215). In a preferred embodiment, the therapeutic comprises a nucleic acid encoding the siRNA as a part of an expression vector. In particular, such a nucleic acid has a promoter operably linked to the siRNA coding region, in which the promoter being inducible or constitutive, and, optionally, tissue-specific. In another particular embodiment, a nucleic acid molecule in which the siRNA coding sequence is flanked by regions that promote homologous recombination at a desired site in the genome is used (see e.g., Koller and Smithies, 1989, Proc. Natl. Acad. Sci. U.S.A. 86:8932-8935; Zijlstra et al., 1989, Nature 342:435-438).

In a specific embodiment, the nucleic acid is directly administered in vivo. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429-4432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. U.S.A. 86:8932-8935; Zijlstra et al., 1989, Nature 342:435-438).

In a specific embodiment, a viral vector that contains the siRNA coding nucleic acid is used. For example, a retroviral vector can be used (see Miller et al., 1993, Meth. Enzymol. 217:581-599). These retroviral vectors have been modified to delete retroviral sequences that are not necessary for packaging of the viral genome and integration into host cell DNA. The siRNA coding nucleic acid to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. Genet. and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993, Current Opinion in Genetics and Development 3:499-503) present a review of adenovirus-based gene therapy. Bout et al. (1994, Human Gene Therapy 5:3-10) demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234. Adeno-associated virus (AAV) may also been used in gene therapy (Walsh et al., 1993, Proc. Soc. Exp. Biol. Med. 204:289-300).

Degree of silencing can be determined using any standard RNA or protein quantification method known in the art. For example, RNA quantification can be performed using Real-time PCR, e.g., using AP Biosystems TaqMan pre-developed assay reagent (#4319442). Primer probe for the appropriate gene can be designed using any standard method known in the art, e.g. using Primer Express software. RNA values can be normalized to RNA for actin (#4326315). Protein levels can be quantified by flow cytometry following staining with appropriate antibody and labeled secondary antibody. Protein levels can also be quantified by western blot of cell lysates with appropriate monoclonal antibodies followed by Kodak image analysis of chemiluminescent immunoblot. Protein levels can also be normalized to actin levels.

Effects of gene silencing on a cell can be evaluated by any known assay. For example, cell growth can be assayed using any suitable proliferation or growth inhibition assays known in the art. In a preferred embodiment, an MTT proliferation assay (see, e.g., van de Loosdrechet, et al., 1994, J. Immunol. Methods 174: 311-320; Ohno et al., 1991, J. Immunol. Methods 145:199-203; Ferrari et al., 1990, J. Immunol. Methods 131: 165-172; Alley et al., 1988, Cancer Res. 48: 589-601; Carmichael et al., 1987, Cancer Res. 47:936-942; Gerlier et al., 1986, J. Immunol. Methods 94:57-63; Mosmann, 1983, J. Immunological Methods 65:55-63) is used to assay the effect of one or more agents in inhibiting the growth of cells. The cells are treated with chosen concentrations of one or more candidate agents for a chosen period of time, e.g., for 4 to 72 hours. The cells are then incubated with a suitable amount of 3-(4,5-dimethylthiazol-2-yl)-2,5-diphenyltetrazolium bromide (MTT) for a chosen period of time, e.g., 1-8 hours, such that viable cells convert MTT into an intracellular deposit of insoluble formazan. After removing the excess MTT contained in the supernatant, a suitable MTT solvent, e.g., a DMSO solution, is added to dissolved the formazan. The concentration of MTT, which is proportional to the number of viable cells, is then measured by determining the optical density at e.g., 570 nm. A plurality of different concentrations of the candidate agent can be assayed to allow the determination of the concentrations of the candidate agent or agents which causes 50% inhibition.

In another preferred embodiment, an alamarBlue™ Assay for cell proliferation is used to screen for one or more candidate agents that can be used to inhibit the growth of cells (see, e.g., Page et al., 1993, Int. J. Oncol. 3:473-476). An alamarBlue™ assay measures cellular respiration and uses it as a measure of the number of living cells. The internal environment of proliferating cells is more reduced than that of non-proliferating cells. For example, the ratios of NADPH/NADP, FADH/FAD, FMNH/FMN, and NADH/NAF increase during proliferation. AlamarBlue can be reduced by these metabolic intermediates and, therefore, can be used to monitor cell proliferation. The cell number of a treated sample as measured by alamarBlue can be expressed in percent relative to that of an untreated control sample. alamarBlue reduction can be measured by either absorption or fluorescence spectroscopy. In one embodiment, the alamarBlue reduction is determined by absorbance and calculated as percent reduced using the equation:

$$\% \text{ Reduced} = \frac{(\varepsilon_{ox}\lambda_2)(A\lambda_1) - (\varepsilon_{ox}\lambda_1)(A\lambda_2)}{(\varepsilon_{red}\lambda_1)(A'\lambda_2) - (\varepsilon_{red}\lambda_2)(A'\lambda_1)} \times 100 \qquad (8)$$

where:
$\lambda_1 = 570$ nm
$\lambda_2 = 600$ nm
$(\epsilon_{red} \lambda_1) = 155{,}677$ (Molar extinction coefficient of reduced alamarBlue at 570 nm)
$(\epsilon_{red} \lambda_2) = 14{,}652$ (Molar extinction coefficient of reduced alamarBlue at 600 nm)
$(\epsilon_{ox} \lambda_1) = 80{,}586$ (Molar extinction coefficient of oxidized alamarBlue at 570 nm)
$(\epsilon_{ox} \lambda_2) = 117{,}216$ (Molar extinction coefficient of oxidized alamarBlue at 600 nm)
$(A \lambda_1) =$ Absorbance of test wells at 570 nm
$(A \lambda_2) =$ Absorbance of test wells at 600 nm
$(A'\lambda_1) =$ Absorbance of negative control wells which contain medium plus alamar Blue but to which no cells have been added at 570 nm.
$(A'\lambda_2) =$ Absorbance of negative control wells which contain medium plus alamar Blue but to which no cells have been added at 600 nm. Preferably, the % Reduced of wells containing no cell was subtracted from the % Reduced of wells containing samples to determine the % Reduced above background.

Cell cycle analysis can be carried out using standard method known in the art. In one embodiment, the supernatant from each well is combined with the cells that have been harvested by trypsinization. The mixture is then centrifuged at a suitable speed. The cells are then fixed with, e.g., ice cold 70% ethanol for a suitable period of time, e.g., ~30 minutes. Fixed cells can be washed once with PBS and resuspended, e.g., in 0.5 ml of PBS containing Propidium Iodide (10 microgram/ml) and RNase A (1 mg/ml), and incubated at a suitable temperature, e.g., 37° C., for a suitable period of time, e.g., 30 min. Flow cytometric analysis is then carried out using a flow cytometer. In one embodiment, the Sub-G1 cell population is used as a measure of cell death. For example, the cells are said to have been sensitized to an agent if the Sub-G1 population from the sample treated with the agent is larger than the Sub-G1 population of sample not treated with the agent.

5.6. Implementation Systems and Methods

The analytical methods of the present invention can preferably be implemented using a computer system, such as the computer system described in this section, according to the following programs and methods. Such a computer system can also preferably store and manipulate measured signals obtained in various experiments that can be used by a computer system implemented with the analytical methods of this invention. Accordingly, such computer systems are also considered part of the present invention.

An exemplary computer system suitable from implementing the analytic methods of this invention is illustrated in FIG. 12. Computer system 1201 is illustrated here as comprising internal components and as being linked to external components. The internal components of this computer system include one or more processor elements 1202 interconnected with a main memory 1203. For example, computer system 1201 can be an Intel Pentium IV®-based processor of 2 GHZ or greater clock rate and with 256 MB or more main memory. In a preferred embodiment, computer system 1201 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 1204. This mass storage can be one or more hard disks that are typically packaged together with the processor and memory. Such hard disk are typically of 10 GB or greater storage capacity and more preferably have at least 40 GB of storage capacity. For example, in a preferred embodiment, described above, wherein a computer system of the invention comprises several nodes, each node can have its own hard drive. The head node preferably has a hard drive with at least 10 GB of storage capacity whereas each sibling node preferably has a hard drive with at least 40 GB of storage capacity. A computer system of the invention can further comprise other mass storage units including, for example, one or more floppy drives, one more CD-ROM drives, one or more DVD drives or one or more DAT drives.

Other external components typically include a user interface device 1205, which is most typically a monitor and a keyboard together with a graphical input device 1206 such as a "mouse." The computer system is also typically linked to a network link 1207 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 12. The software components comprise both software components that are standard in the art and components that are special to the present invention. These software components are typically stored on mass storage such as the hard drive 1204, but can be stored on other computer readable media as well including, for example, one or more floppy disks, one or more CD-ROMs, one or more DVDs or one or more DATs. Software component 1210 represents an operating system which is responsible for managing the computer system and its network interconnections.

The operating system can be, for example, of the Microsoft Windows™ family such as Windows 95, Window 98, Windows NT, Windows 2000 or Windows XP. Alternatively, the operating software can be a Macintosh operating system, a UNIX operating system or a LINUX operating system. Software components 1211 comprises common languages and functions that are preferably present in the system to assist programs implementing methods specific to the present invention. Languages that can be used to program the analytic methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matiab from Mathworks (Natick, Mass.), Mathematica from Wolfram Research (Champaign, Ill.) or S-Plus from MathSoft (Seattle, Wash.).

Software component 1212 comprises any analytic methods of the present invention described supra, preferably programmed in a procedural language or symbolic package. For example, software component 1212 preferably includes programs that cause the processor to implement steps of accepting a plurality of measured signals and storing the measured signals in the memory. For example, the computer system can accept measured signals that are manually entered by a user (e.g., by means of the user interface). More preferably, however, the programs cause the computer system to retrieve measured signals from a database. Such a database can be stored on a mass storage (e.g., a hard drive) or other computer readable medium and loaded into the memory of the computer, or the compendium can be accessed by the computer system by means of the network 1207.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

6. EXAMPLES

The following examples are presented by way of illustration of the present invention, and are not intended to limit the present invention in any way.

6.1. Example 1

Designing siRNA for High Silencing Efficacy

A library of siRNAs targeting more than 700 genes was constructed. The siRNAs in the library were designed by use of a "standard" approach, based on a combination of limited design principles available from the scientific literature (Elbashir et al., 2001, Nature 411:494-8) and a method for predicting off target effects by sequence similarity scoring as described in Section 5.2. A set of 377 siRNAs was tested by Taqman analysis for their ability to silence their respective target genes. The set of 377 siRNAs are listed in Table II. Table II lists the following information for the 377 siRNAs: the ID number of the siRNA, the accession number of the target gene, start position of the target sequence, target sequence, % silencing, the set it belongs (i.e., training or test) in Set 1, the set it belongs in Set 2, and the SEQ ID NO. The results of this test showed that most siRNAs successfully silenced their target genes (median silencing, ~75%), but individual siRNAs still showed a wide range of silencing performance. Good (or poor) silencing ability was not consistently associated with any particular base at any position, overall GC content, the position of the siRNA sequence within the target transcript, or with alternative splicing of target transcripts.

The potential relationship between target gene silencing and the base-composition, thermodynamics and secondary structure of the siRNA and target sequences was explored using a classifier approach. siRNAs were divided into groups containing those with less than median silencing ability ("bad" siRNAs) and those with median or better silencing ability ("good" siRNAs). A number of metrics were evaluated for their ability to distinguish good and bad siRNAs, including base composition in windows of the 19mer siRNA duplex sequence and the flanking target region, secondary structure predictions by various programs and thermodynamic properties. These tests revealed that siRNA efficacy correlated well with siRNA and target gene base composition, but poorly with secondary structure predictions and thermodynamic properties. In particular, the GC content of good siRNAs differed substantially from that of bad siRNAs in a position-specific manner (FIGS. 1-3). For example, good siRNA duplexes were not observed to be associated with any particular sequence, but tended to be GC rich at the 5' end and GC poor at the 3' end. The data indicate that a good siRNA duplex encourages preferential interaction of the antisense strand by being GC poor at its 3' end and discourages interaction of the sense strand by being GC rich at its 5' end. The data further demonstrate that position-specific sequence preferences extend beyond the boundaries of the siRNA target sequence into the adjacent sequence(s). This suggests that steps during RNA silencing other than unwinding of the siRNA duplex are affected by position-specific base composition preferences.

The GC-content difference between good and bad siRNAs shown in FIGS. 1 and 2 was used to develop methods for selecting good siRNAs. Best results were obtained with a position-specific scoring matrix (PSSM) approach. The PSSM provides weights for GC, A or U at every position on the sense strand of the target gene sequence from 10 bases upstream of the start to 10 bases downstream of the end of the siRNA duplex. The siRNA efficacy data were divided into two sets, one to be used for training and the other for an independent test. A random-mutation hill-climbing search algorithm was used to optimize the weights for each base at each position of the PSSM simultaneously. The optimization criterion was the correlation coefficient between the target silencing of the siRNA and its PSSM score. Multiple runs of optimization on the training data set were averaged to complete each PSSM. Each PSSM was then tested on the independent (test) set of siRNAs. The performance of two PSSMs on their training and test data sets is demonstrated in FIG. 2.

An siRNA design method was developed based on a position-specific score matrix (PSSM). A scoring scheme is used to predict the efficacy of siRNA oligos. The score is a weighted sum of 39 bases (10 bases upstream of the 19mer, 19 bases on the siRNA proper, and 10 bases downstream) computed as follows:

$$Score = \sum_{i=1}^{39} \ln(E_i / p_i)$$

where $P_i$ equals the random probability of any base, i.e., 0.25, and $E_i$ the weight assigned to the base A, U, G or C at position i. Therefore, a total of 117 weights (39 positions times 3 base types—G or C, A, U) need to be assigned and optimized.

A random-mutation hill climbing (RMHC) search algorithm was utilized to optimize the weights based on a training oligo set and the resulting profiles applied to a test set, with the optimizing criteria being the correlation coefficient between the knock-down (KD) levels of the oligos and the computed PSSM scores. The metric to measure the effectiveness of the training and testing is the aggregate false detection rate (FDR) based on the ROC curve, and is computed as the average of the FDR scores of the top 33% oligos sorted by the scores given by the trained predictor. In computing the FDR scores, those oligos with silencing levels less than the median are considered false, and those more than the median silencing levels considered true.

Different criteria were used to divide the existing siRNA performance data into training and test sets. The greatest obstacle to an ideal partition is that the vast majority of siRNA oligos are designed with the standard method, which requires an AA dimer immediately before the 19mer oligo sequence. This limitation was found later to be detrimental rather than helpful to the design process and was abolished. To limit the influence of this on the training procedure, several partitions were used and more than one trained predictors, i.e., PSSMs, (rather than single predictors) were combined to assign scores to the test oligos.

Finally, a state-of-the-art siRNA oligo design procedure (also referred to as "pipeline") was constructed. It incorporates the off-target prediction procedure and two ensembles of siRNA oligo efficacy predictors trained and tested on different data sets. A total of 30 siRNA oligos (6 oligos for each of 5 genes) were selected and tested. The results were significantly better than any of the previously existing pipelines.

The initial training and testing results showed that the PSSM is very effective in predicting the on-target efficacy of siRNA oligos. Typically the aggregate FDR scores for training are between 0.02 and 0.08, and those for testing between 0.05 and 0.10. As a reference, random predictions have a mean aggregate FDR of 0.17, with the standard deviation being 0.02 (data computed with 10,000 randomly generated predictions). FIG. 3 illustrates typical ROC curves, generated by an ensemble of about 200 randomly optimized predictors. It could be seen that the performance of the training is better than the test set, which is hardly surprising. Both curves are significantly better than random.

FIG. 5 illustrates the resulting sequence profiles from training and testing on several different oligo sets. This profile illustrates that G or C bases are strongly preferred at the beginning, i.e., the 5' end, and strongly disfavored at the end, i.e., the 3' end, of the 19mer sequence. To confirm this observation, the average knock-down levels for oligos starting and ending with G/C or A/U are computed, and those oligos starting with G/C and ending with A/U have the best performance, far superior to the other three categories. Simply by comparing the weights at different positions, a 19mer oligo having a sequence of GCGTTAATGTGATAATATA (SEQ ID NO: 1), and the oligos that are most similar to this sequence are identified as an siRNA that may have high silencing efficacy.

The design method incorporated both PSSMs shown in FIG. 3 because the combination gave better performance as compared to using either one PSSM alone. The improved siRNA design method selected oligonucleotides based on 4 principles: base composition, off-target identity, position in the transcript, and sequence variety. Certain oligonucleotides containing sequence from features such as untranslated regions, repeats or homopolymeric runs were eliminated. Remaining oligonucleotides were ranked by their PSSM scores. Top-ranking oligonucleotides were selected for variety in GC content, in start position, and in the two bases upstream of the siRNA 19mer duplex. Selected oligonucleotides were then filtered for predicted off-target activity, which was calculated as a position-weighted FASTA alignment score. Remaining oligonucleotides were ranked by PSSM scores, subjected to a second round of selection for variety and finally re-ranked by their PSSM scores. The desired number of siRNAs was retained from the top of this final is ranking.

The improved method was compared to the standard method by side-by-side testing of new siRNAs selected by each. The results obtained with three siRNAs selected by each method are shown in FIG. 3. siRNAs designed by the improved algorithm showed better median efficacy (88%, compared to 78% for the standard method siRNA) and were more uniform in their performance. The distribution of silencing efficacies of the improved algorithm siRNAs was significantly better than that of the standard method siRNAs for the same genes (p=0.004, Wilcoxon rank sum test).

The test results of 30 experimental oligos using the new pipeline proved to be successful. Table III lists the 30 siRNAs. In the past, an siRNA design with the standard method had a median silencing level of 75%. Of the 30 experimental oligos, 28 had silencing levels equal to or better than 75%, 26 better than or equal to 80%, and 37% better than 90%, comparing with only 10% better than 90% using the standard method Two target genes (KIF14 and IGF1R) had been very difficult to silence by siRNAs, with previous oligos achieving only 40% to 70% and no more than 80% silencing levels in the past. The 12 new oligos targeting these gene all achieved silencing of at least 80% and 6 achieved 90% levels. The two oligos among the 30 oligos which had less than 75% silencing level turned out to be targeting an exon that is unique to one target transcript sequence, but absent in all other alternative splice forms of the same gene. Therefore, the failure of these two oligos was due to improper input sequence rather than the PSSM method. Therefore, when given proper input sequences, the pipeline appears to be able to pick oligos that can knock down target genes by at least 75% for 100% of the target genes.

TABLE II

A library of 377 siRNAs

| BioID | accession number | start position | 19 mer sequence | % silencing | Set 1 | Set 2 | SEQ ID NO |
|---|---|---|---|---|---|---|---|
| 31 | NM_000075 | 437 | TGTTGTCCGGCTGATGGAC | 27.0 | Training | Training | 2 |
| 36 | NM_001813 | 1036 | ACTCTTACTGCTCTCCAGT | 86.1 | Test | Training | 3 |
| 37 | NM_001813 | 1278 | CTTAACACGGATGCTGGTG | 60.1 | Test | Training | 4 |
| 38 | NM_001813 | 3427 | GGAGAGCTTTCTAGGACCT | 88.0 | Test | Training | 5 |
| 39 | NM_004073 | 192 | AGTCATCCCGCAGAGCCGC | 55.0 | Training | Training | 6 |
| 40 | NM_004073 | 1745 | ATCGTAGTGCTTGTACTTA | 70.0 | Training | Training | 7 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 41 | NM_004073 | 717 | GGAGACGTACCGCTGCATC | 65.0 | Training | Training | 8 |
| 42 | AK092024 | 437 | GCAGTGATTGCTCAGCAGC | 93.0 | Training | Training | 9 |
| 43 | NM_030932 | 935 | GAGTTTACCGACCACCAAG | 81.0 | Training | Training | 10 |
| 44 | NM_030932 | 1186 | TGCGGATGCCATTCAGTGG | 35.0 | Training | Training | 11 |
| 45 | NM_030932 | 1620 | CACGGTTGGCAGAGTCTAT | 73.0 | Training | Training | 12 |
| 49 | U53530 | 169 | GCAAGTTGAGCTCTACCGC | 59.0 | Training | Training | 13 |
| 50 | U53530 | 190 | TGGCCAGCGCTTACTGGAA | 75.0 | Training | Training | 14 |
| 64 | NM_006101 | 1623 | GTTCAAAAGCTGGATGATC | 79.0 | Test | Training | 15 |
| 65 | NM_006101 | 186 | GGCCTCTATACCCCTCAAA | 74.4 | Test | Training | 16 |
| 66 | NM_006101 | 968 | AGAACCGAATCGTCTAGAG | 80.3 | Test | Training | 17 |
| 67 | NM_000859 | 253 | CACGATGCATAGCCATCCT | 25.0 | Training | Training | 18 |
| 68 | NM_000859 | 1075 | CAGAGACAGAATCTACACT | 45.0 | Training | Training | 19 |
| 69 | NM_000859 | 1720 | CAACAGAAGGTTGTCTTGT | 50.0 | Training | Training | 20 |
| 70 | NM_000859 | 2572 | TTGTGTGTGGGACCGTAAT | 80.0 | Training | Training | 21 |
| 71 | NM_000875 | 276 | GCTCACGGTCATTACCGAG | 63.9 | Training | Training | 22 |
| 72 | NM_000875 | 441 | CCTGAGGAACATTACTCGG | 0.0 | Training | Training | 23 |
| 73 | NM_000875 | 483 | TGCTGACCTCTGTTACCTC | 50.0 | Training | Training | 24 |
| 74 | NM_000875 | 777 | CGACACGGCCTGTGTAGCT | 58.0 | Training | Training | 25 |
| 75 | NM_000875 | 987 | CGGCAGCCAGAGCATGTAC | 63.0 | Training | Training | 26 |
| 76 | NM_000875 | 1320 | CCAGAACTTGCAGCAACTG | 70.0 | Training | Training | 27 |
| 81 | NM_000875 | 351 | CCTCACGGTCATCCGCGGC | 0.0 | Training | Training | 28 |
| 83 | NM_000875 | 387 | CTACGCCCTGGTCATCTTC | 32.0 | Training | Training | 29 |
| 84 | NM_000875 | 417 | TCTCAAGGATATTGGGCTT | 54.0 | Training | Training | 30 |
| 85 | NM_000875 | 423 | GGATATTGGGCTTTACAAC | 71.0 | Training | Training | 31 |
| 86 | NM_000875 | 450 | CATTACTCGGGGGGCCATC | 53.0 | Training | Training | 32 |
| 87 | NM_000875 | 481 | AATGCTGACCTCTGTTACC | 54.6 | Training | Training | 33 |
| 117 | NM_004523 | 1689 | CTGGATCGTAAGAAGGCAG | 74.7 | Training | Test | 34 |
| 118 | NM_004523 | 484 | TGGAAGGTGAAAGGTCACC | 16.0 | Training | Test | 35 |
| 119 | NM_004523 | 802 | GGACAACTGCAGCTACTCT | 84.1 | Training | Test | 36 |
| 139 | NM_002358 | 219 | TACGGACTCACCTTGCTTG | 83.0 | Training | Training | 37 |
| 144 | NM_001315 | 779 | GTATATACATTCAGCTGAC | 78.5 | Training | | 38 |
| 145 | NM_001315 | 1080 | GGAACACCCCCGCTTATC | 27.2 | Training | | 39 |
| 146 | NM_001315 | 1317 | GTGGCCGATCCTTATGATC | 81.3 | Training | | 40 |
| 152 | NM_001315 | 607 | ATGTGATTGGTCTGTTGGA | 95.0 | Training | | 41 |
| 153 | NM_001315 | 1395 | GTCATCAGCTTTGTGCCAC | 92.0 | Training | | 42 |
| 154 | NM_001315 | 799 | TAATTCACAGGGACCTAAA | 82.0 | Training | | 43 |
| 155 | NM_001315 | 1277 | TGCCTACTTTGCTCAGTAC | 95.0 | Training | | 44 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 193 | NM_001315 | 565 | CCTACAGAGAACTGCGGTT | 90.0 | Training | | 45 |
| 190 | NM_001315 | 763 | TTCTCCGAGGTCTAAAGTA | 87.0 | Training | | 46 |
| 192 | NM_001315 | 1314 | CCAGTGGCCGATCCTTATG | 89.0 | Training | | 47 |
| 194 | NM_001315 | 1491 | GGCCTTTTCACGGGAACTC | 97.0 | Training | | 48 |
| 201 | NM_016195 | 2044 | CTGAAGAAGCTACTGCTTG | 80.3 | Test | Training | 49 |
| 202 | NM_016195 | 4053 | GACATGCGAATGACACTAG | 75.9 | Test | Training | 50 |
| 203 | NM_016195 | 3710 | AGAGGAACTCTCTGCAAGC | 84.7 | Test | Training | 51 |
| 204 | NM_014875 | 4478 | AAACTGGGAGGCTACTTAC | 93.0 | Test | Training | 52 |
| 205 | NM_014875 | 1297 | ACTGACAACAAAGTGCAGC | 37.0 | Test | Training | 53 |
| 206 | NM_014875 | 5130 | CTCACATTGTCCACCAGGA | 91.6 | Test | Training | 54 |
| 210 | NM_004523 | 4394 | GACCTGTGCCTTTTAGAGA | 63.7 | Training | Test | 55 |
| 211 | NM_004523 | 2117 | GACTTCATTGACAGTGGCC | 71.0 | Training | Test | 56 |
| 212 | NM_004523 | 799 | AAAGGACAACTGCAGCTAC | 49.0 | Training | Test | 57 |
| 213 | NM_000314 | 2753 | TGGAGGGGAATGCTCAGAA | 40.0 | Training | Training | 58 |
| 214 | NM_000314 | 2510 | TAAAGATGGCACTTTCCCG | 79.0 | Training | Training | 59 |
| 215 | NM_000314 | 2935 | AAGGCAGCTAAAGGAAGTG | 55.0 | Training | Training | 60 |
| 234 | NM_007054 | 963 | TATTGGGCCAGCAGATTAC | 76.9 | Training | Training | 61 |
| 235 | NM_007054 | 593 | TTATGACGCTAGGCCACAA | 74.4 | Training | Training | 62 |
| 236 | NM_007054 | 1926 | GGAGAAAGATCCCTTTGAG | 78.3 | Training | Training | 63 |
| 237 | NM_006845 | 324 | ACAAAAACGGAGATCCGTC | 72.2 | Training | Training | 64 |
| 238 | NM_006845 | 2206 | ATAAGCAGCAAGAAACGGC | 30.9 | Training | Training | 65 |
| 239 | NM_006845 | 766 | GAATTTCGGGCTACTTTGG | 65.8 | Training | Training | 66 |
| 240 | NM_005163 | 454 | CGCACCTTCCATGTGGAGA | 86.8 | Training | Training | 67 |
| 241 | NM_005163 | 1777 | AGACGTTTTTGTGCTGTGG | 76.0 | Training | Training | 68 |
| 242 | NM_005163 | 1026 | GCTGGAGAACCTCATGCTG | 87.8 | Training | Training | 69 |
| 243 | NM_005733 | 2139 | CTCTACCACTGAAGAGTTG | 90.7 | Training | Training | 70 |
| 244 | NM_005733 | 1106 | AAGTGGGTCGTAAGAACCA | 82.5 | Training | Training | 71 |
| 245 | NM_005733 | 696 | GAAGCTGTCCCTGCTAAAT | 93.4 | Training | Training | 72 |
| 246 | NM_001813 | 3928 | GAAGAGATCCCAGTGCTTC | 86.8 | Test | Training | 73 |
| 247 | NM_001813 | 4456 | TCTGAAAGTGACCAGCTCA | 82.5 | Test | Training | 74 |
| 248 | NM_001813 | 2293 | GAAAATGAAGCTTTGCGGG | 78.4 | Test | Training | 75 |
| 249 | NM_005030 | 1135 | AAGAAGAACCAGTGGTTCG | 83.0 | Test | Test | 76 |
| 250 | NM_005030 | 572 | CCGAGTTATTCATCGAGAC | 93.6 | Test | Test | 77 |
| 251 | NM_005030 | 832 | AAGAGACCTACCTCCGGAT | 85.0 | Test | Test | 78 |
| 255 | NM_001315 | 3050 | AATATCCTCAGGGGTGGAG | 36.0 | Training | | 79 |
| 256 | NM_001315 | 1526 | GTGCCTCTTGTTGCAGAGA | 88.0 | Training | | 80 |
| 257 | NM_001315 | 521 | GAAGCTCTCCAGACCATTT | 96.0 | Training | | 81 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 261 | NM_006218 | 456 | AGAAGCTGTGGATCTTAGG | 65.3 | Test | Training | 82 |
| 262 | NM_006218 | 3144 | TGATGCACATCATGGTGGC | 68.9 | Test | Training | 83 |
| 263 | NM_006218 | 2293 | CTAGGAAACCTCAGGCTTA | 94.7 | Test | Training | 84 |
| 264 | NM_000075 | 1073 | GCGAATCTCTGCCTTTCGA | 79.0 | Training | Training | 85 |
| 265 | NM_000075 | 685 | CAGTCAAGCTGGCTGACTT | 78.0 | Training | Training | 86 |
| 266 | NM_000075 | 581 | GGATCTGATGCGCCAGTTT | 77.0 | Training | Training | 87 |
| 288 | NM_020242 | 1829 | GCACAACTCCTGCAAATTC | 87.4 | Training | Training | 88 |
| 289 | NM_020242 | 3566 | GATGGAAGAGCCTCTAAGA | 82.7 | Training | Training | 89 |
| 290 | NM_020242 | 2631 | ACGAAAAGCTGCTTGAGAG | 73.4 | Training | Training | 90 |
| 291 | NM_004073 | 570 | GAAGACCATCTGTGGCACC | 65.0 | Training | Training | 91 |
| 292 | NM_004073 | 1977 | TCAGGGACCAGCTTTACTG | 60.0 | Training | Training | 92 |
| 293 | NM_004073 | 958 | GTTACCAAGAGCCTCTTTG | 75.0 | Training | Training | 93 |
| 294 | NM_005026 | 3279 | AACCAAAGTGAACTGGCTG | 56.3 | Training | Training | 94 |
| 295 | NM_005026 | 2121 | GATCGGCCACTTCCTTTTC | 70.9 | Training | Training | 95 |
| 296 | NM_005026 | 4004 | AGAGATCTGGGCCTCATGT | 67.3 | Training | Training | 96 |
| 303 | NM_000051 | 5373 | AGTTCGATCAGCAGCTGTT | 60.9 | Training | Training | 97 |
| 304 | NM_000051 | 3471 | TAGATTGTTCCAGGACACG | 71.2 | Training | Training | 98 |
| 305 | NM_000051 | 7140 | GAAGTTGGATGCCAGCTGT | 56.3 | Training | Training | 99 |
| 309 | NM_004064 | 1755 | TGGTGATCACTCCAGGTAG | 25.3 | Training | Training | 100 |
| 310 | NM_004064 | 1505 | TGTCCCTTTCAGAGACAGC | 5.0 | Training | Training | 101 |
| 311 | NM_004064 | 1049 | GACGTCAAACGTAAACAGC | 50.2 | Training | Training | 102 |
| 312 | NM_006219 | 1049 | AAGTTCATGTCAGGGCTGG | 76.6 | Test | Training | 103 |
| 313 | NM_006219 | 2631 | CAAAGATGCCCTTCTGAAC | 88.9 | Test | Training | 104 |
| 314 | NM_006219 | 453 | AATGCGCAAATTCAGCGAG | 32.9 | Test | Training | 105 |
| 339 | NM_003600 | 437 | GCACAAAAGCTTGTCTCCA | 96.0 | Test | Training | 106 |
| 340 | NM_003600 | 1071 | TTGCAGATTTTGGGTGGTC | 37.0 | Test | Training | 107 |
| 341 | NM_003600 | 1459 | ACAGTCTTAGGAATCGTGC | 61.1 | Test | Training | 108 |
| 342 | NM_004958 | 1476 | AGGACTTCGCCCATAAGAG | 61.8 | Test | Training | 109 |
| 343 | NM_004958 | 5773 | CAACCTCCAGGATACACTC | 80.9 | Test | Training | 110 |
| 344 | NM_004958 | 7886 | CCAACTTTCTAGCTGCTGT | 71.1 | Test | Training | 111 |
| 348 | NM_004856 | 1999 | GAATGTGAGCGTAGAGTGG | 92.2 | Training | Training | 112 |
| 349 | NM_004856 | 1516 | CCATTGGTTACTGACGTGG | 87.7 | Training | Training | 113 |
| 350 | NM_004856 | 845 | AACCCAAACCTCCACAATC | 71.8 | Training | Training | 114 |
| 369 | XM_294563 | 117 | GAAAGAAGCAGTTGACCTC | 59.9 | Training | Training | 115 |
| 370 | XM_294563 | 2006 | CTAAAAGCTGGGTGGACTC | 69.4 | Training | Training | 116 |
| 371 | XM_294563 | 389 | GAAAGCACCTCTTTGTGTG | 64.2 | Training | Training | 117 |
| 399 | NM_000546 | 1286 | TGAGGCCTTGGAACTCAAG | 17.8 | | | 118 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 400 | NM_000546 | 2066 | CCTCTTGGTCGACCTTAGT | 74.5 | | | 119 |
| 401 | NM_000546 | 1546 | GCACCCAGGACTTCCATTT | 93.2 | | | 120 |
| 417 | NM_001184 | 3790 | GAAACTGCAGCTATCTTCC | 75.8 | Training | Training | 121 |
| 418 | NM_001184 | 7717 | GTTACAATGAGGCTGATGC | 73.0 | Training | Training | 122 |
| 419 | NM_001184 | 5953 | TCACGACTCGCTGAACTGT | 78.8 | Training | Training | 123 |
| 453 | NM_005978 | 323 | GACCGACCCTGAAGCAGAA | 91.3 | Test | Test | 124 |
| 454 | NM_005978 | 254 | TTCCAGGAGTATGCTGTTT | 74.4 | Test | Test | 125 |
| 455 | NM_005978 | 145 | GGAACTTCTGCACAAGGAG | 96.5 | Test | Test | 126 |
| 465 | NM_000551 | 495 | TGTTGACGGACAGCCTATT | 75.5 | Test | Training | 127 |
| 466 | NM_000551 | 1056 | GGCATTGGCATCTGCTTTT | 89.7 | Test | Training | 128 |
| 467 | NM_000551 | 3147 | GTGAATGAGACACTCCAGT | 82.2 | Test | Training | 129 |
| 468 | NM_002658 | 1944 | GAGCTGGTGTCTGATTGTT | 82.8 | Test | Training | 130 |
| 469 | NM_002658 | 1765 | GTGTAAGCAGCTGAGGTCT | 44.4 | Test | Training | 131 |
| 470 | NM_002658 | 232 | CTGCCCAAAGAAATTCGGA | 47.8 | Test | Training | 132 |
| 507 | NM_003391 | 792 | ATTTGCCCGCGCATTTGTG | 27.2 | Test | Training | 133 |
| 508 | NM_003391 | 2171 | AGAAGATGAATGGTCTGGC | 69.4 | Test | Training | 134 |
| 509 | NM_003391 | 981 | AACGGGCGATTATCTCTGG | 43.3 | Test | Training | 135 |
| 540 | NM_002387 | 3490 | GACTTAGAGCTGGGAATCT | 83.7 | Test | Training | 136 |
| 541 | NM_002387 | 4098 | AGTTGAGGAGGTTTCTGCA | 86.1 | Test | Training | 137 |
| 542 | NM_002387 | 1930 | GGATTATATCCAGCAGCTC | 82.3 | Test | Training | 138 |
| 585 | NM_014885 | 509 | GTGGCTGGATTCATGTTCC | 81.5 | Training | Training | 139 |
| 586 | NM_014885 | 798 | CAAGGCATCCGTTATATCT | 84.7 | Training | Training | 140 |
| 587 | NM_014885 | 270 | ACCAGGATTTGGAGTGGAT | 84.7 | Training | Training | 141 |
| 639 | NM_001274 | 250 | CTGAAGAAGCAGTCGCAGT | 77.7 | | | 142 |
| 640 | NM_001274 | 858 | ATCGATTCTGCTCCTCTAG | 86.2 | | | 143 |
| 641 | NM_001274 | 1332 | TGCCTGAAAGAGACTTGTG | 85.4 | | | 144 |
| 651 | NM_001259 | 807 | TCTTGGACGTGATTGGACT | 89.8 | Training | Training | 145 |
| 652 | NM_001259 | 1036 | AGAAAACCTGGATTCCCAC | 88.9 | Training | Training | 146 |
| 653 | NM_001259 | 556 | ACCACAGAACATTCTGGTG | 89.3 | Training | Training | 147 |
| 672 | NM_003161 | 2211 | GAAAGCCAGACAACTTCTG | 87.1 | Test | Training | 148 |
| 673 | NM_003161 | 1223 | CTCTCAGTGAAAGTGCCAA | 91.2 | Test | Training | 149 |
| 674 | NM_003161 | 604 | GACACTGCCTGCTTTTACT | 98.1 | Test | Training | 150 |
| 678 | NM_004972 | 3526 | AAGAACCTGGTGAAAGTCC | 57.2 | Training | Training | 151 |
| 679 | NM_004972 | 4877 | GAAGTGCAGCAGGTTAAGA | 54.8 | Training | Training | 152 |
| 680 | NM_004972 | 1509 | AGCCGAGTTGTAACTATCC | 74.9 | Training | Training | 153 |
| 684 | NM_007194 | 1245 | GATCACAGTGGCAATGAA | 80.9 | | | 154 |
| 685 | NM_007194 | 1432 | AAACTCTTGGAAGTGGTGC | 39.2 | | | 155 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 686 | NM_007194 | 2269 | ATGAATCCACAGCTCTACC | 44.6 | | | 156 |
| 687 | NM_007313 | 3866 | GAATGGAAGCCTGAACTGA | 92.4 | Test | Training | 157 |
| 688 | NM_007313 | 2451 | AGACATCATGGAGTCCAGC | 5.0 | Test | Training | 158 |
| 689 | NM_007313 | 1296 | CAAGTTCTCCATCAAGTCC | 91.1 | Test | Training | 159 |
| 711 | NM_139049 | 129 | GGAATAGTATGCGCAGCTT | 92.5 | Test | Training | 160 |
| 712 | NM_139049 | 369 | GTGATTCAGATGGAGCTAG | 89.0 | Test | Training | 161 |
| 713 | NM_139049 | 969 | CACCCGTACATCAATGTCT | 77.0 | Test | Training | 162 |
| 858 | NM_001253 | 522 | TCATTGGAAGAACAGCGGC | 0.0 | Test | Training | 163 |
| 859 | NM_001253 | 2571 | AAGAAGACGTTCAGCGACA | 93.5 | Test | Training | 164 |
| 860 | NM_001253 | 911 | AAAAAGCCTGCCCTTGGTT | 88.1 | Test | Training | 165 |
| 1110 | NM_006101 | 1847 | CTTGCAACGTCTGTTAGAG | 72.3 | Test | Training | 166 |
| 1111 | NM_006101 | 999 | CTGAAGGCTTCCTTACAAG | 82.9 | Test | Training | 167 |
| 1112 | NM_006101 | 1278 | CAGAAGTTGTGGAATGAGG | 79.1 | Test | Training | 168 |
| 1182 | NM_016231 | 1302 | GCAATGAGGACAGCTTGTG | 79.8 | Test | Training | 169 |
| 1183 | NM_016231 | 1829 | TGTAGCTTTCCACTGGAGT | 79.3 | Test | Training | 170 |
| 1184 | NM_016231 | 1019 | TCTCCTTGTGAACAGCAAC | 62.5 | Test | Training | 171 |
| 1212 | NM_001654 | 1072 | AGTGAAGAACCTGGGGTAC | 79.3 | Test | Training | 172 |
| 1213 | NM_001654 | 595 | GTTCCACCAGCATTGTTCC | 86.2 | Test | Training | 173 |
| 1214 | NM_001654 | 1258 | GAATGAGATGCAGGTGCTC | 86.9 | Test | Training | 174 |
| 1287 | NM_005417 | 2425 | CAATTCGTCGGAGGCATCA | 73.9 | Test | Training | 175 |
| 1288 | NM_005417 | 1077 | GGGGAGTTTGCTGGACTTT | 66.4 | Test | Training | 176 |
| 1289 | NM_005417 | 3338 | GCAGTGCCTGCCTATGAAA | 68.2 | Test | Training | 177 |
| 1290 | NM_001982 | 3223 | CTAGACCTAGACCTAGACT | 63.5 | Test | Training | 178 |
| 1291 | NM_001982 | 3658 | GAGGATGTCAACGGTTATG | 49.4 | Test | Training | 179 |
| 1292 | NM_001982 | 2289 | CAAAGTCTTGGCCAGAATC | 45.3 | Test | Training | 180 |
| 1293 | NM_005400 | 249 | GATCGAGCTGGCTGTCTTT | 85.4 | Test | Training | 181 |
| 1294 | NM_005400 | 1326 | GGTCTTAAAGAAGGACGTC | 63.4 | Test | Training | 182 |
| 1295 | NM_005400 | 1848 | TGAGGACGACCTATTTGAG | 0.0 | Test | Training | 183 |
| 1317 | NM_002086 | 465 | TGAGCTGGTGGATTATCAC | 85.5 | Test | Test | 184 |
| 1318 | NM_002086 | 183 | CTGGTACAAGGCAGAGCTT | 95.5 | Test | Test | 185 |
| 1319 | NM_002086 | 720 | CCGGAACGTCTAAGAGTCA | 92.3 | Test | Test | 186 |
| 1332 | NM_006219 | 2925 | TACAGAAAAGTTTGGCCGG | 20.1 | Test | Training | 187 |
| 1333 | NM_006219 | 2346 | AATGAAGCCTTTGTGGCTG | 22.4 | Test | Training | 188 |
| 1334 | NM_006219 | 2044 | GTGCACATTCCTGCTGTCT | 79.0 | Test | Training | 189 |
| 1335 | NM_003600 | 1618 | CCTCCCTATTCAGAAAGCT | 84.2 | Test | Training | 190 |
| 1336 | NM_003600 | 650 | GACTTTGAAATTGGTCGCC | 52.1 | Test | Training | 191 |
| 1337 | NM_003600 | 538 | CACCCAAAAGAGCAAGCAG | 96.3 | Test | Training | 192 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 1338 | XM_294563 | 2703 | TAAGCCTGGTGGTGATCTT | 78.1 | Training | Training | 193 |
| 1339 | XM_294563 | 1701 | AAGGTCTTTACGCCAGTAC | 29.5 | Training | Training | 194 |
| 1340 | XM_294563 | 789 | GGAATGTATCCGAGCACTG | 73.5 | Training | Training | 195 |
| 1386 | NM_033360 | 493 | GGACTCTGAAGATGTACCT | 91.0 | Test | Training | 196 |
| 1387 | NM_033360 | 897 | GGCATACTAGTACAAGTGG | 84.8 | Test | Training | 197 |
| 1388 | NM_033360 | 704 | GAAAAGACTCCTGGCTGTG | 0.0 | Test | Training | 198 |
| 1389 | NM_024408 | 4735 | CTTTGAATGCCAGGGGAAC | 91.6 | Test | Training | 199 |
| 1390 | NM_024408 | 2674 | CCAAGGAACCTGCTTTGAT | 96.4 | Test | Training | 200 |
| 1391 | NM_024408 | 5159 | GACTCAGACCACTGCTTCA | 95.8 | Test | Training | 201 |
| 1392 | NM_000435 | 6045 | GCTGCTGTTGGACCACTTT | 0.0 | Test | Training | 202 |
| 1393 | NM_000435 | 5495 | TGCCAACTGAAGAGGATGA | 0.0 | Test | Training | 203 |
| 1394 | NM_000435 | 4869 | TGATCACTGCTTCCCCGAT | 0.0 | Test | Training | 204 |
| 1410 | AF308602 | 770 | ATATCGACGATTGTCCAGG | 36.7 | Test | Training | 205 |
| 1411 | AF308602 | 3939 | AGGCAAGCCCTGCAAGAAT | 81.3 | Test | Training | 206 |
| 1412 | AF308602 | 1644 | CACTTACACCTGTGTGTGC | 81.3 | Test | Training | 207 |
| 1581 | NM_005633 | 3593 | TATCAGACCGGACCTCTAT | 70.8 | Test | Training | 208 |
| 1582 | NM_005633 | 364 | ATTGACCACCAGGTTTCTG | 1.4 | Test | Training | 209 |
| 1583 | NM_005633 | 3926 | CTTACAAAAGGGAGCACAC | 66.9 | Test | Training | 210 |
| 1620 | NM_002388 | 1097 | GTCTCAGCTTCTGCGGTAT | 95.0 | Test | Training | 211 |
| 1621 | NM_002388 | 286 | AGGATTTTGTGGCCTCCAT | 94.6 | Test | Training | 212 |
| 1622 | NM_002388 | 2268 | TCCAGGTTGAAGGCATTCA | 92.5 | Test | Training | 213 |
| 1629 | NM_012193 | 3191 | TTGGCAAAGGCTCCTTGTA | 80.0 | Test | Test | 214 |
| 1630 | NM_012193 | 5335 | CCATCTGCTTGAGCTACTT | 85.0 | Test | Test | 215 |
| 1631 | NM_012193 | 2781 | GTTGACTTACCTGACGGAC | 43.1 | Test | Test | 216 |
| 1632 | NM_004380 | 3708 | GACATCCCGAGTCTATAAG | 85.3 | Test | Training | 217 |
| 1633 | NM_004380 | 339 | TGGAGGAGAATTAGGCCTT | 81.1 | Test | Training | 218 |
| 1634 | NM_004380 | 5079 | GCACAAGGAGGTCTTCTTC | 79.0 | Test | Training | 219 |
| 1641 | NM_017412 | 2331 | CAGATCACTCCAGGCATAG | 97.3 | Test | Training | 220 |
| 1643 | NM_017412 | 2783 | ATGTGTGGTGACTGCTTTG | 95.7 | Test | Training | 221 |
| 1695 | NM_001903 | 2137 | TGACATCATTGTGCTGGCC | 38.4 | Test | Training | 222 |
| 1696 | NM_001903 | 655 | CGTTCCGATCCTCTATACT | 97.9 | Test | Training | 223 |
| 1697 | NM_001903 | 3117 | TGACCAAAGATGACCTGTG | 40.1 | Test | Training | 224 |
| 1815 | NM_020168 | 3064 | GAGAAAGAATGGGGTCGGT | 85.0 | Training | Training | 225 |
| 1816 | NM_020168 | 681 | CGACATCCAGAAGTTGTCA | 86.1 | Training | Training | 226 |
| 1817 | NM_020168 | 1917 | TGAGGAGCAGATTGCCACT | 72.1 | Training | Training | 227 |
| 2502 | NM_000271 | 237 | GAGGTACAATTGCGAATAT | 87.0 | Training | Training | 228 |
| 2503 | NM_000271 | 559 | TACTACGTCGGACAGAGTT | 76.0 | Training | Training | 229 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 2504 | NM_000271 | 1783 | AACTACAATAACGCCACTG | 39.0 | Training | Training | 230 |
| 2505 | NM_000271 | 2976 | GCCACAGTCGTCTTGCTGT | 84.0 | Training | Training | 231 |
| 2512 | NM_005030 | 245 | GGGCGGCTTTGCCAAGTGC | 88.6 | Test | Test | 232 |
| 2513 | NM_005030 | 1381 | CACGCCTCATCCTCTACAA | 90.5 | Test | Test | 233 |
| 2514 | NM_005030 | 834 | GAGACCTACCTCCGGATCA | 91.0 | Test | Test | 234 |
| 2521 | NM_000314 | 1316 | CCCACCACAGCTAGAACTT | 93.0 | Training | Training | 235 |
| 2522 | NM_000314 | 1534 | CTATTCCCAGTCAGAGGCG | 89.0 | Training | Training | 236 |
| 2523 | NM_000314 | 2083 | CAGTAGAGGAGCCGTCAAA | 90.0 | Training | Training | 237 |
| 2524 | NM_006622 | 1928 | CAGTTCACTATTACGCAGA | 65.0 | Training | Training | 238 |
| 2525 | NM_006622 | 586 | TGTTACGAGATGACAGATT | 73.0 | Training | Training | 239 |
| 2526 | NM_006622 | 1252 | AACCCAGAGGATCGTCCCA | 70.0 | Training | Training | 240 |
| 2527 | NM_139164 | 200 | CTGTTTGGAGAAAACCCTC | 79.0 | Training | Training | 241 |
| 2528 | NM_139164 | 568 | GACAACCCAAACCAGAGTC | 71.0 | Training | Training | 242 |
| 2529 | NM_139164 | 488 | GTCTTGACTGGGATGAAAA | 66.0 | Training | Training | 243 |
| 2530 | NM_139164 | 578 | ACCAGAGTCTTTTGACAGG | 82.0 | Training | Training | 244 |
| 2546 | NM_014875 | 1090 | TAGACCACCCATTGCTTCC | 63.5 | Test | Training | 245 |
| 2547 | NM_014875 | 1739 | AGAGCCTTCGAAGGCTTCA | 73.2 | Test | Training | 246 |
| 2548 | NM_014875 | 3563 | GACCATAGCATCCGCCATG | 87.1 | Test | Training | 247 |
| 2602 | NM_002387 | 2655 | TAGCTCTGCTAGAGGAGGA | 71.0 | Test | Training | 248 |
| 2603 | NM_002387 | 1418 | ACAGAACGGCTGAATAGCC | 43.5 | Test | Training | 249 |
| 2604 | NM_002387 | 941 | GAGAATGAGAGCCTGACTG | 81.0 | Test | Training | 250 |
| 2605 | NM_016231 | 1683 | GGAAACAGAGTGCCTCTCT | 55.3 | Test | Training | 251 |
| 2606 | NM_016231 | 915 | CCACTCAGCTCAGATCATG | 82.3 | Test | Training | 252 |
| 2607 | NM_016231 | 737 | TCTGGTCTCTTGCAAAAGG | 30.3 | Test | Training | 253 |
| 2611 | NM_004380 | 4230 | ATTTTTGCGGCGCCAGAAT | 79.0 | Test | Training | 254 |
| 2612 | NM_004380 | 2197 | GAAAAACGGAGGTCGCGTT | 85.9 | Test | Training | 255 |
| 2613 | NM_004380 | 5701 | GAAAACAAATGCCCCGTGC | 55.4 | Test | Training | 256 |
| 2614 | NM_005978 | 276 | TGGCACTCATCACTGTCAT | 91.8 | Test | Test | 257 |
| 2615 | NM_005978 | 229 | TGAGAACAGTGACCAGCAG | 91.9 | Test | Test | 258 |
| 2616 | NM_005978 | 369 | GGGCCCAGGACTGTTGATG | 94.5 | Test | Test | 259 |
| 2617 | NM_017412 | 3128 | AGAGATGGGCATTGTTTCC | 94.3 | Test | Training | 260 |
| 2618 | NM_017412 | 814 | GCTCATGGAGATGTTTGGT | 88.7 | Test | Training | 261 |
| 2619 | NM_017412 | 1459 | AGCATTGCTGTTTCACGCC | 93.1 | Test | Training | 262 |
| 2620 | NM_001654 | 1902 | TTGAGCTGCTGCCACGGTC | 67.2 | Test | Training | 263 |
| 2621 | NM_001654 | 1006 | GTCCCCACATTCCAAGTCA | 90.0 | Test | Training | 264 |
| 2622 | NM_001654 | 2327 | CCTCTCTGGAATTTGTGCC | 85.7 | Test | Training | 265 |
| 2623 | NM_002658 | 202 | CAAGTACTTCTCCAACATT | 87.2 | Test | Training | 266 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 2624 | NM_002658 | 181 | TGGAGGAACATGTGTGTCC | 0.0 | Test | Training | 267 |
| 2625 | NM_002658 | 436 | TTACTGCAGGAACCCAGAC | 0.0 | Test | Training | 268 |
| 2629 | NM_006218 | 1334 | TGGCTTTGAATCTTTGGCC | 3.5 | Test | Training | 269 |
| 2630 | NM_006218 | 2613 | AGGTGCACTGCAGTTCAAC | 53.8 | Test | Training | 270 |
| 2631 | NM_006218 | 1910 | TTCAGCTAGTACAGGTCCT | 78.0 | Test | Training | 271 |
| 2632 | NM_003161 | 1834 | TTGATTCCTCGCGACATCT | 88.3 | Test | Training | 272 |
| 2633 | NM_003161 | 1555 | GCTTTTCCCATGATCTCCA | 90.7 | Test | Training | 273 |
| 2634 | NM_003161 | 217 | CTTGGCATGGAACATTGTG | 61.4 | Test | Training | 274 |
| 2635 | NM_003391 | 2072 | GCCTCAGAAAGGGATTGCT | 79.1 | Test | Training | 275 |
| 2636 | NM_003391 | 1318 | GCTCTGGATGTGCACACAT | 60.5 | Test | Training | 276 |
| 2637 | NM_003391 | 1734 | GTGTCTCAAAGGAGCTTTC | 87.1 | Test | Training | 277 |
| 2641 | AF308602 | 4260 | ATTCAACGGGCTCTTGTGC | 0.0 | Test | Training | 278 |
| 2642 | AF308602 | 1974 | GATCGATGGCTACGAGTGT | 84.0 | Test | Training | 279 |
| 2643 | AF308602 | 5142 | CATCCCTACAAGATCGAG | 41.6 | Test | Training | 280 |
| 2644 | NM_024408 | 8232 | GCAACTTTGGTCTCCTTTC | 91.0 | Test | Training | 281 |
| 2645 | NM_024408 | 10503 | GCAATTGGCTGTGATGCTC | 86.6 | Test | Training | 282 |
| 2646 | NM_024408 | 8643 | GAGACAAGTTAACTCGTGC | 89.4 | Test | Training | 283 |
| 2647 | NM_007313 | 4222 | TCCTGGCAAGAAAGCTTGA | 65.6 | Test | Training | 284 |
| 2648 | NM_007313 | 3237 | AAACCTCTACACGTTCTGC | 53.5 | Test | Training | 285 |
| 2649 | NM_007313 | 302 | CTAAAGGTGAAAAGCTCCG | 67.8 | Test | Training | 286 |
| 2650 | NM_000551 | 631 | GATCTGGAAGACCACCCAA | 70.9 | Test | Training | 287 |
| 2651 | NM_000551 | 4678 | CAGAACCCAAAAGGGTAAG | 0.0 | Test | Training | 288 |
| 2652 | NM_000551 | 4382 | AGGAAATAGGCAGGGTGTG | 4.3 | Test | Training | 289 |
| 2653 | NM_001903 | 1888 | AGCAGTGCTGATGATAAGG | 89.1 | Test | Training | 290 |
| 2654 | NM_001903 | 2606 | AAGCCATTGGTGAAGAGAG | 91.9 | Test | Training | 291 |
| 2655 | NM_001903 | 1583 | TGTGTCATTGCTCTCCAAG | 90.3 | Test | Training | 292 |
| 2656 | NM_002388 | 842 | GCAGATGAGCAAGGATGCT | 86.8 | Test | Training | 293 |
| 2657 | NM_002388 | 1754 | GTACATCCATGTGGCCAAA | 94.6 | Test | Training | 294 |
| 2658 | NM_002388 | 2642 | TGGGTCATGAAAGCTGCCA | 93.1 | Test | Training | 295 |
| 2662 | NM_005633 | 3251 | GAACACCGTTAACACCTCC | 31.2 | Test | Training | 296 |
| 2663 | NM_005633 | 2899 | ATAACAGGAGAGATCCAGC | 21.7 | Test | Training | 297 |
| 2664 | NM_005633 | 2607 | TGGTGTCCTTGAGGTTGTC | 75.1 | Test | Training | 298 |
| 2665 | NM_033360 | 329 | ACCTGTCTCTTGGATATTC | 81.4 | Test | Training | 299 |
| 2666 | NM_033360 | 529 | TAAATGTGATTTGCCTTCT | 47.8 | Test | Training | 300 |
| 2667 | NM_033360 | 585 | GAAGTTATGGAATTCCTTT | 94.2 | Test | Training | 301 |
| 2668 | NM_139049 | 745 | CACCATGTCCTGAATTCAT | 80.7 | Test | Training | 302 |
| 2669 | NM_139049 | 433 | TCAAGCACCTTCATTCTGC | 42.6 | Test | Training | 303 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 2670 | NM_139049 | 550 | CGAGTTTTATGATGACGCC | 79.9 | Test | Training | 304 |
| 2671 | NM_002086 | 555 | ATACGTCCAGGCCCTCTTT | 87.9 | Test | Test | 305 |
| 2672 | NM_002086 | 392 | TGCAGCACTTCAAGGTGCT | 36.9 | Test | Test | 306 |
| 2673 | NM_002086 | 675 | CGGGCAGACCGGCATGTTT | 92.6 | Test | Test | 307 |
| 2674 | NM_004958 | 5024 | GACATGAGAACCTGGCTCA | 77.8 | Test | Training | 308 |
| 2675 | NM_004958 | 2155 | CTTGCAGGCCTTGTTTGTG | 83.2 | Test | Training | 309 |
| 2676 | NM_004958 | 6955 | TAATACAGCTGGGGACGAC | 52.3 | Test | Training | 310 |
| 2677 | NM_012193 | 467 | AGAACCTCGGCTACAACGT | 71.5 | Test | Test | 311 |
| 2678 | NM_012193 | 473 | TCGGCTACAACGTGACCAA | 51.3 | Test | Test | 312 |
| 2679 | NM_012193 | 449 | TCCGCATCTCCATGTGCCA | 37.5 | Test | Test | 313 |
| 2680 | NM_005400 | 665 | TCACAAAGTGTGCTGGGTT | 43.9 | Test | Training | 314 |
| 2681 | NM_005400 | 2178 | CCAGGAGGAATTCAAAGGT | 41.6 | Test | Training | 315 |
| 2682 | NM_005400 | 1022 | GCTCACCATCTGAGGAAGA | 64.2 | Test | Training | 316 |
| 2686 | NM_001982 | 948 | TGACAGTGGAGCCTGTGTA | 65.8 | Test | Training | 317 |
| 2687 | NM_001982 | 1800 | CTTTCTGAATGGGGAGCCT | 61.7 | Test | Training | 318 |
| 2688 | NM_001982 | 2860 | TACACACACCAGAGTGATG | 0.0 | Test | Training | 319 |
| 2692 | NM_016195 | 5331 | ATGAAGGAGAGTGATCACC | 10.5 | Test | Training | 320 |
| 2693 | NM_016195 | 4829 | AATGGCAGTGAAACACCCT | 67.3 | Test | Training | 321 |
| 2694 | NM_016195 | 1480 | AAGTTTGTGTCCCAGACAC | 80.5 | Test | Training | 322 |
| 2695 | NM_000435 | 2107 | AATGGCTTCCGCTGCCTCT | 0.0 | Test | Training | 323 |
| 2696 | NM_000435 | 5193 | GAACATGGCCAAGGGTGAG | 15.5 | Test | Training | 324 |
| 2697 | NM_000435 | 7273 | GAGTCTGGGACCTCCTTCT | 0.0 | Test | Training | 325 |
| 2802 | NM_004523 | 46 | CCAGGGAGACTCCGGCCCC | 6.7 | Training | Test | 326 |
| 2803 | NM_004523 | 132 | GGGACCGTCATGGCGTCGC | 8.2 | Training | Test | 327 |
| 2804 | NM_004523 | 221 | ATTTAATTTGGCAGAGCGG | 0.0 | Training | Test | 328 |
| 2805 | NM_004523 | 322 | GCTCAAGGAAAACATACAC | 76.2 | Training | Test | 329 |
| 2806 | NM_004523 | 365 | TACTAAACAGATTGATGTT | 77.9 | Training | Test | 330 |
| 2807 | NM_004523 | 581 | TACTGATAATGGTACTGAA | 93.8 | Training | Test | 331 |
| 2808 | NM_004523 | 716 | AGGAGTGATAATTAAAGGT | 84.8 | Training | Test | 332 |
| 2809 | NM_004523 | 852 | GTTTTCTCTGTTACAATAC | 85.4 | Training | Test | 333 |
| 2810 | NM_004523 | 995 | TGGAAATATAAATCAATCC | 0.0 | Training | Test | 334 |
| 2811 | NM_004523 | 1085 | ACTAACTAGAATCCTCCAG | 0.0 | Training | Test | 335 |
| 2812 | NM_004523 | 1174 | AAACTCTGAGTACATTGGA | 81.9 | Training | Test | 336 |
| 2813 | NM_004523 | 1375 | TAACTGTTCAAGAAGAGCA | 14.1 | Training | Test | 337 |
| 2814 | NM_004523 | 1570 | AAGAAGAATATATCACATC | 0.0 | Training | Test | 338 |
| 2815 | NM_004523 | 1706 | AGTTGACCAACACAATGCA | 86.0 | Training | Test | 339 |
| 2816 | NM_004523 | 2197 | TACATGAACTACAAGAAAA | 90.0 | Training | Test | 340 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 2817 | NM_004523 | 2858 | GACTAAGCTTAATTGCTTT | 87.0 | Training | Test | 341 |
| 2818 | NM_004523 | 3089 | GGGGCAGTATACTGAAGAA | 64.5 | Training | Test | 342 |
| 2819 | NM_004523 | 3878 | TTCTTGTATATTATTAAGT | 0.0 | Training | Test | 343 |
| 2820 | NM_004523 | 4455 | TCTATAATTTATATTCTTT | 9.3 | Training | Test | 344 |
| 2821 | NM_004523 | 4648 | TACAAAGAATAAATTTTCT | 23.5 | Training | Test | 345 |
| 2823 | NM_005030 | 45 | CAGCGCAGCTTCGGGAGCA | 72.1 | Training | Test | 346 |
| 2824 | NM_005030 | 131 | CGGAGTTGCAGCTCCCGGA | 85.7 | Training | Test | 347 |
| 2825 | NM_005030 | 303 | GGCAAGATTGTGCCTAAGT | 80.3 | Training | Test | 348 |
| 2826 | NM_005030 | 346 | GGGAGAAGATGTCCATGGA | 100.0 | Training | Test | 349 |
| 2827 | NM_005030 | 432 | GACTTCGTGTTCGTGGTGT | 89.3 | Training | Test | 350 |
| 2828 | NM_005030 | 519 | GCCCGATACTACCTACGGC | 86.2 | Training | Test | 351 |
| 2829 | NM_005030 | 648 | GGACTGGCAACCAAAGTCG | 86.7 | Training | Test | 352 |
| 2830 | NM_005030 | 777 | TGTATCATGTATACCTTGT | 84.3 | Training | Test | 353 |
| 2831 | NM_005030 | 821 | TTCTTGCCTAAAAGAGACC | 26.8 | Training | Test | 354 |
| 2832 | NM_005030 | 907 | TCCAGAAGATGCTTCAGAC | 90.8 | Training | Test | 355 |
| 2833 | NM_005030 | 952 | ACGAGCTGCTTAATGACGA | 87.7 | Training | Test | 356 |
| 2834 | NM_005030 | 1038 | TCGATTGCTCCCAGCAGCC | 31.4 | Training | Test | 357 |
| 2835 | NM_005030 | 1082 | CACAGTCCTCAATAAAGGC | 62.9 | Training | Test | 358 |
| 2836 | NM_005030 | 1214 | CAATGCCTCCAAGCCCTCG | 0.0 | Training | Test | 359 |
| 2837 | NM_005030 | 1300 | AGTGGGTGGACTATTCGGA | 84.9 | Training | Test | 360 |
| 2838 | NM_005030 | 1515 | TACATGAGCGAGCACTTGC | 20.3 | Training | Test | 361 |
| 2839 | NM_005030 | 1860 | CTCAAGGCCTCCTAATAGC | 74.2 | Training | Test | 362 |
| 2840 | NM_005030 | 1946 | CCGCGGTGCCATGTCTGCA | 79.7 | Training | Test | 363 |
| 2841 | NM_005030 | 2075 | CCCCTCCCCCTCAACCCCA | 34.6 | Training | Test | 364 |
| 3041 | NM_014875 | 4629 | ATTTTCTAGAAAACGGTAA | 91.8 | | | 365 |
| 3042 | NM_014875 | 77 | GAGGGGCGAAGTTTCGGCA | 71.2 | | | 366 |
| 3043 | NM_014875 | 243 | CTGGGACCGGGAAGCCGGA | 0.0 | | | 367 |
| 3044 | NM_014875 | 5094 | CTTCTACTTCTGTTGGCAG | 85.9 | | | 368 |
| 3045 | NM_014875 | 4354 | ACTTACTATTCAGACTGCA | 85.7 | | | 369 |
| 3046 | NM_014875 | 524 | GCCCTCACCCACAGTAGCC | 68.1 | | | 370 |
| 3047 | NM_014875 | 5349 | CAGAGGAATGCACACCCAG | 73.6 | | | 371 |
| 3048 | NM_014875 | 4824 | GATTGATTAGATCTCTTGA | 91.3 | | | 372 |
| 3049 | NM_014875 | 3014 | GTGAGTATTATCCCAGT7G | 41.5 | | | 373 |
| 3050 | NM_014875 | 2959 | ATCTGGGGTGCTGATTGCT | 46.3 | | | 374 |
| 3051 | NM_014875 | 1514 | GTGACAGTGGCAGTACGCG | 67.7 | | | 375 |

TABLE II-continued

A library of 377 siRNAs

| BioID | accession number | start position | 19 mer sequence | % silencing | Set 1 | Set 2 | SEQ ID NO |
|---|---|---|---|---|---|---|---|
| 3052 | NM_014875 | 1114 | TCAGACTGAAGTTGTTAGA | 80.8 | | | 376 |
| 3053 | NM_014875 | 2079 | GTTGGCTAGAATTGGGAAA | 91.8 | | | 377 |
| 3054 | NM_014875 | 3560 | GAAGACCATAGCATCCGCC | 74.8 | | | 378 |

TABLE III 30 siRNAs designed using the method of this example

| BioID | Accession | Gene name | Sequence (sense strand) | % Silencing | SEQ ID NO |
|---|---|---|---|---|---|
| 3844 | NM_014875 | KIF14 | CAGGTAAAGTCAGAGACAT | 87 | 379 |
| 3845 | NM_014875 | KIF14 | GGGATTGACGGCAGTAAGA | 89 | 380 |
| 3846 | NM_014875 | KIF14 | CACTGAATGTGGGAGGTGA | 92 | 381 |
| 3847 | NM_014875 | KIF14 | GTCTGGGTGGAAATTCAAA | 93 | 382 |
| 3848 | NM_014875 | KIF14 | CATCTTTGCTGAATCGAAA | 86 | 383 |
| 3849 | NM_014875 | KIF14 | CAGGGATGCTGTTTGGATA | 95 | 384 |
| 3850 | NM_005030 | PLK | CCCTGTGTGGGACTCCTAA | 87 | 385 |
| 3851 | NM_005030 | PLK | GGTGTTCGCGGGCAAGATT | 86 | 386 |
| 3852 | NM_005030 | PLK | CGCCTCATCCTCTACAATG | 88 | 387 |
| 3853 | NM_005030 | PLK | GTTCTTTACTTCTGGCTAT | 97 | 388 |
| 3854 | NM_005030 | PLK | CTCCTTAAATATTTCCGCA | 92 | 389 |
| 3855 | NM_005030 | PLK | CTGAGCCTGAGGCCCGATA | 75 | 390 |
| 3856 | NM_000875 | IGF1R | CAAATTATGTGTTTCCGAA | 90 | 391 |
| 3857 | NM_000875 | IGF1R | CGCATGTGCTGGCAGTATA | 84 | 392 |
| 3858 | NM_000875 | IGF1R | CCGAAGATTTCACAGTCAA | 79 | 393 |
| 3859 | NM_000875 | IGF1R | ACCATTGATTCTGTTACTT | 86 | 394 |
| 3860 | NM_000875 | IGF1R | ACCGCAAAGTCTTTGAGAA | 88 | 395 |
| 3861 | NM_000875 | IGF1R | GTCCTGACATGCTGTTTGA | 79 | 396 |
| 3862 | NM_001315 | MAPK14 | GGAATTCAATGATGTGTAT | 85 | 397 |
| 3863 | NM_001315 | MAPK14 | GCTGTTGACTGGAAGAACA | 84 | 398 |
| 3864 | NM_001315 | MAPK14 | CTCCTGAGATCATGCTGAA | 81 | 399 |
| 3865 | NM_001315 | MAPK14 | CCATTTCAGTCCATCATTC | 88 | 400 |
| 3866 | NM_001315 | MAPK14 | CAGATTATGCGTCTGACAG | 25 | 401 |
| 3867 | NM_001315 | MAPK14 | CGCTTATCTCATTAACAGG | 14 | 402 |
| 3871 | NM_004523 | KIF11 | GAGCCCAGATCAACCTTTA | 87 | 403 |
| 3872 | NM_004523 | KIF11 | CTGACAAGAGCTCAAGGAA | 89 | 404 |
| 3873 | NM_004523 | KIF11 | GGCATTAACACACTGGAGA | 92 | 405 |
| 3874 | NM_004523 | KIF11 | GATGGCAGCTCAAAGCAAA | 93 | 406 |

TABLE III-continued 30 siRNAs designed using the method of this example

| BioID | Accession | Gene name | Sequence (sense strand) | % Silencing | SEQ ID NO |
|---|---|---|---|---|---|
| 3875 | NM_004523 | KIF11 | CAGCAGAAATCTAAGGATA | 86 | 407 |
| 3876 | NM_004523 | KIF11 | CGTTCTGGAGCTGTTGATA | 95 | 408 |

6.2. Example 2

Selection of siRNAS for Silencing Specificity

The importance of off-target effects of siRNA and sbRNA sequences have been shown. Microarray experiments suggest that most siRNA oligos result in downregulation of off-target genes through direct interactions between dsRNA and the off-target transcripts. While sequence similarity between dsRNA and transcripts appears to play a role in determining which off-target genes will be affected, sequence similarity searches, even combined with thermodynamic models of hybridization, are insufficient to predict off-target effects accurately. However, alignment of off-target transcripts with offending siRNA sequences reveals that some base pairing interactions between the two appear to be more important than others (FIG. 6).

FIG. 6 shows an example of alignments of transcripts of off-target genes to the core 19mer of an siRNA oligo sequence. Off-target genes were selected from the Human 25 k v2.2.1 microarray by selecting for kinetic patterns of transcript abundance consistent with direct effects of siRNA oligos. Alignments were generated with FASTA and edited by hand. The black boxes and grey area demonstrate the higher level of sequence similarity in the 3' half of the alignment.

Figure 7:
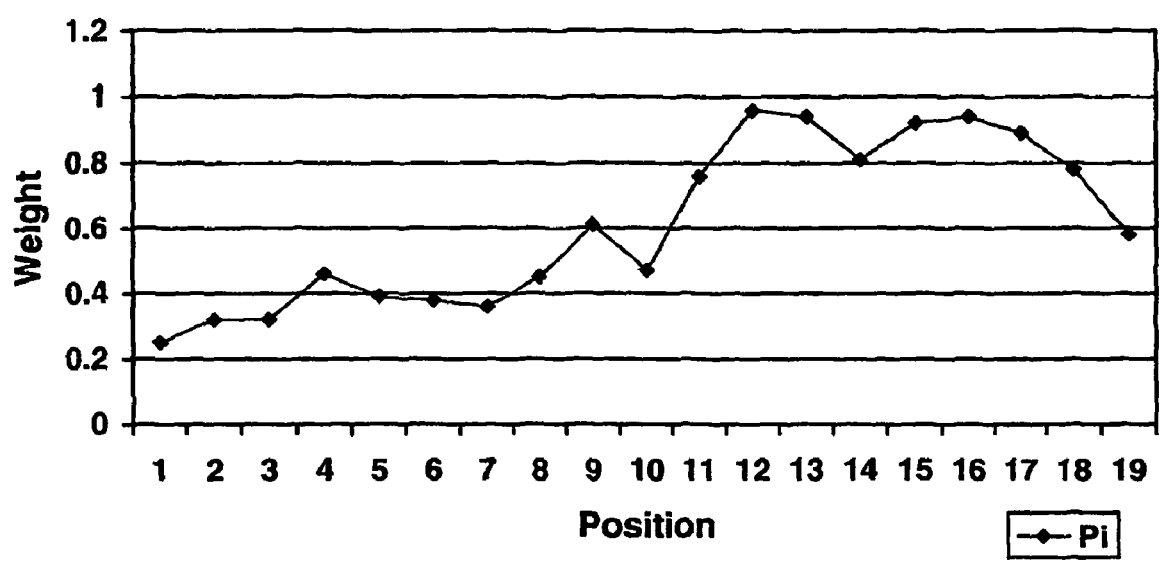

The alignment shown in FIG. 6 and similar data for other siRNAs were combined to generate a position-specific scoring matrix for use in predicting off-target effects. The matrix, which reflects the frequency with which each position in the oligo is found to match affected off-target transcripts, is represented in FIG. 7.

The position-specific scoring matrix is used to calculate scores for alignments between a candidate RNAi sequence and off-target transcript sequences. Alignments of interest are established with a low-stringency FASTA search and the score for each alignment is calculated with the Eq. 6

$$Score = \sum_{i=1}^{n} \ln(E_i / 0.25)$$

where: n is the length of the alignment (generally 19); $E_i = P_i$ from FIG. 7 if position i in the alignment is a match and $E_i = (1-P_i)/3$ if position i is a mismatch. It was observed that the number of alignments for a given siRNA which score above a threshold is predictive of the number of observed off-target effects. The threshold of the score was optimized to maximize the correlation between predicted and observed numbers of effects (FIG. 8). The selection pipeline uses the optimized threshold to favor sequences with relatively small numbers of predicted off-target effects.

6.3. Example 3

Curve Model PSSMS

PSSMs were also generated by a method which hypothesized dependency of the base composition of any one position on its neighboring positions, referred to as "curve models".

The curve models were generated as a sum of normal curves. Each curve represents the probability of finding a particular base in a particular region. The value at each position in the summed normal curves is the weight given to that position for the base represented by the curve. The weights for each base present at each position in each siRNA and its flanking sequences were summed to generate an siRNA's score, i.e., the score is $\Sigma w_i$. The score calculation can also be described as the dot product of the base content in the sequence with the weights in the curve model. As such, it is one way of representing the correlation of the sequence of interest with the model.

Curve models can be initialized to correspond to the major peaks and valleys present in the smoothed base composition difference between good and bad siRNAs, e.g., as described in FIGS. 1A-C and 5A-C. The initial model can be set up for the 3-peak G/C curve model as follows:

Peak 1
    mean: 1.5
    standard deviation: 2
    amplitude: 0.0455
Peak 1 mean, standard deviation and amplitude are set to correspond to the peak in the mean difference in GC content between good and bad siRNAs occurring within bases—2-5 of the siRNA target site in Set 1 training and test sets.
Peak 2
    mean: 11
    standard deviation: 0.5
    amplitude: 0.0337
Peak 2 mean, standard deviation and amplitude are set to correspond to the peak in the mean difference in GC content between good and bad siRNAs occurring within bases 10-12 of the siRNA target site in Set 1 training and test sets.
Peak 3
    mean: 18.5
    standard deviation: 4
    amplitude: −0.0548
Peak 3 mean, standard deviation and amplitude are set to correspond to the peak in the mean difference in GC content between good and bad siRNAs occurring within bases 12-25 of the siRNA target site in Set 1 training and test sets.

Peak height (amplitude), center position in the sequence (mean) and width (standard deviation) of a peak in a curve model can be adjusted. Curve models were optimized by adjusting the amplitude, mean and standard deviation of each peak over a preset grid of values. Curve models were optimized on several training sets and tested on several test sets, e.g., training sets and test sets as described in Table II. Each base—G/C, A or U—was optimized separately, and then combinations of optimized models were screened for best performance.

The optimization criteria for curve models were: (1) the fraction of good oligos in the top 10%, 15%, 20% and 33% of the scores, (2) the false detection rate at 33% and 50% of the siRNAs selected, and (3) the correlation coefficient of siRNA silencing vs. siRNA scores used as a tiebreaker.

When the model is trained, a grid of possible values for amplitude, mean and standard deviation of each peak is explored. The models with the top value or within the top range of values for any of the above criteria were selected and examined further.

G/C models were optimized with 3 or 4 peaks. A models were optimized with 3 peaks. U models were optimized with 5 peaks.

Exemplary optimization ranges for the models are listed below:
3 Peak G/C Models:
  peak 1:
  amplitudes: gc1=0-0.091
  means: gc1=−2.5-1.5
  standard deviations: gc1=2.5-4
  peak 2:
  amplitudes: gc2=0.0337-0.1011
  means: gc2=11-11.5
  standard deviations: gc2=0.5-0.9
  peak 3:
  amplitudes: gc3=−0.1644-−0.0822
  means: gc3=18.75-20.75
  standard deviations: gc3=2.5-3.5
4 Peak G/C models:
  peak 0:
  amplitudes: gc0=0-0.091
  means: gc0=−5.5-−3.5
  standard deviations: gc0=1-2.5
  peak 1:
  amplitudes: gc1=0-0.091
  means: gc1=−2.5-1.5
  standard deviations: gc1=2.5-4
  peak 2:
  amplitudes: gc2=0.0337-0.1011
  means: gc2=11-11.5
  standard deviations: gc2=0.5-0.9
  peak 3:
  amplitudes: gc3=−0.1644-−0.0822
  means: gc3=18.75-20.75
  standard deviations: gc3=2.5-3.5
5 Peak U models:
  U peak 1:
  amplitudes: u1=−0.2-0.0
  means: u1=1-2
  standard deviations: u1=0.75-1.5
  U peak 2:
  amplitudes: u2=0.0-0.16
  means: u2=5-6
  standard deviations: u2=0.75-1.5
  U peak 3:
  amplitudes: u3=0.0-0.1
  means: u3=10-11
  standard deviations: u3=1-2
  U peak 4:
  amplitudes: u4=0.0-0.16
  means: u4=13-14
  standard deviations: u4=0.75-1.5
  U peak 5:
  amplitudes: u5=0.0-0.16
  means: u5=17-18
  standard deviations: u5=1-3
3 Peak A model:
  A peak 1:
  amplitudes: a1=0.0442-0.2210
  means: a1=5.5-6.5
  standard deviations: a1=1-2
  A peak 2:
  amplitudes: a2=−0.05-0
  means: a2=10-12.5
  standard deviations: a2=25-4.5
  A peak 3:
  amplitudes: a3=0.0442-0.2210
  means: a3=18-20
  standard deviations: a3=4-6

An exemplary set of curve models for PSSM is shown in FIG. 11A. FIG. 11B shows the performance of the models on training and test sets.

6.4. Example 4

Base Composition Models for Prediction of Strand Preference of siRNAS

The mean difference in G/C content between good and bad siRNAs provides a model for G/C PSSMs which can be used to classify siRNA functional and resistant motifs. As it is known that both strands of the siRNA can be active (see, e.g., Elbashir et al., 2001, Genes Dev. 15:188-200), it was of interest to discover how well the G/C contents of both sense and antisense strands of siRNAs fit the model of siRNA functional target motif G/C content derived from the mean difference in G/C content between good and bad siRNAs. To this end, the reverse complements of good and bad siRNAs were examined. These reverse complements correspond to the hypothetical perfect match target sites for the sense strands of the siRNA duplexes. The reverse complements were compared to the actual good and bad siRNAs, represented by the actual perfect match target sites of the antisense strands of the siRNA duplexes.

FIG. 14A shows the difference between the mean G/C content of the reverse complements of bad siRNAs with the mean G/C content of the bad siRNAs themselves, within the 19mer siRNA duplex region. The difference between the mean G/C content of good and bad siRNAs is shown for comparison. The curves were smoothed over a window of 5 (or portion of a window of 5, at the edges of the sequence).

FIG. 14B shows the difference between the mean G/C content of the reverse complements of good siRNAs with the mean G/C content of bad siRNAs, within the 19mer siRNA duplex region. The difference between the mean G/C content of good and bad siRNAs is shown for comparison. The curves were smoothed over a window of 5 (or portion of a window of 5, at the edges of the sequence).

The reverse complements of bad siRNAs were seen to be even more different from the bad siRNAs themselves than are good siRNAs. On the average, the reverse complements of bad siRNAs had even stronger G/C content at the 5' end than the good siRNAs did and were similar in G/C content to good siRNAs at the 3' end. In contrast, the reverse complements of good siRNAs were seen to be substantially more similar to bad siRNAs than the good siRNAs were. On average, the reverse complements of good siRNAs hardly differed from bad siRNAs in G/C content at the 5' end and were only slightly less G/C rich than bad siRNAs at the 3' end.

These results appear to imply that the G/C PSSMs are distinguishing siRNAs with strong sense strands as bad siRNAs from siRNAs with weak sense strands as good siRNAs. An siRNA whose G/C PSSM score is greater than the G/C PSSM score of its reverse complement is predicted to have an antisense strand that is more active than its sense strand. In contrast, an siRNA whose G/C PSSM score is less than the G/C PSSM score of its reverse complement is predicted to have a sense strand that is more active than its antisense strand.

It has been shown that increased efficacy corresponds to greater antisense strand activity and lesser sense strand activity. Thus the G/C PSSMs of this invention would appear to distinguish good siRNAs with greater efficacy due to dominant antisense strand activity ("antisense-active" siRNAs) from siRNAs with dominant sense strand activity ("sense-active" siRNAs).

The relevance of comparison of G/C PSSMs of siRNAs and their reverse complements for prediction of strand bias was tested by comparison with estimation of strand bias from siRNA expression profiles by the 3'-biased method.

siRNAs and their reverse complements were scored using the smoothed G/C content difference between good and bad siRNAs within the 19mer, shown in FIG. 14A, as the weight matrix. The G/C PSSM score of each strand was the dot product of the siRNA strand G/C content with the G/C content difference matrix, following the score calculation method of curve model PSSMs.

siRNAs were called sense-active by the 3'-biased method of expression profile analysis if the antisense-identical score exceeded the sense-identical score. siRNAs were called sense-active by the G/C PSSM method if their reverse complement G/C PSSM score exceeded their own G/C PSSM score.

In FIG. 15, siRNAs were binned by measured silencing efficacy, and the frequency of sense-active calls by the expression profile and G/C PSSM methods was compared. Although these techniques are based on distinct analyses, the agreement is quite good. Both show that a higher proportion of low-silencing siRNAs vs. high-silencing siRNAs are predicted to be sense active. The correlation coefficient for (siRNA G/C PSSM score—reverse complement G/C PSSM score) vs. $\log_{10}$(sense-identity score/antisense-identity score) is 0.59 for the set of 61 siRNAs binned in FIG. 15.

6.5. Example 5

Designing siRNAS For Silencing Genes Having Low Transcript Levels

In the previous examples, an improved siRNA design algorithm that permits selection of siRNAs with greater and more uniform silencing ability was described. Despite this dramatic improvement, some genes remain difficult to silence with high efficacy. A general trend toward poorer silencing for poorly-expressed genes (less than −0.5 intensity on microarray; <5 copies per cell; FIG. 16) was observed. This example describes identification of parameters affecting silencing efficacy of siRNAs to poorly expressed genes.

Twenty-four poorly-expressed genes were selected for detailed analysis of parameters affecting siRNA silencing efficacy. A number of criteria were evaluated for their ability to distinguish good and bad siRNAs, including base composition of the 19mer siRNA duplex sequence and the flanking target region. In addition, the contribution of the GC content of the target transcript was considered. These tests revealed that siRNA efficacy correlated well with siRNA and target gene base composition. In particular, the GC content of good siRNAs differed substantially from that of bad siRNAs in a region-specific manner (FIG. 17). The sequences of siRNAs used in generating FIG. 17 are listed in Table IV. Good siRNA duplexes tended to be GC poor at positions 2-7 of the 5' end of the sense strand, and GC poor at the 3' end (positions 18-19). Furthermore, siRNA efficacy correlated with low GC content in the transcript sequence flanking the siRNA binding site. The requirement for low GC content as a determinant of siRNA efficacy may explain the difficulty in silencing the poorly-expressed transcripts, as these transcripts tend to be GC rich overall. Base composition of the siRNA duplex also affected silencing of poorly expressed genes. In particular, the GC content of good siRNAs differed substantially from that of bad siRNAs in a region-specific manner (FIG. 17). Good siRNA duplexes tended to be GC rich at the first position, GC poor at positions 2-7 of the 5' end of the sense strand, and GC poor at the 3' end (positions 18-19.) Of the criteria examined, low GC content in positions 2-7 of the sense strand (FIG. 17, dotted line) produced the greatest improvement in silencing efficacy. This is consistent with the region of the siRNA implicated in the catalysis step of transcript silencing. Low GC content in this region may provide accessibility or optimal helical geometry for enhanced cleavage. Requiring low GC content in this region of the siRNA may also select for target sites that contain low GC content flanking the binding site, which also correlated with silencing efficacy.

The base composition for good siRNAs to poorly-expressed genes diverges somewhat from our previously-derived base composition criteria for good siRNAs to well-expressed genes (FIG. 17, solid line). Good siRNAs to both types of genes show a preference for high GC at position 1, and low GC at the 3' end. However, siRNAs for well-expressed genes show an extreme asymmetry in GC content between the two termini, while siRNAs for poorly-expressed genes prefer a more moderate asymmetry. Our previous design algorithm seeks to maximize asymmetry, in accordance with the features seen in good siRNAs to well-expressed genes. Our current results indicate that base composition of more than one region of the siRNA can influence efficacy. Different regions of the siRNA may be more critical for silencing of different targets, perhaps depending on target transcript features such as expression level or overall GC content. Consistent with this idea, different commercially available design algorithms work well on different subsets of genes (data not shown).

A new siRNA design algorithm was developed based on the GC composition derived for poorly-expressed genes. The new algorithm includes the following adjustments to the previous algorithm:

(1) selection for 1-3 G+C in sense 19mer bases 2-7, (2) sense 19mer base 1 & 19 asymmetry (position 1, G or C; position 19, A or T), (3) −300<pssm score<+200, (4) greatest off-target BLAST match no more than 16, and (5) 200 bases on either side of the 19mer are not repeat or low-complexity sequences. The new algorithm was compared to the algorithm described in previous examples, by side-by-side testing of new siRNAs selected by each. The results obtained with three siRNAs selected by each method are shown in FIG. 18. siRNAs designed by the new algorithm of the present example showed better median efficacy (80%, compared to 60% for the standard method siRNA) and were more uniform in their performance. The distribution of silencing efficacies of siRNAs obtained by the new algorithm was significantly better than that of the previous algorithm for the same genes ($p=10^{-5}$, Wilcoxon rank-sum). siRNAs designed using the new design algorithm also appear effective at silencing more highly-expressed transcripts, based on an examination of 12 highly-expressed genes.

The new design criteria may capture features important to siRNA functionality in general (FIG. 19), and emphasize that different regions of siRNAs have different functions in transcript recognition, cleavage, and product release. Bases near the 5' end of the guide strand are implicated in transcript binding (both on- and off-target transcripts), and have recently been shown to be sufficient for target RNA-binding energy. The design criteria are also consistent with available data on how siRNAs interact with RISC, the protein-RNA complex that mediates RNA silencing. These studies show that weaker base pairing at the 5' end of the antisense strand (3' end of the duplex) encourages preferential interaction of the antisense strand with RISC, perhaps by facilitating unwinding of the siRNA duplex by a 5'-3' helicase component of RISC. As in the previous design, our new design maintains the base composition asymmetry that encourages preferential interaction of the antisense strand. This suggests that the previous inefficiency of silencing poorly-expressed transcripts is not due to inefficient association with RISC, but rather is likely due to inefficient targeting of the RISC complex to the target transcript, or inefficient cleavage and release of the target transcript. The designs described in these examples include a preference for U at position 10 of the sense strand, which has been associated with improved cleavage efficiency by RISC as it is in most endonucleases. The observed preference for low GC content flanking the cleavage site may enhance accessibility of the RISC/nuclease complex for cleavage, or release of the cleaved transcript, consistent with recent studies demonstrating that base pairs formed by the central and 3' regions of the siRNA guide strand provide a helical geometry required for catalysis. The new design criteria may increase the efficiency of these and additional steps in the RNAi pathway, thereby providing efficient silencing of transcripts at different levels of expression.

TABLE IV siRNAs for FIG. 17

| ACCESSION NUMBER | GENE | sIRNA sequence | SEQ ID NO |
|---|---|---|---|
| AK092024_NM_030932 | DIAPH3 | GCAGTGATTGCTCAGCAGC | 409 |
| AK092024_NM_030932 | DIAPH3 | GAGTTTACCGACCACCAAG | 410 |
| AK092024_NM_030932 | DIAPH3 | CACGGTTGGCAGAGTCTAT | 411 |
| AK092024_NM_030932 | DIAPH3 | TGCGGATGCCATTCAGTGG | 412 |
| NM_014875 | KIF14 | AAACTGGGAGGCTACTTAC | 413 |
| NM_014875 | KIF14 | CTCACATTGTCCACCAGGA | 414 |
| NM_014875 | KIF14 | GACCATAGCATCCGCCATG | 415 |
| NM_014875 | KIF14 | AGAGCCTTCGAAGGCTTCA | 416 |
| NM_014875 | KIF14 | TAGACCACCCATTGCTTCC | 417 |
| NM_014875 | KIF14 | ACTGACAACAAAGTGCAGC | 418 |
| U53530 | DNCH1 | TGGCCAGCGCTTACTGGAA | 419 |
| U53530 | DNCH1 | GCAAGTTGAGCTCTACCGC | 420 |
| NM_000859 | HMGCR | TTGTGTGTGGGACCGTAAT | 421 |

TABLE IV-continued siRNAs for FIG. 17

| ACCESSION NUMBER | GENE | sIRNA sequence | SEQ ID NO |
|---|---|---|---|
| NM_000859 | HMGCR | CAACAGAAGGTTGTCTTGT | 422 |
| NM_000859 | HMGCR | CAGAGACAGAATCTACACT | 423 |
| NM_000859 | HMGCR | CACGATGCATAGCCATCCT | 424 |
| NM_000271 | NPC1 | GAGGTACAATTCCGAATAT | 425 |
| NM_000271 | NPC1 | GCCACAGTCGTCTTGCTGT | 426 |
| NM_000271 | NPC1 | TACTACGTCGGACAGAGTT | 427 |
| NM_000271 | NPC1 | AACTACAATAACGCCACTG | 428 |
| NM_004523 | KNSL1 | TACTGATAATCGTACTGAA | 429 |
| NM_004523 | KNSL1 | TACATGAACTACAAGAAAA | 430 |
| NM_004523 | KNSL1 | GACTAAGCTTAATTGCTTT | 431 |
| NM_004523 | KNSL1 | AGTTGACCAACACAATGCA | 432 |
| NM_004523 | KNSL1 | GTTTTCTCTGTTACAATAC | 433 |
| NM_004523 | KNSL1 | AGGAGTGATAATTAAAGGT | 434 |
| NM_004523 | KNSL1 | AAACTCTGAGTACATTGGA | 435 |
| NM_004523 | KNSL1 | TACTAAACAGATTGATGTT | 436 |
| NM_004523 | KNSL1 | GCTCAAGGAAAACATACAC | 437 |
| NM_004523 | KNSL1 | CTGGATCGTAAGAAGGCAG | 438 |
| NM_004523 | KNSL1 | GACTTCATTGACAGTGGCC | 439 |
| NM_004523 | KNSL1 | GGACAACTGCAGCTACTCT | 440 |
| NM_004523 | KNSL1 | GGGGCAGTATACTGAAGAA | 441 |
| NM_004523 | KNSL1 | GACCTGTGCCTTTTAGAGA | 442 |
| NM_004523 | KNSL1 | AAAGGACAACTGCAGCTAC | 443 |
| NM_004523 | KNSL1 | TACAAAGAATAAATTTTCT | 444 |
| NM_004523 | KNSL1 | TGGAAGGTGAAAGGTCACC | 445 |
| NM_004523 | KNSL1 | TAACTGTTCAAGAAGAGCA | 446 |
| NM_004523 | KNSL1 | TCTATAATTTATATTCTTT | 447 |
| NM_004523 | KNSL1 | GGGACCGTCATGGCGTCGC | 448 |
| NM_004523 | KNSL1 | CCAGGGAGACTCCGGCCCC | 449 |
| NM_004523 | KNSL1 | ATTTAATTTGGCAGAGCGG | 450 |
| NM_004523 | KNSL1 | TGGAAATATAAATCAATCC | 451 |
| NM_004523 | KNSL1 | ACTAACTAGAATCCTCCAG | 452 |
| NM_004523 | KNSL1 | AAGAAGAATATATCACATC | 453 |
| NM_004523 | KNSL1 | TTCTTGTATATTATTAAGT | 454 |
| NM_004064 | CDKN1B | GACGTCAAACGTAAACAGC | 455 |
| NM_004064 | CDKN1B | TGGTGATCACTCCAGGTAG | 456 |
| NM_004064 | CDKN1B | TGTCCCTTTCAGAGACAGC | 457 |
| NM_004073 | CNK | GTTACCAAGAGCCTCTTTG | 458 |

TABLE IV-continued siRNAs for FIG. 17

| ACCESSION NUMBER | GENE | sIRNA sequence | SEQ ID NO |
|---|---|---|---|
| NM_004073 | CNK | ATCGTAGTGCTTGTACTTA | 459 |
| NM_004073 | CNK | GAAGACCATCTGTGGCACC | 460 |
| NM_004073 | CNK | GGAGACGTACCGCTGCATC | 461 |
| NM_004073 | CNK | TCAGGGACCAGCTTTACTG | 462 |
| NM_004073 | CNK | AGTCATCCCGCAGAGCCGC | 463 |
| NM_001315 | MAPK14 | GGCCTTTTCACGGGAACTC | 464 |
| NM_001315 | MAPK14 | GAAGCTCTCCAGACCATTT | 465 |
| NM_001315 | MAPK14 | TGCCTACTTTGCTCAGTAC | 466 |
| NM_001315 | MAPK14 | ATGTGATTGGTCTGTTGGA | 467 |
| NM_001315 | MAPK14 | GTCATCAGCTTTGTGCCAC | 468 |
| NM_001315 | MAPK14 | CCTACAGAGAACTGCGGTT | 469 |
| NM_001315 | MAPK14 | CCAGTGGCCGATCCTTATG | 470 |
| NM_001315 | MAPK14 | GTGCCTCTTGTTGCAGAGA | 471 |
| NM_001315 | MAPK14 | TTCTCCGAGGTCTAAAGTA | 472 |
| NM_001315 | MAPK14 | TAATTCACAGGGACCTAAA | 473 |
| NM_001315 | MAPK14 | GTGGCCGATCCTTATGATC | 474 |
| NM_001315 | MAPK14 | GTATATACATTCAGCTGAC | 475 |
| NM_001315 | MAPK14 | AATATCCTCAGGGGTGGAG | 476 |
| NM_001315 | MAPK14 | GGAACACCCCCCGCTTATC | 477 |
| NM_006101 | HEC | CTGAAGGCTTCCTTACAAG | 478 |
| NM_006101 | HEC | AGAACCGAATCGTCTAGAG | 479 |
| NM_006101 | HEC | CAGAAGTTGTGGAATGAGG | 480 |
| NM_006101 | HEC | GTTCAAAAGCTGGATGATC | 481 |
| NM_006101 | HEC | GGCCTCTATACCCCTCAAA | 482 |
| NM_006101 | HEC | CTTGCAACGTCTGTTAGAG | 483 |
| NM_000314 | PTEN | CCCACCACAGCTAGAACTT | 484 |
| NM_000314 | PTEN | CAGTAGAGGAGCCGTCAAA | 485 |
| NM_000314 | PTEN | CTATTCCCAGTCAGAGGCG | 486 |
| NM_000314 | PTEN | TAAAGATGGCACTTTCCCG | 487 |
| NM_000314 | PTEN | AAGGCAGCTAAAGGAAGTG | 488 |
| NM_000314 | PTEN | TGGAGGGGAATGCTCAGAA | 489 |
| NM_000075 | CDK4 | GCGAATCTCTGCCTTTCGA | 490 |
| NM_000075 | CDK4 | CAGTCAAGCTGGCTGACTT | 491 |
| NM_000075 | CDK4 | GGATCTGATGCGCCAGTTT | 492 |
| NM_000075 | CDK4 | TGTTGTCCGGCTGATGGAC | 493 |
| NM_006622 | SNK | TGTTACGAGATGACAGATT | 494 |
| NM_006622 | SNK | AACCCAGAGGATCGTCCCA | 495 |
| NM_006622 | SNK | CAGTTCACTATTACGCAGA | 496 |
| NM_139164 | STARD4 | ACCAGAGTCTTTTGACAGG | 497 |
| NM_139164 | STARD4 | CTGTTTGGAGAAAACCCTC | 498 |
| NM_139164 | STARD4 | GACAACCCAAACCAGAGTC | 499 |
| NM_139164 | STARD4 | GTCTTGACTGGGATGAAAA | 500 |
| NM_005030 | PLK | GGGAGAAGATGTCCATGGA | 501 |
| NM_005030 | PLK | CCGAGTTATTCATCGAGAC | 502 |
| NM_005030 | PLK | GAGACCTACCTCCGGATCA | 503 |
| NM_005030 | PLK | TCCAGAAGATGCTTCAGAC | 504 |
| NM_005030 | PLK | CACGCCTCATCCTCTACAA | 505 |
| NM_005030 | PLK | GACTTCGTGTTCGTGGTGT | 506 |
| NM_005030 | PLK | GGGCGGCTTTGCCAAGTGC | 507 |
| NM_005030 | PLK | ACGAGCTGCTTAATGACGA | 508 |
| NM_005030 | PLK | GGACTGGCAACCAAAGTCG | 509 |
| NM_005030 | PLK | GCCCGATACTACCTACGGC | 510 |
| NM_005030 | PLK | CGGAGTTGCAGCTCCCGGA | 511 |
| NM_005030 | PLK | AAGAGACCTACCTCCGGAT | 512 |
| NM_005030 | PLK | AGTGGGTGGACTATTCGGA | 513 |
| NM_005030 | PLK | TGTATCATGTATACCTTGT | 514 |
| NM_005030 | PLK | AAGAAGAACCAGTGGTTCG | 515 |
| NM_005030 | PLK | GGCAAGATTGTGCCTAAGT | 516 |
| NM_005030 | PLK | CCGCGGTGCCATGTCTGCA | 517 |
| NM_005030 | PLK | CTCAAGGCCTCCTAATAGC | 518 |
| NM_005030 | PLK | CAGCGCAGCTTCGGGAGCA | 519 |
| NM_005030 | PLK | CACAGTCCTCAATAAAGGC | 520 |
| NM_005030 | PLK | CCCCTCCCCCTCAACCCCA | 521 |
| NM_005030 | PLK | TCGATTGCTCCCAGCAGCC | 522 |
| NM_005030 | PLK | TTCTTGCCTAAAAGAGACC | 523 |
| NM_005030 | PLK | TACATGAGCGAGCACTTGC | 524 |
| NM_005030 | PLK | CAATGCCTCCAAGCCCTCG | 525 |
| NM_000875 | IGF1R | GGATATTGGGCTTTACAAC | 526 |
| NM_000875 | IGF1R | CTTGCAGCAACTGTGGGAC | 527 |
| NM_000875 | IGF1R | GCTCACGGTCATTACCGAG | 528 |
| NM_000875 | IGF1R | GATGATTCAGATGGCCGGA | 529 |
| NM_000875 | IGF1R | CGACACGGCCTGTGTAGCT | 530 |
| NM_000875 | IGF1R | AATGCTGACCTCTGTTACC | 531 |
| NM_000875 | IGF1R | TCTCAAGGATATTGGGCTT | 532 |

TABLE IV-continued siRNAs for FIG. 17

| ACCESSION NUMBER | GENE | sIRNA sequence | SEQ ID NO |
|---|---|---|---|
| NM_000875 | IGF1R | CATTACTCGGGGGGCCATC | 533 |
| NM_000875 | IGF1R | TGCTGACCTCTGTTACCTC | 534 |
| NM_000875 | IGF1R | CTACGCCCTGGTCATCTTC | 535 |
| NM_000875 | IGF1R | CCTCACGGTCATCCGCGGC | 536 |
| NM_000875 | IGF1R | CCTGAGGAACATTACTCGG | 537 |
| NM_001813 | CENPE | GGAGAGCTTTCTAGGACCT | 538 |
| NM_001813 | CENPE | GAAGAGATCCCAGTGCTTC | 539 |
| NM_001813 | CENPE | ACTCTTACTGCTCTCCAGT | 540 |
| NM_001813 | CENPE | TCTGAAAGTGACCAGCTCA | 541 |
| NM_001813 | CENPE | GAAAATGAAGCTTTGCGGG | 542 |
| NM_001813 | CENPE | CTTAACACGGATGCTGGTG | 543 |
| NM_004958 | FRAP1 | CTTGCAGGCCTTGTTTGTG | 544 |
| NM_004958 | FRAP1 | CAACCTCCAGGATACACTC | 545 |
| NM_004958 | FRAP1 | GACATGAGAACCTGGCTCA | 546 |
| NM_004958 | FRAP1 | CCAACTTTCTAGCTGCTGT | 547 |
| NM_004958 | FRAP1 | AGGACTTCGCCCATAAGAG | 548 |
| NM_004958 | FRAP1 | TAATACAGCTGGGGACGAC | 549 |
| NM_005163 | AKT1 | GCTGGAGAACCTCATGCTG | 550 |
| NM_005163 | AKT1 | CGCACCTTCCATGTGGAGA | 551 |
| NM_005163 | AKT1 | AGACGTTTTGTGCTGTGG | 552 |
| NM_002358 | MAD2L1 | TACGGACTCACCTTGCTTG | 553 |
| NM_000551 | VHL | GGCATTGGCATCTGCTTTT | 554 |
| NM_000551 | VHL | GTGAATGAGACACTCCAGT | 555 |
| NM_000551 | VHL | TGTTGACGGACAGCCTATT | 556 |
| NM_000551 | VHL | GATCTGGAAGACCACCCAA | 557 |
| NM_000551 | VHL | AGGAAATAGGCAGGGTGTG | 558 |
| NM_000551 | VHL | CAGAACCCAAAAGGGTAAG | 559 |
| NM_001654 | ARAF1 | GTCCCCACATTCCAAGTCA | 560 |
| NM_001654 | ARAF1 | GAATGAGATGCAGGTGCTC | 561 |
| NM_001654 | ARAF1 | GTTCCACCAGCATTGTTCC | 562 |
| NM_001654 | ARAF1 | CCTCTCTGGAATTTGTGCC | 563 |
| NM_001654 | ARAF1 | AGTGAAGAACCTGGGGTAC | 564 |
| NM_001654 | ARAF1 | TTGAGCTGCTGCAACGGTC | 565 |
| NM_000435 | NOTCH3 | GAACATGGCCAAGGGTGAG | 566 |
| NM_000435 | NOTCH3 | GAGTCTGGGACCTCCTTCT | 567 |
| NM_000435 | NOTCH3 | AATGGCTTCCGCTGCCTCT | 568 |
| NM_000435 | NOTCH3 | TGATCACTGCTTCCCCGAT | 569 |
| NM_000435 | NOTCH3 | TGCCAACTGAAGAGGATGA | 570 |
| NM_000435 | NOTCH3 | GCTGCTGTTGGACCACTTT | 571 |
| NM_024408 | NOTCH2 | CCAAGGAACCTGCTTTGAT | 572 |
| NM_024408 | NOTCH2 | GACTCAGACCACTGCTTCA | 573 |
| NM_024408 | NOTCH2 | CTTTGAATGCCAGGGGAAC | 574 |
| NM_024408 | NOTCH2 | GCAACTTTGGTCTCCTTTC | 575 |
| NM_024408 | NOTCH2 | GAGACAAGTTAACTCGTGC | 576 |
| NM_024408 | NOTCH2 | GCAATTGGCTGTGATGCTC | 577 |
| NM_012193 | FZD4 | CCATCTGCTTGAGCTACTT | 578 |
| NM_012193 | FZD4 | TTGGCAAAGGCTCCTTGTA | 579 |
| NM_012193 | FZD4 | AGAACCTCGGCTACAACGT | 580 |
| NM_012193 | FZD4 | TCGGCTACAACGTGACCAA | 581 |
| NM_012193 | FZD4 | GTTGACTTACCTGACGGAC | 582 |
| NM_012193 | FZD4 | TCCGCATCTCCATGTGCCA | 583 |
| NM_007313 | ABL1 | GAATGGAAGCCTGAACTGA | 584 |
| NM_007313 | ABL1 | CAAGTTCTCCATCAAGTCC | 585 |
| NM_007313 | ABL1 | CTAAAGGTGAAAAGCTCCG | 586 |
| NM_007313 | ABL1 | TCCTGGCAAGAAAGCTTGA | 587 |
| NM_007313 | ABL1 | AAACCTCTACAGTTCTGC | 588 |
| NM_007313 | ABL1 | AGACATCATGGAGTCCAGC | 589 |
| NM_017412 | FZD3 | CAGATCACTCCAGGCATAG | 590 |
| NM_017412 | FZD3 | ATGTGTGGTGACTGCTTTG | 591 |
| NM_017412 | FZD3 | AGAGATGGGCATTGTTTCC | 592 |
| NM_017412 | FZD3 | AGCATTGCTGTTTCACGCC | 593 |
| NM_017412 | FZD3 | GCTCATGGAGATGTTTGGT | 594 |
| NM_005633 | SOS1 | TGGTGTCCTTGAGGTTGTC | 595 |
| NM_005633 | SOS1 | TATCAGACCGGACCTCTAT | 596 |
| NM_005633 | SOS1 | CTTACAAAAGGGAGCACAC | 597 |
| NM_005633 | SOS1 | GAACACCGTTAACACCTCC | 598 |
| NM_005633 | SOS1 | ATAACAGGAGAGATCCAGC | 599 |
| NM_005633 | SOS1 | ATTGACCACCAGGTTTCTG | 600 |
| NM_005417 | SRC | CAATTCGTCGGAGGCATCA | 601 |
| NM_005417 | SRC | GCAGTGCCTGCCTATGAAA | 602 |
| NM_005417 | SRC | GGGGAGTTTGCTGGACTTT | 603 |
| NM_005400 | PRKCE | GATCGAGCTGGCTGTCTTT | 604 |
| NM_005400 | PRKCE | GCTCACCATCTGAGGAAGA | 605 |
| NM_005400 | PRKCE | GGTCTTAAAGAAGGACGTC | 606 |

TABLE IV-continued siRNAs for FIG. 17

| ACCESSION NUMBER | GENE | sIRNA sequence | SEQ ID NO |
|---|---|---|---|
| NM_005400 | PRKCE | TCACAAAGTGTGCTGGGTT | 607 |
| NM_005400 | PRKCE | CCAGGAGGAATTCAAAGGT | 608 |
| NM_005400 | PRKCE | TGAGGACGACCTATTTGAG | 609 |
| NM_002388 | MCM3 | GTCTCAGCTTCTGCGGTAT | 610 |
| NM_002388 | MCM3 | GTACATCCATGTGGCCAAA | 611 |
| NM_002388 | MCM3 | AGGATTTTGTGGCCTCCAT | 612 |
| NM_002388 | MCM3 | TGGGTCATGAAAGCTGCCA | 613 |
| NM_002388 | MCM3 | TCCAGGTTGAAGGCATTCA | 614 |
| NM_002388 | MCM3 | GCAGATGAGCAAGGATGCT | 615 |
| NM_004380 | CREBBP | GAAAAACGGAGGTCGCGTT | 616 |
| NM_004380 | CREBBP | GACATCCGAGTCTATAAG | 617 |
| NM_004380 | CREBBP | TGGAGGAGAATTAGGCCTT | 618 |
| NM_004380 | CREBBP | ATTTTTGCGGCGCCAGAAT | 619 |
| NM_004380 | CREBBP | GCACAAGGAGGTCTTCTTC | 620 |
| NM_004380 | CREBBP | GAAAACAAATGCCCCGTGC | 621 |
| NM_006219 | PIK3CB | CAAAGATGCCCTTCTGAAC | 622 |
| NM_006219 | PIK3CB | GTGCACATTCCTGCTGTCT | 623 |
| NM_006219 | PIK3CB | AAGTTCATGTCAGGGCTGG | 624 |
| NM_006219 | PIK3CB | AATGCGCAAATTCAGCGAG | 625 |
| NM_006219 | PIK3CB | AATGAAGCCTTTGTGGCTG | 626 |
| NM_006219 | PIK3CB | TACAGAAAAGTTTGGCCGG | 627 |
| NM_006218 | PIK3CA | CTAGGAAACCTCAGGCTTA | 628 |
| NM_006218 | PIK3CA | TTCAGCTAGTACAGGTCCT | 629 |
| NM_006218 | PIK3CA | TGATGCACATCATGGTGGC | 630 |
| NM_006218 | PIK3CA | AGAAGCTGTGGATCTTAGG | 631 |
| NM_006218 | PIK3CA | AGGTGCACTGCAGTTCAAC | 632 |
| NM_006218 | PIK3CA | TGGCTTTGAATCTTTGGCC | 633 |
| NM_002086 | GRB2 | CTGGTACAAGGCAGAGCTT | 634 |
| NM_002086 | GRB2 | CGGGCAGACCGGCATGTTT | 635 |
| NM_002086 | GRB2 | CCGGAACGTCTAAGAGTCA | 636 |
| NM_002086 | GRB2 | ATACGTCCAGGCCCTCTTT | 637 |
| NM_002086 | GRB2 | TGAGCTGGTGGATTATCAC | 638 |
| NM_002086 | GRB2 | TGCAGCACTTCAAGGTGCT | 639 |
| NM_001982 | ERBB3 | TGACAGTGGAGCCTGTGTA | 640 |
| NM_001982 | ERBB3 | CTAGACCTAGACCTAGACT | 641 |
| NM_001982 | ERBB3 | CTTTCTGAATGGGGAGCCT | 642 |
| NM_001982 | ERBB3 | GAGGATGTCAACGGTTATG | 643 |
| NM_001982 | ERBB3 | CAAAGTCTTGGCCAGAATC | 644 |
| NM_001982 | ERBB3 | TACACACACCAGAGTGATG | 645 |
| NM_001903 | CTNNAI | CGTTCCGATCCTCTATACT | 646 |
| NM_001903 | CTNNAI | AAGCCATTGGTGAAGAGAG | 647 |
| NM_001903 | CTNNAI | TGTGTCATTGCTCTCCAAG | 648 |
| NM_001903 | CTNNAI | AGCAGTGCTGATGATAAGG | 649 |
| NM_001903 | CTNNAI | TGACCAAAGATGACCTGTG | 650 |
| NM_001903 | CTNNAI | TGACATCATTGTGCTGGCC | 651 |
| NM_003600 | STK6 | CACCCAAAAGAGCAAGCAG | 652 |
| NM_003600 | STK6 | GCACAAAAGCTTGTCTCCA | 653 |
| NM_003600 | STK6 | CCTCCCTATTCAGAAAGCT | 654 |
| NM_003600 | STK6 | ACAGTCTTAGGAATCGTGC | 655 |
| NM_003600 | STK6 | GACTTTGAAATTGGTCGCC | 656 |
| NM_003600 | STK6 | TTGCAGATTTTGGGTGGTC | 657 |
| NM_003161 | RPS6KB1 | GACACTGCCTGCTTTTACT | 658 |
| NM_003161 | RPS6KB1 | CTCTCAGTGAAAGTGCCAA | 659 |
| NM_003161 | RPS6KB1 | GCTTTTCCCATGATCTCCA | 660 |
| NM_003161 | RPS6KB1 | TTGATTCCTCGCGACATCT | 661 |
| NM_003161 | RPS6KB1 | GAAAGCCAGACAACTTCTG | 662 |
| NM_003161 | RPS6KB1 | CTTGGCATGGAACATTGTG | 663 |
| AF308602 | NOTCH1 | GATCGATGGCTACGAGTGT | 664 |
| AF308602 | NOTCH1 | CACTTACACCTGTGTGTGC | 665 |
| AF308602 | NOTCH1 | AGGCAAGCCCTGCAAGAAT | 666 |
| AF308602 | NOTCH1 | CATCCCCTACAAGATCGAG | 667 |
| AF308602 | NOTCH1 | ATATCGACGATTGTCCAGG | 668 |
| AF308602 | NOTCH1 | ATTCAACGGGCTCTTGTGC | 669 |
| NM_016231 | NLK | CCACTCAGCTCAGATCATG | 670 |
| NM_016231 | NLK | GCAATGAGGACAGCTTGTG | 671 |
| NM_016231 | NLK | TGTAGCTTTCCACTGGAGT | 672 |
| NM_016231 | NLK | TCTCCTTGTGAACAGCAAC | 673 |
| NM_016231 | NLK | GGAAACAGAGTGCCTCTCT | 674 |
| NM_016231 | NLK | TCTGGTCTCTTGCAAAAGG | 675 |
| NM_001253 | CDC5L | AAGAAGACGTTCAGCGACA | 676 |
| NM_001253 | CDC5L | AAAAAGCCTGCCCTTGGTT | 677 |
| NM_001253 | CDC5L | TCATTGGAAGAACAGCGGC | 678 |
| NM_003391 | WNT2 | GTGTCTCAAAGGAGCTTTC | 679 |
| NM_003391 | WNT2 | GCCTCAGAAAGGGATTGCT | 680 |

TABLE IV-continued siRNAs for FIG. 17

| ACCESSION NUMBER | GENE | sIRNA sequence | SEQ ID NO |
|---|---|---|---|
| NM_003391 | WNT2 | AGAAGATGAATGGTCTGGC | 681 |
| NM_003391 | WNT2 | GCTCTGGATGTGCACACAT | 682 |
| NM_003391 | WNT2 | AACGGGCGATTATCTCTGG | 683 |
| NM_003391 | WNT2 | ATTTGCCCGCGCATTTGTG | 684 |
| NM_002387 | MCC | AGTTGAGGAGGTTTCTGCA | 685 |
| NM_002387 | MCC | GACTTAGAGCTGGGAATCT | 686 |
| NM_002387 | MCC | GGATTATATCCAGCAGCTC | 687 |
| NM_002387 | MCC | GAGAATGAGAGCCTGACTG | 688 |
| NM_002387 | MCC | TAGCTCTGCTAGAGGAGGA | 689 |
| NM_002387 | MCC | ACAGAACGGCTGAATAGCC | 690 |
| NM_005978 | S100A2 | GGAACTTCTGCACAAGGAG | 691 |
| NM_005978 | S100A2 | GGGCCCAGGACTGTTGATG | 692 |
| NM_005978 | S100A2 | TGAGAACAGTGACCAGCAG | 693 |
| NM_005978 | S100A2 | TGGCACTCATCACTGTCAT | 694 |
| NM_005978 | S100A2 | GACCGACCCTGAAGCAGAA | 695 |
| NM_005978 | S100A2 | TTCCAGGAGTATGCTGTTT | 696 |
| NM_033360 | KRAS2 | GAAGTTATGGAATTCCTTT | 697 |
| NM_033360 | KRAS2 | GGACTCTGAAGATGTACCT | 698 |
| NM_033360 | KRAS2 | GGCATACTAGTACAAGTGG | 699 |
| NM_033360 | KRAS2 | ACCTGTCTCTTGGATATTC | 700 |
| NM_033360 | KRAS2 | TAAATGTGATTTGCCTTCT | 701 |
| NM_033360 | KRAS2 | GAAAAGACTCCTGGCTGTG | 702 |
| NM_139049 | MAPK8 | GGAATAGTATGCGCAGCTT | 703 |
| NM_139049 | MAPK8 | GTGATTCAGATGGAGCTAG | 704 |
| NM_139049 | MAPK8 | CACCATGTCCTGAATTCAT | 705 |
| NM_139049 | MAPK8 | CGAGTTTTATGATGACGCC | 706 |
| NM_139049 | MAPK8 | CACCCGTACATCAATGTCT | 707 |
| NM_139049 | MAPK8 | TCAAGCACCTTCATTCTGC | 708 |
| NM_002658 | PLAU | CAAGTACTTCTCCAACATT | 709 |
| NM_002658 | PLAU | GAGCTGGTGTCTGATTGTT | 710 |
| NM_002658 | PLAU | CTGCCCAAAGAAATTCGGA | 711 |
| NM_002658 | PLAU | GTGTAAGCAGCTGAGGTCT | 712 |
| NM_002658 | PLAU | TGGAGGAACATGTGTGTCC | 713 |
| NM_002658 | PLAU | TTACTGCAGGAACCCAGAC | 714 |
| NM_016195 | MPHOSPH1 | AGAGGAACTCTCTGCAAGC | 715 |
| NM_016195 | MPHOSPH1 | AAGTTTGTGTCCCAGACAC | 716 |
| NM_016195 | MPHOSPH1 | CTGAAGAAGCTACTGCTTG | 717 |
| NM_016195 | MPHOSPH1 | GACATGCGAATGACACTAG | 718 |
| NM_016195 | MPHOSPH1 | AATGGCAGTGAAACACCCT | 719 |
| NM_016195 | MPHOSPH1 | ATGAAGGAGAGTGATCACC | 720 |
| NM_020168 | PAK6 | CGACATCCAGAAGTTGTCA | 721 |
| NM_020168 | PAK6 | GAGAAAGAATGGGGTCGGT | 722 |
| NM_020168 | PAK6 | TGAGGAGCAGATTGCCACT | 723 |
| NM_000051 | ATM | TAGATTGTTCCAGGACACG | 724 |
| NM_000051 | ATM | AGTTCGATCAGCAGCTGTT | 725 |
| NM_000051 | ATM | GAAGTTGGATGCCAGCTGT | 726 |
| NM_001259 | CDK6 | TCTTGGACGTGATTGGACT | 727 |
| NM_001259 | CDK6 | ACCACAGAACATTCTGGTG | 728 |
| NM_001259 | CDK6 | AGAAAACCTGGATTCCCAC | 729 |
| NM_004856 | KNSL5 | GAATGTGAGCGTAGAGTGG | 730 |
| NM_004856 | KNSL5 | CCATTGGTTACTGACGTGG | 731 |
| NM_004856 | KNSL5 | AACCCAAACCTCCACAATC | 732 |
| NM_006845 | KNSL6 | ACAAAAACGGAGATCCGTC | 733 |
| NM_006845 | KNSL6 | GAATTTCGGGCTACTTTGG | 734 |
| NM_006845 | KNSL6 | ATAAGCAGCAAGAAACGGC | 735 |
| NM_004972 | JAK2 | AGCCGAGTTGTAACTATCC | 736 |
| NM_004972 | JAK2 | AAGAACCTGGTGAAAGTCC | 737 |
| NM_004972 | JAK2 | GAAGTGCAGCAGGTTAAGA | 738 |
| NM_005026 | PIK3CD | GATCGGCCACTTCCTTTTC | 739 |
| NM_005026 | PIK3CD | AGAGATCTGGGCCTCATGT | 740 |
| NM_005026 | PIK3CD | AACCAAAGTGAACTGGCTG | 741 |
| NM_014885 | APC10 | CAAGGCATCCGTTATATCT | 742 |
| NM_014885 | APC10 | ACCAGGATTTGGAGTGGAT | 743 |
| NM_014885 | APC10 | GTGGCTGGATTCATGTTCC | 744 |
| NM_005733 | RAB6KIFL | GAAGCTGTCCCTGCTAAAT | 745 |
| NM_005733 | RAB6KIFL | CTCTACCACTGAAGAGTTG | 746 |
| NM_005733 | RAB6KIFL | AAGTGGGTCGTAAGAACCA | 747 |
| NM_007054 | KIF3A | GGAGAAAGATCCCTTTGAG | 748 |
| NM_007054 | KIF3A | TATTGGGCCAGCAGATTAC | 749 |
| NM_007054 | KIF3A | TTATGACGCTAGGCCACAA | 750 |
| NM_020242 | KNSL7 | GCACAACTCCTGCAAATTC | 751 |
| NM_020242 | KNSL7 | GATGGAAGAGCCTCTAAGA | 752 |
| NM_020242 | KNSL7 | ACGAAAAGCTGCTTGAGAG | 753 |
| NM_001184 | ATR | TCACGACTCGCTGAACTGT | 754 |

TABLE IV-continued siRNAs for FIG. 17

| ACCESSION NUMBER | GENE | sIRNA sequence | SEQ ID NO |
|---|---|---|---|
| NM_001184 | ATR | GAAACTGCAGCTATCTTCC | 755 |
| NM_001184 | ATR | GTTACAATGAGGCTGATGC | 756 |
| NM_014875 | KIF14 | ATTTTCTAGAAAACGGTAA | 757 |
| NM_014875 | KIF14 | GAGGCGCGAAGTTTCGGCA | 758 |
| NM_014875 | KIF14 | CTGGGACCGGGAAGCCGGA | 759 |
| NM_014875 | KIF14 | CTTCTACTTCTGTTGGCAG | 760 |
| NM_014875 | KIF14 | ACTTACTATTCAGACTGCA | 761 |
| NM_014875 | KIF14 | GCCCTCACCCACAGTAGCC | 762 |
| NM_014875 | KIF14 | CAGAGGAATGCACACCCAG | 763 |
| NM_014875 | KIF14 | GATTGATTAGATCTCTTGA | 764 |
| NM_014875 | KIF14 | GTGAGTATTATCCCAGTTG | 765 |
| NM_014875 | KIF14 | ATCTGGGGTGCTGATTGCT | 766 |
| NM_014875 | KIF14 | GTGACAGTGGCAGTACGCG | 767 |
| NM_014875 | KIF14 | TCAGACTGAAGTTGTTAGA | 768 |
| NM_014875 | KIF14 | GTTGGCTAGAATTGGGAAA | 769 |
| NM_014875 | KIF14 | GAAGACCATAGCATCCGCC | 770 |
| NM_001274 | CHEK1 | TGCCTGAAAGAGACTTGTG | 771 |
| NM_001274 | CHEK1 | ATCGATTCTGCTCCTCTAG | 772 |
| NM_001274 | CHEK1 | CTGAAGAAGCAGTCGCAGT | 773 |
| NM_007194 | CHEK2 | GATCACAGTGGCAATGGAA | 774 |
| NM_007194 | CHEK2 | ATGAATCCACAGCTCTACC | 775 |
| NM_007194 | CHEK2 | AAACTCTTGGAAGTGGTGC | 776 |
| NM_000546 | TP53 | GCACCCAGGACTTCCATTT | 777 |
| NM_000546 | TP53 | CCTCTTGGTCGACCTTAGT | 778 |
| NM_000546 | TP53 | TGAGGCCTTGGAACTCAAG | 779 |
| NM_005400 | PRKCE | AGCGCCTGGGCCTGGATGA | 780 |
| NM_005400 | PRKCE | ACCGGGCAGCATCGTCTCC | 781 |
| NM_005400 | PRKCE | CAGCGGCCAGAGAAGGAAA | 782 |
| NM_005400 | PRKCE | CAGAAGGAAGAGTGTATGT | 783 |
| NM_005400 | PRKCE | TGCAGTGTAAAGTCTGCAA | 784 |
| NM_005400 | PRKCE | GCGCATCGGCCAAACGGCC | 785 |
| NM_005400 | PRKCE | ATTGCAGAGACTTCATCTG | 786 |
| NM_005400 | PRKCE | GAAGAGCCGGTACTCACCC | 787 |
| NM_005400 | PRKCE | AGTACTGGCCGACCTGGGC | 788 |
| NM_005400 | PRKCE | GGATGCAGAAGGTCACTGC | 789 |
| NM_005400 | PRKCE | CGTGAGCTTGAAGCCCACA | 790 |
| NM_005400 | PRKCE | CACAAAGTGTGCTGGGTTA | 791 |
| NM_005400 | PRKCE | GACGAAGCAATTGTAAAGC | 792 |
| NM_005400 | PRKCE | CACCCTTCAAACCACGCAT | 793 |
| NM_005400 | PRKCE | GTCAGCATCTTGAAAGCTT | 794 |
| NM_005400 | PRKCE | CAACCGAGGAGAGGAGCAC | 795 |
| NM_005400 | PRKCE | TACATTGCCCTCAATGTGG | 796 |
| NM_005400 | PRKCE | GAGGAATCGCCAAAGTACT | 797 |
| NM_005400 | PRKCE | GGGATTTGAAACTGGACAA | 798 |
| NM_006218 | PIK3CA | TTACACGTTCATGTGCTGG | 799 |
| NM_006218 | PIK3CA | CACAATCCATGAACAGCAT | 800 |
| NM_006218 | PIK3CA | CAATCAAACCTGAACAGGC | 801 |
| NM_006218 | PIF3CA | CAGTTCAACAGCCACACAC | 802 |
| NM_006218 | PIK3CA | GTGTTACAAGGCTTATCTA | 803 |
| NM_006218 | PIK3CA | GATCCTATGGTTCGAGGTT | 804 |
| NM_006218 | PIK3CA | CTCCAAATAATGACAAGCA | 805 |
| NM_006218 | PIK3CA | ACTTTGCCTTTCCATTTGC | 806 |
| NM_006218 | PIK3CA | AGAATATCAGGGCAAGTAC | 807 |
| NM_006218 | PIK3CA | TTGGATCTTCCACACAATT | 808 |
| NM_006218 | PIK3CA | AGTAGGCAACCGTGAAGAA | 809 |
| NM_006218 | PIK3CA | CAGGGCTTGCTGTCTCCTC | 810 |
| NM_006218 | PIK3CA | GAGCCCAAGAATGCACAAA | 811 |
| NM_006218 | PIK3CA | GCCAGAACAAGTAATTGCT | 812 |
| NM_006218 | PIK3CA | GGATGCCCTACAGGGCTTG | 833 |
| NM_006218 | PIK3CA | TCAAATTATTCGTATTATG | 814 |
| NM_006218 | PIK3CA | GAATTGGAGATCGTCACAA | 815 |
| NM_006218 | PIK3CA | TGAGGTGGTGCGAAATTCT | 816 |
| NM_006218 | PIK3CA | GATTTACGGCAAGATATGC | 817 |
| NM_006218 | PIK3CA | TGATGAATACTTCCTAGAA | 818 |
| NM_001982 | ERBB3 | GCTGCTGGGACTATGCCCA | 819 |
| NM_001982 | ERBB3 | ATCTGCACAATTGATGTCT | 820 |
| NM_001982 | ERBB3 | CTTTGAACTGGACCAAGGT | 821 |
| NM_001982 | ERBB3 | CATCATGCCCACTGCAGGC | 822 |
| NM_001982 | ERBB3 | AACTTTCCAGCTGGAACCC | 823 |
| NM_001982 | ERBB3 | TGAAGGAAATTAGTGCTGG | 824 |
| NM_001982 | ERBB3 | AATTCGCCAGCGGTTCAGG | 825 |
| NM_001982 | ERBB3 | ACCAGAGCTTCAAGACTGT | 826 |
| NM_001982 | ERBB3 | GAGGCTACAGACTCTGCCT | 827 |
| NM_001982 | ERBB3 | TGGAGCCAGAACTAGACCT | 828 |

TABLE IV-continued siRNAs for FIG. 17

| ACCESSION NUMBER | GENE | sIRNA sequence | SEQ ID NO |
|---|---|---|---|
| NM_001982 | ERBB3 | ACACTGTACAAGCTCTACG | 829 |
| NM_001982 | ERBB3 | TAATGGTCACTGCTTTGGG | 830 |
| NM_001982 | ERBB3 | ACAGGCACTCCTGGAGATA | 831 |
| NM_001982 | ERBB3 | GTTTAGGACAAACACTGGT | 832 |
| NM_001982 | ERBB3 | GATTACTGGCATAGCAGGC | 833 |
| NM_001982 | ERBB3 | ATGAATACATGAACCGGAG | 834 |
| NM_001982 | ERBB3 | CACTTAATCGGCCACGTGG | 835 |
| NM_001982 | ERBB3 | GGCCTGTCCTCCTGACAAG | 836 |
| NM_001982 | ERBB3 | TCTGCGGAGTCATGAGGGC | 837 |
| NM_001982 | ERBB3 | TAGACCTAGACTTGGAAGC | 838 |
| NM_004283 | RAB3D | GATTTCAGGTCTCCCTGTC | 839 |
| NM_004283 | RAB3D | GCCACAGTGGTTATCTCCA | 840 |
| NM_004283 | RAB3D | GCAATCCCTTCCCTCCTGT | 841 |
| NM_004283 | RAB3D | TCTCTGATCCTGAAGTGAA | 842 |
| NM_004283 | RAB3D | CATCAATGTGAAGCAGGTC | 843 |
| NM_004283 | RAB3D | CATGAGCTTGCTGCTTTCC | 844 |
| NM_004283 | RAB3D | AACGTGTTGTGCCTGCTGA | 845 |
| NM_004283 | RAB3D | CTGCTTTCCAGGGTGTGTT | 846 |
| NM_004283 | RAB3D | GCGGCCAGGGCCAAGCCGC | 847 |
| NM_004283 | RAB3D | CTTCTAGCTTAGAACCATT | 848 |
| NM_004283 | RAB3D | CAGGGTGTGTTGAGGGTGG | 849 |
| NM_004283 | RAB3D | CTCTTTCTCAGGTCCTGCA | 850 |
| NM_004283 | RAB3D | CTTGTGCCAAGATGGCATC | 851 |
| NM_004283 | RAB3D | GCACCATCACCACGGCCTA | 852 |
| NM_004283 | RAB3D | CGCGGACGACTCCTTCACT | 853 |
| NM_004283 | RAB3D | TCATCCAGGGAAGGCGGCG | 854 |
| NM_004283 | RAB3D | GACACTGACGTGCATCAGC | 855 |
| NM_004283 | RAB3D | CCCTCCCAGGCCCTGTTTA | 856 |
| NM_004283 | RAB3D | AGGTCTTCGAGCGCCTGGT | 857 |
| NM_004283 | RAB3D | CCTCTTTCTCAGGTCCTGC | 858 |
| NM_003620 | PPM1D | TTGCCCGGGAGCACTTGTG | 859 |
| NM_003620 | PPM1D | CGTGTGCGACGGGCACGGC | 860 |
| NM_003620 | PPM1D | ATTAGGTCTTAAAGTAGTT | 861 |
| NM_003620 | PPM1D | AGCCCTGACTTTAAGGATA | 862 |
| NM_003620 | PPM1D | TGTGGAGCCCGAACCGACG | 863 |
| NM_003620 | PPM1D | GCGACGGGCACGGCGGGCG | 864 |
| NM_003620 | PPM1D | GATTATATGGGTATATATT | 865 |
| NM_003620 | PPM1D | TTAGAAGGAGCACAGTTAT | 866 |
| NM_003620 | PPM1D | CCGGCCAGCCGGCCATGGC | 867 |
| NM_003620 | PPM1D | GAGCAGATAACACTAGTGC | 868 |
| NM_003620 | PPM1D | AGATCCCATCTCAATGTGC | 869 |
| NM_003620 | PPM1D | GCGGCACAGTTTGCCCGGG | 870 |
| NM_003620 | PPM1D | CGTAGCAATGCCTTCTCAG | 871 |
| NM_003620 | PPM1D | TATATGGGTATATATTCAT | 872 |
| NM_003620 | PPM1D | GCTGCTAATTCCCAACATT | 873 |
| NM_003620 | PPM1D | ACAACTGCCAGTGTGGTCA | 874 |
| NM_003620 | PPM1D | TTGACCCTCAGAAGCACAA | 875 |
| NM_003620 | PPM1D | GTCTTAAAGTAGTTACTCC | 876 |
| NM_003620 | PPM1D | ATGCTCCGAGCAGATAACA | 877 |
| NM_003620 | PPM1D | GCGCCTAGTGTGTCTCCCG | 878 |
| NM_022048 | CSNKIG1 | TAGCCATCCAGCTGCTTTC | 879 |
| NM_022048 | CSNKIG1 | TTCTCATTGGAAGGGACTC | 880 |
| NM_022048 | CSNKIG1 | CACGCATCTTGGCAAAGAG | 881 |
| NM_022048 | CSNKIG1 | TAGCTTGGAGGACTTGTTT | 882 |
| NM_022048 | CSNKIG1 | ACTCAATTGTACCTGCAGC | 883 |
| NM_022048 | CSNKIG1 | CTAAGTGCTGCTGTTTCTT | 884 |
| NM_022048 | CSNKIG1 | GCAAAGCCGGAGAGATGAT | 885 |
| NM_022048 | CSNKIG1 | CCTCTTCACAGACCTCTTT | 886 |
| NM_022048 | CSNKIG1 | GAAGGGACTCCTCTTTGGG | 887 |
| NM_022048 | CSNKIG1 | GAGAGCTCAGATTAGGTAA | 888 |
| NM_022048 | CSNKIG1 | CACGTAGATTCTGGTGCAT | 889 |
| NM_022048 | CSNKIG1 | ATGAGTATTTACGGACCCT | 890 |
| NM_022048 | CSNKIG1 | GGTGGGACCCAACTTCAGG | 891 |
| NM_022048 | CSNKIG1 | AGAGCTGAATGTTGATGAT | 892 |
| NM_022048 | CSNKIG1 | GATTCTGGTGCATCTGCAA | 893 |
| NM_022048 | CSNKIG1 | AACTTCAGGGTTGGCAAGA | 894 |
| NM_022048 | CSNKIG1 | TCTCGAATGGAATACGTGC | 895 |
| NM_022048 | CSNKIG1 | CCGAGGAGAGTGGGAAATT | 896 |
| NM_022048 | CSNKIG1 | GGGAGCCCACTCCAATGCA | 897 |
| NM_022048 | CSNKIG1 | GTCAAGCCAGAGAACTTCC | 898 |
| NM_000082 | CKN1 | TTAGCAGTTTCCTGGTCTC | 899 |
| NM_000082 | CKN1 | ATGTGAGAAGAGCATCAGG | 900 |
| NM_000082 | CKN1 | AGCAGTGTGTTCCATTGGC | 901 |
| NM_000082 | CKN1 | GGATCCTGTTCTCACATTC | 902 |

TABLE IV-continued siRNAs for FIG. 17

| ACCESSION NUMBER | GENE | sIRNA sequence | SEQ ID NO |
|---|---|---|---|
| NM_000082 | CKN1 | CAGCAGTGATGAAGAAGGA | 903 |
| NM_000082 | CKN1 | GATAACTATGCTTAAGGGA | 904 |
| NM_000082 | CKN1 | TGGACTTCACCTCCTCACT | 905 |
| NM_000082 | CKN1 | TTGAAGTCTGGATCCTGTT | 906 |
| NM_000082 | CKN1 | AGGAACTTTATAGTGGTAG | 907 |
| NM_000082 | CKN1 | AAGTGATGGACTTCACCTC | 908 |
| NM_000082 | CKN1 | TGTTTATACAGTTTACTCA | 909 |
| NM_000082 | CKN1 | GAAGGGAGATACATGTTAT | 910 |
| NM_000082 | CKN1 | GGGTTTGGAGGACCCTCTT | 911 |
| NM_000082 | CKN1 | ATATGTCTCCAGTCTCCAC | 912 |
| NM_000082 | CKN1 | GATGGACTTCACCTCCTCA | 913 |
| NM_000082 | CKN1 | TGAAAGTATGGGATACAAA | 914 |
| NM_000082 | CKN1 | ATGTAAAGCAGTGTGTTCC | 915 |
| NM_000082 | CKN1 | TCTACAGGGTCACAGACAA | 916 |
| NM_000082 | CKN1 | GAGGCCATCAGTATTGACT | 917 |
| NM_000082 | CKN1 | ACTGTTTGGTAGCAGTTGG | 918 |
| NM_002843 | PTPRJ | AGGAGGAGGCGAAGGAGAC | 919 |
| NM_002843 | PTPRJ | CTACGTCACCACCACGGAG | 920 |
| NM_002843 | PTPRJ | TCGCCTAATTCCAAAGGAA | 921 |
| NM_002843 | PTPRJ | CAAGTATGTAGTAAAGCAT | 922 |
| NM_002843 | PTPRJ | AAGCTGGTCACCCTTCTGC | 923 |
| NM_002843 | PTPRJ | CACAGAAGGTGGCTTGGAT | 924 |
| NM_002843 | PTPRJ | TGGAATCTAGCCGATGGAA | 925 |
| NM_002843 | PTPRJ | ATAAACAGAATGGAACTGG | 926 |
| NM_002843 | PTPRJ | CCTGGAGAGCTGCTCCTCT | 927 |
| NM_002843 | PTPRJ | AACTTTAAGTTGGCAGAAC | 928 |
| NM_002843 | PTPRJ | ACACAGTGGAGATCTTTGC | 929 |
| NM_002843 | PTPRJ | CAGTACACACGGCCCAGCA | 930 |
| NM_002843 | PTPRJ | TTGAACAGGGAAGAACCAA | 931 |
| NM_002843 | PTPRJ | ATTATGTTGACTAAATGTG | 932 |
| NM_002843 | PTPRJ | TGACTCAAGACTCAAGACT | 933 |
| NM_002843 | PTPRJ | AACTTCGGTCCAGACCCA | 934 |
| NM_002843 | PTPRJ | GGCCAGACCACGGTGTTCC | 935 |
| NM_002843 | PTPRJ | TCACTGGAACCTGGCCGGA | 936 |
| NM_002843 | PTPRJ | ACACAGGAGGGAGCTGGCA | 937 |
| NM_002843 | PTPRJ | TGTTCTCATTTGATCAGGG | 938 |
| NM_004037 | AMPD2 | TCATCCGGGAGAAGTACAT | 939 |
| NM_004037 | AMPD2 | ACCCAACTATACCAAGGAA | 940 |
| NM_004037 | AMPD2 | CCTGCATGAACCAGAAGCA | 941 |
| NM_004037 | AMPD2 | CTGCGGGAGGTCTTTGAGA | 942 |
| NM_004037 | AMPD2 | GCCTCTTTGATGTGTACCG | 943 |
| NM_004037 | AMPD2 | GACAACATGAGAAATCGTG | 944 |
| NM_004037 | AMPD2 | GCCACCCAGTGAAAGCAAA | 945 |
| NM_004037 | AMPD2 | CAGGAACACTTTCCATCGC | 946 |
| NM_004037 | AMPD2 | TGTGGGAGAGGCAGCTGCC | 947 |
| NM_004037 | AMPD2 | GCCGTGAACAGACGCTGCG | 948 |
| NM_004037 | AMPD2 | AAATATCCCTTTAAGAAGC | 949 |
| NM_004037 | AMPD2 | GTAAAGAGCCACTGGCTGG | 950 |
| NM_004037 | AMPD2 | CGTCCTGCATGAACCAGAA | 951 |
| NM_004037 | AMPD2 | GCTCAGCAACAACAGCCTC | 952 |
| NM_004037 | AMPD2 | CACATCATCAAGGAGGTGA | 953 |
| NM_004037 | AMPD2 | CTCATTGTTGTTTGGGCTC | 954 |
| NM_004037 | AMPD2 | AAGCTCAGCTCCTGCGATA | 955 |
| NM_004037 | AMPD2 | TGCGATATGTGTGAGCTGG | 956 |
| NM_004037 | AMPD2 | CTGGGCCCATCCACCACCT | 957 |
| NM_004037 | AMPD2 | GAAGGACCAGCTAGCCTGG | 958 |
| NM_016218 | POLK | TATTTCATTTCTTGTCAAT | 959 |
| NM_016218 | POLK | GACGAGGGATGGAGAGAGG | 960 |
| NM_016218 | POLK | AGTAGATTGTATAGCTTTA | 961 |
| NM_016218 | POLK | TATAGATAACTCATCTAAA | 962 |
| NM_016218 | POLK | AAGAACTTTGCAGTGAGCT | 963 |
| NM_016218 | POLK | GAATTAGAACAAAGCCGAA | 964 |
| NM_016218 | POLK | TGTGCTATCAATGAGTTCT | 965 |
| NM_016218 | POLK | ACACCTGACGAGGGATGGA | 966 |
| NM_016218 | POLK | TGCATCTACAGTTTCATCT | 967 |
| NM_016218 | POLK | ACACACCTGACCAGGGATG | 968 |
| NM_016218 | POLK | TGGATAGCACAAAGGAGAA | 969 |
| NM_016218 | POLK | AGGGTGCATCAGTCTGGAA | 970 |
| NM_016218 | POLK | TATAGCTTTAGTAGATACT | 971 |
| NM_016218 | POLK | TGTTTCTACTGCAGAAGAA | 972 |
| NM_016218 | POLK | GTTGTTTCTACTGCAGAAG | 973 |
| NM_016218 | POLK | CTGACAAAGATAAGTTTGT | 974 |
| NM_016218 | POLK | GCATCAGTCTGGAAGCCTT | 975 |
| NM_016218 | POLK | CTCAGGATCTACAGAAAGA | 976 |

TABLE IV-continued siRNAs for FIG. 17

| ACCESSION NUMBER | GENE | sIRNA sequence | SEQ ID NO |
|---|---|---|---|
| NM_016218 | POLK | AAGGAGATTTGGTGTTCGT | 977 |
| NM_016218 | POLK | TAGTGCACATTGACATGGA | 978 |

This application includes a Sequence Listing submitted on compact disc, recorded on two compact discs, including one duplicate, containing file name NEW SEQLIST 9301-244-999.TXT, of size 205 kilo-bytes, created Apr. 21, 2008. The Sequence Listing on the compact discs is incorporated by reference herein in its entirety.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for selecting from a plurality of different siRNAs one or more siRNAs for silencing a target gene in an organism, each different siRNA in said plurality of different siRNAs targeting a different target sequence in a transcript of said target gene, said method comprising (a) calculating a score for a corresponding targeted sequence motif in said transcript, for each said different siRNA in said plurality of different siRNAs, wherein said score is calculated using a position-specific score matrix (PSSM), wherein each said sequence motif is a nucleotide sequence of L nucleotides, L being an integer, and wherein said PSSM is $\{\log(e_{ij}/p_{ij})\}$, where $e_{ij}$ is the weight of nucleotide i at position j, $p_{ij}$ is the weight of nucleotide i at position j in a random sequence, and i=G or C, A, U(T), j=1, . . . L, wherein each of said targeted sequence motifs comprises at least a portion of the target sequence of the corresponding siRNA and/or a second sequence in a sequence region flanking said target sequence;

(b) ranking said plurality of different siRNAs according to said scores; and (c) selecting one or more siRNAs from said ranked siRNAs, wherein at least one of steps (a), (b) or (c) is performed by a suitably programmed computer.

2. The method of claim 1, wherein each said sequence motif comprises said target sequence of said targeting siRNA.

3. The method of claim 1, wherein said score for each said siRNA is calculated according to equation $$Score = \sum_{t=1}^{L} \ln(e_t / p_t)$$

wherein said $e_t$ and $p_t$ are respectively weights of the nucleotide at position t in said sequence motif as determined according to said position-specific score matrix and in a random sequence.

4. The method of claim 3, wherein each said sequence motif comprises said target sequence of said targeting siRNA and at least one flanking sequence.

5. The method of claim 4, wherein each said sequence motif comprises said target sequence of said targeting siRNA and a 5' flanking sequence and a 3' flanking sequence.

6. The method of claim 5, wherein said 5' flanking sequence and said 3' flanking sequence are each a sequence of D nucleotides, D being an integer.

7. The method of claim 6, wherein each said target sequence is a sequence of 19 nucleotides, and each said 5' flanking sequence and 3' flanking sequence are a sequence of 10 nucleotides.

8. The method of claim 5, wherein each said target sequence is a sequence of 19 nucleotides, and each said 5' flanking sequence and 3' flanking sequence are a sequence of 50 nucleotides.

9. The method of claim 1, further comprising a step of selecting one or more siRNAs based on silencing specificity, said step of selecting based on silencing specificity comprising, (i) for each of said plurality of siRNAs, predicting off-target genes of said siRNA from among a plurality of genes, wherein said off-target genes are genes other than said target gene and are directly silenced by said siRNA; (ii) ranking said plurality of siRNAs according to the number of off-target genes; and (iii) selecting one or more siRNAs for which said number of off-target genes is below a given threshold.

10. The method of claim 9, wherein said predicting comprises (i1) evaluating sequence of each of said plurality of genes based on a predetermined siRNA sequence match pattern; and (i2) predicting said gene as an off-target gene if said gene comprise a sequence that matches said siRNA based on said sequence match pattern.

11. The method of claim 10, wherein said step of evaluating comprises identifying an alignment of said siRNA to a sequence in a gene by a low stringency FASTA alignment.

12. The method of claim 11, wherein each said siRNA has L nucleotides in its duplex region, and wherein said match pattern is represented by a position match position-specific score matrix (pmPSSM), said position match position-specific score matrix consisting of weights of different positions in an siRNA to match transcript sequence positions in an off-target transcript $\{P_j\}$, where $j=1, \ldots, L$, $P_j$ is the weight of a match at position j.

13. The method of claim 12, wherein said step (i1) comprises calculating a position match score pmScore according to equation $$pmScore = \sum_{i=1}^{L} \ln(E_i/0.25)$$

where $E_i = P_i$ if position i is a match and $E_i = (1-P_i)/3$ if position i is a mismatch; and said step (i2) comprises predicting said gene as an off-target gene if said position match score is greater than a given threshold.

14. The method of claim 13, wherein L is 19, and wherein said pmPSSM is given by Table I.

15. The method of claim 14, wherein said plurality of genes comprises all known unique genes of said organism other than said target gene.

16. The method of claim 7, wherein said position-specific score matrix (PSSM) is obtained by a method comprising
    (aa) identifying a plurality of N siRNAs consisting of siRNAs having 19-nucleotide duplex region and having a silencing efficacy above a chosen threshold;
    (bb) identifying for each said siRNA a functional sequence motif, said functional sequence motif comprising a 19-nucleotide target sequence of said siRNA and a 10-nucleotide 5' flanking sequence and a 10-nucleotide 3' flanking sequence;
    (cc) calculating a frequency matrix $\{f_{ij}\}$, where i=G, C, A, U(T); j=1, 2, ..., L, and where $f_{ij}$ is the frequency of the ith nucleotide at the jth position, based on said siRNAs functional sequence motifs according to equation $$f_{ij} = \sum_{k=1}^{N} \delta_{ik}(j), \text{ where } \delta_{ik}(j) = \begin{cases} 1, \text{ if } k = i \\ 0, \text{ if } k \neq i \end{cases}, \text{ and}$$

(dd) determining said PSSM by calculating $e_{ij}$ according to equation $$e_{ij} = \frac{f_{ij}}{N}.$$

17. The method of claim 16, wherein said plurality of N siRNAs target a plurality of different genes having different transcript abundances in a cell.

18. The method of claim 17, wherein said step (c) is carried out by selecting one or more siRNAs having the highest scores.

19. The method of claim 17, wherein said step (c) is carried out by selecting one or more siRNAs having a score closest to a predetermined value, wherein said predetermined value is the score value corresponding to the maximum median silencing efficacy of a plurality of siRNA sequence motifs.

20. The method of claim 19, wherein said plurality of siRNA sequence motifs are sequence motifs in transcript having abundance level of less than about 3-5 copies per cell.

21. The method of claim 17, wherein said step (c) is carried out by selecting one or more siRNAs having a score within a predetermined range, wherein said predetermined range is a score range corresponding to a plurality of siRNAs sequence motifs having a given level of silencing efficacy.

22. The method of claim 21, wherein said silencing efficacy is above 50% at an siRNA dose of about 100 nM.

23. The method of claim 22, wherein said plurality of siRNA sequence motifs are sequence motifs in transcript having abundance level of less than about 3-5 copies per cell.

24. The method of claim 1, wherein said position-specific score matrix (PSSM) is obtained by a method comprising
    (aa) initializing said PSSM with random weights;
    (bb) selecting randomly a weight $w_{ij}$ obtained in (aa);
    (cc) changing the value of said selected weight to generate a test psPSSM comprising said selected weight having said changed value;
    (dd) calculating a score for each of a plurality of siRNAs functional sequence motifs using said test PSSM according to equation $$Score = \sum_{k=1}^{L} \ln(w_k/p_k)$$

wherein said $w_k$ and $p_k$ are respectively weights of a nucleotide at position k in said functional sequence motif and in a random sequence;

(ee) calculating correlation of said score and a metric of a characteristic of an siRNA among said plurality of siRNAs functional sequence motifs;

(ff) repeating steps (cc)-(ee) for a plurality of different values of said selected weight in a given range and retain the value that corresponds to the best correlation for said selected weight; and (gg) repeating steps (bb)-(ff) for a chosen number of times; thereby determining said PSSM.

25. The method of claim 24, further comprising selecting said plurality of siRNA functional sequence motifs by a method comprising
    (i) identifying a plurality of siRNAs consisting of siRNAs having different values in said metric;
    (ii) identifying a plurality of siRNA functional sequence motifs each corresponding to an siRNA in said plurality of siRNAs.

26. The method of claim 25, wherein said characteristic is silencing efficacy.

27. The method of claim 26, wherein said plurality of N siRNAs target a plurality of different genes having different transcript abundances in a cell.

28. The method of claim 27, wherein said step (c) is carried out by selecting one or more siRNAs having the highest scores.

29. The method of claim 27, wherein said step (bb) is carried out by selecting one or more siRNAs having a score closest to a predetermined value, wherein said predetermined value is the score value corresponding to the maximum median silencing efficacy of a plurality of siRNA sequence motifs.

30. The method of claim 29, wherein said plurality of siRNA sequence motifs are sequence motifs in transcript having abundance level of less than about 3-5 copies per cell.

31. The method of claim 27, wherein said step (bb) is carried out by selecting one or more siRNAs having a score within a predetermined range, wherein said predetermined range is a score range corresponding to a plurality of siRNAs sequence motifs having a given level of silencing efficacy.

32. The method of claim 31, wherein said silencing efficacy is above 50% at an siRNA dose of about 100 nM.

33. The method of claim 32, wherein said plurality of siRNA sequence motifs are sequence motifs in transcript having abundance level of less than about 3-5 copies per cell.

34. The method of claim 24, wherein said position-specific score matrix (PSSM) comprises $w_k$, k=1, ..., L, $w_k$ being a difference in probability of finding nucleotide G or C at sequence position k between a first type of siRNA and a second type of siRNA, and wherein said score for each said strand is calculated according to equation $$Score = \sum_{k=1}^{L} w_k.$$

35. The method of claim 34, wherein said first type of siRNA consists of one or more siRNAs having silencing efficacy no less than a first threshold and said second type of siRNA consists of one or more siRNAs having silencing efficacy less than a second threshold.

36. The method of claim 35, wherein said difference in probability is described by a sum of Gaussian curves, each of said Gaussian curves representing the difference in probability of finding a G or C at a different sequence position.

37. The method of claim 36, wherein said first and second thresholds are both 75% at an siRNA dose of 100 nM.

* * * * *